(12) United States Patent
de Sauvage et al.

(10) Patent No.: US 9,914,774 B2
(45) Date of Patent: Mar. 13, 2018

(54) NOTCH PATHWAY INHIBITION

(71) Applicants: Genentech, Inc., South San Francisco, CA (US); The Regents of the University of California, Oakland, CA (US)

(72) Inventors: Fred de Sauvage, Foster City, CA (US); Christian Siebel, Berkeley, CA (US); Brian Biehs, San Francisco, CA (US); Hua Tian, San Francisco, CA (US); Ophir Klein, San Francisco, CA (US)

(73) Assignees: Genentech, Inc., South San Francisco, CA (US); The Regents of the University of California, Oakland, CA (US)

( * ) Notice: Subject to any disclaimer, the term of this patent is extended or adjusted under 35 U.S.C. 154(b) by 52 days.

(21) Appl. No.: 14/795,761

(22) Filed: Jul. 9, 2015

(65) Prior Publication Data

US 2016/0068596 A1    Mar. 10, 2016

Related U.S. Application Data

(60) Provisional application No. 62/089,425, filed on Dec. 9, 2014, provisional application No. 62/023,554, filed on Jul. 11, 2014.

(51) Int. Cl.
| | | |
|---|---|---|
| *C07K 16/18* | (2006.01) | |
| *C07K 16/22* | (2006.01) | |
| *C07K 16/28* | (2006.01) | |
| *A61K 39/395* | (2006.01) | |
| *C07K 14/705* | (2006.01) | |
| *A61K 31/497* | (2006.01) | |
| *A61K 31/519* | (2006.01) | |
| *C07K 14/475* | (2006.01) | |
| *C07K 14/71* | (2006.01) | |
| *A61K 39/00* | (2006.01) | |

(52) U.S. Cl.
CPC .......... *C07K 16/28* (2013.01); *A61K 31/497* (2013.01); *A61K 31/519* (2013.01); *A61K 39/3955* (2013.01); *C07K 14/705* (2013.01); *C07K 16/18* (2013.01); *C07K 16/22* (2013.01); *C07K 16/2863* (2013.01); *A61K 2039/505* (2013.01); *A61K 2039/507* (2013.01); *C07K 2317/21* (2013.01); *C07K 2317/31* (2013.01); *C07K 2317/524* (2013.01); *C07K 2317/73* (2013.01); *C07K 2317/76* (2013.01); *C07K 2319/30* (2013.01); *C07K 2319/32* (2013.01)

(58) Field of Classification Search
CPC .......... A61K 2300/00; A61K 39/39558; A61K 2039/505; A61K 39/3955; A61K 38/177; C07K 2317/76; C07K 16/28; C07K 16/2863; C07K 2317/565; C07K 14/705; C07K 16/22; C07K 16/18; C07K 14/475; C07K 2316/96

See application file for complete search history.

(56) References Cited

U.S. PATENT DOCUMENTS

| | | |
|---|---|---|
| 6,756,511 B2 | 6/2004 | Castro Pineiro et al. |
| 6,890,956 B2 | 5/2005 | Churcher et al. |
| 6,984,626 B2 | 1/2006 | Nadin et al. |
| 7,049,296 B2 | 5/2006 | Castro Pineiro et al. |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Castro Pineiro et al. |
| 7,723,477 B2 | 5/2010 | Gurney et al. |
| 7,803,377 B2 | 9/2010 | Yan et al. |
| 7,919,092 B2 | 4/2011 | Lewicki et al. |
| 7,935,791 B2 | 5/2011 | Fung et al. |
| 7,947,277 B2 | 5/2011 | Ernst et al. |
| 7,982,013 B2 | 7/2011 | Gurney et al. |
| 7,994,285 B2 | 8/2011 | Li et al. |
| 8,088,617 B2 | 1/2012 | Gurney et al. |
| 8,148,106 B2 | 4/2012 | Fung et al. |
| 8,206,713 B2 | 6/2012 | Lewicki et al. |
| 8,226,943 B2 | 7/2012 | Gurney et al. |
| 8,329,868 B2 | 12/2012 | Fung et al. |
| 8,377,886 B2 | 2/2013 | Susztak et al. |
| 8,404,239 B2 | 3/2013 | Siebel et al. |
| 8,425,903 B2 | 4/2013 | Gurney et al. |
| 8,404,237 B2 | 5/2013 | Lewicki et al. |
| 8,435,513 B2 | 5/2013 | Gurney |
| 8,445,491 B2 | 5/2013 | Lum et al. |
| 8,450,340 B2 | 5/2013 | Hood et al. |
| 8,460,661 B2 | 6/2013 | Gurney et al. |
| 8,507,442 B2 | 8/2013 | Gurney et al. |
| 8,513,388 B2 | 8/2013 | Li et al. |

(Continued)

FOREIGN PATENT DOCUMENTS

| | | |
|---|---|---|
| WO | 2006/052128 | 5/2006 |
| WO | 2008/031009 A2 | 3/2008 |

(Continued)

OTHER PUBLICATIONS

Purow, B. Notch inhibition as a promising new approach to cancer therapy. Adv Exp Med Biol 727L 305-319, 2012.*

(Continued)

*Primary Examiner* — Bridget E Bunner
(74) *Attorney, Agent, or Firm* — McNeill Baur PLLC

(57) ABSTRACT

The invention provides Notch pathway inhibition with reduced toxicity.

37 Claims, 10 Drawing Sheets

(10 of 10 Drawing Sheet(s) Filed in Color)

(56) References Cited

U.S. PATENT DOCUMENTS

| | | | |
|---|---|---|---|
| 8,551,789 | B2 | 10/2013 | Gurney |
| 8,802,097 | B2 | 8/2014 | Gurney et al. |
| 2008/0317760 | A1 | 12/2008 | Gurney et al. |
| 2009/0258026 | A2 | 10/2009 | Siebel et al. |
| 2010/0080808 | A1 | 4/2010 | Siebel et al. |
| 2010/0196385 | A1 | 8/2010 | Bedian et al. |
| 2010/0317098 | A1 | 12/2010 | Gurney et al. |
| 2011/0243963 | A1 | 10/2011 | Abo et al. |
| 2011/0256127 | A1 | 10/2011 | Bourhis et al. |
| 2011/0305695 | A1* | 12/2011 | Satyal ............... C07K 14/705 424/134.1 |
| 2011/0311552 | A1 | 12/2011 | Gurney et al. |
| 2012/0027778 | A1 | 2/2012 | Gurney |
| 2012/0093813 | A1 | 4/2012 | Kang et al. |
| 2012/0213786 | A1 | 8/2012 | Van der Horst |
| 2012/0276089 | A1 | 11/2012 | Lee et al. |
| 2012/0301489 | A1 | 11/2012 | Gurney et al. |
| 2012/0328608 | A1 | 12/2012 | Siebel |
| 2013/0034551 | A2 | 2/2013 | Satyal et al. |
| 2013/0045209 | A1 | 2/2013 | Gurney et al. |
| 2013/0064823 | A1 | 3/2013 | Cong et al. |
| 2013/0095104 | A1 | 4/2013 | Cummings et al. |
| 2013/0144040 | A1 | 6/2013 | Fung et al. |
| 2013/0164295 | A1 | 6/2013 | Gurney et al. |
| 2013/0183320 | A1 | 7/2013 | Wu et al. |
| 2013/0190258 | A1 | 7/2013 | Cashman et al. |
| 2013/0209473 | A1 | 8/2013 | de Sauvage et al. |
| 2013/0225576 | A1 | 8/2013 | Hood et al. |
| 2013/0266594 | A1 | 10/2013 | Geles et al. |
| 2013/0267495 | A1 | 10/2013 | Hood et al. |
| 2013/0273058 | A1 | 10/2013 | Tarasova et al. |
| 2013/0295106 | A1 | 11/2013 | Gurney et al. |
| 2013/0296344 | A1 | 11/2013 | Boutros et al. |
| 2013/0323248 | A1 | 12/2013 | Gros et al. |
| 2013/0323257 | A1 | 12/2013 | Gurney et al. |
| 2013/0323265 | A1 | 12/2013 | Stagg et al. |
| 2013/0323266 | A1 | 12/2013 | Hoey et al. |
| 2014/0005164 | A1 | 1/2014 | Varrone et al. |
| 2014/0010810 | A1 | 1/2014 | West et al. |
| 2014/0031374 | A1 | 1/2014 | Holsworth et al. |
| 2014/0093521 | A1 | 4/2014 | Benatuil et al. |

FOREIGN PATENT DOCUMENTS

| | | |
|---|---|---|
| WO | 2010/037041 | 4/2010 |
| WO | 2011/088123 | 7/2011 |
| WO | 2011/119661 A1 | 9/2011 |
| WO | 2014/012007 A2 | 1/2014 |
| WO | 2014/028446 A1 | 2/2014 |
| WO | 2014/111704 A1 | 7/2014 |

OTHER PUBLICATIONS

Van Es et al. Notch and Wnt inhibitors as potential new drugs for intestinal neoplastic disease. TRENDS Mol Med 11(11): 496-502, 2005.*

Cubillo et al., "A Ph1b Study of Demcizumab (DEM, anti-DLL4) with Gemcitabine (GEM) in Patients with 1st Line Locally Advanced or Metastatic Pancreatic Cancer" Poster (2013) (1 page).

Cubillo et al., "A Phase 1b Study of the Anti-Cancer Stem Cell Agent Demcizumab (DEM, anti-DLL4) and Gemcitabine (GEM) with or without Nab-Paclitaxel in Patients with Pancreatic Cancer" Poster, 2016 Gastrointestinal Cancers Symposium, pp. 1 (2016).

Davis et al., "A first-in-human phase I study of the novel cancer stem cell (CSC) targeting antibody OMP-52M51 (anti-Notch1) administered intravenously to patients with certain advanced solid tumors" Poster AACR-NCI-EORTC International Conference: Molecular Targets and Cancer Therapeutics, (Oct. 2013) (1 page).

Dupont, "OMP-59R5: A Novel Therapeutic Antibody in Clinical Development for Patients with Cancer" Slides (22 pages).

U.S. Appl. No. 11/851,596, filed Sep. 7, 2007.

U.S. Appl. No. 13/069,582, filed Mar. 23, 2011.

International Search Report and Written Opinion for International Patent Application No. PCT/US2007/077845 dated May 7, 2009 (11 pages).

McKeage et al., "A Phase 1b Study of Demcizumab plus Pemetrexed and Carboplatin in Patients with 1st line Non-Squamous Non-Small Cell Lung Cancer (NSCLC)." 2014 ASCO Annual Meeting, (2014).

Notification of Transmittal of the International Search Report and the Written Opinion of the International Searching Authority, or the Declaration, pp. 13 (dated Sep. 29, 2015).

O'Reilly, "A Phase 1b of anti-cancer stem cell antibody OMP-59R5 (anti-Notch2/3) with nab-paclitaxel and gemcitabine (Nab-P+Gem) in patients (pts) with untreated metastatic pancreatic cancer (mPC)" Poster 2014 Gastrointestinal Cancers Symposium, San Francisco, CA, USA, (Jan. 2014).

Papadopoulos et al., "A Phase in study in patients with advanced solid tumors for the human monoclonal antibody vantictumab (OMP-18R5; anti-Frizzled) targeting the WNT pathway" Poster European Cancer Congress 2013 (ECCO-ESMO-ESTRO), Amsterdam, (Sep. 29, 2013).

Ridgway, "Chronic DLL4 blockade induces vascular neoplasms" Nature 463(11):E6-E7 (Feb. 11, 2010).

Smith et al., "A First-In-Human, Phase I Trial of the Anti-DLL4 Antibody (OMP-21M18) Targeting Cancer Stem Cells (CSCs) in Patients with Advanced Solid Tumors" pp. 1 (Nov. 2010).

Smith et al., "A First-in-human Phase I Study to Evaluate the Fully Human Monoclonal Antibody OMP-59R5 (anti-Notch2/3) Administered Intravenously to Patients with Advanced Solid Tumors" Slides 24th Annual EORTC NCI AACR Symposium on Moecular Targets and Cancer Therapuetics, Dublin, Ireland, (Nov. 2012).

Smith et al., "First-in-human evaluation of the human monoclonal antibody vantictumab (OMP-18R5; anti-Frizzled) targeting the WNT pathway in a Phase I study for patients with advanced solid tumors" Poster 2013 ASCO Annual Meeting, Chicago, IL (Jun. 2013).

Smith et al., "A first-in-human Phase 1 study of anti-cancer stem cell (CSC) agent OMP-54F28 (FZD8-Fc) targeting the WNT pathway in patients with advanced solid tumors" Poster 2013 AACR-NCI-EORTC Molecular Targets and Cancer Therapeutics Conference, Boston, MA, 1 page, (Oct. 21, 2013).

Smith, "Biomarker analysis in the first-in-human Phase 1a study for vantictumab (OMP-18R5; anti-Frizzled) demonstrates pharmacodynamic (PD) modulation of the Wnt pathway in patients with advanced solid tumors" Poster AACR-NCI-EORTC International Conference: Molecular Targets and Cancer Therapeutic, Boston MA, (Oct. 29, 2013) (1 page).

Tolcher et al., "A First-in-Human Phase I Study to Evaluate the Fully Human Monoclonal Antibody OMP-59R5 (Anti-Notch2/3) Administered Intravenously to Patients with Advanced Solid Tumors: Study 59R5-001" Poster 2012 ASCO Annual Meeting, Chicago, IL, (Jun. 2012).

Tolcher et al., "Biomarker analysis in the first-in-human OMP-59R5 (anti-Notch2/3) phase I study demonstrates pharmacodynamic (PD) modulation of the Notch Pathway in patients with advanced solid tumors" Poster 26th EORTC-NCI-AACR Symposium on Molecular Targets and Cancer Therapeutics Meeting, Dublin, Ireland, (Nov. 2012).

Wu et al. et al., "Therapeutic Antibody targeting of individual Notch receptors"Nature 464:1052-1057.

Hoey, "Development of FZD8-Fc (OMP-54F28), a Wnt signaling antagonist that inhibits tumor growth and reduces tumor initiating cell frequency" Slides 2013 AACR Annual Meeting, pp. 1-26.

McKeage et al., "Phase 1b Study of Demcizumab plus Pemetrexed and Carboplatin in Patients with 1st line Non-Small Cell Lung Cancer (NSCLC)" Poster 2013 AACR-NCI-EORTC Molecular Targets and Cancer Therapeutics Conference, pp. 1 (Oct. 21, 2013).

Zecchini et al., "Notch signaling regulates the differentiation of post-mitotic intestinal epithelial cells" Genes & Development 19:1686-1691 ( 2005).

Landman et al., "Small molecule inhibitors of WNT/β-catenin signaling block IL-1β- and TNFα-induced cartilage degradation" Arthritis Res. Ther. 15( SUPPL R93):1-11, 2013.

(56) References Cited

OTHER PUBLICATIONS

Tian et al., "Oppsoing Activities of Notch and Wnt Signaling Regulate Intestinal Stem Cells and Gut Homeostasis" Cell Reports 11:33-42 (Apr. 7, 2015).

Kuhnert et al., "Essential requirement for Wnt signaling in proliferation of adult small intestine and colon revealed by adenoviral expression of Dickkopf-1" PNAS 101(1):266-271 (Jan. 6, 2004).

Pinto et al., "Canonical Wnt signals are essential for homeostasis of the intestinal epithelium" Genes & Development 17:1709-1713 ( 2003).

Chen et al., "Selection and analysis of an optimized anti-VEGF antibody: crystal structure of an affinity-matured Fab in compled with antigen" J Mol Biol 293(4):865-881 ( 1999).

Chen et al., "Small molecule-mediated disruption of Wnt-dependent signaling in tissue regeneration and cancer" Nature Chem Biol 5:100-107 (Feb. 2009).

* cited by examiner

SEQUENCE LISTING

<160> NUMBER OF SEQ ID NOS: 324

<210> SEQ ID NO 1
<211> LENGTH: 1218
<212> TYPE: PRT
<213> ORGANISM: Homo sapiens

<400> SEQUENCE: 1

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365
```

-continued

```
Pro Thr Cys Ser Thr Asn Ile Asp Asp Cys Ser Pro Asn Asn Cys Ser
    370             375             380

His Gly Gly Thr Cys Gln Asp Leu Val Asn Gly Phe Lys Cys Val Cys
385             390             395             400

Pro Pro Gln Trp Thr Gly Lys Thr Cys Gln Leu Asp Ala Asn Glu Cys
            405             410             415

Glu Ala Lys Pro Cys Val Asn Ala Lys Ser Cys Lys Asn Leu Ile Ala
            420             425             430

Ser Tyr Tyr Cys Asp Cys Leu Pro Gly Trp Met Gly Gln Asn Cys Asp
    435             440             445

Ile Asn Ile Asn Asp Cys Leu Gly Gln Cys Gln Asn Asp Ala Ser Cys
450             455             460

Arg Asp Leu Val Asn Gly Tyr Arg Cys Ile Cys Pro Pro Gly Tyr Ala
465             470             475             480

Gly Asp His Cys Glu Arg Asp Ile Asp Glu Cys Ala Ser Asn Pro Cys
                485             490             495

Leu Asn Gly Gly His Cys Gln Asn Glu Ile Asn Arg Phe Gln Cys Leu
            500             505             510

Cys Pro Thr Gly Phe Ser Gly Asn Leu Cys Gln Leu Asp Ile Asp Tyr
    515             520             525

Cys Glu Pro Asn Pro Cys Gln Asn Gly Ala Gln Cys Tyr Asn Arg Ala
    530             535             540

Ser Asp Tyr Phe Cys Lys Cys Pro Glu Asp Tyr Glu Gly Lys Asn Cys
545             550             555             560

Ser His Leu Lys Asp His Cys Arg Thr Thr Pro Cys Glu Val Ile Asp
            565             570             575

Ser Cys Thr Val Ala Met Ala Ser Asn Asp Thr Pro Glu Gly Val Arg
        580             585             590

Tyr Ile Ser Ser Asn Val Cys Gly Pro His Gly Lys Cys Lys Ser Gln
        595             600             605

Ser Gly Gly Lys Phe Thr Cys Asp Cys Asn Lys Gly Phe Thr Gly Thr
    610             615             620

Tyr Cys His Glu Asn Ile Asn Asp Cys Glu Ser Asn Pro Cys Arg Asn
625             630             635             640

Gly Gly Thr Cys Ile Asp Gly Val Asn Ser Tyr Lys Cys Ile Cys Ser
            645             650             655

Asp Gly Trp Glu Gly Ala Tyr Cys Glu Thr Asn Ile Asn Asp Cys Ser
            660             665             670

Gln Asn Pro Cys His Asn Gly Gly Thr Cys Arg Asp Leu Val Asn Asp
            675             680             685

Phe Tyr Cys Asp Cys Lys Asn Gly Trp Lys Gly Lys Thr Cys His Ser
    690             695             700

Arg Asp Ser Gln Cys Asp Glu Ala Thr Cys Asn Asn Gly Gly Thr Cys
705             710             715             720

Tyr Asp Glu Gly Asp Ala Phe Lys Cys Met Cys Pro Gly Gly Trp Glu
            725             730             735

Gly Thr Thr Cys Asn Ile Ala Arg Asn Ser Ser Cys Leu Pro Asn Pro
            740             745             750

Cys His Asn Gly Gly Thr Cys Val Asn Gly Glu Ser Phe Thr Cys
            755             760             765

Val Cys Lys Glu Gly Trp Glu Gly Pro Ile Cys Ala Gln Asn Thr Asn
    770             775             780

Asp Cys Ser Pro His Pro Cys Tyr Asn Ser Gly Thr Cys Val Asp Gly
```

```
                785                 790                 795                 800
Asp Asn Trp Tyr Arg Cys Glu Cys Ala Pro Gly Phe Ala Gly Pro Asp
                    805                 810                 815

Cys Arg Ile Asn Ile Asn Glu Cys Gln Ser Ser Pro Cys Ala Phe Gly
                    820                 825                 830

Ala Thr Cys Val Asp Glu Ile Asn Gly Tyr Arg Cys Val Cys Pro Pro
                    835                 840                 845

Gly His Ser Gly Ala Lys Cys Gln Glu Val Ser Gly Arg Pro Cys Ile
        850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
                900                 905                 910

Ser Gly Gln Ser Cys Ile Pro Ile Leu Asp Asp Gln Cys Phe Val His
            915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
    1010                1015                1020

Asp Gly Asn Pro Ile Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Ala Arg Phe Ala Lys Gln
    1160                1165                1170

Pro Ala Tyr Thr Leu Val Asp Arg Glu Glu Lys Pro Pro Asn Gly
    1175                1180                1185

Thr Pro Thr Lys His Pro Asn Trp Thr Asn Lys Gln Asp Asn Arg
    1190                1195                1200
```

Asp Leu Glu Ser Ala Gln Ser Leu Asn Arg Met Glu Tyr Ile Val
    1205                1210                1215

<210> SEQ ID NO 2
<211> LENGTH: 1218
<212> TYPE: PRT
<213> ORGANISM: Mus musculus

<400> SEQUENCE: 2

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Val Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Asp Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Thr Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Arg Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly

```
              355                 360                 365
Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
        755                 760                 765

Val Cys Lys Glu Gly Trp Glu Gly Pro Ile Cys Thr Gln Asn Thr Asn
    770                 775                 780
```

```
Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
            835                 840                 845

Gly His Ser Gly Ala Lys Cys His Glu Val Ser Gly Arg Ser Cys Ile
        850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Leu Ser Ala
        995                 1000                1005

Asn Asn Glu Ile His Val Ala Ile Ser Ala Glu Asp Ile Arg Asp
    1010                1015                1020

Asp Gly Asn Pro Val Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Val Cys
    1070                1075                1080

Cys Leu Val Thr Ala Phe Tyr Trp Cys Val Arg Lys Arg Arg Lys
    1085                1090                1095

Pro Ser Ser His Thr His Ser Ala Pro Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Val Arg Phe Ala Lys Gln
    1160                1165                1170

Pro Val Tyr Thr Leu Val Asp Arg Glu Glu Lys Ala Pro Ser Gly
    1175                1180                1185
```

-continued

```
Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 3
<211> LENGTH: 1238
<212> TYPE: PRT
<213> ORGANISM: Homo sapiens

<400> SEQUENCE: 3

Met Arg Ala Gln Gly Arg Gly Arg Leu Pro Arg Arg Leu Leu Leu
1               5                   10                  15

Leu Ala Leu Trp Val Gln Ala Ala Arg Pro Met Gly Tyr Phe Glu Leu
                20                  25                  30

Gln Leu Ser Ala Leu Arg Asn Val Asn Gly Glu Leu Leu Ser Gly Ala
                35                  40                  45

Cys Cys Asp Gly Asp Gly Arg Thr Thr Arg Ala Gly Gly Cys Gly His
50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
                100                 105                 110

Asp Arg Ala Arg Ala Arg Ala Arg Ala Gly Gly Asp Gln Asp Pro Gly
                115                 120                 125

Leu Val Val Ile Pro Phe Gln Phe Ala Trp Pro Arg Ser Phe Thr Leu
130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
                180                 185                 190

Gln Ile Arg Val Arg Cys Asp Glu Asn Tyr Tyr Ser Ala Thr Cys Asn
                195                 200                 205

Lys Phe Cys Arg Pro Arg Asn Asp Phe Phe Gly His Tyr Thr Cys Asp
                210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
                260                 265                 270

Cys Asp Glu Cys Val Pro Tyr Pro Gly Cys Val His Gly Ser Cys Val
                275                 280                 285

Glu Pro Trp Gln Cys Asn Cys Glu Thr Asn Trp Gly Gly Leu Leu Cys
                290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
                340                 345                 350
```

```
Ser Asn Pro Cys Ala Asn Gly Gly Ser Cys His Glu Val Pro Ser Gly
        355                 360                 365

Phe Glu Cys His Cys Pro Ser Gly Trp Ser Gly Pro Thr Cys Ala Leu
        370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
                420                 425                 430

Leu Asn Ala Phe Ser Cys Lys Asn Leu Ile Gly Tyr Tyr Cys Asp
        435                 440                 445

Cys Ile Pro Gly Trp Lys Gly Ile Asn Cys His Ile Asn Val Asn Asp
450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495

Leu Glu Arg Asp Glu Cys Ala Ser Ser Pro Cys His Ser Gly Gly Leu
            500                 505                 510

Cys Glu Asp Leu Ala Asp Gly Phe His Cys His Cys Pro Gln Gly Phe
        515                 520                 525

Ser Gly Pro Leu Cys Glu Val Asp Val Asp Leu Cys Glu Pro Ser Pro
        530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
                565                 570                 575

Pro Cys Pro Gly Gly Ala Cys Arg Val Ile Asp Gly Cys Gly Ser Asp
            580                 585                 590

Ala Gly Pro Gly Met Pro Gly Thr Ala Ala Ser Gly Val Cys Gly Pro
        595                 600                 605

His Gly Arg Cys Val Ser Gln Pro Gly Gly Asn Phe Ser Cys Ile Cys
        610                 615                 620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
                645                 650                 655

Ala Phe Arg Cys Phe Cys Pro Ser Gly Trp Glu Gly Glu Leu Cys Asp
                660                 665                 670

Thr Asn Pro Asn Asp Cys Leu Pro Asp Pro Cys His Ser Arg Gly Arg
        675                 680                 685

Cys Tyr Asp Leu Val Asn Asp Phe Tyr Cys Ala Cys Asp Asp Gly Trp
        690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
        755                 760                 765
```

```
Ser Gly Ala Ser Phe Ser Cys Ile Cys Arg Asp Gly Trp Glu Gly Arg
770                 775                 780
Thr Cys Thr His Asn Thr Asn Asp Cys Asn Pro Leu Pro Cys Tyr Asn
785                 790                 795                 800
Gly Gly Ile Cys Val Asp Gly Val Asn Trp Phe Arg Cys Glu Cys Ala
                805                 810                 815
Pro Gly Phe Ala Gly Pro Asp Cys Arg Ile Asn Ile Asp Glu Cys Gln
                820                 825                 830
Ser Ser Pro Cys Ala Tyr Gly Ala Thr Cys Val Asp Glu Ile Asn Gly
                835                 840                 845
Tyr Arg Cys Ser Cys Pro Pro Gly Arg Ala Gly Pro Arg Cys Gln Glu
850                 855                 860
Val Ile Gly Phe Gly Arg Ser Cys Trp Ser Arg Gly Thr Pro Phe Pro
865                 870                 875                 880
His Gly Ser Ser Trp Val Glu Asp Cys Asn Ser Cys Arg Cys Leu Asp
                885                 890                 895
Gly Arg Arg Asp Cys Ser Lys Val Trp Cys Gly Trp Lys Pro Cys Leu
                900                 905                 910
Leu Ala Gly Gln Pro Glu Ala Leu Ser Ala Gln Cys Pro Leu Gly Gln
                915                 920                 925
Arg Cys Leu Glu Lys Ala Pro Gly Gln Cys Leu Arg Pro Pro Cys Glu
                930                 935                 940
Ala Trp Gly Glu Cys Gly Ala Glu Glu Pro Pro Ser Thr Pro Cys Leu
945                 950                 955                 960
Pro Arg Ser Gly His Leu Asp Asn Asn Cys Ala Arg Leu Thr Leu His
                965                 970                 975
Phe Asn Arg Asp His Val Pro Gln Gly Thr Thr Val Gly Ala Ile Cys
                980                 985                 990
Ser Gly Ile Arg Ser Leu Pro Ala Thr Arg Ala Val Ala Arg Asp Arg
                995                 1000                1005
Leu Leu Val Leu Leu Cys Asp Arg Ala Ser Ser Gly Ala Ser Ala
                1010                1015                1020
Val Glu Val Ala Val Ser Phe Ser Pro Ala Arg Asp Leu Pro Asp
                1025                1030                1035
Ser Ser Leu Ile Gln Gly Ala Ala His Ala Ile Val Ala Ala Ile
                1040                1045                1050
Thr Gln Arg Gly Asn Ser Ser Leu Leu Leu Ala Val Thr Glu Val
                1055                1060                1065
Lys Val Glu Thr Val Val Thr Gly Gly Ser Ser Thr Gly Leu Leu
                1070                1075                1080
Val Pro Val Leu Cys Gly Ala Phe Ser Val Leu Trp Leu Ala Cys
                1085                1090                1095
Val Val Leu Cys Val Trp Trp Thr Arg Lys Arg Arg Lys Glu Arg
                1100                1105                1110
Glu Arg Ser Arg Leu Pro Arg Glu Glu Ser Ala Asn Asn Gln Trp
                1115                1120                1125
Ala Pro Leu Asn Pro Ile Arg Asn Pro Ile Glu Arg Pro Gly Gly
                1130                1135                1140
His Lys Asp Val Leu Tyr Gln Cys Lys Asn Phe Thr Pro Pro Pro
                1145                1150                1155
Arg Arg Ala Asp Glu Ala Leu Pro Gly Pro Ala Gly His Ala Ala
                1160                1165                1170
Val Arg Glu Asp Glu Glu Asp Glu Asp Leu Gly Arg Gly Glu Glu
```

-continued

```
            1175                1180                1185

Asp Ser Leu Glu Ala Glu Lys Phe Leu Ser His Lys Phe Thr Lys
    1190                1195                1200

Asp Pro Gly Arg Ser Pro Gly Arg Pro Ala His Trp Ala Ser Gly
    1205                1210                1215

Pro Lys Val Asp Asn Arg Ala Val Arg Ser Ile Asn Glu Ala Arg
    1220                1225                1230

Tyr Ala Gly Lys Glu
    1235

<210> SEQ ID NO 4
<211> LENGTH: 1247
<212> TYPE: PRT
<213> ORGANISM: Mus musculus

<400> SEQUENCE: 4

Met Arg Ala Arg Gly Trp Gly Arg Leu Pro Arg Arg Leu Leu Leu
1               5                   10                  15

Leu Val Leu Cys Val Gln Ala Thr Arg Pro Met Gly Tyr Phe Glu Leu
            20                  25                  30

Gln Leu Ser Ala Leu Arg Asn Val Asn Gly Glu Leu Leu Ser Gly Ala
            35                  40                  45

Cys Cys Asp Gly Asp Gly Arg Thr Thr Arg Ala Gly Gly Cys Gly Arg
    50                  55                  60

Asp Glu Cys Asp Thr Tyr Val Arg Val Cys Leu Lys Glu Tyr Gln Ala
65              70                  75                  80

Lys Val Thr Pro Thr Gly Pro Cys Ser Tyr Gly Tyr Gly Ala Thr Pro
                85                  90                  95

Val Leu Gly Gly Asn Ser Phe Tyr Leu Pro Pro Ala Gly Ala Ala Gly
                100                 105                 110

Asp Arg Ala Arg Ala Arg Ser Arg Thr Gly Gly His Gln Asp Pro Gly
            115                 120                 125

Leu Val Val Ile Pro Phe Gln Phe Ala Trp Pro Arg Ser Phe Thr Leu
            130                 135                 140

Ile Val Glu Ala Trp Asp Trp Asp Asn Asp Thr Thr Pro Asp Glu Glu
145             150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
                180                 185                 190

Gln Ile Arg Val Arg Cys Asp Glu Asn Tyr Tyr Ser Ala Thr Cys Asn
            195                 200                 205

Lys Phe Cys Arg Pro Arg Asn Asp Phe Phe Gly His Tyr Thr Cys Asp
    210                 215                 220

Gln Tyr Gly Asn Lys Ala Cys Met Asp Gly Trp Met Gly Lys Glu Cys
225             230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Lys Phe
                260                 265                 270

Cys Asp Glu Cys Val Pro Tyr Pro Gly Cys Val His Gly Ser Cys Val
            275                 280                 285

Glu Pro Trp His Cys Asp Cys Glu Thr Asn Trp Gly Gly Leu Leu Cys
    290                 295                 300
```

```
Asp Lys Asp Leu Asn Tyr Cys Gly Ser His His Pro Cys Val Asn Gly
305                 310                 315                 320

Gly Thr Cys Ile Asn Ala Glu Pro Asp Gln Tyr Leu Cys Ala Cys Pro
            325                 330                 335

Asp Gly Tyr Leu Gly Lys Asn Cys Glu Arg Ala Glu His Ala Cys Ala
                340                 345                 350

Ser Asn Pro Cys Ala Asn Gly Gly Ser Cys His Glu Val Pro Ser Gly
            355                 360                 365

Phe Glu Cys His Cys Pro Ser Gly Trp Ser Gly Pro Thr Cys Ala Leu
    370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
            420                 425                 430

Leu Asn Ala Phe Ser Cys Lys Asn Leu Ile Gly Gly Tyr Tyr Cys Asp
                435                 440                 445

Cys Leu Pro Gly Trp Lys Gly Ile Asn Cys Gln Ile Asn Ile Asn Asp
450                 455                 460

Cys His Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495

Leu Glu Tyr Asp Lys Cys Ala Ser Ser Pro Cys Arg Arg Gly Gly Ile
            500                 505                 510

Cys Glu Asp Leu Val Asp Gly Phe Arg Cys His Cys Pro Arg Gly Leu
    515                 520                 525

Ser Gly Leu His Cys Glu Val Asp Met Asp Leu Cys Glu Pro Ser Pro
    530                 535                 540

Cys Leu Asn Gly Ala Arg Cys Tyr Asn Leu Glu Gly Asp Tyr Tyr Cys
545                 550                 555                 560

Ala Cys Pro Glu Asp Phe Gly Gly Lys Asn Cys Ser Val Pro Arg Asp
                565                 570                 575

Thr Cys Pro Gly Gly Ala Cys Arg Val Ile Asp Gly Cys Gly Phe Glu
            580                 585                 590

Ala Gly Ser Arg Ala Arg Gly Val Ala Pro Ser Gly Ile Cys Gly Pro
                595                 600                 605

His Gly His Cys Val Ser Leu Pro Gly Gly Asn Phe Ser Cys Ile Cys
    610                 615                 620

Asp Ser Gly Phe Thr Gly Thr Tyr Cys His Glu Asn Ile Asp Asp Cys
625                 630                 635                 640

Met Gly Gln Pro Cys Arg Asn Gly Gly Thr Cys Ile Asp Glu Val Asp
            645                 650                 655

Ser Phe Arg Cys Phe Cys Pro Ser Gly Trp Glu Gly Glu Leu Cys Asp
            660                 665                 670

Ile Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
    690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
```

```
                    725                 730                 735
Ala Cys Pro Pro Gly Trp Lys Gly Ser Thr Cys Thr Ile Ala Lys Asn
                740                 745                 750

Ser Ser Cys Val Pro Asn Pro Cys Val Asn Gly Gly Thr Cys Val Gly
                755                 760                 765

Ser Gly Asp Ser Phe Ser Cys Ile Cys Arg Asp Gly Trp Glu Gly Arg
            770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
                805                 810                 815

Pro Gly Phe Ala Gly Pro Asp Cys Arg Ile Asn Ile Asp Glu Cys Gln
                820                 825                 830

Ser Ser Pro Cys Ala Tyr Gly Ala Thr Cys Val Asp Glu Ile Asn Gly
                835                 840                 845

Tyr Arg Cys Ser Cys Pro Pro Gly Arg Ser Gly Pro Arg Cys Gln Glu
            850                 855                 860

Val Val Ile Phe Thr Arg Pro Cys Trp Ser Arg Gly Met Ser Phe Pro
865                 870                 875                 880

His Gly Ser Ser Trp Met Glu Asp Cys Asn Ser Cys Arg Cys Leu Asp
                    885                 890                 895

Gly His Arg Asp Cys Ser Lys Val Trp Cys Gly Trp Lys Pro Cys Leu
            900                 905                 910

Leu Ser Gly Gln Pro Ser Asp Pro Ser Ala Gln Cys Pro Pro Gly Gln
            915                 920                 925

Gln Cys Gln Glu Lys Ala Val Gly Gln Cys Leu Gln Pro Pro Cys Glu
930                 935                 940

Asn Trp Gly Glu Cys Thr Ala Glu Glu Pro Leu Pro Pro Ser Thr Pro
945                 950                 955                 960

Cys Gln Pro Arg Ser Ser His Leu Asp Asn Asn Cys Ala Arg Leu Thr
                965                 970                 975

Leu Arg Phe Asn Arg Asp Gln Val Pro Gln Gly Thr Thr Val Gly Ala
                980                 985                 990

Ile Cys Ser Gly Ile Arg Ala Leu  Pro Ala Thr Arg Ala  Ala Ala His
                995                 1000                1005

Asp Arg Leu Leu Leu Leu  Cys Asp Arg Ala Ser  Ser Gly Ala
            1010                1015                1020

Ser Ala Val Glu Val Ala Met  Ser Phe Ser Pro Ala  Arg Asp Leu
            1025                1030                1035

Pro Asp  Ser Ser Leu Ile Gln  Ser Thr Ala His Ala  Ile Val Ala
            1040                1045                1050

Ala Ile  Thr Gln Arg Gly Asn  Ser Ser Leu Leu Leu  Ala Val Thr
            1055                1060                1065

Glu Val  Lys Val Glu Thr Val  Val Met Gly Gly Ser  Ser Thr Gly
            1070                1075                1080

Leu Leu  Val Pro Val Leu Cys  Ser Val Phe Ser Val  Leu Trp Leu
            1085                1090                1095

Ala Cys  Val Val Ile Cys Val  Trp Trp Thr Arg Lys  Arg Arg Lys
            1100                1105                1110

Glu Arg  Glu Arg Ser Arg Leu  Pro Arg Asp Glu Ser  Thr Asn Asn
            1115                1120                1125

Gln Trp  Ala Pro Leu Asn Pro  Ile Arg Asn Pro Ile  Glu Arg Pro
            1130                1135                1140
```

```
Gly Gly Ser Gly Leu Gly Thr Gly Gly His Lys Asp Ile Leu Tyr
    1145                1150                1155

Gln Cys Lys Asn Phe Thr Pro Pro Arg Ala Gly Glu Ala
    1160                1165                1170

Leu Pro Gly Pro Ala Gly His Gly Ala Gly Gly Glu Asp Glu Glu
    1175                1180                1185

Asp Glu Glu Leu Ser Arg Gly Asp Gly Asp Ser Pro Glu Ala Glu
    1190                1195                1200

Lys Phe Ile Ser His Lys Phe Thr Lys Asp Pro Ser Cys Ser Leu
    1205                1210                1215

Gly Arg Pro Ala Cys Trp Ala Pro Gly Pro Lys Val Asp Asn Arg
    1220                1225                1230

Ala Val Arg Ser Thr Lys Asp Val Arg Arg Ala Gly Arg Glu
    1235                1240                1245

<210> SEQ ID NO 5
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Asp Leu Gly Ser Gln Phe Glu Leu Glu Ile Leu Ser Met Gln Asn
1               5                   10                  15

Val Asn Gly Glu Leu Gln Asn Gly Asn Cys Cys Gly Val Arg Asn
            20                  25                  30

Pro Gly Asp Arg Lys Cys Thr Arg Asp Glu Cys Asp Thr Tyr Phe Lys
        35                  40                  45

Val Cys Leu Lys Glu Tyr Gln Ser Arg Val Thr Ala Gly Gly Pro Cys
    50                  55                  60

Ser Phe Gly Ser Gly Ser Thr Pro Val Ile Gly Gly Asn Thr Phe Asn
65                  70                  75                  80

Leu Lys Ala Ser Arg Gly Asn Asp Arg Asn Arg Ile Val Leu Pro Phe
                85                  90                  95

Ser Phe Ala Trp Pro Arg Ser Tyr Thr Leu Leu Val Glu Ala Trp Asp
            100                 105                 110

Ser Ser Asn Asp Thr Ile Gln Pro Asp Ser Ile Ile Glu Lys Ala Ser
        115                 120                 125

His Ser Gly Met Ile Asn Pro Ser Arg Gln Trp Gln Thr Leu Lys Gln
    130                 135                 140

Asn Thr Gly Ile Ala His Phe Glu Tyr Gln Ile Arg Val Thr Cys Asp
145                 150                 155                 160

Asp His Tyr Tyr Gly Phe Gly Cys Asn Lys Phe Cys Arg Pro Arg Asp
                165                 170                 175

Asp Phe Phe Gly His Tyr Ala Cys Asp Gln Asn Gly Asn Lys Thr Cys
            180                 185                 190

Met Glu Gly Trp Met Gly Pro Asp Cys Asn Lys Ala Ile Cys Arg Gln
        195                 200                 205

Gly Cys Ser Pro Lys His Gly Ser Cys Lys Leu Pro Gly Asp Cys Arg
    210                 215                 220

Cys Gln Tyr Gly Trp Gln Gly Leu Tyr Cys Asp Lys Cys Ile Pro His
225                 230                 235                 240
```

```
Pro Gly Cys Val His Gly Thr Cys Asn Glu Pro Trp Gln Cys Leu Cys
            245                 250                 255

Glu Thr Asn Trp Gly Gly Gln Leu Cys Asp Lys Asp Leu Asn Tyr Cys
        260                 265                 270

Gly Thr His Gln Pro Cys Leu Asn Arg Gly Thr Cys Ser Asn Thr Gly
        275                 280                 285

Pro Asp Lys Tyr Gln Cys Ser Cys Pro Glu Gly Tyr Ser Gly Pro Asn
        290                 295                 300

Cys Glu Ile Ala Glu His Ala Cys Leu Ser Asp Pro Cys His Asn Arg
305                 310                 315                 320

Gly Ser Cys Lys Glu Thr Ser Ser Gly Phe Glu Cys Glu Cys Ser Pro
                325                 330                 335

Gly Trp Thr Gly Pro Thr Cys Ser Thr Asn Ile Asp Asp Glu Phe Gly
                340                 345                 350

Leu Val Pro Arg Gly Ser Gly His His His His His
                355                 360                 365

<210> SEQ ID NO 6
<211> LENGTH: 343
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Phe Glu Leu Glu Ile Leu Ser Met Gln Asn Val Asn Gly Glu Leu
1               5                   10                  15

Gln Asn Gly Asn Cys Cys Gly Gly Ala Arg Asn Pro Gly Asp Arg Lys
            20                  25                  30

Cys Thr Arg Asp Glu Cys Asp Thr Tyr Phe Lys Val Cys Leu Lys Glu
        35                  40                  45

Tyr Gln Ser Arg Val Thr Ala Gly Gly Pro Cys Ser Phe Gly Ser Gly
    50                  55                  60

Ser Thr Pro Val Ile Gly Gly Asn Thr Phe Asn Leu Lys Ala Ser Arg
65                  70                  75                  80

Gly Asn Asp Arg Asn Arg Ile Val Leu Pro Phe Ser Phe Ala Trp Pro
                85                  90                  95

Arg Ser Tyr Thr Leu Leu Val Glu Ala Trp Asp Ser Ser Asn Asp Thr
                100                 105                 110

Val Gln Pro Asp Ser Ile Ile Glu Lys Ala Ser His Ser Gly Met Ile
        115                 120                 125

Asn Pro Ser Arg Gln Trp Gln Thr Leu Lys Gln Asn Thr Gly Val Ala
    130                 135                 140

His Phe Glu Tyr Gln Ile Arg Val Thr Cys Asp Asp Tyr Tyr Tyr Gly
145                 150                 155                 160

Phe Gly Cys Asn Lys Phe Cys Arg Pro Arg Asp Asp Phe Phe Gly His
                165                 170                 175

Tyr Ala Cys Asp Gln Asn Gly Asn Lys Thr Cys Met Glu Gly Trp Met
            180                 185                 190

Gly Pro Glu Cys Asn Arg Ala Ile Cys Arg Gln Gly Cys Ser Pro Lys
        195                 200                 205

His Gly Ser Cys Lys Leu Gly Asp Cys Arg Cys Gln Tyr Gly Trp Gln
    210                 215                 220

Gly Leu Tyr Cys Asp Lys Cys Ile Pro His Pro Gly Cys Val His Gly
```

```
            225                 230                 235                 240

Ile Cys Asn Glu Pro Trp Gln Cys Leu Cys Glu Thr Asn Trp Gly Gly
                    245                 250                 255

Gln Leu Cys Asp Lys Asp Leu Asn Tyr Cys Gly Thr His Gln Pro Cys
                260                 265                 270

Leu Asn Gly Gly Thr Cys Ser Asn Thr Gly Pro Asp Lys Tyr Gln Cys
            275                 280                 285

Ser Cys Pro Glu Gly Tyr Ser Gly Pro Asn Cys Glu Ile Ala Glu His
    290                 295                 300

Ala Cys Leu Ser Asp Pro Cys His Asn Arg Gly Ser Cys Lys Glu Thr
305                 310                 315                 320

Ser Leu Gly Phe Glu Cys Glu Cys Ser Pro Gly Trp Thr Gly Pro Thr
                325                 330                 335

Cys Ser Thr Asn Ile Asp Asp
            340

<210> SEQ ID NO 7
<211> LENGTH: 383
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Asp Leu Gly Ser Met Gly Tyr Phe Glu Leu Gln Leu Ser Ala Leu
1               5                   10                  15

Arg Asn Val Asn Gly Glu Leu Leu Ser Gly Ala Cys Cys Asp Gly Asp
                20                  25                  30

Gly Arg Thr Thr Arg Ala Gly Gly Cys Gly Arg Asp Glu Cys Asp Thr
            35                  40                  45

Tyr Val Arg Val Cys Leu Lys Glu Tyr Gln Ala Lys Val Thr Pro Thr
    50                  55                  60

Gly Pro Cys Ser Tyr Gly Tyr Gly Ala Thr Pro Val Leu Gly Gly Asn
65                  70                  75                  80

Ser Phe Tyr Leu Pro Pro Ala Gly Ala Ala Gly Asp Arg Ala Arg Ala
                85                  90                  95

Arg Ser Arg Thr Gly Gly His Gln Asp Pro Gly Leu Val Val Ile Pro
            100                 105                 110

Phe Gln Phe Ala Trp Pro Arg Ser Phe Thr Leu Ile Val Glu Ala Trp
        115                 120                 125

Asp Trp Asp Asn Asp Thr Thr Pro Asp Glu Glu Leu Leu Ile Glu Arg
    130                 135                 140

Val Ser His Ala Gly Met Ile Asn Pro Glu Asp Arg Trp Lys Ser Leu
145                 150                 155                 160

His Phe Ser Gly His Val Ala His Leu Glu Leu Gln Ile Arg Val Arg
                165                 170                 175

Cys Asp Glu Asn Tyr Tyr Ser Ala Thr Cys Asn Lys Phe Cys Arg Pro
            180                 185                 190

Arg Asn Asp Phe Phe Gly His Tyr Thr Cys Asp Gln Tyr Gly Asn Lys
        195                 200                 205

Ala Cys Met Asp Gly Trp Met Gly Lys Glu Cys Lys Glu Ala Val Cys
    210                 215                 220

Lys Gln Gly Cys Asn Leu Leu His Gly Gly Cys Thr Val Pro Gly Glu
225                 230                 235                 240
```

```
Cys Arg Cys Ser Tyr Gly Trp Gln Gly Lys Phe Cys Asp Glu Cys Val
            245                 250                 255

Pro Tyr Pro Gly Cys Val His Gly Ser Cys Val Glu Pro Trp His Cys
            260                 265                 270

Asp Cys Glu Thr Asn Trp Gly Gly Leu Leu Cys Asp Lys Asp Leu Asn
            275                 280                 285

Tyr Cys Gly Ser His His Pro Cys Val Asn Gly Thr Cys Ile Asn
            290                 295                 300

Ala Glu Pro Asp Gln Tyr Leu Cys Ala Cys Pro Asp Gly Tyr Leu Gly
305                 310                 315                 320

Lys Asn Cys Glu Arg Ala Glu His Ala Cys Ala Ser Asn Pro Cys Ala
            325                 330                 335

Asn Gly Gly Ser Cys His Glu Val Pro Ser Gly Phe Glu Cys His Cys
            340                 345                 350

Pro Ser Gly Trp Asn Gly Pro Thr Cys Ala Leu Asp Ile Asp Glu Glu
            355                 360                 365

Phe Gly Leu Val Pro Arg Gly Ser Gly His His His His His His
370                 375                 380
```

<210> SEQ ID NO 8
<211> LENGTH: 381
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Ala Arg Pro Met Gly Tyr Phe Glu Leu Gln Leu Ser Ala Leu Arg Asn
1               5                   10                  15

Val Asn Gly Glu Leu Leu Ser Gly Ala Cys Cys Asp Gly Asp Gly Arg
            20                  25                  30

Thr Thr Arg Ala Gly Gly Cys Gly His Asp Glu Cys Asp Thr Tyr Val
            35                  40                  45

Arg Val Cys Leu Lys Glu Tyr Gln Ala Lys Val Thr Pro Thr Gly Pro
50                  55                  60

Cys Ser Tyr Gly His Gly Ala Thr Pro Val Leu Gly Gly Asn Ser Phe
65                  70                  75                  80

Tyr Leu Pro Pro Ala Gly Ala Ala Gly Asp Arg Ala Arg Ala Arg Ala
            85                  90                  95

Arg Ala Gly Gly Asp Gln Asp Pro Gly Leu Val Val Ile Pro Phe Gln
            100                 105                 110

Phe Ala Trp Pro Arg Ser Phe Thr Leu Ile Val Glu Ala Trp Asp Trp
            115                 120                 125

Asp Asn Asp Thr Thr Pro Asn Glu Glu Leu Leu Ile Glu Arg Val Ser
130                 135                 140

His Ala Gly Met Ile Asn Pro Glu Asp Arg Trp Lys Ser Leu His Phe
145                 150                 155                 160

Ser Gly His Val Ala His Leu Glu Leu Gln Ile Arg Val Arg Cys Asp
            165                 170                 175

Glu Asn Tyr Tyr Ser Ala Thr Cys Asn Lys Phe Cys Arg Pro Arg Asn
            180                 185                 190

Asp Phe Phe Gly His Tyr Thr Cys Asp Gln Tyr Gly Asn Lys Ala Cys
            195                 200                 205
```

-continued

```
Met Asp Gly Trp Met Gly Lys Glu Cys Lys Glu Ala Val Cys Lys Gln
        210                 215                 220

Gly Cys Asn Leu Leu His Gly Gly Cys Thr Val Pro Gly Glu Cys Arg
225                 230                 235                 240

Cys Ser Tyr Gly Trp Gln Gly Arg Phe Cys Asp Glu Cys Val Pro Tyr
            245                 250                 255

Pro Gly Cys Val His Gly Ser Cys Val Glu Pro Trp Gln Cys Asn Cys
        260                 265                 270

Glu Thr Asn Trp Gly Gly Leu Leu Cys Asp Lys Asp Leu Asn Tyr Cys
    275                 280                 285

Gly Ser His His Pro Cys Thr Asn Gly Gly Thr Cys Ile Asn Ala Glu
290                 295                 300

Pro Asp Gln Tyr Arg Cys Thr Cys Pro Asp Gly Tyr Ser Gly Arg Asn
305                 310                 315                 320

Cys Glu Lys Ala Glu His Ala Cys Thr Ser Asn Pro Cys Ala Asn Gly
            325                 330                 335

Gly Ser Cys His Glu Val Pro Ser Gly Phe Glu Cys His Cys Pro Ser
        340                 345                 350

Gly Trp Ser Gly Pro Thr Cys Ala Leu Asp Ile Asp Glu Glu Phe Gly
    355                 360                 365

Leu Val Pro Arg Gly Ser Gly His His His His His His
370                 375                 380

<210> SEQ ID NO 9
<211> LENGTH: 2555
<212> TYPE: PRT
<213> ORGANISM: Homo sapiens

<400> SEQUENCE: 9

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
            85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
            165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205
```

```
Thr His Thr Gly Pro Asn Cys Glu Arg Pro Tyr Val Pro Cys Ser Pro
210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
            245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
            355                 360                 365
Leu Cys His Leu Asn Asp Ala Cys Ile Ser Asn Pro Cys Asn Glu Gly
370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
            405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Val Ser Asn Pro Cys Gln Asn Asp
450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
            565                 570                 575
Tyr Gly Ser Cys Lys Asp Gly Val Ala Thr Phe Thr Cys Leu Cys Arg
            580                 585                 590
Pro Gly Tyr Thr Gly His His Cys Glu Thr Asn Ile Asn Glu Cys Ser
        595                 600                 605
Ser Gln Pro Cys Arg His Gly Gly Thr Cys Gln Asp Arg Asp Asn Ala
610                 615                 620
```

```
Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
        645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
    675                 680                 685

Asn Gly Gly Thr Cys Glu Asp Gly Ile Asn Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
                755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
            850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
            965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
            995                 1000                1005

Cys Pro Pro Gly Phe Thr Gly Ser Tyr Cys Gln His Asp Val Asn
        1010                1015                1020

Glu Cys Asp Ser Gln Pro Cys Leu His Gly Gly Thr Cys Gln Asp
        1025                1030                1035

Gly Cys Gly Ser Tyr Arg Cys Thr Cys Pro Gln Gly Tyr Thr Gly
```

```
            1040                1045                1050
Pro Asn Cys Gln Asn Leu Val His Trp Cys Asp Ser Ser Pro Cys
            1055                1060                1065
Lys Asn Gly Gly Lys Cys Trp Gln Thr His Thr Gln Tyr Arg Cys
            1070                1075                1080
Glu Cys Pro Ser Gly Trp Thr Gly Leu Tyr Cys Asp Val Pro Ser
            1085                1090                1095
Val Ser Cys Glu Val Ala Ala Gln Arg Gln Gly Val Asp Val Ala
            1100                1105                1110
Arg Leu Cys Gln His Gly Gly Leu Cys Val Asp Ala Gly Asn Thr
            1115                1120                1125
His His Cys Arg Cys Gln Ala Gly Tyr Thr Gly Ser Tyr Cys Glu
            1130                1135                1140
Asp Leu Val Asp Glu Cys Ser Pro Ser Pro Cys Gln Asn Gly Ala
            1145                1150                1155
Thr Cys Thr Asp Tyr Leu Gly Gly Tyr Ser Cys Lys Cys Val Ala
            1160                1165                1170
Gly Tyr His Gly Val Asn Cys Ser Glu Glu Ile Asp Glu Cys Leu
            1175                1180                1185
Ser His Pro Cys Gln Asn Gly Gly Thr Cys Leu Asp Leu Pro Asn
            1190                1195                1200
Thr Tyr Lys Cys Ser Cys Pro Arg Gly Thr Gln Gly Val His Cys
            1205                1210                1215
Glu Ile Asn Val Asp Asp Cys Asn Pro Pro Val Asp Pro Val Ser
            1220                1225                1230
Arg Ser Pro Lys Cys Phe Asn Asn Gly Thr Cys Val Asp Gln Val
            1235                1240                1245
Gly Gly Tyr Ser Cys Thr Cys Pro Pro Gly Phe Val Gly Glu Arg
            1250                1255                1260
Cys Glu Gly Asp Val Asn Glu Cys Leu Ser Asn Pro Cys Asp Ala
            1265                1270                1275
Arg Gly Thr Gln Asn Cys Val Gln Arg Val Asn Asp Phe His Cys
            1280                1285                1290
Glu Cys Arg Ala Gly His Thr Gly Arg Arg Cys Glu Ser Val Ile
            1295                1300                1305
Asn Gly Cys Lys Gly Lys Pro Cys Lys Asn Gly Gly Thr Cys Ala
            1310                1315                1320
Val Ala Ser Asn Thr Ala Arg Gly Phe Ile Cys Lys Cys Pro Ala
            1325                1330                1335
Gly Phe Glu Gly Ala Thr Cys Glu Asn Asp Ala Arg Thr Cys Gly
            1340                1345                1350
Ser Leu Arg Cys Leu Asn Gly Gly Thr Cys Ile Ser Gly Pro Arg
            1355                1360                1365
Ser Pro Thr Cys Leu Cys Leu Gly Pro Phe Thr Gly Pro Glu Cys
            1370                1375                1380
Gln Phe Pro Ala Ser Ser Pro Cys Leu Gly Gly Asn Pro Cys Tyr
            1385                1390                1395
Asn Gln Gly Thr Cys Glu Pro Thr Ser Glu Ser Pro Phe Tyr Arg
            1400                1405                1410
Cys Leu Cys Pro Ala Lys Phe Asn Gly Leu Leu Cys His Ile Leu
            1415                1420                1425
Asp Tyr Ser Phe Gly Gly Gly Ala Gly Arg Asp Ile Pro Pro Pro
            1430                1435                1440
```

```
Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830
```

```
Leu Asp Asp Gln Thr Asp His Arg Gln Trp Thr Gln Gln His Leu
1835                1840                1845

Asp Ala Ala Asp Leu Arg Met Ser Ala Met Ala Pro Thr Pro Pro
1850                1855                1860

Gln Gly Glu Val Asp Ala Asp Cys Met Asp Val Asn Val Arg Gly
1865                1870                1875

Pro Asp Gly Phe Thr Pro Leu Met Ile Ala Ser Cys Ser Gly Gly
1880                1885                1890

Gly Leu Glu Thr Gly Asn Ser Glu Glu Glu Glu Asp Ala Pro Ala
1895                1900                1905

Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
1925                1930                1935

Ser Arg Ser Asp Ala Ala Lys Arg Leu Leu Glu Ala Ser Ala Asp
1940                1945                1950

Ala Asn Ile Gln Asp Asn Met Gly Arg Thr Pro Leu His Ala Ala
1955                1960                1965

Val Ser Ala Asp Ala Gln Gly Val Phe Gln Ile Leu Ile Arg Asn
1970                1975                1980

Arg Ala Thr Asp Leu Asp Ala Arg Met His Asp Gly Thr Thr Pro
1985                1990                1995

Leu Ile Leu Ala Ala Arg Leu Ala Val Glu Gly Met Leu Glu Asp
2000                2005                2010

Leu Ile Asn Ser His Ala Asp Val Asn Ala Val Asp Asp Leu Gly
2015                2020                2025

Lys Ser Ala Leu His Trp Ala Ala Ala Val Asn Asn Val Asp Ala
2030                2035                2040

Ala Val Val Leu Leu Lys Asn Gly Ala Asn Lys Asp Met Gln Asn
2045                2050                2055

Asn Arg Glu Glu Thr Pro Leu Phe Leu Ala Ala Arg Glu Gly Ser
2060                2065                2070

Tyr Glu Thr Ala Lys Val Leu Leu Asp His Phe Ala Asn Arg Asp
2075                2080                2085

Ile Thr Asp His Met Asp Arg Leu Pro Arg Asp Ile Ala Gln Glu
2090                2095                2100

Arg Met His His Asp Ile Val Arg Leu Leu Asp Glu Tyr Asn Leu
2105                2110                2115

Val Arg Ser Pro Gln Leu His Gly Ala Pro Leu Gly Gly Thr Pro
2120                2125                2130

Thr Leu Ser Pro Pro Leu Cys Ser Pro Asn Gly Tyr Leu Gly Ser
2135                2140                2145

Leu Lys Pro Gly Val Gln Gly Lys Lys Val Arg Lys Pro Ser Ser
2150                2155                2160

Lys Gly Leu Ala Cys Gly Ser Lys Glu Ala Lys Asp Leu Lys Ala
2165                2170                2175

Arg Arg Lys Lys Ser Gln Asp Gly Lys Gly Cys Leu Leu Asp Ser
2180                2185                2190

Ser Gly Met Leu Ser Pro Val Asp Ser Leu Glu Ser Pro His Gly
2195                2200                2205

Tyr Leu Ser Asp Val Ala Ser Pro Pro Leu Leu Pro Ser Pro Phe
2210                2215                2220

Gln Gln Ser Pro Ser Val Pro Leu Asn His Leu Pro Gly Met Pro
```

-continued

Asp Thr His Leu Gly Ile Gly His Leu Asn Val Ala Ala Lys Pro
            2240                2245                2250

Glu Met Ala Ala Leu Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 10
<211> LENGTH: 2471
<212> TYPE: PRT
<213> ORGANISM: Homo sapiens

<400> SEQUENCE: 10

Met Pro Ala Leu Arg Pro Ala Leu Leu Trp Ala Leu Leu Ala Leu Trp
1               5                   10                  15

```
Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
```

```
            435                 440                 445
Ala Gly Pro Arg Cys Glu Met Asp Ile Asn Glu Cys His Ser Asp Pro
450                 455                 460

Cys Gln Asn Asp Ala Thr Cys Leu Asp Lys Ile Gly Phe Thr Cys
465                 470                 475             480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
            515                 520                 525

Cys Gln Ile Asp Ile Asp Asp Cys Ser Ser Thr Pro Cys Leu Asn Gly
530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
            595                 600                 605

Asp Glu Cys Tyr Ser Ser Pro Cys Leu Asn Asp Gly Arg Cys Ile Asp
            610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                    645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
            675                 680                 685

Asn Pro Cys Arg Lys Gly Ala Thr Cys Ile Asn Gly Val Asn Gly Phe
            690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
                740                 745                 750

Asn Cys Glu Val Asp Lys Asn Glu Cys Leu Ser Asn Pro Cys Gln Asn
            755                 760                 765

Gly Gly Thr Cys Asp Asn Leu Val Asn Gly Tyr Arg Cys Thr Cys Lys
            770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
850                 855                 860
```

-continued

```
Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
            885                 890                 895

Cys Glu Cys Pro Pro Gly Phe Ser Gly Met Asp Cys Glu Glu Asp Ile
        900                 905                 910

Asp Asp Cys Leu Ala Asn Pro Cys Gln Asn Gly Gly Ser Cys Met Asp
            915                 920                 925

Gly Val Asn Thr Phe Ser Cys Leu Cys Leu Pro Gly Phe Thr Gly Asp
        930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
            965                 970                 975

Ala Gly Phe Asp Gly Val His Cys Glu Asn Asn Ile Asn Glu Cys Thr
        980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215

Gly Leu Leu Cys Glu Glu Asn Ile Asp Asp Cys Ala Arg Gly Pro
    1220                1225                1230

His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly
    1250                1255                1260
```

```
Asp Ile Asn Glu Cys Leu Ser Asn Pro Cys Ser Ser Glu Gly Ser
    1265                1270                1275

Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335

Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
    1640                1645                1650

Ala Ile Gln Gly Thr Leu Ser Tyr Pro Leu Val Ser Val Val Ser
```

```
                1655                1660                 1665
Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
    1730                1735                1740

Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
    1760                1765                1770

Glu Ala Leu Leu Ser Glu Glu Asp Asp Pro Ile Asp Arg Arg Pro
    1775                1780                1785

Trp Thr Gln Gln His Leu Glu Ala Ala Asp Ile Arg Arg Thr Pro
    1790                1795                1800

Ser Leu Ala Leu Thr Pro Pro Gln Ala Glu Gln Glu Val Asp Val
    1805                1810                1815

Leu Asp Val Asn Val Arg Gly Pro Asp Gly Cys Thr Pro Leu Met
    1820                1825                1830

Leu Ala Ser Leu Arg Gly Gly Ser Ser Asp Leu Ser Asp Glu Asp
    1835                1840                1845

Glu Asp Ala Glu Asp Ser Ser Ala Asn Ile Ile Thr Asp Leu Val
    1850                1855                1860

Tyr Gln Gly Ala Ser Leu Gln Ala Gln Thr Asp Arg Thr Gly Glu
    1865                1870                1875

Met Ala Leu His Leu Ala Ala Arg Tyr Ser Arg Ala Asp Ala Ala
    1880                1885                1890

Lys Arg Leu Leu Asp Ala Gly Ala Asp Ala Asn Ala Gln Asp Asn
    1895                1900                1905

Met Gly Arg Cys Pro Leu His Ala Ala Val Ala Ala Asp Ala Gln
    1910                1915                1920

Gly Val Phe Gln Ile Leu Ile Arg Asn Arg Val Thr Asp Leu Asp
    1925                1930                1935

Ala Arg Met Asn Asp Gly Thr Thr Pro Leu Ile Leu Ala Ala Arg
    1940                1945                1950

Leu Ala Val Glu Gly Met Val Ala Glu Leu Ile Asn Cys Gln Ala
    1955                1960                1965

Asp Val Asn Ala Val Asp Asp His Gly Lys Ser Ala Leu His Trp
    1970                1975                1980

Ala Ala Ala Val Asn Asn Val Glu Ala Thr Leu Leu Leu Leu Lys
    1985                1990                1995

Asn Gly Ala Asn Arg Asp Met Gln Asp Asn Lys Glu Glu Thr Pro
    2000                2005                2010

Leu Phe Leu Ala Ala Arg Glu Gly Ser Tyr Glu Ala Ala Lys Ile
    2015                2020                2025

Leu Leu Asp His Phe Ala Asn Arg Asp Ile Thr Asp His Met Asp
    2030                2035                2040

Arg Leu Pro Arg Asp Val Ala Arg Asp Arg Met His His Asp Ile
    2045                2050                2055
```

-continued

Val Arg Leu Leu Asp Glu Tyr Asn Val Thr Pro Ser Pro Pro Gly
2060                2065                2070

Thr Val Leu Thr Ser Ala Leu Ser Pro Val Ile Cys Gly Pro Asn
2075                2080                2085

Arg Ser Phe Leu Ser Leu Lys His Thr Pro Met Gly Lys Lys Ser
2090                2095                2100

Arg Arg Pro Ser Ala Lys Ser Thr Met Pro Thr Ser Leu Pro Asn
2105                2110                2115

Leu Ala Lys Glu Ala Lys Asp Ala Lys Gly Ser Arg Arg Lys Lys
2120                2125                2130

Ser Leu Ser Glu Lys Val Gln Leu Ser Glu Ser Ser Val Thr Leu
2135                2140                2145

Ser Pro Val Asp Ser Leu Glu Ser Pro His Thr Tyr Val Ser Asp
2150                2155                2160

Thr Thr Ser Ser Pro Met Ile Thr Ser Pro Gly Ile Leu Gln Ala
2165                2170                2175

Ser Pro Asn Pro Met Leu Ala Thr Ala Ala Pro Pro Ala Pro Val
2180                2185                2190

His Ala Gln His Ala Leu Ser Phe Ser Asn Leu His Glu Met Gln
2195                2200                2205

Pro Leu Ala His Gly Ala Ser Thr Val Leu Pro Ser Val Ser Gln
2210                2215                2220

Leu Leu Ser His His His Ile Val Ser Pro Gly Ser Gly Ser Ala
2225                2230                2235

Gly Ser Leu Ser Arg Leu His Pro Val Pro Val Pro Ala Asp Trp
2240                2245                2250

Met Asn Arg Met Glu Val Asn Glu Thr Gln Tyr Asn Glu Met Phe
2255                2260                2265

Gly Met Val Leu Ala Pro Glu Gly Thr His Pro Gly Ile Ala
2270                2275                2280

Pro Gln Ser Arg Pro Pro Glu Gly Lys His Ile Thr Thr Pro Arg
2285                2290                2295

Glu Pro Leu Pro Pro Ile Val Thr Phe Gln Leu Ile Pro Lys Gly
2300                2305                2310

Ser Ile Ala Gln Pro Ala Gly Ala Pro Gln Pro Gln Ser Thr Cys
2315                2320                2325

Pro Pro Ala Val Ala Gly Pro Leu Pro Thr Met Tyr Gln Ile Pro
2330                2335                2340

Glu Met Ala Arg Leu Pro Ser Val Ala Phe Pro Thr Ala Met Met
2345                2350                2355

Pro Gln Gln Asp Gly Gln Val Ala Gln Thr Ile Leu Pro Ala Tyr
2360                2365                2370

His Pro Phe Pro Ala Ser Val Gly Lys Tyr Pro Thr Pro Pro Ser
2375                2380                2385

Gln His Ser Tyr Ala Ser Ser Asn Ala Ala Glu Arg Thr Pro Ser
2390                2395                2400

His Ser Gly His Leu Gln Gly Glu His Pro Tyr Leu Thr Pro Ser
2405                2410                2415

Pro Glu Ser Pro Asp Gln Trp Ser Ser Ser Ser Pro His Ser Ala
2420                2425                2430

Ser Asp Trp Ser Asp Val Thr Thr Ser Pro Thr Pro Gly Gly Ala
2435                2440                2445

-continued

```
Gly Gly Gly Gln Arg Gly Pro Gly Thr His Met Ser Glu Pro Pro
    2450            2455                2460

His Asn Asn Met Gln Val Tyr Ala
    2465                2470

<210> SEQ ID NO 11
<211> LENGTH: 2321
<212> TYPE: PRT
<213> ORGANISM: Homo sapiens

<400> SEQUENCE: 11

Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Pro Pro Cys Leu Asp Gly Ser Pro
            35                  40                  45

Cys Ala Asn Gly Gly Arg Cys Thr Gln Leu Pro Ser Arg Glu Ala Ala
50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
        130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
        210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
        290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350
```

```
Asp Ala Cys Val Ser Asn Pro Cys His Glu Asp Ala Ile Cys Asp Thr
            355                 360                 365

Asn Pro Val Asn Gly Arg Ala Ile Cys Thr Cys Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
            450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765
```

-continued

Cys Glu Leu Leu Ser Pro Cys Thr Pro Asn Pro Cys Glu His Gly Gly
770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
                820                 825                 830

Phe Ser Cys Thr Cys His Gly Gly Tyr Thr Gly Pro Ser Cys Asp Gln
                835                 840                 845

Asp Ile Asn Asp Cys Asp Pro Asn Pro Cys Leu Asn Gly Gly Ser Cys
850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
                900                 905                 910

Pro Pro Gly Tyr Gly Gly Phe His Cys Glu Gln Asp Leu Pro Asp Cys
                915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
                980                 985                 990

Thr Gly Pro Gln Cys Gln Thr Leu Val Asp Trp Cys Ser Arg Gln Pro
                995                 1000                1005

Cys Gln Asn Gly Gly Arg Cys Val Gln Thr Gly Ala Tyr Cys Leu
            1010                1015                1020

Cys Pro Pro Gly Trp Ser Gly Arg Leu Cys Asp Ile Arg Ser Leu
            1025                1030                1035

Pro Cys Arg Glu Ala Ala Ala Gln Ile Gly Val Arg Leu Glu Gln
            1040                1045                1050

Leu Cys Gln Ala Gly Gly Gln Cys Val Asp Glu Asp Ser Ser His
            1055                1060                1065

Tyr Cys Val Cys Pro Glu Gly Arg Thr Gly Ser His Cys Glu Gln
            1070                1075                1080

Glu Val Asp Pro Cys Leu Ala Gln Pro Cys Gln His Gly Gly Thr
            1085                1090                1095

Cys Arg Gly Tyr Met Gly Gly Tyr Met Cys Glu Cys Leu Pro Gly
            1100                1105                1110

Tyr Asn Gly Asp Asn Cys Glu Asp Asp Val Asp Glu Cys Ala Ser
            1115                1120                1125

Gln Pro Cys Gln His Gly Gly Ser Cys Ile Asp Leu Val Ala Arg
            1130                1135                1140

Tyr Leu Cys Ser Cys Pro Pro Gly Thr Leu Gly Val Leu Cys Glu
            1145                1150                1155

Ile Asn Glu Asp Asp Cys Gly Pro Gly Pro Pro Leu Asp Ser Gly
            1160                1165                1170

Pro Arg Cys Leu His Asn Gly Thr Cys Val Asp Leu Val Gly Gly

-continued

```
                1175                1180                1185

Phe Arg Cys Thr Cys Pro Pro Gly Tyr Thr Gly Leu Arg Cys Glu
    1190                1195                1200

Ala Asp Ile Asn Glu Cys Arg Ser Gly Ala Cys His Ala Ala His
    1205                1210                1215

Thr Arg Asp Cys Leu Gln Asp Pro Gly Gly Phe Arg Cys Leu
    1220                1225                1230

Cys His Ala Gly Phe Ser Gly Pro Arg Cys Gln Thr Val Leu Ser
    1235                1240                1245

Pro Cys Glu Ser Gln Pro Cys Gln His Gly Gly Gln Cys Arg Pro
    1250                1255                1260

Ser Pro Gly Pro Gly Gly Leu Thr Phe Thr Cys His Cys Ala
    1265                1270                1275

Gln Pro Phe Trp Gly Pro Arg Cys Glu Arg Val Ala Arg Ser Cys
    1280                1285                1290

Arg Glu Leu Gln Cys Pro Val Gly Val Pro Cys Gln Gln Thr Pro
    1295                1300                1305

Arg Gly Pro Arg Cys Ala Cys Pro Pro Gly Leu Ser Gly Pro Ser
    1310                1315                1320

Cys Arg Ser Phe Pro Gly Ser Pro Pro Gly Ala Ser Asn Ala Ser
    1325                1330                1335

Cys Ala Ala Ala Pro Cys Leu His Gly Gly Ser Cys Arg Pro Ala
    1340                1345                1350

Pro Leu Ala Pro Phe Phe Arg Cys Ala Cys Ala Gln Gly Trp Thr
    1355                1360                1365

Gly Pro Arg Cys Glu Ala Pro Ala Ala Ala Pro Glu Val Ser Glu
    1370                1375                1380

Glu Pro Arg Cys Pro Arg Ala Ala Cys Gln Ala Lys Arg Gly Asp
    1385                1390                1395

Gln Arg Cys Asp Arg Glu Cys Asn Ser Pro Gly Cys Gly Trp Asp
    1400                1405                1410

Gly Gly Asp Cys Ser Leu Ser Val Gly Asp Pro Trp Arg Gln Cys
    1415                1420                1425

Glu Ala Leu Gln Cys Trp Arg Leu Phe Asn Asn Ser Arg Cys Asp
    1430                1435                1440

Pro Ala Cys Ser Ser Pro Ala Cys Leu Tyr Asp Asn Phe Asp Cys
    1445                1450                1455

His Ala Gly Gly Arg Glu Arg Thr Cys Asn Pro Val Tyr Glu Lys
    1460                1465                1470

Tyr Cys Ala Asp His Phe Ala Asp Gly Arg Cys Asp Gln Gly Cys
    1475                1480                1485

Asn Thr Glu Glu Cys Gly Trp Asp Gly Leu Asp Cys Ala Ser Glu
    1490                1495                1500

Val Pro Ala Leu Leu Ala Arg Gly Val Leu Val Leu Thr Val Leu
    1505                1510                1515

Leu Pro Pro Glu Glu Leu Leu Arg Ser Ser Ala Asp Phe Leu Gln
    1520                1525                1530

Arg Leu Ser Ala Ile Leu Arg Thr Ser Leu Arg Phe Arg Leu Asp
    1535                1540                1545

Ala His Gly Gln Ala Met Val Phe Pro Tyr His Arg Pro Ser Pro
    1550                1555                1560

Gly Ser Glu Pro Arg Ala Arg Arg Glu Leu Ala Pro Glu Val Ile
    1565                1570                1575
```

```
Gly Ser Val Val Met Leu Glu Ile Asp Asn Arg Leu Cys Leu Gln
    1580                1585                1590

Ser Pro Glu Asn Asp His Cys Phe Pro Asp Ala Gln Ser Ala Ala
    1595                1600                1605

Asp Tyr Leu Gly Ala Leu Ser Ala Val Glu Arg Leu Asp Phe Pro
    1610                1615                1620

Tyr Pro Leu Arg Asp Val Arg Gly Glu Pro Leu Glu Pro Pro Glu
    1625                1630                1635

Pro Ser Val Pro Leu Leu Pro Leu Leu Val Ala Gly Ala Val Leu
    1640                1645                1650

Leu Leu Val Ile Leu Val Leu Gly Val Met Val Ala Arg Arg Lys
    1655                1660                1665

Arg Glu His Ser Thr Leu Trp Phe Pro Glu Gly Phe Ser Leu His
    1670                1675                1680

Lys Asp Val Ala Ser Gly His Lys Gly Arg Arg Glu Pro Val Gly
    1685                1690                1695

Gln Asp Ala Leu Gly Met Lys Asn Met Ala Lys Gly Glu Ser Leu
    1700                1705                1710

Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu
    1730                1735                1740

Ala Val Asp Cys Arg Gln Trp Thr Gln His His Leu Val Ala Ala
    1745                1750                1755

Asp Ile Arg Val Ala Pro Ala Met Ala Leu Thr Pro Pro Gln Gly
    1760                1765                1770

Asp Ala Asp Ala Asp Gly Met Asp Val Asn Val Arg Gly Pro Asp
    1775                1780                1785

Gly Phe Thr Pro Leu Met Leu Ala Ser Phe Cys Gly Gly Ala Leu
    1790                1795                1800

Glu Pro Met Pro Thr Glu Glu Asp Glu Ala Asp Asp Thr Ser Ala
    1805                1810                1815

Ser Ile Ile Ser Asp Leu Ile Cys Gln Gly Ala Gln Leu Gly Ala
    1820                1825                1830

Arg Thr Asp Arg Thr Gly Glu Thr Ala Leu His Leu Ala Ala Arg
    1835                1840                1845

Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920

Glu Leu Ile Ala Ser His Ala Asp Val Asn Ala Val Asp Glu Leu
    1925                1930                1935

Gly Lys Ser Ala Leu His Trp Ala Ala Ala Val Asn Asn Val Glu
    1940                1945                1950

Ala Thr Leu Ala Leu Leu Lys Asn Gly Ala Asn Lys Asp Met Gln
    1955                1960                1965
```

```
Asp Ser Lys Glu Glu Thr Pro Leu Phe Leu Ala Ala Arg Glu Gly
    1970                1975                1980

Ser Tyr Glu Ala Ala Lys Leu Leu Leu Asp His Phe Ala Asn Arg
    1985                1990                1995

Glu Ile Thr Asp His Leu Asp Arg Leu Pro Arg Asp Val Ala Gln
    2000                2005                2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
    2030                2035                2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
    2060                2065                2070

Pro Gln Gly Pro Arg Gly Arg Gly Lys Lys Leu Thr Leu Ala Cys
    2075                2080                2085

Pro Gly Pro Leu Ala Asp Ser Ser Val Thr Leu Ser Pro Val Asp
    2090                2095                2100

Ser Leu Asp Ser Pro Arg Pro Phe Gly Gly Pro Ala Ser Pro
    2105                2110                2115

Gly Gly Phe Pro Leu Glu Gly Pro Tyr Ala Ala Ala Thr Ala Thr
    2120                2125                2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
    2150                2155                2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
    2180                2185                2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Ala
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250

His Trp Ala Ser Pro Ser Pro Pro Ser Leu Ser Asp Trp Ser Glu
    2255                2260                2265

Ser Thr Pro Ser Pro Ala Thr Ala Thr Gly Ala Met Ala Thr Thr
    2270                2275                2280

Thr Gly Ala Leu Pro Ala Gln Pro Leu Pro Leu Ser Val Pro Ser
    2285                2290                2295

Ser Leu Ala Gln Ala Gln Thr Gln Leu Gly Pro Gln Pro Glu Val
    2300                2305                2310

Thr Pro Lys Arg Gln Val Leu Ala
    2315                2320

<210> SEQ ID NO 12
<211> LENGTH: 2003
<212> TYPE: PRT
<213> ORGANISM: Homo sapiens

<400> SEQUENCE: 12
```

```
Met Gln Pro Pro Ser Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
            35                  40                  45

Gly Thr Cys Gln Cys Ala Pro Gly Phe Leu Gly Glu Thr Cys Gln Phe
        50                  55                  60

Pro Asp Pro Cys Gln Asn Ala Gln Leu Cys Gln Asn Gly Gly Ser Cys
65                      70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
                100                 105                 110

Arg Cys Gln Ala Lys Leu Glu Asp Pro Cys Pro Pro Ser Phe Cys Ser
            115                 120                 125

Lys Arg Gly Arg Cys His Ile Gln Ala Ser Gly Arg Pro Gln Cys Ser
        130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
        210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
            245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
            275                 280                 285

Gly Thr Cys Gln Asp Gly Leu Asp Thr Tyr Thr Cys Leu Cys Pro Glu
        290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
            325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
            355                 360                 365

Thr Cys Ile Asp Arg Val Gly Ser Phe Ser Cys Leu Cys Pro Pro Gly
        370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415
```

-continued

```
Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
            435                 440                 445

Gly Gly Ser Cys Leu Asn Thr Pro Gly Ser Phe Asn Cys Leu Cys Pro
450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
            515                 520                 525

His Asp Leu Leu Asn Gly Phe Gln Cys Ile Cys Leu Pro Gly Phe Ser
        530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
            595                 600                 605

Gly Ala Phe Phe Cys Leu Cys Pro Ser Gly Phe Thr Gly Gln Leu Cys
610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
            675                 680                 685

Glu Ala Glu Leu Gly Gly Cys Ile Ser Ala Pro Cys Ala His Gly Gly
        690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
            755                 760                 765

Asp Tyr Cys Val Ser Ala Pro Cys Phe Asn Gly Gly Thr Cys Val Asn
        770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
                805                 810                 815

Asn Arg Ala Thr Cys Gln Asp Ser Pro Gln Gly Pro Arg Cys Leu Cys
            820                 825                 830

Pro Thr Gly Tyr Thr Gly Gly Ser Cys Gln Thr Leu Met Asp Leu Cys
```

-continued

```
                835                 840                 845
Ala Gln Lys Pro Cys Pro Arg Asn Ser His Cys Leu Gln Thr Gly Pro
        850                 855                 860
Ser Phe His Cys Leu Cys Leu Gln Gly Trp Thr Gly Pro Leu Cys Asn
865                 870                 875                 880
Leu Pro Leu Ser Ser Cys Gln Lys Ala Ala Leu Ser Gln Gly Ile Asp
                885                 890                 895
Val Ser Ser Leu Cys His Asn Gly Gly Leu Cys Val Asp Ser Gly Pro
        900                 905                 910
Ser Tyr Phe Cys His Cys Pro Pro Gly Phe Gln Gly Ser Leu Cys Gln
            915                 920                 925
Asp His Val Asn Pro Cys Glu Ser Arg Pro Cys Gln Asn Gly Ala Thr
        930                 935                 940
Cys Met Ala Gln Pro Ser Gly Tyr Leu Cys Gln Cys Ala Pro Gly Tyr
945                 950                 955                 960
Asp Gly Gln Asn Cys Ser Lys Glu Leu Asp Ala Cys Gln Ser Gln Pro
                965                 970                 975
Cys His Asn His Gly Thr Cys Thr Pro Lys Pro Gly Gly Phe His Cys
                980                 985                 990
Ala Cys Pro Pro Gly Phe Val Gly Leu Arg Cys Glu Gly Asp Val Asp
            995                1000                1005
Glu Cys Leu Asp Gln Pro Cys His Pro Thr Gly Thr Ala Ala Cys
   1010                1015                1020
His Ser Leu Ala Asn Ala Phe Tyr Cys Gln Cys Leu Pro Gly His
   1025                1030                1035
Thr Gly Gln Trp Cys Glu Val Glu Ile Asp Pro Cys His Ser Gln
   1040                1045                1050
Pro Cys Phe His Gly Gly Thr Cys Glu Ala Thr Ala Gly Ser Pro
   1055                1060                1065
Leu Gly Phe Ile Cys His Cys Pro Lys Gly Phe Glu Gly Pro Thr
   1070                1075                1080
Cys Ser His Arg Ala Pro Ser Cys Gly Phe His His Cys His His
   1085                1090                1095
Gly Gly Leu Cys Leu Pro Ser Pro Lys Pro Gly Phe Pro Pro Arg
   1100                1105                1110
Cys Ala Cys Leu Ser Gly Tyr Gly Gly Pro Asp Cys Leu Thr Pro
   1115                1120                1125
Pro Ala Pro Lys Gly Cys Gly Pro Pro Ser Pro Cys Leu Tyr Asn
   1130                1135                1140
Gly Ser Cys Ser Glu Thr Thr Gly Leu Gly Gly Pro Gly Phe Arg
   1145                1150                1155
Cys Ser Cys Pro His Ser Ser Pro Gly Pro Arg Cys Gln Lys Pro
   1160                1165                1170
Gly Ala Lys Gly Cys Glu Gly Arg Ser Gly Asp Gly Ala Cys Asp
   1175                1180                1185
Ala Gly Cys Ser Gly Pro Gly Gly Asn Trp Asp Gly Gly Asp Cys
   1190                1195                1200
Ser Leu Gly Val Pro Asp Pro Trp Lys Gly Cys Pro Ser His Ser
   1205                1210                1215
Arg Cys Trp Leu Leu Phe Arg Asp Gly Gln Cys His Pro Gln Cys
   1220                1225                1230
Asp Ser Glu Glu Cys Leu Phe Asp Gly Tyr Asp Cys Glu Thr Pro
   1235                1240                1245
```

-continued

```
Pro Ala Cys Thr Pro Ala Tyr Asp Gln Tyr Cys His Asp His Phe
    1250                1255                1260

His Asn Gly His Cys Glu Lys Gly Cys Asn Thr Ala Glu Cys Gly
    1265                1270                1275

Trp Asp Gly Gly Asp Cys Arg Pro Glu Asp Gly Asp Pro Glu Trp
    1280                1285                1290

Gly Pro Ser Leu Ala Leu Leu Val Val Leu Ser Pro Pro Ala Leu
    1295                1300                1305

Asp Gln Gln Leu Phe Ala Leu Ala Arg Val Leu Ser Leu Thr Leu
    1310                1315                1320

Arg Val Gly Leu Trp Val Arg Lys Asp Arg Asp Gly Arg Asp Met
    1325                1330                1335

Val Tyr Pro Tyr Pro Gly Ala Arg Ala Glu Glu Lys Leu Gly Gly
    1340                1345                1350

Thr Arg Asp Pro Thr Tyr Gln Glu Arg Ala Ala Pro Gln Thr Gln
    1355                1360                1365

Pro Leu Gly Lys Glu Thr Asp Ser Leu Ser Ala Gly Phe Val Val
    1370                1375                1380

Val Met Gly Val Asp Leu Ser Arg Cys Gly Pro Asp His Pro Ala
    1385                1390                1395

Ser Arg Cys Pro Trp Asp Pro Gly Leu Leu Leu Arg Phe Leu Ala
    1400                1405                1410

Ala Met Ala Ala Val Gly Ala Leu Glu Pro Leu Leu Pro Gly Pro
    1415                1420                1425

Leu Leu Ala Val His Pro His Ala Gly Thr Ala Pro Pro Ala Asn
    1430                1435                1440

Gln Leu Pro Trp Pro Val Leu Cys Ser Pro Val Ala Gly Val Ile
    1445                1450                1455

Leu Leu Ala Leu Gly Ala Leu Leu Val Leu Gln Leu Ile Arg Arg
    1460                1465                1470

Arg Arg Arg Glu His Gly Ala Leu Trp Leu Pro Pro Gly Phe Thr
    1475                1480                1485

Arg Arg Pro Arg Thr Gln Ser Ala Pro His Arg Arg Arg Pro Pro
    1490                1495                1500

Leu Gly Glu Asp Ser Ile Gly Leu Lys Ala Leu Lys Pro Lys Ala
    1505                1510                1515

Glu Val Asp Glu Asp Gly Val Val Met Cys Ser Gly Pro Glu Glu
    1520                1525                1530

Gly Glu Glu Val Gly Gln Ala Glu Glu Thr Gly Pro Pro Ser Thr
    1535                1540                1545

Cys Gln Leu Trp Ser Leu Ser Gly Gly Cys Gly Ala Leu Pro Gln
    1550                1555                1560

Ala Ala Met Leu Thr Pro Pro Gln Glu Ser Glu Met Glu Ala Pro
    1565                1570                1575

Asp Leu Asp Thr Arg Gly Pro Asp Gly Val Thr Pro Leu Met Ser
    1580                1585                1590

Ala Val Cys Cys Gly Glu Val Gln Ser Gly Thr Phe Gln Gly Ala
    1595                1600                1605

Trp Leu Gly Cys Pro Glu Pro Trp Glu Pro Leu Leu Asp Gly Gly
    1610                1615                1620

Ala Cys Pro Gln Ala His Thr Val Gly Thr Gly Glu Thr Pro Leu
    1625                1630                1635
```

His Leu Ala Ala Arg Phe Ser Arg Pro Thr Ala Ala Arg Arg Leu
1640                1645                1650

Leu Glu Ala Gly Ala Asn Pro Asn Gln Pro Asp Arg Ala Gly Arg
    1655                1660                1665

Thr Pro Leu His Ala Ala Val Ala Ala Asp Ala Arg Glu Val Cys
    1670                1675                1680

Gln Leu Leu Leu Arg Ser Arg Gln Thr Ala Val Asp Ala Arg Thr
    1685                1690                1695

Glu Asp Gly Thr Thr Pro Leu Met Leu Ala Ala Arg Leu Ala Val
    1700                1705                1710

Glu Asp Leu Val Glu Glu Leu Ile Ala Ala Gln Ala Asp Val Gly
    1715                1720                1725

Ala Arg Asp Lys Trp Gly Lys Thr Ala Leu His Trp Ala Ala Ala
    1730                1735                1740

Val Asn Asn Ala Arg Ala Ala Arg Ser Leu Leu Gln Ala Gly Ala
    1745                1750                1755

Asp Lys Asp Ala Gln Asp Asn Arg Glu Gln Thr Pro Leu Phe Leu
    1760                1765                1770

Ala Ala Arg Glu Gly Ala Val Glu Val Ala Gln Leu Leu Leu Gly
    1775                1780                1785

Leu Gly Ala Ala Arg Glu Leu Arg Asp Gln Ala Gly Leu Ala Pro
    1790                1795                1800

Ala Asp Val Ala His Gln Arg Asn His Trp Asp Leu Leu Thr Leu
    1805                1810                1815

Leu Glu Gly Ala Gly Pro Pro Glu Ala Arg His Lys Ala Thr Pro
    1820                1825                1830

Gly Arg Glu Ala Gly Pro Phe Pro Arg Ala Arg Thr Val Ser Val
    1835                1840                1845

Ser Val Pro Pro His Gly Gly Gly Ala Leu Pro Arg Cys Arg Thr
    1850                1855                1860

Leu Ser Ala Gly Ala Gly Pro Arg Gly Gly Gly Ala Cys Leu Gln
    1865                1870                1875

Ala Arg Thr Trp Ser Val Asp Leu Ala Ala Arg Gly Gly Gly Ala
    1880                1885                1890

Tyr Ser His Cys Arg Ser Leu Ser Gly Val Gly Ala Gly Gly Gly
    1895                1900                1905

Pro Thr Pro Arg Gly Arg Arg Phe Ser Ala Gly Met Arg Gly Pro
    1910                1915                1920

Arg Pro Asn Pro Ala Ile Met Arg Gly Arg Tyr Gly Val Ala Ala
    1925                1930                1935

Gly Arg Gly Gly Arg Val Ser Thr Asp Asp Trp Pro Cys Asp Trp
    1940                1945                1950

Val Ala Leu Gly Ala Cys Gly Ser Ala Ser Asn Ile Pro Ile Pro
    1955                1960                1965

Pro Pro Cys Leu Thr Pro Ser Pro Glu Arg Gly Ser Pro Gln Leu
    1970                1975                1980

Asp Cys Gly Pro Pro Ala Leu Gln Glu Met Pro Ile Asn Gln Gly
    1985                1990                1995

Gly Glu Gly Lys Lys
    2000

<210> SEQ ID NO 13
<211> LENGTH: 497
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Leu Gly Ser Asp Tyr Lys Asp Asp
        35                  40                  45

Asp Asp Lys Gly Ser Gly Val Ile Asn Gly Cys Lys Gly Lys Pro Cys
50                  55                  60

Lys Asn Gly Gly Thr Cys Ala Val Ala Ser Asn Thr Ala Arg Gly Phe
65                  70                  75                  80

Ile Cys Lys Cys Pro Ala Gly Phe Glu Gly Ala Thr Cys Glu Asn Asp
                85                  90                  95

Ala Arg Thr Cys Gly Ser Leu Arg Cys Leu Asn Gly Gly Thr Cys Ile
            100                 105                 110

Ser Gly Pro Arg Ser Pro Thr Cys Leu Cys Leu Gly Pro Phe Thr Gly
        115                 120                 125

Pro Glu Cys Gln Phe Pro Ala Ser Ser Pro Cys Leu Gly Gly Asn Pro
130                 135                 140

Cys Tyr Asn Gln Gly Thr Cys Glu Pro Thr Ser Glu Ser Pro Phe Tyr
145                 150                 155                 160

Arg Cys Leu Cys Pro Ala Lys Phe Asn Gly Leu Leu Cys His Ile Leu
                165                 170                 175

Asp Tyr Ser Phe Gly Gly Gly Ala Gly Arg Asp Ile Pro Pro Pro Leu
            180                 185                 190

Ile Glu Glu Ala Cys Glu Leu Pro Glu Cys Gln Glu Asp Ala Gly Asn
        195                 200                 205

Lys Val Cys Ser Leu Gln Cys Asn Asn His Ala Cys Gly Trp Asp Gly
210                 215                 220

Gly Asp Cys Ser Leu Asn Phe Asn Asp Pro Trp Lys Asn Cys Thr Gln
225                 230                 235                 240

Ser Leu Gln Cys Trp Lys Tyr Phe Ser Asp Gly His Cys Asp Ser Gln
                245                 250                 255

Cys Asn Ser Ala Gly Cys Leu Phe Asp Gly Phe Asp Cys Gln Arg Ala
            260                 265                 270

Glu Gly Gln Cys Asn Pro Leu Tyr Asp Gln Tyr Cys Lys Asp His Phe
        275                 280                 285

Ser Asp Gly His Cys Asp Gln Gly Cys Asn Ser Ala Glu Cys Glu Trp
290                 295                 300

Asp Gly Leu Asp Cys Ala Glu His Val Pro Glu Arg Leu Ala Ala Gly
305                 310                 315                 320

Thr Leu Val Val Val Val Leu Met Pro Pro Glu Gln Leu Arg Asn Ser
                325                 330                 335

Ser Phe His Phe Leu Arg Glu Leu Ser Arg Val Leu His Thr Asn Val
            340                 345                 350

Val Phe Lys Arg Asp Ala His Gly Gln Gln Met Ile Phe Pro Tyr Tyr
        355                 360                 365

Gly Arg Glu Glu Glu Leu Arg Lys His Pro Ile Lys Arg Ala Ala Glu
370                 375                 380

```
Gly Trp Ala Ala Pro Asp Ala Leu Leu Gly Gln Val Lys Ala Ser Leu
385                 390                 395                 400

Leu Pro Gly Gly Ser Glu Gly Gly Arg Arg Arg Glu Leu Asp Pro
            405                 410                 415

Met Asp Val Arg Gly Ser Ile Val Tyr Leu Glu Ile Asp Asn Arg Gln
            420                 425                 430

Cys Val Gln Ala Ser Ser Gln Cys Phe Gln Ser Ala Thr Asp Val Ala
            435                 440                 445

Ala Phe Leu Gly Ala Leu Ala Ser Leu Gly Ser Leu Asn Ile Pro Tyr
            450                 455                 460

Lys Ile Glu Ala Val Gln Ser Glu Thr Val Glu Pro Pro Pro Pro Ala
465                 470                 475                 480

Gln Glu Phe Gly Leu Val Pro Arg Gly Ser Gly His His His His His
            485                 490                 495

His
```

```
<210> SEQ ID NO 14
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Gly Gly Thr Ala Ala Arg Leu Gly Ala Val Ile Leu Phe Val Val
1               5                   10                  15

Ile Val Gly Leu His Gly Val Arg Gly Lys Asp Tyr Lys Asp Asp Asp
                20                  25                  30

Asp Lys Leu Glu Val Ile Asn Gly Cys Arg Gly Lys Pro Cys Lys Asn
            35                  40                  45

Gly Gly Val Cys Ala Val Ala Ser Asn Thr Ala Arg Gly Phe Ile Cys
        50                  55                  60

Arg Cys Pro Ala Gly Phe Glu Gly Ala Thr Cys Glu Asn Asp Ala Arg
65                  70                  75                  80

Thr Cys Gly Ser Leu Arg Cys Leu Asn Gly Gly Thr Cys Ile Ser Gly
                85                  90                  95

Pro Arg Ser Pro Thr Cys Leu Cys Leu Gly Ser Phe Thr Gly Pro Glu
            100                 105                 110

Cys Gln Phe Pro Ala Ser Ser Pro Cys Val Gly Ser Asn Pro Cys Tyr
        115                 120                 125

Asn Gln Gly Thr Cys Glu Pro Thr Ser Glu Asn Pro Phe Tyr Arg Cys
130                 135                 140

Leu Cys Pro Ala Lys Phe Asn Gly Leu Leu Cys His Ile Leu Asp Tyr
145                 150                 155                 160

Ser Phe Thr Gly Gly Ala Gly Arg Asp Ile Pro Pro Gln Ile Glu
                165                 170                 175

Glu Ala Cys Glu Leu Pro Glu Cys Gln Val Asp Ala Gly Asn Lys Val
            180                 185                 190

Cys Asn Leu Gln Cys Asn His Ala Cys Gly Trp Asp Gly Gly Asp
        195                 200                 205

Cys Ser Leu Asn Phe Asn Asp Pro Trp Lys Asn Cys Thr Gln Ser Leu
        210                 215                 220

Gln Cys Trp Lys Tyr Phe Ser Asp Gly His Cys Asp Ser Gln Cys Asn
```

```
            225                 230                 235                 240
Ser Ala Gly Cys Leu Phe Asp Gly Phe Asp Cys Gln Leu Thr Glu Gly
                245                 250                 255

Gln Cys Asn Pro Leu Tyr Asp Gln Tyr Cys Lys Asp His Phe Ser Asp
                260                 265                 270

Gly His Cys Asp Gln Gly Cys Asn Ser Ala Glu Cys Glu Trp Asp Gly
                275                 280                 285

Leu Asp Cys Ala Glu His Val Pro Glu Arg Leu Ala Ala Gly Thr Leu
                290                 295                 300

Val Leu Val Val Leu Leu Pro Pro Asp Gln Leu Arg Asn Asn Ser Phe
305                 310                 315                 320

His Phe Leu Arg Glu Leu Ser His Val Leu His Thr Asn Val Val Phe
                325                 330                 335

Lys Arg Asp Ala Gln Gly Gln Gln Met Ile Phe Pro Tyr Tyr Gly His
                340                 345                 350

Glu Glu Glu Leu Arg Lys His Pro Ile Lys Arg Ser Thr Val Gly Trp
                355                 360                 365

Ala Thr Ser Ser Leu Leu Pro Gly Thr Ser Gly Gly Arg Gln Arg Arg
                370                 375                 380

Glu Leu Asp Pro Met Asp Ile Arg Gly Ser Ile Val Tyr Leu Glu Ile
385                 390                 395                 400

Asp Asn Arg Gln Cys Val Gln Ser Ser Gln Cys Phe Gln Ser Ala
                405                 410                 415

Thr Asp Val Ala Ala Phe Leu Gly Ala Leu Ala Ser Leu Gly Ser Leu
                420                 425                 430

Asn Ile Pro Tyr Lys Ile Glu Ala Val Lys Ser Glu Pro Val Glu Pro
                435                 440                 445

Pro Leu Pro Ser Gln Gly Ser Gly His His His His His His
                450                 455                 460
```

<210> SEQ ID NO 15
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Lys Asp Asp Asp Lys Gly Ser Gly Asp Val Cys Pro Gln Met Pro
1               5                   10                  15

Cys Leu Asn Gly Gly Thr Cys Ala Val Ala Ser Asn Met Pro Asp Gly
                20                  25                  30

Phe Ile Cys Arg Cys Pro Pro Gly Phe Ser Gly Ala Arg Cys Gln Ser
                35                  40                  45

Ser Cys Gly Gln Val Lys Cys Arg Lys Gly Glu Gln Cys Val His Thr
                50                  55                  60

Ala Ser Gly Pro Arg Cys Phe Cys Pro Ser Pro Arg Asp Cys Glu Ser
65                  70                  75                  80

Gly Cys Ala Ser Ser Pro Cys Gln His Gly Gly Ser Cys His Pro Gln
                85                  90                  95

Arg Gln Pro Pro Tyr Tyr Ser Cys Gln Cys Ala Pro Pro Phe Ser Gly
                100                 105                 110

Ser Arg Cys Glu Leu Tyr Thr Ala Pro Pro Ser Thr Pro Pro Ala Thr
                115                 120                 125
```

-continued

```
Cys Leu Ser Gln Tyr Cys Ala Asp Lys Ala Arg Asp Gly Val Cys Asp
        130                 135                 140

Glu Ala Cys Asn Ser His Ala Cys Gln Trp Asp Gly Gly Asp Cys Ser
145                 150                 155                 160

Leu Thr Met Glu Asn Pro Trp Ala Asn Cys Ser Ser Pro Leu Pro Cys
            165                 170                 175

Trp Asp Tyr Ile Asn Asn Gln Cys Asp Glu Leu Cys Asn Thr Val Glu
            180                 185                 190

Cys Leu Phe Asp Asn Phe Glu Cys Gln Gly Asn Ser Lys Thr Cys Lys
        195                 200                 205

Tyr Asp Lys Tyr Cys Ala Asp His Phe Lys Asp Asn His Cys Asn Gln
    210                 215                 220

Gly Cys Asn Ser Glu Glu Cys Gly Trp Asp Gly Leu Asp Cys Ala Ala
225                 230                 235                 240

Asp Gln Pro Glu Asn Leu Ala Glu Gly Thr Leu Val Ile Val Val Leu
            245                 250                 255

Met Pro Pro Glu Gln Leu Leu Gln Asp Ala Arg Ser Phe Leu Arg Ala
            260                 265                 270

Leu Gly Thr Leu Leu His Thr Asn Leu Arg Ile Lys Arg Asp Ser Gln
        275                 280                 285

Gly Glu Leu Met Val Tyr Pro Tyr Tyr Gly Glu Lys Ser Ala Ala Met
    290                 295                 300

Lys Lys Gln Arg Met Thr Arg Arg Ser Leu Pro Gly Glu Gln Glu Gln
305                 310                 315                 320

Glu Val Ala Gly Ser Lys Val Phe Leu Glu Ile Asp Asn Arg Gln Cys
            325                 330                 335

Val Gln Asp Ser Asp His Cys Phe Lys Asn Thr Asp Ala Ala Ala Ala
            340                 345                 350

Leu Leu Ala Ser His Ala Ile Gln Gly Thr Leu Ser Tyr Pro Leu Val
        355                 360                 365

Ser Val Val Ser Glu Ser Leu Thr Pro Glu Arg Thr Glu Phe Gly Leu
    370                 375                 380

Val Pro Arg Gly Ser Gly His His His His His His
385                 390                 395
```

<210> SEQ ID NO 16
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Ala Asp Val Cys Pro Gln Lys Pro Cys Leu Asn Gly Gly Thr Cys Ala
1               5                   10                  15

Val Ala Ser Asn Met Pro Asp Gly Phe Ile Cys Arg Cys Pro Pro Gly
            20                  25                  30

Phe Ser Gly Ala Arg Cys Gln Ser Ser Cys Gly Gln Val Lys Cys Arg
        35                  40                  45

Arg Gly Glu Gln Cys Ile His Thr Asp Ser Gly Pro Arg Cys Phe Cys
    50                  55                  60

Leu Asn Pro Lys Asp Cys Glu Ser Gly Cys Ala Ser Asn Pro Cys Gln
65                  70                  75                  80
```

-continued

His Gly Gly Thr Cys Tyr Pro Gln Arg Gln Pro His Tyr Ser Cys
            85                  90                  95

Arg Cys Pro Pro Ser Phe Gly Ser His Cys Glu Leu Tyr Thr Ala
        100                 105                 110

Pro Thr Ser Thr Pro Pro Ala Thr Cys Gln Ser Gln Tyr Cys Ala Asp
        115                 120                 125

Lys Ala Arg Asp Gly Ile Cys Asp Glu Ala Cys Asn Ser His Ala Cys
130                 135                 140

Gln Trp Asp Gly Gly Asp Cys Ser Leu Thr Met Glu Asp Pro Trp Ala
145                 150                 155                 160

Asn Cys Thr Ser Thr Leu Arg Cys Trp Glu Tyr Ile Asn Asn Gln Cys
                165                 170                 175

Asp Glu Gln Cys Asn Thr Ala Glu Cys Leu Phe Asp Asn Phe Glu Cys
            180                 185                 190

Gln Arg Asn Ser Lys Thr Cys Lys Tyr Asp Lys Tyr Cys Ala Asp His
        195                 200                 205

Phe Lys Asp Asn His Cys Asp Gln Gly Cys Asn Ser Glu Glu Cys Gly
    210                 215                 220

Trp Asp Gly Leu Asp Cys Ala Ser Asp Gln Pro Glu Asn Leu Ala Glu
225                 230                 235                 240

Gly Thr Leu Ile Ile Val Val Leu Leu Pro Pro Glu Gln Leu Leu Gln
                245                 250                 255

Asp Ser Arg Ser Phe Leu Arg Ala Leu Gly Thr Leu Leu His Thr Asn
            260                 265                 270

Leu Arg Ile Lys Gln Asp Ser Gln Gly Ala Leu Met Val Tyr Pro Tyr
        275                 280                 285

Phe Gly Glu Lys Ser Ala Ala Met Lys Lys Gln Lys Met Thr Arg Arg
    290                 295                 300

Ser Leu Pro Glu Glu Gln Glu Gln Glu Val Ile Gly Ser Lys
305                 310                 315                 320

Ile Phe Leu Glu Ile Asp Asn Arg Gln Cys Val Gln Asp Ser Asp Gln
                325                 330                 335

Cys Phe Lys Asn Thr Asp Ala Ala Ala Ala Leu Leu Ala Ser His Ala
            340                 345                 350

Ile Gln Gly Thr Leu Ser Tyr Pro Leu Val Ser Val Phe Ser Glu Leu
        355                 360                 365

Glu Ser Pro Arg Asn Ala Arg Arg Ala Gly Ser Gly Asp Tyr Lys Asp
    370                 375                 380

Asp Asp Asp Lys Glu Asn Leu Tyr Phe Gln
385                 390

<210> SEQ ID NO 17
<211> LENGTH: 723
<212> TYPE: PRT
<213> ORGANISM: Homo sapiens

<400> SEQUENCE: 17

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

```
Lys His Tyr Gln Ala Ser Val Ser Pro Glu Pro Cys Thr Tyr Gly
 65                  70                  75                  80

Ser Ala Val Thr Pro Val Leu Gly Val Asp Ser Phe Ser Leu Pro Asp
                 85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
            290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480
```

```
Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Gly Pro Ala
        515                 520                 525

Val Val Asp Leu Thr Glu Lys Leu Glu Gly Gln Gly Pro Phe Pro
    530                 535                 540

Trp Val Ala Val Cys Ala Gly Val Ile Leu Val Leu Met Leu Leu Leu
545                 550                 555                 560

Gly Cys Ala Ala Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
                595                 600                 605

Ala Thr Gln Ile Lys Asn Thr Asn Lys Lys Ala Asp Phe His Gly Asp
            610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
    690                 695                 700

Gln Ser Val Tyr Val Ile Ser Glu Glu Lys Asp Glu Cys Val Ile Ala
705                 710                 715                 720

Thr Glu Val

<210> SEQ ID NO 18
<211> LENGTH: 685
<212> TYPE: PRT
<213> ORGANISM: Homo sapiens

<400> SEQUENCE: 18

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
        50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125
```

-continued

```
Leu Arg Pro Glu Ala Leu Pro Pro Asp Ala Leu Ile Ser Lys Ile Ala
    130                 135                 140
Ile Gln Gly Ser Leu Ala Val Gly Gln Asn Trp Leu Leu Asp Glu Gln
145                 150                 155                 160
Thr Ser Thr Leu Thr Arg Leu Arg Tyr Ser Tyr Arg Val Ile Cys Ser
                165                 170                 175
Asp Asn Tyr Tyr Gly Asp Asn Cys Ser Arg Leu Cys Lys Lys Arg Asn
            180                 185                 190
Asp His Phe Gly His Tyr Val Cys Gln Pro Asp Gly Asn Leu Ser Cys
        195                 200                 205
Leu Pro Gly Trp Thr Gly Glu Tyr Cys Gln Gln Pro Ile Cys Leu Ser
    210                 215                 220
Gly Cys His Glu Gln Asn Gly Tyr Cys Ser Lys Pro Ala Glu Cys Leu
225                 230                 235                 240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
            260                 265                 270
Asp Glu Gly Trp Gly Gly Leu Phe Cys Asp Gln Asp Leu Asn Tyr Cys
        275                 280                 285
Thr His His Ser Pro Cys Lys Asn Gly Ala Thr Cys Ser Asn Ser Gly
    290                 295                 300
Gln Arg Ser Tyr Thr Cys Thr Cys Arg Pro Gly Tyr Thr Gly Val Asp
305                 310                 315                 320
Cys Glu Leu Glu Leu Ser Glu Cys Asp Ser Asn Pro Cys Arg Asn Gly
                325                 330                 335
Gly Ser Cys Lys Asp Gln Glu Asp Gly Tyr His Cys Leu Cys Pro Pro
            340                 345                 350
Gly Tyr Tyr Gly Leu His Cys Glu His Ser Thr Leu Ser Cys Ala Asp
        355                 360                 365
Ser Pro Cys Phe Asn Gly Gly Ser Cys Arg Glu Arg Asn Gln Gly Ala
    370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
            420                 425                 430
Thr Gly Thr Tyr Cys Glu Leu His Val Ser Asp Cys Ala Arg Asn Pro
        435                 440                 445
Cys Ala His Gly Gly Thr Cys His Asp Leu Glu Asn Gly Leu Met Cys
    450                 455                 460
Thr Cys Pro Ala Gly Phe Ser Gly Arg Arg Cys Glu Val Arg Thr Ser
465                 470                 475                 480
Ile Asp Ala Cys Ala Ser Ser Pro Cys Phe Asn Arg Ala Thr Cys Tyr
                485                 490                 495
Thr Asp Leu Ser Thr Asp Thr Phe Val Cys Asn Cys Pro Tyr Gly Phe
            500                 505                 510
Val Gly Ser Arg Cys Glu Phe Pro Val Gly Leu Pro Pro Ser Phe Pro
        515                 520                 525
Trp Val Ala Val Ser Leu Gly Val Gly Leu Ala Val Leu Leu Val Leu
    530                 535                 540
Leu Gly Met Val Ala Val Ala Val Arg Gln Leu Arg Leu Arg Arg Pro
```

```
                545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
                580                 585                 590

Glu Leu Glu Val Asp Cys Gly Leu Asp Lys Ser Asn Cys Gly Lys Gln
                595                 600                 605

Gln Asn His Thr Leu Asp Tyr Asn Leu Ala Pro Gly Pro Leu Gly Arg
                610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
                660                 665                 670

Ser Glu Glu Arg Asn Glu Cys Val Ile Ala Thr Glu Val
                675                 680                 685

<210> SEQ ID NO 19
<211> LENGTH: 574
<212> TYPE: PRT
<213> ORGANISM: Homo sapiens

<400> SEQUENCE: 19

Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30

Gln Pro Tyr His Gly Glu Lys Gly Ile Ser Val Pro Asp His Gly Phe
                35                  40                  45

Cys Gln Pro Ile Ser Ile Pro Leu Cys Thr Asp Ile Ala Tyr Asn Gln
                50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
                100                 105                 110

Leu Asp Gln Ala Ile Pro Pro Cys Arg Ser Leu Cys Glu Arg Ala Arg
                115                 120                 125

Gln Gly Cys Glu Ala Leu Met Asn Lys Phe Gly Phe Gln Trp Pro Glu
                130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
                180                 185                 190

Leu Pro Pro Gly Ala Ser Asp Gly Arg Gly Arg Pro Ala Phe Pro Phe
                195                 200                 205

Ser Cys Pro Arg Gln Leu Lys Val Pro Pro Tyr Leu Gly Tyr Arg Phe
                210                 215                 220

Leu Gly Glu Arg Asp Cys Gly Ala Pro Cys Glu Pro Gly Arg Ala Asn
225                 230                 235                 240
```

```
Gly Leu Met Tyr Phe Lys Glu Glu Arg Phe Ala Arg Leu Trp
            245                 250                 255

Val Gly Val Trp Ser Val Leu Cys Cys Ala Ser Thr Leu Phe Thr Val
        260                 265                 270

Leu Thr Tyr Leu Val Asp Met Arg Arg Phe Ser Tyr Pro Glu Arg Pro
            275                 280                 285

Ile Ile Phe Leu Ser Gly Cys Tyr Phe Met Val Ala Val His Val
        290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
            325                 330                 335

Thr Ile Leu Phe Met Val Leu Tyr Phe Phe Gly Met Ala Ser Ser Ile
            340                 345                 350

Trp Trp Val Ile Leu Ser Leu Thr Trp Phe Leu Ala Ala Gly Met Lys
        355                 360                 365

Trp Gly His Glu Ala Ile Glu Ala Asn Ser Gln Tyr Phe His Leu Ala
        370                 375                 380

Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
            405                 410                 415

Ser Val Asp Ala Leu Arg Gly Phe Val Leu Ala Pro Leu Phe Val Tyr
            420                 425                 430

Leu Phe Ile Gly Thr Ser Phe Leu Leu Ala Gly Phe Val Ser Leu Phe
            435                 440                 445

Arg Ile Arg Thr Ile Met Lys His Asp Gly Thr Lys Thr Glu Lys Leu
450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
            485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Pro Met Ser Pro Asp Phe Thr
        515                 520                 525

Val Phe Met Ile Lys Tyr Leu Met Thr Met Ile Val Gly Ile Thr Thr
        530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
            565                 570

<210> SEQ ID NO 20
<211> LENGTH: 694
<212> TYPE: PRT
<213> ORGANISM: Homo sapiens

<400> SEQUENCE: 20

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45
```

```
Asn Tyr Thr Tyr Met Pro Asn Gln Phe Asn His Asp Thr Gln Asp Glu
 50                  55                  60

Ala Gly Leu Glu Val His Gln Phe Trp Pro Leu Val Glu Ile Gln Cys
 65                  70                  75                  80

Ser Pro Asp Leu Lys Phe Phe Leu Cys Ser Met Tyr Thr Pro Ile Cys
                     85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
        130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
        195                 200                 205

Ala Arg Gly Gly Gly Gly Gly Lys Ala Arg Pro Pro Gly Gly Gly
210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
            340                 345                 350

Ala Gly Gly Ala Ala Ala Gly Ala Gly Ala Gly Ala Gly Ala Gly
        355                 360                 365

Gly Pro Gly Gly Arg Gly Glu Tyr Glu Glu Leu Gly Ala Val Glu Gln
370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
            420                 425                 430

Ala Ile Ala Gly Tyr Ser Gln Tyr Phe His Leu Ala Ala Trp Leu Val
        435                 440                 445

Pro Ser Val Lys Ser Ile Ala Val Leu Ala Leu Ser Ser Val Asp Gly
450                 455                 460
```

-continued

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
            485                 490                 495

Thr Met Phe Leu Leu Ala Gly Phe Val Ser Leu Phe Arg Ile Arg Ser
        500                 505                 510

Val Ile Lys Gln Gln Asp Gly Pro Thr Lys Thr His Lys Leu Glu Lys
    515                 520                 525

Leu Met Ile Arg Leu Gly Leu Phe Thr Val Leu Tyr Thr Val Pro Ala
530                 535                 540

Ala Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
            565                 570                 575

Gln Ala Arg Arg Pro Asp Tyr Ala Val Phe Met Leu Lys Tyr Phe Met
            580                 585                 590

Cys Leu Val Val Gly Ile Thr Ser Gly Val Trp Val Trp Ser Gly Lys
        595                 600                 605

Thr Leu Glu Ser Trp Arg Ser Leu Cys Thr Arg Cys Cys Trp Ala Ser
    610                 615                 620

Lys Gly Ala Ala Val Gly Gly Ala Gly Ala Thr Ala Ala Gly Gly
625                 630                 635                 640

Gly Gly Gly Pro Gly Gly Gly Gly Gly Pro Gly Gly Gly
            645                 650                 655

Gly Pro Gly Gly Gly Gly Ser Leu Tyr Ser Asp Val Ser Thr Gly
            660                 665                 670

Leu Thr Trp Arg Ser Gly Thr Ala Ser Ser Val Ser Tyr Pro Lys Gln
            675                 680                 685

Met Pro Leu Ser Gln Val
            690

<210> SEQ ID NO 21
<211> LENGTH: 1615
<212> TYPE: PRT
<213> ORGANISM: Homo sapiens

<400> SEQUENCE: 21

Met Glu Ala Ala Pro Gly Pro Pro Trp Pro Leu Leu Leu Leu Leu
1               5                   10                  15

Leu Leu Leu Leu Ala Leu Cys Gly Cys Pro Ala Pro Ala Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
            85                  90                  95

Ala Ala Val Gln Asn Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

```
Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560
```

```
Thr Asp Trp Gln Arg Arg Ser Ile Glu Arg Val His Lys Val Lys Ala
                565                 570                 575
Ser Arg Asp Val Ile Ile Asp Gln Leu Pro Asp Leu Met Gly Leu Lys
            580                 585                 590
Ala Val Asn Val Ala Lys Val Gly Thr Asn Pro Cys Ala Asp Arg
        595                 600                 605
Asn Gly Gly Cys Ser His Leu Cys Phe Phe Thr Pro His Ala Thr Arg
    610                 615                 620
Cys Gly Cys Pro Ile Gly Leu Glu Leu Leu Ser Asp Met Lys Thr Cys
625                 630                 635                 640
Ile Val Pro Glu Ala Phe Leu Val Phe Thr Ser Arg Ala Ala Ile His
            645                 650                 655
Arg Ile Ser Leu Glu Thr Asn Asn Asn Asp Val Ala Ile Pro Leu Thr
            660                 665                 670
Gly Val Lys Glu Ala Ser Ala Leu Asp Phe Asp Val Ser Asn Asn His
        675                 680                 685
Ile Tyr Trp Thr Asp Val Ser Leu Lys Thr Ile Ser Arg Ala Phe Met
    690                 695                 700
Asn Gly Ser Ser Val Glu His Val Val Glu Phe Gly Leu Asp Tyr Pro
705                 710                 715                 720
Glu Gly Met Ala Val Asp Trp Met Gly Lys Asn Leu Tyr Trp Ala Asp
            725                 730                 735
Thr Gly Thr Asn Arg Ile Glu Val Ala Arg Leu Asp Gly Gln Phe Arg
            740                 745                 750
Gln Val Leu Val Trp Arg Asp Leu Asp Asn Pro Arg Ser Leu Ala Leu
        755                 760                 765
Asp Pro Thr Lys Gly Tyr Ile Tyr Trp Thr Glu Trp Gly Gly Lys Pro
770                 775                 780
Arg Ile Val Arg Ala Phe Met Asp Gly Thr Asn Cys Met Thr Leu Val
785                 790                 795                 800
Asp Lys Val Gly Arg Ala Asn Asp Leu Thr Ile Asp Tyr Ala Asp Gln
            805                 810                 815
Arg Leu Tyr Trp Thr Asp Leu Asp Thr Asn Met Ile Glu Ser Ser Asn
            820                 825                 830
Met Leu Gly Gln Glu Arg Val Val Ile Ala Asp Asp Leu Pro His Pro
835                 840                 845
Phe Gly Leu Thr Gln Tyr Ser Asp Tyr Ile Tyr Trp Thr Asp Trp Asn
        850                 855                 860
Leu His Ser Ile Glu Arg Ala Asp Lys Thr Ser Gly Arg Asn Arg Thr
865                 870                 875                 880
Leu Ile Gln Gly His Leu Asp Phe Val Met Asp Ile Leu Val Phe His
            885                 890                 895
Ser Ser Arg Gln Asp Gly Leu Asn Asp Cys Met His Asn Asn Gly Gln
        900                 905                 910
Cys Gly Gln Leu Cys Leu Ala Ile Pro Gly Gly His Arg Cys Gly Cys
            915                 920                 925
Ala Ser His Tyr Thr Leu Asp Pro Ser Arg Asn Cys Ser Pro Pro
        930                 935                 940
Thr Thr Phe Leu Leu Phe Ser Gln Lys Ser Ala Ile Ser Arg Met Ile
945                 950                 955                 960
Pro Asp Asp Gln His Ser Pro Asp Leu Ile Leu Pro Leu His Gly Leu
                965                 970                 975
Arg Asn Val Lys Ala Ile Asp Tyr Asp Pro Leu Asp Lys Phe Ile Tyr
```

-continued

```
                980               985                990
Trp Val Asp Gly Arg Gln Asn Ile  Lys Arg Ala Lys  Asp Asp Gly Thr
                    995               1000              1005
Gln Pro Phe Val Leu Thr Ser  Leu Ser Gln Gly Gln  Asn Pro Asp
    1010              1015              1020
Arg Gln Pro His Asp Leu Ser  Ile Asp Ile Tyr Ser  Arg Thr Leu
    1025              1030              1035
Phe Trp Thr Cys Glu Ala Thr  Asn Thr Ile Asn Val  His Arg Leu
    1040              1045              1050
Ser Gly Glu Ala Met Gly Val  Val Leu Arg Gly Asp  Arg Asp Lys
    1055              1060              1065
Pro Arg Ala Ile Val Val Asn  Ala Glu Arg Gly Tyr  Leu Tyr Phe
    1070              1075              1080
Thr Asn Met Gln Asp Arg Ala  Ala Lys Ile Glu Arg  Ala Ala Leu
    1085              1090              1095
Asp Gly Thr Glu Arg Glu Val  Leu Phe Thr Thr Gly  Leu Ile Arg
    1100              1105              1110
Pro Val Ala Leu Val Val Asp  Asn Thr Leu Gly Lys  Leu Phe Trp
    1115              1120              1125
Val Asp Ala Asp Leu Lys Arg  Ile Glu Ser Cys Asp  Leu Ser Gly
    1130              1135              1140
Ala Asn Arg Leu Thr Leu Glu  Asp Ala Asn Ile Val  Gln Pro Leu
    1145              1150              1155
Gly Leu Thr Ile Leu Gly Lys  His Leu Tyr Trp Ile  Asp Arg Gln
    1160              1165              1170
Gln Gln Met Ile Glu Arg Val  Glu Lys Thr Thr Gly  Asp Lys Arg
    1175              1180              1185
Thr Arg Ile Gln Gly Arg Val  Ala His Leu Thr Gly  Ile His Ala
    1190              1195              1200
Val Glu Glu Val Ser Leu Glu  Glu Phe Ser Ala His  Pro Cys Ala
    1205              1210              1215
Arg Asp Asn Gly Gly Cys Ser  His Ile Cys Ile Ala  Lys Gly Asp
    1220              1225              1230
Gly Thr Pro Arg Cys Ser Cys  Pro Val His Leu Val  Leu Leu Gln
    1235              1240              1245
Asn Leu Leu Thr Cys Gly Glu  Pro Pro Thr Cys Ser  Pro Asp Gln
    1250              1255              1260
Phe Ala Cys Ala Thr Gly Glu  Ile Asp Cys Ile Pro  Gly Ala Trp
    1265              1270              1275
Arg Cys Asp Gly Phe Pro Glu  Cys Asp Asp Gln Ser  Asp Glu Glu
    1280              1285              1290
Gly Cys Pro Val Cys Ser Ala  Ala Gln Phe Pro Cys  Ala Arg Gly
    1295              1300              1305
Gln Cys Val Asp Leu Arg Leu  Arg Cys Asp Gly Glu  Ala Asp Cys
    1310              1315              1320
Gln Asp Arg Ser Asp Glu Ala  Asp Cys Asp Ala Ile  Cys Leu Pro
    1325              1330              1335
Asn Gln Phe Arg Cys Ala Ser  Gly Gln Cys Val Leu  Ile Lys Gln
    1340              1345              1350
Gln Cys Asp Ser Phe Pro Asp  Cys Ile Asp Gly Ser  Asp Glu Leu
    1355              1360              1365
Met Cys Glu Ile Thr Lys Pro  Pro Ser Asp Asp Ser  Pro Ala His
    1370              1375              1380
```

Ser Ser Ala Ile Gly Pro Val Ile Gly Ile Ile Leu Ser Leu Phe
    1385                1390                1395

Val Met Gly Gly Val Tyr Phe Val Cys Gln Arg Val Val Cys Gln
    1400                1405                1410

Arg Tyr Ala Gly Ala Asn Gly Pro Phe Pro His Glu Tyr Val Ser
    1415                1420                1425

Gly Thr Pro His Val Pro Leu Asn Phe Ile Ala Pro Gly Gly Ser
    1430                1435                1440

Gln His Gly Pro Phe Thr Gly Ile Ala Cys Gly Lys Ser Met Met
    1445                1450                1455

Ser Ser Val Ser Leu Met Gly Gly Arg Gly Gly Val Pro Leu Tyr
    1460                1465                1470

Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser
    1490                1495                1500

Pro Ala Thr Asp Pro Ser Leu Tyr Asn Met Asp Met Phe Tyr Ser
    1505                1510                1515

Ser Asn Ile Pro Ala Thr Ala Arg Pro Tyr Arg Pro Tyr Ile Ile
    1520                1525                1530

Arg Gly Met Ala Pro Pro Thr Thr Pro Cys Ser Thr Asp Val Cys
    1535                1540                1545

Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
    1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
    1595                1600                1605

Ser Pro Cys Thr Asp Ser Ser
    1610                1615

<210> SEQ ID NO 22
<211> LENGTH: 1613
<212> TYPE: PRT
<213> ORGANISM: Homo sapiens

<400> SEQUENCE: 22

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu

-continued

```
            115                 120                 125
Arg Lys Val Leu Phe Trp Gln Glu Leu Asp Gln Pro Arg Ala Ile Ala
        130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
        435                 440                 445

Arg Ala Ile Val Leu Asp Pro Met Val Gly Tyr Met Tyr Trp Thr Asp
450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
        515                 520                 525

Glu Asp Lys Ile Pro His Ile Phe Gly Phe Thr Leu Leu Gly Asp Tyr
530                 535                 540
```

```
Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
            565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
            595                 600                 605

Gly Leu Arg Cys Ala Cys Pro Ile Gly Phe Glu Leu Ile Ser Asp Met
            610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
            675                 680                 685

Ala Phe Met Asn Gly Ser Ala Leu Glu His Val Glu Phe Gly Leu
            690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
            755                 760                 765

Gly Lys Pro Lys Ile Asp Arg Ala Ala Met Asp Gly Ser Glu Arg Thr
            770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
                820                 825                 830

Pro His Pro Phe Gly Leu Thr Gln Tyr Gln Asp Tyr Ile Tyr Trp Thr
            835                 840                 845

Asp Trp Ser Arg Arg Ser Ile Glu Arg Ala Asn Lys Thr Ser Gly Gln
            850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Thr Thr Phe Leu Leu Phe Ser Gln Lys Ser Ala Ile
            930                 935                 940

Asn Arg Met Val Ile Asp Glu Gln Gln Ser Pro Asp Ile Ile Leu Pro
945                 950                 955                 960
```

```
Ile His Ser Leu Arg Asn Val Arg Ala Ile Asp Tyr Asp Pro Leu Asp
            965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Ser Ser Val Pro
            995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
```

```
                    1355                1360                1365
Gln Ala Thr Asn Thr Val Gly Ser Val Ile Gly Val Ile Val Thr
            1370                1375                1380
Ile Phe Val Ser Gly Thr Val Tyr Phe Ile Cys Gln Arg Met Leu
        1385                1390                1395
Cys Pro Arg Met Lys Gly Asp Gly Glu Thr Met Thr Asn Asp Tyr
    1400                1405                1410
Val Val His Gly Pro Ala Ser Val Pro Leu Gly Tyr Val Pro His
    1415                1420                1425
Pro Ser Ser Leu Ser Gly Ser Leu Pro Gly Met Ser Arg Gly Lys
    1430                1435                1440
Ser Met Ile Ser Ser Leu Ser Ile Met Gly Gly Ser Ser Gly Pro
    1445                1450                1455
Pro Tyr Asp Arg Ala His Val Thr Gly Ala Ser Ser Ser Ser Ser
    1460                1465                1470
Ser Ser Thr Lys Gly Thr Tyr Phe Pro Ala Ile Leu Asn Pro Pro
    1475                1480                1485
Pro Ser Pro Ala Thr Glu Arg Ser His Tyr Thr Met Glu Phe Gly
    1490                1495                1500
Tyr Ser Ser Asn Ser Pro Ser Thr His Arg Ser Tyr Ser Tyr Arg
    1505                1510                1515
Pro Tyr Ser Tyr Arg His Phe Ala Pro Pro Thr Pro Cys Ser
    1520                1525                1530
Thr Asp Val Cys Asp Ser Asp Tyr Ala Pro Ser Arg Arg Met Thr
    1535                1540                1545
Ser Val Ala Thr Ala Lys Gly Tyr Thr Ser Asp Leu Asn Tyr Asp
    1550                1555                1560
Ser Glu Pro Val Pro Pro Pro Thr Pro Arg Ser Gln Tyr Leu
    1565                1570                1575
Ser Ala Glu Glu Asn Tyr Glu Ser Cys Pro Pro Ser Pro Tyr Thr
    1580                1585                1590
Glu Arg Ser Tyr Ser His His Leu Tyr Pro Pro Pro Ser Pro
    1595                1600                1605
Cys Thr Asp Ser Ser
    1610

<210> SEQ ID NO 23
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Gln Gln Ser Gly Ala Glu Leu Met Lys Pro Gly Ala
1               5                   10                  15

Ser Val Lys Ile Ser Cys Lys Ala Ala Gly Tyr Thr Met Arg Gly Tyr
            20                  25                  30

Trp Ile Glu Trp Ile Lys Gln Arg Pro Gly His Gly Leu Glu Trp Ile
        35                  40                  45

Gly Gln Ile Leu Pro Gly Thr Gly Arg Thr Asn Tyr Asn Glu Lys Phe
    50                  55                  60

Lys Gly Lys Ala Thr Phe Thr Ala Asp Thr Ser Ser Asn Thr Ala Asn
65                  70                  75                  80
```

```
Met Gln Leu Ser Ser Leu Thr Ser Glu Asp Ser Ala Val Tyr Tyr Cys
                85                  90                  95

Ala Arg Phe Asp Gly Asn Tyr Gly Tyr Tyr Ala Met Asp Tyr Trp Gly
            100                 105                 110

Gln Gly Ser Ser Val Thr Val Ser Ser Ala
        115                 120

<210> SEQ ID NO 24
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 25
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Gln Ser Gly Ala Glu Val Lys Lys Pro Gly Ala
1               5                   10                  15

Ser Val Lys Ile Ser Cys Lys Val Ser Gly Tyr Thr Leu Arg Gly Tyr
            20                  25                  30

Trp Ile Glu Trp Val Arg Gln Ala Pro Gly Lys Gly Leu Glu Trp Ile
        35                  40                  45

Gly Gln Ile Leu Pro Gly Thr Gly Arg Thr Asn Tyr Asn Glu Lys Phe
    50                  55                  60

Lys Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Asp Gly Asn Tyr Gly Tyr Tyr Ala Met Asp Tyr Trp Gly
            100                 105                 110

Gln Gly Thr Thr Val Thr Val Ser Ser Ala
        115                 120
```

<210> SEQ ID NO 26
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Ser Gly Val Asp Ser Gln Ala Val Val Thr Gln Glu Pro Ser Leu Thr
1               5                   10                  15
Val Ser Pro Gly Gly Thr Val Thr Leu Thr Cys Arg Ser Ser Thr Gly
            20                  25                  30
Ala Val Thr Thr Ser Asn Tyr Ala Asn Trp Phe Gln Gln Lys Pro Gly
        35                  40                  45
Gln Ala Pro Arg Thr Leu Ile Gly Gly Thr Asn Asn Arg Ala Pro Gly
    50                  55                  60
Val Pro Ala Arg Phe Ser Gly Ser Leu Leu Gly Gly Lys Ala Ala Leu
65                  70                  75                  80
Thr Leu Ser Gly Ala Gln Pro Glu Asp Glu Ala Glu Tyr Tyr Cys Ala
                85                  90                  95
Leu Trp Tyr Ser Asn His Trp Val Phe Gly Gly Gly Thr Lys Leu Thr
            100                 105                 110
Val Leu Gly
        115

<210> SEQ ID NO 27
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

Arg Gly Tyr Trp Ile Glu
1               5

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Gln Ile Leu Pro Gly Thr Gly Arg Thr Asn Tyr Asn Glu Lys Phe Lys
1               5                   10                  15
Gly

<210> SEQ ID NO 29
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

```
Phe Asp Gly Asn Tyr Gly Tyr Tyr Ala Met Asp Tyr
1               5                   10
```

<210> SEQ ID NO 30
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

```
Arg Ser Ser Thr Gly Ala Val Thr Thr Ser Asn Tyr Ala Asn
1               5                   10
```

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

```
Gly Thr Asn Asn Arg Ala Pro
1               5
```

<210> SEQ ID NO 32
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

```
Ala Leu Trp Tyr Ser Asn His Trp Val Phe Gly Gly Gly Thr Lys Leu
1               5                   10                  15
```

<210> SEQ ID NO 33
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
                20                  25                  30

Gly Met Ser Trp Val Arg Gln Ala Pro Gly Lys Gly Leu Glu Trp Val
            35                  40                  45

Ser Val Ile Ala Ser Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ser Ile Phe Tyr Thr Thr Trp Gly Gln Gly Thr Leu Val Thr
            100                 105                 110

Val Ser Ser
        115

<210> SEQ ID NO 34
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser Asn Phe Pro
                85                  90                  95

Ile Thr Phe Gly Gln Gly Thr Lys Val Glu Ile Lys Arg
            100                 105

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ser Ser Ser Gly Met Ser
1               5

<210> SEQ ID NO 36
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Val Ile Ala Ser Ser Gly Ser Asn Thr Tyr Tyr Ala Asp Ser Val Lys
1               5                   10                  15

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Ile Phe Tyr Thr Thr
1               5

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Arg Ala Ser Gln Ser Val Arg Ser Asn Tyr Leu
1               5                   10

<210> SEQ ID NO 39
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Ala Ser Ser Arg Ala
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Gln Tyr Ser Asn Phe Pro Ile
1               5

<210> SEQ ID NO 41
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

```
Ala Arg Gly Ser Gly Phe Arg Trp Val Met Asp Tyr Trp Gly Gln Gly
            100                 105                 110

Thr Leu Val Thr Val Ser Ser
        115

<210> SEQ ID NO 42
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Thr Thr Pro Ser
                85                  90                  95

Thr Phe Gly Gln Gly Thr Lys Val Glu Ile Lys Arg
            100                 105

<210> SEQ ID NO 43
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Phe Thr Phe Ser Ser Tyr Trp Ile His
1               5                   10

<210> SEQ ID NO 44
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ala Arg Ile Asn Pro Ser Asn Gly Ser Thr Asn Tyr Ala Asp Ser Val
1               5                   10                  15

Lys Gly

<210> SEQ ID NO 45
<211> LENGTH: 18
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 45

Ala Arg Ile Asn Pro Ser Asn Gly Ser Ala His Tyr Ala Asp Ser Val
1               5                   10                  15

Lys Gly

<210> SEQ ID NO 46
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ala Arg Ile Asn Pro Ser Asn Arg Ser Asn Gln Tyr Ala Asp Ser Val
1               5                   10                  15

Lys Gly

<210> SEQ ID NO 47
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Arg Ile Asn Pro Ser Asn Gly Ser Thr Arg Tyr Ala Asp Ser Val
1               5                   10                  15

Lys Gly

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Arg Gly Ser Gly Phe Arg Trp Val Met Asp Tyr
1               5                   10

<210> SEQ ID NO 49
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg Ala Ser Gln Asp Val Ser Thr Ala Val Ala
1               5                   10

<210> SEQ ID NO 50
<211> LENGTH: 7
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 50

Ser Ala Ser Phe Leu Tyr Ser
1               5

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Gln Ser Tyr Thr Thr Pro Pro Thr
1               5

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gln Gln Ser Tyr Thr Thr Pro Ala Thr
1               5

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gln Gln Phe Tyr Thr Thr Pro Ser Thr
1               5

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Gln Ser Phe Ser Thr Pro Ala Thr
1               5

<210> SEQ ID NO 55
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Gly Met Ser Trp Val Arg Gln Ala Pro Gly Lys Gly Leu Glu Trp Val
        35                  40                  45

Ser Tyr Ile Tyr Pro Tyr Ser Gly Ala Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Tyr Arg Ile Ser Ser Ala Met Asp Val Trp
            100                 105                 110

Gly Gln Gly Thr Leu Val Thr Val Ser Ala
        115                 120

<210> SEQ ID NO 56
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Arg Phe
            20                  25                  30

Leu Ala Trp Tyr Gln Gln Lys Pro Gly Lys Ala Pro Lys Leu Leu Ile
        35                  40                  45

Tyr Gly Ala Ser Thr Arg Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Arg Ser Pro His
                85                  90                  95

Thr Phe Gly Gln Gly Thr Lys Val Glu Ile Lys Arg
            100                 105

<210> SEQ ID NO 57
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Tyr Ser Phe Thr Ser Tyr Gly Met Ser
1               5                   10

<210> SEQ ID NO 58
<211> LENGTH: 10
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Tyr Thr Phe Ser Ser Tyr Gly Met Ser
1               5                   10

<210> SEQ ID NO 59
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ser Tyr Ile Tyr Pro Tyr Ser Gly Ala Thr Tyr Tyr Ala Asp Ser Val
1               5                   10                  15

Lys Gly

<210> SEQ ID NO 60
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

His Ser Gly Tyr Tyr Arg Ile Ser Ser Ala Met Asp Val
1               5                   10

<210> SEQ ID NO 61
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Arg Ala Ser Gln Ser Ile Ser Ser Tyr Leu Ala
1               5                   10

<210> SEQ ID NO 62
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Arg Ala Ser Gln Ser Asn Arg Arg Phe Leu Ala
1               5                   10

<210> SEQ ID NO 63
<211> LENGTH: 11
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 63

Arg Ala Ser Gln Ser Val Arg Ser Phe Leu Ala
1               5                   10

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Arg Ala Ser Gln Asn Ile Lys Arg Phe Leu Ala
1               5                   10

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gly Ala Ser Ser Arg Ala Ser
1               5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Arg Ala Ser Ile Arg Ala Ser
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Ala Ser Thr Arg Glu Ser
1               5

<210> SEQ ID NO 68
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 68

Gln Gln Tyr Tyr Ser Ser Pro Leu Thr
1               5

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gln Gln Tyr Tyr Ile Ser Pro Leu Thr
1               5

<210> SEQ ID NO 70
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gln Gln Tyr Tyr Ile Ser Pro Trp Thr
1               5

<210> SEQ ID NO 71
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gln Gln Tyr Tyr Arg Ser Pro His Thr
1               5

<210> SEQ ID NO 72
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser His Tyr
            20                  25                  30

Tyr Met Ser Trp Val Arg Gln Thr Pro Glu Lys Arg Leu Glu Trp Val
        35                  40                  45

Ala Tyr Ile Ser Asn Gly Gly Arg Thr Asp Tyr Pro Asp Ser Val
    50                  55                  60

Lys Gly Arg Phe Thr Ile Ser Arg Asp Asn Ala Lys Asn Thr Leu His
65                  70                  75                  80

Leu Gln Met Ser Ser Leu Lys Ser Glu Asp Thr Ala Met Tyr Tyr Cys
                85                  90                  95

```
Thr Arg Leu Asp Tyr Phe Gly Gly Ser Pro Tyr Phe Asp Tyr Trp Gly
            100                 105                 110

Gln Gly Thr Thr Leu Thr Val Ser Ser Ala
        115                 120

<210> SEQ ID NO 73
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Pro Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Lys Arg Ala Asp Ala Ala Pro
            100                 105                 110

Thr Val

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Phe Thr Phe Ser His Tyr Tyr Met Ser
1               5                   10

<210> SEQ ID NO 75
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ile Ser Asn Gly Gly Gly Arg Thr Asp
1               5

<210> SEQ ID NO 76
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 76

Tyr Ile Asn Ser Gly Gly Gly Arg Thr Asp
1               5                   10

<210> SEQ ID NO 77
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Arg Leu Asp Tyr Phe Gly Gly Ser Pro Tyr Phe Asp Tyr
1               5                   10

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Leu Asp Tyr Tyr Gly Gly Ser Pro Tyr Phe Asp Tyr
1               5                   10

<210> SEQ ID NO 79
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Ser Ala Ser Ser Ser Val Ser Tyr Met His
1               5                   10

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Glu Ile Ser Lys Leu Ala Ser
1               5

<210> SEQ ID NO 81
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81
```

Gln Gln Trp Asn Tyr Pro Leu Ile Thr
1               5

<210> SEQ ID NO 82
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Ser Asp Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Tyr Tyr Trp Asn Trp Ile Arg Gln Phe Pro Gly Asn Lys Leu Glu
        35                  40                  45

Trp Met Gly Phe Ile Ser Tyr Asp Gly Ser Asn Asn Tyr Asn Pro Ser
    50                  55                  60

Leu Lys Asn Arg Ile Ser Ile Thr Arg Asp Thr Ser Lys Asn Gln Phe
65                  70                  75                  80

Phe Leu Lys Leu Asn Ser Val Thr Thr Glu Asp Thr Ala Thr Phe Tyr
                85                  90                  95

Cys Ala Thr Leu Tyr Tyr Asp Tyr Asp Gly Asn Tyr Phe Asp Tyr Trp
            100                 105                 110

Gly Gln Gly Thr Thr Leu Thr Val Ser Ser Ala
        115                 120

<210> SEQ ID NO 83
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Cys Asp Ile Gln Met Thr Gln Thr Thr Ser Ser Leu Ser Ala Ser Leu
1               5                   10                  15

Gly Asp Arg Val Thr Ile Ser Cys Arg Thr Ser Gln Asp Ile Ser Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Ala Leu Pro
                85                  90                  95

Leu Thr Phe Gly Pro Gly Thr Lys Leu Glu Leu Lys Arg Ala Asp Ala
            100                 105                 110

Ala Pro Thr Val
        115

<210> SEQ ID NO 84
<211> LENGTH: 12

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Gly Tyr Ser Ile Thr Ser Gly Tyr Tyr Trp Asn Trp
1               5                   10

<210> SEQ ID NO 85
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Ile Ser Tyr Asp Gly Ser Asn Asn Tyr Asn
1               5                   10

<210> SEQ ID NO 86
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Leu Tyr Tyr Asp Tyr Asp Gly Asn Tyr Phe Asp Tyr
1               5                   10

<210> SEQ ID NO 87
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Arg Thr Ser Gln Asp Ile Ser Asn Tyr Leu Asn
1               5                   10

<210> SEQ ID NO 88
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Tyr Thr Ser Arg Leu His Ser
1               5

<210> SEQ ID NO 89
<211> LENGTH: 8
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 89

Gln Gln Gly Asn Ala Leu Pro Thr
1               5

<210> SEQ ID NO 90
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Cys Gln Val Gln Leu Gln Gln Ser Gly Asp Asp Leu Val Lys Pro Gly
1               5                   10                  15

Ala Ser Val Lys Leu Ser Cys Lys Ala Ser Gly Tyr Thr Phe Thr Ser
            20                  25                  30

Tyr Trp Ile Asn Trp Ile Lys Gln Arg Pro Gly Gln Gly Leu Glu Trp
        35                  40                  45

Ile Gly His Ile Gly Pro Gly Ser Gly Ser Thr Tyr Tyr Asn Glu Ile
    50                  55                  60

Phe Lys Gly Lys Ala Thr Leu Thr Val Asp Thr Ser Ser Ser Thr Ala
65                  70                  75                  80

Tyr Ile Gln Leu Ser Ser Leu Ser Ser Glu Asp Ser Ala Val Tyr Phe
                85                  90                  95

Cys Val Leu Thr Arg Tyr Phe Tyr Ala Met Asp Tyr Trp Gly Gln Gly
            100                 105                 110

Thr Ser Val Thr Val Ser Ser Ala
        115                 120

<210> SEQ ID NO 91
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Asp Ile Val Met Thr Gln Ser Pro Ser Ser Leu Ala Val Thr Ala Gly
1               5                   10                  15

Glu Lys Val Thr Met Arg Cys Lys Ser Ser Gln Ser Leu Leu Trp Ser
            20                  25                  30

Val Asn Gln Asn Asn Tyr Leu Ser Trp Tyr Gln Gln Lys Gln Gly Gln
        35                  40                  45

Pro Pro Lys Leu Leu Ile Tyr Gly Ala Ser Ile Arg Glu Ser Trp Val
    50                  55                  60

Pro Asp Arg Phe Thr Gly Ser Gly Ser Gly Thr Asp Phe Thr Leu Thr
65                  70                  75                  80

Ile Ser Asn Val His Val Glu Asp Leu Ala Val Tyr Tyr Cys Gln His
                85                  90                  95

Asn His Gly Ser Phe Leu Pro Leu Thr Phe Gly Ala Gly Thr Lys Leu
            100                 105                 110

Glu Leu Lys Arg Ala Asp Ala Ala Pro Thr Val
        115                 120

```
<210> SEQ ID NO 92
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Tyr Thr Phe Thr Ser Tyr Trp Ile Asn
1               5                   10

<210> SEQ ID NO 93
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

His Ile Gly Pro Gly Ser Gly Ser Thr Tyr Tyr Asn
1               5                   10

<210> SEQ ID NO 94
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Thr Arg Tyr Phe Tyr Ala Met Asp Tyr
1               5

<210> SEQ ID NO 95
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Lys Ser Ser Gln Ser Leu Leu Trp Ser Val Asn Gln Asn Asn Tyr Leu
1               5                   10                  15

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ala Ser Ile Arg Glu Ser
1               5

<210> SEQ ID NO 97
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gln His Asn His Gly Ser Phe Leu Pro Leu Thr
1               5                   10

<210> SEQ ID NO 98
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Ser Gln Val Gln Leu Gln Gln Ser Gly Ala Glu Leu Ala Lys Pro Gly
1               5                   10                  15

Thr Ser Val Lys Met Ala Cys Lys Ala Ser Gly Tyr Thr Phe Thr Thr
                20                  25                  30

His Trp Met Asn Trp Val Lys Gln Arg Pro Gly Gln Gly Leu Glu Trp
            35                  40                  45

Ile Gly Thr Ile Asn Pro Ser Asn Asp Phe Thr Asp Cys Asn Gln Lys
        50                  55                  60

Phe Lys Asp Lys Ala Ile Leu Thr Ala Asp Lys Ser Ser Ser Thr Ala
65                  70                  75                  80

Tyr Met Gln Leu Ser Ser Leu Thr Ser Glu Asp Ser Ala Ile Tyr Tyr
                85                  90                  95

Cys Ala Ser Gly Leu Thr Ala Arg Ala Trp Phe Ala Tyr Trp Gly Gln
            100                 105                 110

Gly Thr Leu Val Thr Val Ser Ala Ala
        115                 120

<210> SEQ ID NO 99
<211> LENGTH: 102
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Arg Ala Thr Ile Ser Cys Arg Ala Ser Gln Ser Val Thr Thr Ser Asn
1               5                   10                  15

Tyr Ser Tyr Met His Trp Phe Gln Gln Lys Pro Gly Gln Pro Pro Lys
                20                  25                  30

Leu Leu Ile Lys Tyr Ala Ser Asn Leu Asp Ser Gly Val Pro Ala Arg
            35                  40                  45

Phe Ser Gly Ser Gly Ser Gly Thr Asp Phe Thr Leu Asn Ile His Pro
        50                  55                  60

Val Glu Glu Glu Asp Thr Ala Thr Phe Tyr Cys Gln His Ser Trp Glu
65                  70                  75                  80

Ile Pro Tyr Thr Phe Gly Gly Gly Thr Asn Leu Glu Ile Lys Arg Ala
                85                  90                  95

Asp Ala Ala Pro Thr Val
```

```
<210> SEQ ID NO 100
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Tyr Thr Phe Thr Thr His Trp Met Asn Trp
1               5                   10

<210> SEQ ID NO 101
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ile Asn Pro Ser Asn Asp Phe Thr Asp Cys Asn
1               5                   10

<210> SEQ ID NO 102
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Thr Ala Arg Ala Trp Phe Ala Tyr
1               5

<210> SEQ ID NO 103
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Arg Ala Ser Gln Ser Val Thr Thr Ser Asn Tyr Ser Tyr Met His
1               5                   10                  15

<210> SEQ ID NO 104
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Tyr Ala Ser Asn Leu Asp Ser Gly
1               5

<210> SEQ ID NO 105
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gln His Ser Trp Glu Ile Pro Tyr Thr
1               5

<210> SEQ ID NO 106
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Trp Phe Ala Tyr Trp Gly Gln Gly Thr Leu Val
            100                 105                 110

Thr Val Ser Ser
        115

<210> SEQ ID NO 107
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95
```

```
Thr Phe Gly Gln Gly Thr Lys Val Glu Ile Lys
            100                 105
```

<210> SEQ ID NO 108
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

```
Gly Phe Thr Phe Ser Asn Tyr Gly Ile His
1               5                   10
```

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

```
Trp Ile Thr Gly Asn Gly Gly Tyr Ser Asp Tyr Ala Asp Ser Val Lys
1               5                   10                  15

Gly
```

<210> SEQ ID NO 110
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

```
Ala Gly Ser Trp Phe Ala Tyr
1               5
```

<210> SEQ ID NO 111
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

```
Arg Ala Ser Gln Asp Val Ser Thr Ala Val Ala
1               5                   10
```

<210> SEQ ID NO 112
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

```
Ser Ala Ser Phe Leu Tyr Ser
1               5
```

<210> SEQ ID NO 113
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gln Gln Ser Tyr Thr Thr Pro Pro Thr
1               5

<210> SEQ ID NO 114
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Phe Val Gly Ser Gly Met Asp Tyr
            100                 105                 110

Trp Gly Gln Gly Thr Leu Val Thr Val Ser Ser
        115                 120

<210> SEQ ID NO 115
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Phe Thr Ala Pro Pro
                85                  90                  95
Thr Phe Gly Gln Gly Thr Lys Val Glu Ile Lys
            100                 105

<210> SEQ ID NO 116
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Gly Phe Thr Phe Thr Ser Tyr Asp Ile His
1               5                   10

<210> SEQ ID NO 117
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gly Ile Ser Pro Ala Asp Gly Asp Thr Asp Tyr Ala Asn Ser Val Lys
1               5                   10                  15
Gly

<210> SEQ ID NO 118
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Asn Asp Tyr Asp Val Arg Phe Val Gly Ser Gly Met Asp Tyr
1               5                   10

<210> SEQ ID NO 119
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Arg Ala Ser Gln Asp Val Ser Thr Ala Val Ala
1               5                   10

<210> SEQ ID NO 120
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120
```

Ser Ala Ser Phe Leu Tyr Ser
1               5

<210> SEQ ID NO 121
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gln Gln Ser Phe Thr Ala Pro Pro Thr
1               5

<210> SEQ ID NO 122
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Ser
            20                  25                  30

Asp Ile His Trp Val Arg Gln Ala Pro Gly Lys Gly Leu Glu Trp Val
        35                  40                  45

Gly Gly Ile Thr Pro Ala Asp Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Trp Ser Ser Ser Pro Gly Ser Ala Phe Asp Tyr Trp
            100                 105                 110

Gly Gln Gly Thr Leu Val Thr Val Ser Ser
        115                 120

<210> SEQ ID NO 123
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ile Ser Pro Ser
                 85                  90                  95

Thr Phe Gly Gln Gly Thr Lys Val Glu Ile Lys
            100                 105

<210> SEQ ID NO 124
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Gly Phe Thr Phe Thr Asn Ser Asp Ile His
 1               5                  10

<210> SEQ ID NO 125
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Ile Thr Pro Ala Asp Gly Tyr Thr Asp Tyr Ala Asp Ser Val Lys
 1               5                  10                  15

Gly

<210> SEQ ID NO 126
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ser Tyr Trp Ser Ser Ser Pro Gly Ser Ala Phe Asp Tyr
 1               5                  10

<210> SEQ ID NO 127
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Arg Ala Ser Gln Asp Val Ser Thr Ala Val Ala
 1               5                  10

<210> SEQ ID NO 128
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 128

Ser Ala Ser Phe Leu Tyr Ser
1               5

<210> SEQ ID NO 129
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gln Gln Ser Tyr Ile Ser Pro Ser Thr
1               5

<210> SEQ ID NO 130
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 131
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Val Ala Pro Pro
                 85                  90                  95

Leu Phe Gly Gln Gly Thr Lys Val Glu Ile Lys Arg
                100                 105
```

<210> SEQ ID NO 132
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                 90                  95

Ala Arg Asp Lys Tyr Asp Ile Pro Asp Ala Phe Asp Ile Trp Gly Gln
                100                 105                 110

Gly Thr Leu Val Thr Val Ser Ser
            115                 120
```

<210> SEQ ID NO 133
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

```
Asp Ile Arg Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Asp
                20                  25                  30

Leu Ala Trp Tyr Gln Gln Lys Pro Gly Lys Val Pro Arg Leu Leu Ile
            35                  40                  45

Tyr Ala Thr Ser Thr Leu Gln Ser Gly Val Pro Ser Arg Phe Ser Gly
        50                  55                  60

Ser Gly Ser Ala Thr Asp Phe Thr Leu Thr Ile Ser Ser Leu Gln Pro
 65                  70                  75                  80

Glu Asp Val Ala Thr Tyr Tyr Cys Gln Gln Ser Tyr Asn Ala Pro Ile
                 85                  90                  95

Thr Phe Gly Gln Gly Thr Arg Leu Glu Ile Lys
```

<210> SEQ ID NO 134
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

Ser Tyr Ala Met His
1               5

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

Val Ile Ser Tyr Asp Gly Ser Asn Lys Tyr Tyr Ala Asp Ser Val Lys
1               5                   10                  15

Gly

<210> SEQ ID NO 136
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 136

Asp Lys Tyr Asp Ile Pro Asp Ala Phe Asp Ile
1               5                   10

<210> SEQ ID NO 137
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 137

Arg Ala Ser Gln Gly Ile Ser Asn Asp Leu Ala
1               5                   10

<210> SEQ ID NO 138
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 138

Ala Thr Ser Thr Leu Gln Ser
1               5

<210> SEQ ID NO 139
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Gln Gln Ser Tyr Asn Ala Pro Ile
1               5

<210> SEQ ID NO 140
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 140

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ala Ile Tyr Pro Asp Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Tyr Asp Ile Pro Asp Ala Phe Asp Ile Trp Gly Gln
            100                 105                 110

Gly Thr Leu Val Thr Val Ser
        115

<210> SEQ ID NO 141
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asp
            20                  25                  30

Leu Ala Trp Tyr Gln Gln Lys Pro Gly Lys Val Pro Arg Leu Leu Ile
        35                  40                  45

Tyr Ala Thr Ser Thr Leu Gln Ser Gly Val Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Val Ala Thr Tyr Tyr Cys Gln Gln Ser Tyr Asn Ala Pro Ile

```
                      85                  90                  95

Thr Phe Gly Gln Gly Thr Arg Leu Glu Ile Lys
                100                 105

<210> SEQ ID NO 142
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Ser Tyr Ala Met His
1               5

<210> SEQ ID NO 143
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ala Ile Tyr Pro Asp Ser Ser Asn Lys Tyr Tyr Ala Asp Ser Val Lys
1               5                   10                  15

Gly

<210> SEQ ID NO 144
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Asp Lys Tyr Asp Ile Pro Asp Ala Phe Asp Ile
1               5                   10

<210> SEQ ID NO 145
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Arg Ala Ser Gln Gly Ile Ser Asn Asp Leu Ala
1               5                   10

<210> SEQ ID NO 146
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146
```

Ala Thr Ser Thr Leu Gln Ser
1               5

<210> SEQ ID NO 147
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Gln Gln Ser Tyr Asn Ala Pro Ile
1               5

<210> SEQ ID NO 148
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ala Ile Ser Pro Glu Ala Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Tyr Asp Ile Pro Asp Ala Phe Asp Ile Trp Gly Gln
            100                 105                 110

Gly Thr Leu Val Thr Val Ser
        115

<210> SEQ ID NO 149
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asp
            20                  25                  30

Leu Ala Trp Tyr Gln Gln Lys Pro Gly Lys Val Pro Arg Leu Leu Ile
        35                  40                  45

Tyr Ala Thr Ser Thr Leu Gln Ser Gly Val Pro Ser Arg Phe Ser Gly
    50                  55                  60

Ser Gly Ser Ala Thr Asp Phe Thr Leu Thr Ile Ser Ser Leu Gln Pro

```
                65                  70                  75                  80
Glu Asp Val Ala Thr Tyr Tyr Cys Gln Gln Ser Tyr Asn Ala Pro Ile
                    85                  90                  95
Thr Phe Gly Gln Gly Thr Arg Leu Glu Ile Lys
            100                 105

<210> SEQ ID NO 150
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ser Tyr Ala Met His
1               5

<210> SEQ ID NO 151
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Ala Ile Ser Pro Glu Ala Ser Asn Lys Tyr Tyr Ala Asp Ser Val Lys
1               5                   10                  15
Gly

<210> SEQ ID NO 152
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Asp Lys Tyr Asp Ile Pro Asp Ala Phe Asp Ile
1               5                   10

<210> SEQ ID NO 153
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Arg Ala Ser Gln Gly Ile Ser Asn Asp Leu Ala
1               5                   10

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 154

Ala Thr Ser Thr Leu Gln Ser
1               5

<210> SEQ ID NO 155
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Gln Gln Ser Tyr Asn Ala Pro Ile
1               5

<210> SEQ ID NO 156
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ala Ile Tyr Pro Ala Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Tyr Asp Ile Pro Ala Phe Asp Ile Trp Gly Gln Gly
            100                 105                 110

Gly Thr Leu Val Thr Val Ser
        115

<210> SEQ ID NO 157
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asp
            20                  25                  30

Leu Ala Trp Tyr Gln Gln Lys Pro Gly Lys Val Pro Arg Leu Leu Ile
        35                  40                  45

Tyr Ala Thr Ser Thr Leu Gln Ser Gly Val Pro Ser Arg Phe Ser Gly

```
                    50                  55                  60
Ser Gly Ser Ala Thr Asp Phe Thr Leu Thr Ile Ser Ser Leu Gln Pro
 65                  70                  75                  80

Glu Asp Val Ala Thr Tyr Tyr Cys Gln Gln Ser Tyr Asn Ala Pro Ile
                 85                  90                  95

Thr Phe Gly Gln Gly Thr Arg Leu Glu Ile Lys
            100                 105

<210> SEQ ID NO 158
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ser Tyr Ala Met His
 1               5

<210> SEQ ID NO 159
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Ala Ile Tyr Pro Ala Ser Ser Asn Lys Tyr Tyr Ala Asp Ser Val Lys
 1               5                  10                  15

Gly

<210> SEQ ID NO 160
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Asp Lys Tyr Asp Ile Pro Asp Ala Phe Asp Ile
 1               5                  10

<210> SEQ ID NO 161
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Arg Ala Ser Gln Gly Ile Ser Asn Asp Leu Ala
 1               5                  10

<210> SEQ ID NO 162
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 162

Ala Thr Ser Thr Leu Gln Ser
1               5

<210> SEQ ID NO 163
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Gln Gln Ser Tyr Asn Ala Pro Ile
1               5

<210> SEQ ID NO 164
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Gln Val Gln Leu Lys Gln Ser Gly Ala Glu Leu Val Arg Pro Gly Thr
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
        35                  40                  45

Ala Arg Ile Tyr Pro Gly Ile Gly Ser Thr Tyr Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Lys Asn Gly Gly Phe Phe Asp Tyr Trp Gly Gln Gly Thr Thr Leu
            100                 105                 110

Thr Val Ser Ser
        115

<210> SEQ ID NO 165
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
```

35                  40                  45
Lys Leu Leu Ile Tyr Arg Ala Ser Asn Leu Glu Ser Gly Ile Pro Ala
         50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Trp Thr Phe Gly Gly Gly Thr Lys Leu Glu Ile Lys
            100                 105                 110

<210> SEQ ID NO 166
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Ser Tyr Trp Ile His
1               5

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Arg Ile Tyr Pro Gly Ile Gly Ser Thr Tyr Tyr Asn Glu Lys Phe Lys
1               5                   10                  15

Asp

<210> SEQ ID NO 168
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Asn Gly Gly Phe Phe Asp Tyr
1               5

<210> SEQ ID NO 169
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Arg Ala Ser Glu Ser Val Asp Ser Tyr Gly Asn Ser Phe Met His
1               5                   10                  15

<210> SEQ ID NO 170
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Arg Ala Ser Asn Leu Glu Ser
1               5

<210> SEQ ID NO 171
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gln Gln Ser Asn Asp Pro Trp Thr
1               5

<210> SEQ ID NO 172
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Gln Val Gln Leu Gln Glu Ser Gly Pro Gly Leu Val Lys Pro Ser Gly
1               5                   10                  15

Thr Leu Ser Leu Thr Cys Thr Val Ser Gly Asp Ser Ile Ser Ser Ser
            20                  25                  30

Asn Trp Trp Ser Trp Val Arg Gln Pro Pro Gly Gln Gly Leu Glu Trp
        35                  40                  45

Ile Gly Glu Ile Phe His Gly Glu Asn Thr Asn Tyr Asn Pro Ser Leu
    50                  55                  60

Lys Ser Arg Val Thr Ile Ser Val Asp Lys Ser Lys Asn Gln Ile Ser
65                  70                  75                  80

Leu Asn Leu Thr Ser Ala Thr Ala Ala Asp Thr Ala Val Tyr Tyr Cys
                85                  90                  95

Ala Arg Asn Pro Gly Ile Gly Ala Ala Lys Phe Asp Ser Trp Gly Gln
            100                 105                 110

Gly Thr Leu Val Thr Val Ser Ser
        115                 120

<210> SEQ ID NO 173
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
```

```
                20                  25                  30
Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Ile Asp Phe Pro Phe Thr Phe Gly Gln Gly Thr Lys Leu Glu Ile Lys
            100                 105                 110

<210> SEQ ID NO 174
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Ser Ser Asn Trp Trp Ser
1               5

<210> SEQ ID NO 175
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Glu Ile Phe His Gly Glu Asn Thr Asn Tyr Asn Pro Ser Leu Lys Ser
1               5                   10                  15

<210> SEQ ID NO 176
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Asn Pro Gly Ile Gly Ala Ala Lys Phe Asp Ser
1               5                   10

<210> SEQ ID NO 177
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Lys Ser Ser Gln Ser Leu Leu His Ser Asp Gly Lys Thr Tyr Leu Tyr
1               5                   10                  15

<210> SEQ ID NO 178
```

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 178

Glu Val Ser Asn Arg Phe Ser
1               5

<210> SEQ ID NO 179
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 179

Met Gln His Ile Asp Phe Pro
1               5

<210> SEQ ID NO 180
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Asn
            20                  25                  30

Trp Ile Ser Trp Val Arg Gln Ala Pro Gly Lys Gly Leu Glu Trp Val
        35                  40                  45

Gly Tyr Ile Ser Pro Asn Ser Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Asn Phe Gly Gly Tyr Phe Asp Tyr Trp Gly Gln Gly Thr
            100                 105                 110

Leu Val

<210> SEQ ID NO 181
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala

```
                     20                  25                  30
Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Gly Thr Val
                 85                  90                  95

Thr Phe Gly Gln Gly Thr Lys Val Glu Ile Lys Arg
            100                 105
```

<210> SEQ ID NO 182
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

```
Gly Phe Thr Phe Thr Asp Asn Trp Ile Ser
 1               5                  10
```

<210> SEQ ID NO 183
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

```
Gly Tyr Ile Ser Pro Asn Ser Gly Phe Thr Tyr Tyr Ala Asp Ser Val
 1               5                  10                  15

Lys Gly
```

<210> SEQ ID NO 184
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

```
Val Tyr Tyr Cys Ala Arg Asp Asn Phe Gly Gly Tyr Phe Asp Tyr
 1               5                  10                  15
```

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

```
Arg Ala Ser Gln Asp Val Ser Thr Ala Val Ala
 1               5                  10
```

<210> SEQ ID NO 186
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 186

Ser Ala Ser Phe Leu Tyr Ser
1               5

<210> SEQ ID NO 187
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 187

Gln Gln Ser Tyr Thr Gly Thr Val Thr
1               5

<210> SEQ ID NO 188
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 188

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 189
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 189

Asp Ile Val Met Thr Gln Ser Pro Asp Ser Leu Ala Val Ser Leu Gly

```
                1               5                  10                  15
Glu Arg Ala Thr Ile Ser Cys Arg Ala Ser Glu Ser Val Asp Asn Tyr
                    20                  25                  30

Gly Ile Ser Phe Met Lys Trp Phe Gln Gln Lys Pro Gly Gln Pro Pro
            35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys
                100                 105                 110

<210> SEQ ID NO 190
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Thr Ala Tyr Tyr Ile His
1               5

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Tyr Ile Ser Ser Tyr Asn Gly Ala Thr Asn Tyr Asn Gln Lys Phe Lys
1               5                   10                  15

Gly

<210> SEQ ID NO 192
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Arg Asp Tyr Asp Tyr Asp Val Gly Met Asp Tyr
1               5                   10

<210> SEQ ID NO 193
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193
```

Arg Ala Ser Glu Ser Val Asp Asn Tyr Gly Ile Ser Phe Met Lys
1               5                   10                  15

<210> SEQ ID NO 194
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Ala Ala Ser Asn Gln Gly Ser
1               5

<210> SEQ ID NO 195
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Gln Gln Ser Lys Glu Val Pro Trp Thr Phe Gly Gly
1               5                   10

<210> SEQ ID NO 196
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Tyr
            20                  25                  30

Tyr Ile Ser Trp Val Arg Gln Ala Pro Gly Lys Gly Leu Glu Trp Val
        35                  40                  45

Ala Glu Ile Ser Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Leu Arg Ala Arg Pro Pro Ile Arg Leu His Pro Arg Gly Ser Val
            100                 105                 110

Met Asp Tyr Trp Gly Gln
        115

<210> SEQ ID NO 197
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 198
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Tyr Tyr Tyr Ile Ser
1               5

<210> SEQ ID NO 199
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Glu Ile Ser Pro Tyr Ser Gly Ser Thr Tyr Tyr Ala Asp Ser Val Lys
1               5                   10                  15

Gly

<210> SEQ ID NO 200
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Arg Ala Arg Pro Pro Ile Arg Leu His Pro Arg Gly Ser Val
1               5                   10

<210> SEQ ID NO 201
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Arg Ala Ser Gln Asp Val Ser Thr Ala Val Ala
1               5                   10

<210> SEQ ID NO 202
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ser Ala Ser Phe Leu Tyr Ser
1               5

<210> SEQ ID NO 203
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Gln Gln Ser Tyr Thr Thr Pro Pro Thr
1               5

<210> SEQ ID NO 204
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Ser
            20                  25                  30

Tyr Ile His Trp Val Arg Gln Ala Pro Gly Lys Gly Leu Glu Trp Val
        35                  40                  45

Gly Trp Ile Thr Pro Tyr Gly Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly His Val Asn Ala Val Lys Asn Tyr Gly Tyr Val
            100                 105                 110

Met Asp Tyr Trp Gly Gln
        115

<210> SEQ ID NO 205
<211> LENGTH: 108
<212> TYPE: PRT
<213> ORGANISM: Artificial Sequence
<220> FEATURE:
<221> NAME/KEY: source -continued
<223> OTHER INFORMATION: /note="Description of Artificial Sequence:
      Synthetic polypeptide"

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 206
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Asn Ser Tyr Ile
1

<210> SEQ ID NO 207
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Trp Ile Thr Pro Tyr Gly Gly Tyr Thr Asn Tyr Ala Asp Ser Val Lys
1               5                   10                  15

<210> SEQ ID NO 208
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Gly Ser Gly His Val Asn Ala Val Lys Asn Tyr Gly Tyr Val
1               5                   10

<210> SEQ ID NO 209
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 209

Arg Ala Ser Gln Asp Val Ser Thr Ala Val Ala
1               5                   10

<210> SEQ ID NO 210
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Ser Ala Ser Phe Leu Tyr Ser
1               5

<210> SEQ ID NO 211
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Gln Gln Ser Tyr Thr Thr Pro Pro Thr
1               5

<210> SEQ ID NO 212
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Arg Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ile Pro Gln Ser Tyr Pro Phe Ala Ser Tyr Lys Ser Gly
            100                 105                 110

Phe Asp Tyr Trp Gly Gln
        115

<210> SEQ ID NO 213
<211> LENGTH: 108
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Met Gly Tyr Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105

<210> SEQ ID NO 214
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 214

Gly Phe Thr Phe Ser Ser Tyr Ala Met His
1               5                   10

<210> SEQ ID NO 215
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 215

Ser Arg Ile Ser Ser Asn Gly Gly Ser Thr Tyr Tyr Ala Asp Ser Val
1               5                   10                  15

Lys Gly

<210> SEQ ID NO 216
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 216

Trp Ile Pro Gln Ser Tyr Pro Phe Ala Ser Tyr Lys Ser Gly Phe Asp
1               5                   10                  15

Tyr

<210> SEQ ID NO 217
<211> LENGTH: 11

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Arg Ala Ser Gln Val Met Gly Tyr Tyr Leu Ala
1               5                   10

<210> SEQ ID NO 218
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Asp Ala Ser Ser Leu Glu Ser
1               5

<210> SEQ ID NO 219
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gln Gln Tyr Tyr Ser Tyr Pro Phe Thr
1               5

<210> SEQ ID NO 220
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 220

Gln Val Gln Leu Lys Glu Ser Gly Pro Gly Leu Val Ala Ser Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Gly Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Gly Thr Gly Ser Trp Phe Ala Tyr Trp Gly Gln Gly Thr Leu Val Thr
            100                 105                 110

Val Ser Ala
        115
```

<210> SEQ ID NO 221
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 221

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105

<210> SEQ ID NO 222
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Thr Leu Ser Trp Val Arg Gln Ala Pro Gly Lys Gly Leu Glu Trp Val
        35                  40                  45

Ser Val Ile Ser Gly Asp Gly Ser Tyr Thr Tyr Tyr Ala Asp Ser Val
    50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Ile Lys Tyr Val Phe Ala Asn Trp Gly Gln Gly Thr
            100                 105                 110

Leu Val Thr Val Ser Ser
        115

<210> SEQ ID NO 223
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 223

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Asn Thr Leu Ser Leu
                85                  90                  95

Val Phe Gly Gly Gly Thr Lys Leu Thr Val Leu Gly
                100                 105
```

<210> SEQ ID NO 224
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

```
Gly Phe Thr Phe Ser His Tyr Thr Leu Ser
1               5                   10
```

<210> SEQ ID NO 225
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

```
Val Ile Ser Gly Asp Gly Ser Tyr Thr Tyr Tyr Ala Asp Ser Val Lys
1               5                   10                  15

Gly
```

<210> SEQ ID NO 226
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

```
Asn Phe Ile Lys Tyr Val Phe Ala Asn
1               5
```

<210> SEQ ID NO 227
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Ser Gly Asp Asn Ile Gly Ser Phe Tyr Val His
1               5                   10

<210> SEQ ID NO 228
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Asp Lys Ser Asn Arg Pro Ser Gly
1               5

<210> SEQ ID NO 229
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Gln Ser Tyr Ala Asn Thr Leu Ser Leu
1               5

<210> SEQ ID NO 230
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Gly Ile Asp Asp Asp Gly Ser Tyr Pro Asn Tyr Gly Ser Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Tyr Gly Gly Ser Trp Gly Gly Tyr Ile Ala Asp Asp
            100                 105                 110

Ile Asp Ala Trp Gly Gln Gly Thr Leu Val Thr Val Ser Ser
        115                 120                 125

<210> SEQ ID NO 231
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 231

Glu Leu Thr Gln Pro Pro Ser Val Ser Val Ser Pro Gly Gln Thr Ala
1               5                   10                  15

Arg Ile Thr Cys Ser Gly Asp Gly Ser Tyr Ala Gly Ser Tyr Tyr Tyr
            20                  25                  30

Gly Trp Tyr Gln Gln Lys Pro Gly Gln Ala Pro Val Thr Leu Ile Tyr
        35                  40                  45

Tyr Asn Asn Lys Arg Pro Ser Gly Ile Pro Glu Arg Phe Ser Gly Ser
    50                  55                  60

Leu Ser Gly Ser Thr Asn Thr Leu Thr Ile Ser Gly Val Gln Ala Glu
65                  70                  75                  80

Asp Glu Ala Asp Tyr Tyr Cys Gly Ser Ala Asp Asn Ser Gly Ala Ala
                85                  90                  95

Phe Gly Gly Gly Thr Lys Leu Thr Val Leu
            100                 105

<210> SEQ ID NO 232
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Ser Phe Asn Met Phe
1               5

<210> SEQ ID NO 233
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Gly Ile Asp Asp Asp Gly Ser Tyr Pro Asn Tyr Gly Ser Ala Val Lys
1               5                   10                  15

Gly

<210> SEQ ID NO 234
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Ser Gly Tyr Gly Gly Ser Trp Gly Gly Tyr Ile Ala Asp Asp Ile Asp
1               5                   10                  15

Ala

<210> SEQ ID NO 235
<211> LENGTH: 13
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 235

Ser Gly Asp Gly Ser Tyr Ala Gly Ser Tyr Tyr Tyr Gly
1               5                   10

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Tyr Asn Asn Lys Arg Pro Ser
1               5

<210> SEQ ID NO 237
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Gly Ser Ala Asp Asn Ser Gly Ala Ala
1               5

<210> SEQ ID NO 238
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Asp Gln Ala Ile Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu Asn Phe Pro Val His Gly Ala Gly Glu Ile Cys
            100                 105                 110

<210> SEQ ID NO 239
<211> LENGTH: 112
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 239

Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Lys Phe Phe Leu Cys Ser Met Tyr Thr Pro Ile Cys Leu Glu
    50                  55                  60

Asp Tyr Lys Lys Pro Leu Pro Pro Cys Arg Ser Val Cys Glu Arg Ala
65                  70                  75                  80

Lys Ala Gly Cys Ala Pro Leu Met Arg Gln Tyr Gly Phe Ala Trp Pro
                85                  90                  95

Asp Arg Met Arg Cys Asp Arg Leu Pro Glu Gln Gly Asn Pro Asp Thr
            100                 105                 110

<210> SEQ ID NO 240
<211> LENGTH: 363
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Glu Pro Lys Ser Ser Asp Lys Thr His Thr Cys Pro Pro
    130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
```

```
                    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                    245                 250                 255

Gly Gln Pro Arg Glu Pro Gln Val Tyr Thr Leu Pro Pro Ser Arg Asp
                260                 265                 270

Glu Leu Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
        290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                    325                 330                 335

Asn Val Phe Ser Cys Ser Val Met His Glu Ala Leu His Asn His Tyr
                340                 345                 350

Thr Gln Lys Ser Leu Ser Leu Ser Pro Gly Lys
        355                 360

<210> SEQ ID NO 241
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Met Glu Trp Val Lys Gln Arg Pro Gly His Gly Leu Glu Trp Ile
        35                  40                  45

Gly Glu Ile Leu Pro Gly Arg Gly Arg Thr Asn Tyr Asn Glu Asn Phe
    50                  55                  60

Lys Gly Lys Ala Thr Phe Thr Ala Asp Thr Ser Ser Asn Thr Val Tyr
65                  70                  75                  80

Met Gln Leu Asn Ser Leu Thr Ser Glu Asp Ser Ala Val Tyr Tyr Cys
                85                  90                  95

Ala Arg Phe His Ser Ser Ala Tyr Tyr Tyr Thr Met Asp Tyr Trp Gly
            100                 105                 110

Gln Arg Thr Ser Val Thr Val Ser Ser
        115                 120

<210> SEQ ID NO 242
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Gln Ala Val Val Thr Gln Glu Ser Ala Leu Thr Thr Ser Pro Gly Glu
1               5                   10                  15
```

```
Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Asn Arg Ala Pro Gly Ile Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 243
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Asn Tyr Trp Met Glu
1               5

<210> SEQ ID NO 244
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Glu Ile Leu Pro Gly Arg Gly Arg Thr Asn Tyr Asn Glu Asn Phe Lys
1               5                   10                  15

<210> SEQ ID NO 245
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Phe His Ser Ser Ala Tyr Tyr Tyr Thr Met Asp Tyr
1               5                   10

<210> SEQ ID NO 246
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Arg Ser Ser Thr Gly Ala Val Thr Thr Ser Asn Tyr Ala Asn
1               5                   10
```

<210> SEQ ID NO 247
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 247

Gly Thr Asn Asn Arg Ala Pro
1               5

<210> SEQ ID NO 248
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 248

Ala Leu Trp Tyr Ser Asn His Trp Val
1               5

<210> SEQ ID NO 249
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 249

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Asn Tyr Asn Arg Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 250
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 250

Asp Ile Val Met Thr Gln Ser Pro Asp Ser Leu Ala Val Ser Leu Gly

```
                1               5                  10                 15
            Glu Arg Ala Thr Ile Ser Cys Arg Ala Ser Glu Ser Val Asp Asn Tyr
                        20                  25                 30
            Gly Ile Ser Phe Met Lys Trp Phe Gln Gln Lys Pro Gly Gln Pro Pro
                    35                  40                  45
            Lys Leu Leu Ile Tyr Ala Ala Ser Asn Gln Gly Ser Gly Val Pro Asp
                50                  55                  60
            Arg Phe Ser Gly Ser Gly Ser Gly Thr Asp Phe Thr Leu Thr Ile Ser
            65                  70                  75                  80
            Ser Leu Gln Ala Glu Asp Val Ala Val Tyr Tyr Cys Gln Gln Ser Lys
                            85                  90                  95
            Glu Val Pro Trp Thr Phe Gly Gly Gly Thr Lys Val Glu Ile Lys
                        100                 105                 110

<210> SEQ ID NO 251
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Thr Ala Tyr Tyr Ile His
1               5

<210> SEQ ID NO 252
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Tyr Ile Ser Asn Tyr Asn Arg Ala Thr Asn Tyr Asn Gln Lys Phe Lys
1               5                   10                  15

<210> SEQ ID NO 253
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Arg Asp Tyr Asp Tyr Asp Val Gly Met Asp Tyr
1               5                   10

<210> SEQ ID NO 254
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Arg Ala Ser Glu Ser Val Asp Asn Tyr Gly Ile Ser Phe Met Lys
1               5                   10                  15
```

<210> SEQ ID NO 255
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 255

Ala Ala Ser Asn Gln Gly Ser
1               5

<210> SEQ ID NO 256
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 256

Gln Gln Ser Lys Glu Val Pro Trp Thr Phe Gly Gly
1               5                   10

<210> SEQ ID NO 257
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 257

Met Glu Trp Gly Tyr Leu Leu Glu Val Thr Ser Leu Leu Ala Ala Leu
1               5                   10                  15

Ala Val Leu Gln Arg Ser Ser Gly Ala Ala Ala Ser Ala Lys Glu
                20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
        50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Glu Ser Gly Gly
145                 150                 155                 160

Gly Gly Val Thr Asp Lys Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

-continued

```
Asp Thr Leu Met Ile Ser Arg Thr Pro Glu Val Thr Cys Val Val Val
            195                 200                 205

Asp Val Ser His Glu Asp Pro Glu Val Lys Phe Asn Trp Tyr Val Asp
210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Glu Glu Met Thr Lys
290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 258
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Asp Tyr Ala Ile His
1               5

<210> SEQ ID NO 259
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Asn Thr Tyr Tyr Gly Asp Ser Lys Tyr Asn Gln Lys Phe Lys Asp
1               5                   10                  15

<210> SEQ ID NO 260
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 260

Asn Thr Tyr Tyr Gly Asp Ser Lys Tyr Ala Gln Lys Phe Gln Gly
1               5                   10                  15

<210> SEQ ID NO 261
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Gly Tyr Asp Gly Phe Ala Tyr
1               5

<210> SEQ ID NO 262
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Arg Thr Ser Glu Asn Ile Tyr Ser Tyr Leu Thr
1               5                   10

<210> SEQ ID NO 263
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Asn Ala Lys Ile Leu Ala Ala Gly Val
1               5

<210> SEQ ID NO 264
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Asn Ala Lys Thr Leu Ala Ser Gly Val
1               5

<210> SEQ ID NO 265
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Asn Ala Lys Ile Leu Asp Ser Gly Val
1               5
```

```
<210> SEQ ID NO 266
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

His Ala Lys Ile Leu Asp Ser Gly Val
1               5

<210> SEQ ID NO 267
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gln His His Tyr Asp Ile Pro Trp Thr
1               5

<210> SEQ ID NO 268
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 268

Met Ser Val Pro Thr Gln Val Leu Gly Leu Leu Leu Trp Leu Thr
1               5                   10                  15

Asp Ala Arg Cys Asp Ile Gln Leu Thr Gln Ser Pro Ala Ser Leu Ser
                20                  25                  30

Ala Ser Val Gly Glu Thr Val Thr Phe Thr Cys Arg Thr Ser Glu Asn
            35                  40                  45

Ile Tyr Ser Tyr Leu Thr Trp Tyr Gln Gln Lys Gln Gly Lys Ser Pro
        50                  55                  60

Gln Leu Leu Val Tyr Asn Ala Lys Ile Leu Ala Ala Gly Val Pro Ser
65                  70                  75                  80

Arg Phe Ser Gly Tyr Gly Ser Gly Thr Gln Phe Ser Leu Lys Ile Asn
                85                  90                  95

Ser Leu Gln Pro Glu Asp Phe Gly Thr Tyr Tyr Cys Gln His His Tyr
            100                 105                 110

Asp Ile Pro Trp Thr Phe Gly Gly Gly Thr Lys Leu Glu Ile Lys Arg
        115                 120                 125

Thr

<210> SEQ ID NO 269
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 269

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Glu Asn
        35                  40                  45

Ile Tyr Ser Tyr Leu Thr Trp Tyr Gln Gln Lys Pro Gly Lys Ala Pro
    50                  55                  60

Lys Leu Leu Val Tyr Asn Ala Lys Ile Leu Ala Ala Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys His His Tyr
            100                 105                 110

Asp Ile Pro Trp Thr Phe Gly Gly Thr Lys Leu Glu Ile Lys Arg
        115                 120                 125

Thr

<210> SEQ ID NO 270
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 270

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Glu Asn
        35                  40                  45

Ile Tyr Ser Tyr Leu Thr Trp Tyr Gln Gln Lys Pro Gly Lys Ala Pro
    50                  55                  60

Lys Leu Leu Ile Tyr Asn Ala Lys Thr Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln His His Tyr
            100                 105                 110

Asp Ile Pro Trp Thr Phe Gly Gly Thr Lys Leu Glu Ile Lys Arg
        115                 120                 125

Thr

<210> SEQ ID NO 271
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 271

Met Ser Val Pro Thr Gln Val Leu Gly Leu Leu Leu Trp Leu Thr

```
              1               5                  10                 15
Met Ser Val Pro Thr Gln Val Leu Gly Leu Leu Leu Leu Trp Leu Thr
              1               5                  10                 15

Asp Ala Arg Cys Asp Ile Gln Met Thr Gln Ser Pro Ser Ser Leu Ser
                    20                  25                 30

Ala Ser Val Gly Asp Arg Val Thr Ile Thr Cys Arg Thr Ser Glu Asn
                    35                  40                 45

Ile Tyr Ser Tyr Leu Thr Trp Tyr Gln Gln Lys Pro Gly Lys Ala Pro
                50                  55                 60

Lys Leu Leu Ile Tyr Asn Ala Lys Ile Leu Asp Ser Gly Val Pro Ser
65                  70                  75                         80

Arg Phe Ser Gly Ser Gly Ser Gly Thr Asp Phe Thr Leu Thr Ile Ser
                    85                  90                 95

Ser Leu Gln Pro Glu Asp Phe Ala Thr Tyr Tyr Cys Gln His His Tyr
                    100                 105                110

Asp Ile Pro Trp Thr Phe Gly Gly Gly Thr Lys Leu Glu Ile Lys Arg
                    115                 120                125

Thr
```

<210> SEQ ID NO 272
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 272

```
Met Ser Val Pro Thr Gln Val Leu Gly Leu Leu Leu Leu Trp Leu Thr
1               5                  10                 15

Asp Ala Arg Cys Asp Ile Gln Met Thr Gln Ser Pro Ser Ser Leu Ser
                    20                  25                 30

Ala Ser Val Gly Asp Arg Val Thr Ile Thr Cys Arg Thr Ser Glu Asn
                    35                  40                 45

Ile Tyr Ser Tyr Leu Thr Trp Tyr Gln Gln Lys Pro Gly Lys Ala Pro
                50                  55                 60

Lys Leu Leu Ile Tyr His Ala Lys Ile Leu Asp Ser Gly Val Pro Ser
65                  70                  75                         80

Arg Phe Ser Gly Ser Gly Ser Gly Thr Asp Phe Thr Leu Thr Ile Ser
                    85                  90                 95

Ser Leu Gln Pro Glu Asp Phe Ala Thr Tyr Tyr Cys Gln His His Tyr
                    100                 105                110

Asp Ile Pro Trp Thr Phe Gly Gly Gly Thr Lys Leu Glu Ile Lys Arg
                    115                 120                125

Thr
```

<210> SEQ ID NO 273
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 273

```
Met Glu Trp Ser Trp Val Phe Leu Phe Phe Leu Ser Val Thr Thr Gly
1               5                  10                 15

Val His Ser Gln Val Gln Leu Gln Gln Pro Gly Thr Glu Leu Val Arg
```

```
                    20                  25                  30

Pro Gly Val Ser Val Lys Ile Ser Cys Lys Val Ser Gly Tyr Ala Phe
            35                  40                  45

Thr Asp Tyr Ala Ile His Trp Ile Met Gln Ser His Ala Lys Ser Leu
        50                  55                  60

Glu Trp Ile Gly Ile Ile Asn Thr Tyr Tyr Gly Asp Ser Lys Tyr Asn
65                  70                  75                  80

Gln Lys Phe Lys Asp Lys Ala Thr Met Thr Val Asp Lys Ser Ser Asn
                85                  90                  95

Thr Ala Tyr Met Glu Leu Ala Arg Leu Thr Ser Glu Asp Ser Ala Ile
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140

<210> SEQ ID NO 274
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 274

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
                20                  25                  30

Pro Gly Ala Ser Val Lys Val Ser Cys Lys Val Ser Gly Tyr Ala Phe
            35                  40                  45

Thr Asp Tyr Ala Ile His Trp Ile Arg Gln Ala Pro Gly Gln Gly Leu
        50                  55                  60

Glu Trp Met Gly Ile Ile Asn Thr Tyr Tyr Gly Asp Ser Lys Tyr Asn
65                  70                  75                  80

Gln Lys Phe Lys Asp Arg Val Thr Met Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140

<210> SEQ ID NO 275
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 275

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
                20                  25                  30
```

Pro Gly Ala Ser Val Lys Val Ser Cys Lys Val Ser Gly Tyr Ala Phe
            35                  40                  45

Thr Asp Tyr Ala Ile His Trp Ile Arg Gln Ala Pro Gly Gln Gly Leu
        50                  55                  60

Glu Trp Met Gly Ile Ile Asn Thr Tyr Tyr Gly Asp Ser Lys Tyr Ala
 65                  70                  75                  80

Gln Lys Phe Gln Gly Arg Val Thr Met Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140

<210> SEQ ID NO 276
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ala Ser Val Lys Val Ser Cys Lys Val Ser Gly Tyr Ala Phe
        35                  40                  45

Thr Asp Tyr Ala Ile His Trp Val Arg Gln Ala Pro Gly Gln Gly Leu
    50                  55                  60

Glu Trp Met Gly Ile Ile Asn Thr Tyr Tyr Gly Asp Ser Lys Tyr Ala
65                  70                  75                  80

Gln Lys Phe Gln Gly Arg Val Thr Met Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Gly Phe Ala Tyr Trp Gly Gln Gly
        115                 120                 125

Thr Leu Val Thr Val Ser Ser Ala Ser Thr Lys Gly Pro
    130                 135                 140

<210> SEQ ID NO 277
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

```
Pro Gly Ala Ser Val Lys Val Ser Cys Lys Ala Ser Gly Tyr Thr Phe
                35                  40                  45

Thr Asp Tyr Ala Ile His Trp Val Arg Gln Ala Pro Gly Gln Gly Leu
 50                  55                  60

Glu Trp Met Gly Ile Ile Asn Thr Tyr Gly Asp Ser Lys Tyr Ala
 65                  70                  75                  80

Gln Lys Phe Gln Gly Arg Val Thr Met Thr Val Asp Thr Ser Thr Ser
                85                  90                  95

Thr Ala Tyr Met Glu Leu Ser Ser Leu Arg Ser Glu Asp Thr Ala Val
                    100                 105                 110

Tyr Tyr Cys Ala Arg Gly Tyr Asp Gly Phe Ala Tyr Trp Gly Gln Gly
                115                 120                 125

Thr Leu Val Thr Val Ser Ser Ala Ser Thr Lys Gly Pro
    130                 135                 140

<210> SEQ ID NO 278
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Asp Tyr Glu Met His
 1               5

<210> SEQ ID NO 279
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Gln Pro Gly Gly Gly Gly Thr Ala Tyr Asn Gln Lys Phe Lys Gly
 1               5                  10                  15

<210> SEQ ID NO 280
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Gln Pro Gly Gly Gly Gly Thr Ala Tyr Ala Gln Lys Phe Lys Gly
 1               5                  10                  15

<210> SEQ ID NO 281
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Gln Pro Gly Gly Gly Gly Thr Ala Tyr Ala Gln Lys Phe Gln Gly
```

```
                1               5                  10                  15

<210> SEQ ID NO 282
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Arg Gly Tyr Asp Asp Tyr Pro Phe Ala Tyr
1               5                  10

<210> SEQ ID NO 283
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Arg Ala Ser Gly Asn Ile His Asn Tyr Leu Ala
1               5                  10

<210> SEQ ID NO 284
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Arg Ala Ser Gln Gly Ile His Asn Tyr Leu Ala
1               5                  10

<210> SEQ ID NO 285
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Asn Ala Lys Thr Leu Ala Asp Asp Ile
1               5

<210> SEQ ID NO 286
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Asn Ala Lys Thr Leu Ala Asp Asp Val
1               5

<210> SEQ ID NO 287
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Asn Ala Lys Thr Leu Ala Asp Ala Val
1               5

<210> SEQ ID NO 288
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Gln His Phe Trp Ser Ala Pro Trp Thr
1               5

<210> SEQ ID NO 289
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Gln Gln Phe Trp Ser Ala Pro Trp Thr
1               5

<210> SEQ ID NO 290
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 290

Met Ser Val Pro Thr Gln Val Leu Gly Leu Leu Leu Leu Trp Leu Thr
1               5                   10                  15

Asp Ala Arg Cys Asp Ile Gln Leu Gln Ser Pro Ala Ser Leu Ser Ala
            20                  25                  30

Ser Val Gly Glu Thr Val Thr Ile Thr Cys Arg Ala Ser Gly Asn Ile
        35                  40                  45

His Asn Tyr Leu Ala Trp Tyr Gln Gln Lys Gln Gly Lys Ser Pro Gln
    50                  55                  60

Leu Leu Val Tyr Asn Ala Lys Thr Leu Ala Asp Asp Ile Pro Ser Arg
65                  70                  75                  80

Phe Ser Gly Ser Gly Ser Gly Thr Gln Tyr Ser Leu Lys Ile Asn Ser
                85                  90                  95

Leu Gln Pro Glu Asp Phe Gly Ser Tyr Tyr Cys Gln His Phe Trp Ser
            100                 105                 110

Ala Pro Trp Thr Phe Gly Gly Gly Thr Lys Leu Glu Ile Lys Arg Thr
        115                 120                 125
```

<210> SEQ ID NO 291
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 291

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
        35                  40                  45

Ile His Asn Tyr Leu Ala Trp Tyr Gln Gln Lys Pro Gly Lys Ala Pro
    50                  55                  60

Lys Leu Leu Ile Tyr Asn Ala Lys Thr Leu Ala Asp Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln His Phe Trp
            100                 105                 110

Ser Ala Pro Trp Thr Phe Gly Gly Gly Thr Lys Leu Glu Ile Lys Arg
        115                 120                 125

Thr

<210> SEQ ID NO 292
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 292

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
        35                  40                  45

Ile His Asn Tyr Leu Ala Trp Tyr Gln Gln Lys Pro Gly Lys Ala Pro
    50                  55                  60

Lys Leu Leu Ile Tyr Asn Ala Lys Thr Leu Ala Asp Ala Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln His Phe Trp
            100                 105                 110

Ser Ala Pro Trp Thr Phe Gly Gly Gly Thr Lys Leu Glu Ile Lys Arg
        115                 120                 125

Thr

<210> SEQ ID NO 293
<211> LENGTH: 129

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 293

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
        35                  40                  45

Ile His Asn Tyr Leu Ala Trp Tyr Gln Gln Lys Pro Gly Lys Ala Pro
    50                  55                  60

Lys Leu Leu Ile Tyr Asn Ala Lys Thr Leu Ala Asp Ala Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln His Phe Trp
            100                 105                 110

Ser Ala Pro Trp Thr Phe Gly Gln Gly Thr Lys Leu Glu Ile Lys Arg
        115                 120                 125

Thr

<210> SEQ ID NO 294
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 294

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile His Asn Tyr Leu Ala Trp Tyr Gln Gln Lys Pro Gly Lys Ala Pro
    50                  55                  60

Lys Leu Leu Ile Tyr Asn Ala Lys Thr Leu Ala Asp Ala Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Phe Trp
            100                 105                 110

Ser Ala Pro Trp Thr Phe Gly Gln Gly Thr Lys Leu Glu Ile Lys Arg
        115                 120                 125

Thr

<210> SEQ ID NO 295
<211> LENGTH: 144
<212> TYPE: PRT
<213> ORGANISM: Artificial Sequence
<220> FEATURE:
```

<210> SEQ ID NO 296
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 295

```
Met Glu Trp Ser Trp Val Phe Leu Phe Phe Leu Ser Val Thr Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Leu Gly Tyr Thr Phe
        35                  40                  45

Thr Asp Tyr Glu Met His Trp Val Lys Glu Thr Pro Val His Gly Leu
    50                  55                  60

Glu Trp Ile Gly Ala Ile Gln Pro Gly Gly Gly Thr Ala Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140
```

<210> SEQ ID NO 296
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 296

```
Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Asn
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140
```

<210> SEQ ID NO 297
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 297

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Leu Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Ala
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 298
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 298

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Ala
65                  70                  75                  80

Gln Lys Phe Gln Gly Arg Val Thr Leu Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 299
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 299

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Glu Met His Trp Val Arg Gln Ala Pro Gly Gln Gly Leu
    50                  55                  60

Glu Trp Met Gly Ala Ile Gln Pro Gly Gly Gly Thr Ala Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Arg Gly Tyr Asp Asp Tyr Pro Phe Ala Tyr Trp
        115                 120                 125

Gly Gln Gly Thr Leu Val Thr Val Ser Ser Ala Ser Thr Lys Gly Pro
    130                 135                 140

<210> SEQ ID NO 300
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Lys Ala Ser Gly Tyr Thr Phe Thr Asp Tyr Ser
1               5                   10

<210> SEQ ID NO 301
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Ile Tyr Pro Ser Asn Gly Asp Ser
1               5

<210> SEQ ID NO 302
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Ala Thr Tyr Phe Ala Asn Asn Phe Asp Tyr
1               5                   10

<210> SEQ ID NO 303
<211> LENGTH: 11

```
-continued

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gln Ser Val Asp Tyr Asp Gly Asp Ser Tyr Met
1               5                   10

<210> SEQ ID NO 304
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Ala Ala Ser Asn Leu Glu Ser
1               5

<210> SEQ ID NO 305
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Gln Gln Ser Asn Glu Asp Pro Leu Thr
1               5

<210> SEQ ID NO 306
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 306

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile His Trp Val Arg Gln Ala Pro Gly Gln Gly Leu Glu Trp Ile
        35                  40                  45

Gly Tyr Ile Tyr Pro Ser Asn Gly Asp Ser Gly Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser
        115
```

-continued

```
<210> SEQ ID NO 307
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Pro Val Gln Ala Glu Asp Phe Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

Thr

<210> SEQ ID NO 308
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Thr Gly Tyr Thr Met His
1               5

<210> SEQ ID NO 309
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Gly Ile Asn Pro Asn Asn Gly Gly Thr Thr Tyr Asn Gln Asn Phe Lys
1               5                   10                  15

Gly

<210> SEQ ID NO 310
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Lys Glu Phe Ser Asp Gly Tyr Tyr Phe Phe Ala Tyr
```

<210> SEQ ID NO 311
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 311

```
Lys Ala Ser Gln Asp Val Ile Phe Ala Val Ala
1               5                   10
```

<210> SEQ ID NO 312
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 312

```
Trp Ala Ser Thr Arg His Thr
1               5
```

<210> SEQ ID NO 313
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 313

```
Gln Gln His Tyr Ser Thr Pro Trp
1               5
```

<210> SEQ ID NO 314
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 314

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Gly Tyr
            20                  25                  30

Thr Met His Trp Val Arg Gln Ser His Gly Lys Thr Leu Glu Trp Ile
        35                  40                  45

Gly Gly Ile Asn Pro Asn Asn Gly Gly Thr Thr Tyr Asn Gln Asn Phe
    50                  55                  60

Lys Gly Lys Ala Thr Leu Thr Val Glu Lys Ser Ser Thr Thr Ala Tyr
65                  70                  75                  80

Leu Glu Leu Arg Ser Leu Thr Ser Glu Asp Ser Ala Leu Tyr Tyr Cys
                85                  90                  95

Ala Arg Lys Glu Phe Ser Asp Gly Tyr Tyr Phe Phe Ala Tyr Trp Gly
            100                 105                 110
```

Gln Gly Thr Leu Val Thr Val Ser Ala
        115                 120

<210> SEQ ID NO 315
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 315

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Ile Phe Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Val Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 316
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Ser Ser Tyr Ala Met Ser
1               5

<210> SEQ ID NO 317
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Ser Ile Ser Ser Gly Gly Ser Thr Tyr Tyr Pro Asp Ser Val Lys Gly
1               5                   10                  15

<210> SEQ ID NO 318
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

```
Arg Gly Gly Asp Pro Gly Val Tyr Asn Gly Asp Tyr Glu Asp Ala Met
1               5                   10                  15

Asp Tyr

<210> SEQ ID NO 319
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Lys Ala Ser Gln Asp Val Ser Ser Ala Val Ala
1               5                   10

<210> SEQ ID NO 320
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Trp Ala Ser Thr Arg His Thr
1               5

<210> SEQ ID NO 321
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Gln Gln His Tyr Ser Thr Pro
1               5

<210> SEQ ID NO 322
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322

Glu Val Lys Leu Val Glu Ser Gly Gly Gly Leu Val Lys Pro Gly Gly
1               5                   10                  15

Ser Leu Lys Phe Ser Cys Ala Ala Ser Gly Phe Ser Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Ala Ser Glu Asp Thr Ala Met Tyr Phe Cys Ala
                85                  90                  95
```

Arg Gly Asp Pro Gly Val Tyr Asn Gly Asp Tyr Glu Asp Ala Met
            100                 105                 110
Asp Tyr Trp Gly Gln Gly Thr Ser Val Thr Val Ser Ser
        115                 120                 125

<210> SEQ ID NO 323
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 323

Asp Ile Val Met Thr Gln Ser His Lys Phe Met Ser Thr Ser Val Gly
1               5                   10                  15
Asp Arg Val Ser Ile Thr Cys Lys Ala Ser Gln Asp Val Ser Ser Ala
            20                  25                  30
Val Ala Trp Tyr Gln Gln Lys Pro Gly Gln Ser Pro Lys Leu Leu Ile
        35                  40                  45
Tyr Trp Ala Ser Thr Arg His Thr Gly Val Pro Asp Arg Phe Thr Asn
50                  55                  60
Ser Gly Ser Gly Thr Asp Tyr Thr Leu Thr Ile Ser Ser Val Gln Ala
65                  70                  75                  80
Glu Asp Leu Ala Leu Tyr Tyr Cys Gln Gln His Tyr Ser Thr Pro Trp
                85                  90                  95
Thr Phe Gly Gly Gly Thr Lys Leu Glu Ile Lys
            100                 105

<210> SEQ ID NO 324
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 324

His His His His His His
1               5

NOTCH PATHWAY INHIBITION

CROSS-REFERENCE TO RELATED APPLICATIONS

This application claims the benefit of priority of U.S. Provisional Application No. 62/089,425, filed Dec. 9, 2014, and U.S. Provisional Application No. 62/023,554, filed Jul. 11, 2014, each of which is incorporated by reference herein in its entirety for any purpose.

STATEMENT REGARDING FEDERALLY SPONSORED RESEARCH OR DEVELOPMENT

This invention was made with government support under Grant No. OD007191 awarded by the National Institutes of Health. The government has certain rights in the invention.

SEQUENCE LISTING

This application contains a Sequence Listing which has been submitted via EFS-Web and is hereby incorporated by reference in its entirety. Said ASCII copy, created Jul. 8, 2015, is named 2015-07-09_01146-0036-00US_seq_listing.txt and is 370,450 bytes in size.

FIELD OF THE INVENTION

The present invention relates to Notch pathway inhibition.

BACKGROUND

The Notch signaling pathway regulates a diverse array of cell functions (Kopan et al., *Cell* 137, 216-233 (2009)). Four Notch receptors have been identified in mammals, i.e., Notch 1-4, that share basic structural elements that include an extracellular domain, a transmembrane domain, and an intracellular domain. Similarly, the canonical ligands of Notch share certain structural similarities but a number of non-canonical ligands of Notch have also been identified (Kopan et al., *Cell* 137, 216-233 (2009)). The five canonical ligands in mammals are Delta-like 1, Delta-like 3, Delta-like 4, Jagged1 and Jagged2. Binding of a Notch ligand to the extracellular domain of a Notch receptor sets a signaling cascade in motion that begins with proteolytic cleavage at the extracellular S2 site by an alpha secretase of the ADAM (a disintegrin and metalloprotease) family. Cleavage at S2 is followed by proteolytic cleavage by a gamma secretase at the intracellular S3 site, which results in release of the intracellular domain and downstream events that ultimately activate Notch-dependent transcription factors such as Hes1 and Hey.

Because aberrant Notch expression and signaling has been implicated in a number of diseases, including cancer (Koch et al., *Cell. Mol. Life Sci.* 64, 2746-2762 (2007)), modulators of Notch signaling have been investigated as possible therapeutic agents for such diseases. For example, gamma secretase inhibitors have been tested in clinical trials for their effectiveness in treating various malignancies (Shih et al, *Cancer Res.* 67, 1879-1882 (2007)). Gamma secretase inhibitors prevent cleavage at S3 and thereby prevent signaling through Notch receptors. However, gamma secretase inhibitors do not distinguish individual Notch family members and therefore inhibit signaling through multiple receptors at once, as well as through unrelated pathways (Beel et al., *Cell. Mol. Life Sci.* 65, 1311-1334 (2008)). Moreover, administration of gamma secretase inhibitors is associated with intestinal toxicity marked by weight loss and intestinal goblet cell metaplasia, indicative of a role for Notch in determining cell fate by maintaining proliferation of intestinal crypt progenitor cells and prohibiting differentiation to a secretory cell fate (see van Es et al., *Nature* 435:959-963 (2005)). Similarly, inhibition of both Notch1 and Notch2 signaling via conditional Notch gene knockout (Riccio et al., *EMBO Rep.* 9:377-383 (2008)) or via antagonist antibody inhibition (US Patent Application Publication No. 2010/0080808) also causes intestinal goblet cell metaplasia.

The mouse intestinal epithelium provides an important model for studying tissue regeneration. Continuous turnover of the epithelium is supported by intestinal stem cells (ISCs) located near the base of the crypts. Genetic lineage tracing studies have led to the identification of distinct ISC populations, including crypt base columnar cells (CBCs) that are marked by Lgr5 expression, a Wnt target gene (Barker, van Es et al. 2007). CBCs reside at the bottom of crypts, occupying cell positions +1 through +5 from the base, where they are intercalated between post-mitotic Paneth cells, which constitute the stem cell niche (Sato, van Es et al. 2011). CBCs contribute to all intestinal cell types, including the secretory and absorptive lineages, through a population of rapidly proliferating intermediates known as transit-amplifying (TA) cells (Barker, van Es et al. 2007). Continuous replacement and sloughing of old cells leads the intestinal epithelium to renew approximately every 5 days.

Development of the small intestine and adult intestinal homeostasis requires canonical Wnt signaling. Lef/Tcf4, the transcription factor that mediates canonical Wnt signaling, is essential for the formation of proliferative compartments in prospective crypt regions of neonatal mice (Korinek, Barker et al. 1998). Lef/Tcf4 is also required for adult intestinal homeostasis (van Es, Haegebarth et al. 2012), as is the Wnt effector β-catenin (Fevr, Robine et al. 2007). Conversely, administration of the Wnt signaling agonist R-spondin1 leads to expansion of the ISC compartment (Yan, Chia et al. 2012), which can mitigate loss of ISCs during chemoradiation (Zhou, Geng et al. 2013). In adult animals, the central role of Wnt signaling is highlighted by the Wnt-dependent expression of numerous ISC markers, including Lgr5. (de Lau, Barker et al. 2011). In addition to its role in maintaining ISCs, Wnt signaling confers competence for the secretory fate decision. Wnt signaling plays specific roles in Paneth cell differentiation (Andreu, Colnot et al. 2005; van Es, Jay et al. 2005; Andreu, Peignon et al. 2008; van Es, Haegebarth et al. 2012), whereas overexpression of the Wnt inhibitor DKK1 leads to loss of all secretory cells (Pinto, Gregorieff et al. 2003).

The Notch pathway affects intestinal homeostasis by regulating CBCs and by promoting the absorptive cell fate. Compromising Notch signaling in adult mice with the γ-secretase inhibitor DAPT, which blocks the conversion of the Notch receptor into its transcriptionally active state, causes a loss of proliferating Lgr5-positive CBCs and an overall increase in secretory cells (VanDussen, Carulli et al. 2012). Secretory cell hyperplasia in the gut also occurs with deletion of the Notch effector Rbp-j (van Es, van Gijn et al. 2005; VanDussen, Carulli et al. 2012). Conversely, the activation of constitutive Notch signaling in the small intestine of perinatal mice causes an expansion of the proliferative compartment as well as a decrease in the number of secretory cells (Fre, Huyghe et al. 2005; Stanger, Datar et al. 2005). Genetic evidence suggests that Notch signaling exerts its negative regulatory effect on secretory cell differentiation entirely through repression of Math1/Atoh1, a transcription factor required for the formation of secretory cells (Yang, Bermingham et al. 2001), as conditional deletion of Math1 rescues the Rbp-j loss of function phenotype (Kim and Shivdasani 2011). However, while Math1 is up-regulated in the absence of Notch (VanDussen, Carulli et al. 2012), the signal(s) required for positively maintaining normal levels of Math1 in the small intestine are unknown.

There is a need in the art for anti-Notch pathway therapeutic regimens that lack the toxicity associated with inhibition of Notch receptors.

SUMMARY

In some embodiments, methods of alleviating toxicity associated with Notch pathway inhibition are provided. In some embodiments, a method comprises administering to an individual being treated with a Notch pathway inhibitor an effective amount of at least one Wnt pathway inhibitor. In some embodiments, the Wnt pathway inhibitor is administered after the individual has been administered at least one dose of a Notch pathway inhibitor. In some embodiments, the Wnt pathway inhibitor is administered at the same time that the individual is administered a Notch pathway inhibitor. In some embodiments, the Wnt pathway inhibitor is administered before the individual is administered a Notch pathway inhibitor. In some embodiments, the toxicity comprises one or more of secretory metaplasia, liver toxicity, lung toxicity, heart toxicity, subcutaneous tumors, and thymic atrophy. In some embodiments, the toxicity comprises diarrhea or gastrointestinal bleeding or both. In some embodiments, administration of at least one Wnt pathway inhibitor alleviates the diarrhea or gastrointestinal bleeding or both. In some embodiments, the liver toxicity comprises one or more of sinusoidal dilation, centrilobular hepatocyte atrophy, bile ductula proliferation, and elevated alanine aminotransferase. In some embodiments, the heart toxicity and/or lung toxicity comprises necrotic lesions.

In some embodiments, methods of treating cancer are provided, comprising administering to an individual with cancer an effective amount of at least one Notch pathway inhibitor and an effective amount of at least one Wnt pathway inhibitor. In some embodiments, the method results in reduced toxicity compared to toxicity observed with the at least one Notch pathway inhibitor alone. In some embodiments, the cancer is selected from breast cancer, lung cancer, brain cancer, cervical cancer, colon cancer, liver cancer, bile duct cancer, pancreatic cancer, skin cancer, B-cell malignancies, and T-cell malignancies.

In some embodiments, the Notch pathway inhibitor is a gamma-secretase inhibitor. In some embodiments, the Notch pathway inhibitor inhibits at least one protein selected from Notch1, Notch2, Notch3, Notch4, DLL1, DLL4, Jagged1, and Jagged2.

In some embodiments, the Notch pathway inhibitor inhibits at last two proteins selected from Notch1, Notch2, Notch3, and Notch4. In some embodiments, the Notch pathway inhibitor inhibits Notch1 and Notch2. In some embodiments, the Notch pathway inhibitor inhibits Notch 2 and Notch 3. In some embodiments, the Notch pathway inhibitor is an anti-Notch antibody. In some embodiments, the anti-Notch antibody is an anti-Notch NRR antibody. In some embodiments, the anti-Notch antibody binds to the EGF-like repeat domain of Notch. In some embodiments, the anti-Notch antibody is selected from:

a) an antibody comprising HVR-H1, HVR-H2, HVR-H3, HVR-L1, HVR-L2, and HVR-L3 shown in SEQ ID NOs: 35 to 40, respectively;

b) an antibody comprising a heavy chain variable region and a light chain variable region shown in SEQ ID NOs: 33 and 34, respectively;

c) an antibody comprising HVR-H1, HVR-H2, HVR-H3, HVR-L1, HVR-L2, and HVR-L3 shown in SEQ ID NOs: 27 to 32, respectively;

d) an antibody comprising a heavy chain variable region and a light chain variable region shown in SEQ ID NOs: 25 and 26, respectively;

e) an antibody comprising HVR-H1, HVR-H2, HVR-H3, HVR-L1, HVR-L2, and HVR-L3 shown in SEQ ID NOs: 43, 46, 48, 49, 50, and 53, respectively;

f) an antibody comprising a heavy chain variable region and a light chain variable region shown in SEQ ID NOs: 41 and 42, respectively;

g) an antibody comprising HVR-H1, HVR-H2, HVR-H3, HVR-L1, HVR-L2, and HVR-L3 shown in SEQ ID NOs: 58 to 60, 64, 67, and 71, respectively;

h) an antibody comprising a heavy chain variable region and a light chain variable region shown in SEQ ID NOs: 55 and 56, respectively;

i) an antibody comprising HVR-H1, HVR-H2, HVR-H3, HVR-L1, HVR-L2, and HVR-L3 shown in SEQ ID NOs: 74, 75, 77, and 79-81, respectively; and j) an antibody comprising a heavy chain variable region and a light chain variable region shown in SEQ ID NOs: 72 and 73, respectively k) an antibody comprising HVR-H1, HVR-H2, HVR-H3, HVR-L1, HVR-L2, and HVR-L3 shown in SEQ ID NOs: 243 to 248, respectively; and l) an antibody comprising a heavy chain variable region and a light chain variable region shown in SEQ ID NOs: 241 and 242, respectively.

In some embodiments, the antibody is a monoclonal antibody. In some embodiments, the antibody is a human, humanized, or chimeric antibody.

In some embodiments, the Notch pathway inhibitor inhibits at least one protein selected from Jagged1 and Jagged2. In some embodiments, the Notch pathway inhibitor inhibits Jagged1 and Jagged2. In some embodiments, the Notch pathway inhibitor is an anti-Jagged antibody. In some embodiments, the anti-Jagged antibody is selected from:

a) an antibody comprising HVR-H1, HVR-H2, HVR-H3, HVR-L1, HVR-L2, and HVR-L3 shown in SEQ ID NOs: 108-113, respectively;

b) an antibody comprising a heavy chain variable region and a light chain variable region shown in SEQ ID NOs: 106 and 107, respectively;

c) an antibody comprising HVR-H1, HVR-H2, HVR-H3, HVR-L1, HVR-L2, and HVR-L3 shown in SEQ ID NOs: 116-121, respectively;

d) an antibody comprising a heavy chain variable region and a light chain variable region shown in SEQ ID NOs: 114 and 115, respectively;

e) an antibody comprising HVR-H1, HVR-H2, HVR-H3, HVR-L1, HVR-L2, and HVR-L3 shown in SEQ ID NOs: 124-129, respectively;

f) an antibody comprising a heavy chain variable region and a light chain variable region shown in SEQ ID NOs: 122 and 123, respectively;

g) an antibody comprising a heavy chain variable region and a light chain variable region shown in SEQ ID NOs: 130 and 131, respectively;

h) an antibody comprising HVR-H1, HVR-H2, HVR-H3, HVR-L1, HVR-L2, and HVR-L3 shown in SEQ ID NOs: 134-139, respectively;

i) an antibody comprising a heavy chain variable region and a light chain variable region shown in SEQ ID NOs: 132 and 133, respectively;
j) an antibody comprising HVR-H1, HVR-H2, HVR-H3, HVR-L1, HVR-L2, and HVR-L3 shown in SEQ ID NOs: 142-147, respectively;
k) an antibody comprising a heavy chain variable region and a light chain variable region shown in SEQ ID NOs: 140 and 141, respectively;
l) an antibody comprising HVR-H1, HVR-H2, HVR-H3, HVR-L1, HVR-L2, and HVR-L3 shown in SEQ ID NOs: 150-155, respectively;
m) an antibody comprising a heavy chain variable region and a light chain variable region shown in SEQ ID NOs: 148 and 149, respectively;
n) an antibody comprising HVR-H1, HVR-H2, HVR-H3, HVR-L1, HVR-L2, and HVR-L3 shown in SEQ ID NOs: 158-163, respectively;
o) an antibody comprising a heavy chain variable region and a light chain variable region shown in SEQ ID NOs: 156 and 157, respectively;
p) an antibody comprising HVR-H1, HVR-H2, HVR-H3, HVR-L1, HVR-L2, and HVR-L3 shown in SEQ ID NOs: 166-171, respectively;
q) an antibody comprising a heavy chain variable region and a light chain variable region shown in SEQ ID NOs: 164 and 165, respectively;
r) an antibody comprising HVR-H1, HVR-H2, HVR-H3, HVR-L1, HVR-L2, and HVR-L3 shown in SEQ ID NOs: 174-179, respectively;
s) an antibody comprising a heavy chain variable region and a light chain variable region shown in SEQ ID NOs: 172 and 173, respectively;
t) an antibody comprising an HVR-H1 of SEQ ID NO: 258, and HVR-H2 selected from SEQ ID NOs: 259 and 260, and HVR-H3 of SEQ ID NO: 261, and HVR-L1 of SEQ ID NO: 262, and HVR-L2 selected from SEQ ID NOs: 263 to 266; and an HVR-L3 of SEQ ID NO: 267;
u) an antibody comprising a heavy chain variable region selected from SEQ ID NOs: 273 to 277 and a light chain variable region selected from SEQ ID NOs: 268 to 272;
v) an antibody comprising an HVR-H1 of SEQ ID NO: 278, and HVR-H2 selected from SEQ ID NOs: 279 to 281, and HVR-H3 of SEQ ID NO: 282, and HVR-L1 selected from SEQ ID NOs: 283 ad 284, and HVR-L2 selected from SEQ ID NOs: 285 to 287; and an HVR-L3 selected from SEQ ID NOs: 288 and 289; and
w) an antibody comprising a heavy chain variable region selected from SEQ ID NOs: 295 to 299 and a light chain variable region selected from SEQ ID NOs: 290 to 294.

In some embodiments, the antibody is a monoclonal antibody. In some embodiments, the antibody is a human, humanized, or chimeric antibody.

In some embodiments, the Notch pathway inhibitor inhibits at least one protein selected from DLL1 and DLL4. In some embodiments, the Notch pathway inhibitor is an anti-DLL antibody. In some embodiments, the anti-DLL antibody is an anti-DLL4 antibody. In some embodiments, the anti-DLL antibody is an antibody selected from:
a) an antibody comprising HVR-H1, HVR-H2, HVR-H3, HVR-L1, HVR-L2, and HVR-L3 shown in SEQ ID NOs: 182-187, respectively;
b) an antibody comprising a heavy chain variable region and a light chain variable region shown in SEQ ID NOs: 180 and 181, respectively;
c) an antibody comprising HVR-H1, HVR-H2, HVR-H3, HVR-L1, HVR-L2, and HVR-L3 shown in SEQ ID NOs: 190-195, respectively;
d) an antibody comprising a heavy chain variable region and a light chain variable region shown in SEQ ID NOs: 188 and 189, respectively;
e) an antibody comprising HVR-H1, HVR-H2, HVR-H3, HVR-L1, HVR-L2, and HVR-L3 shown in SEQ ID NOs: 251-256, respectively; and
f) an antibody comprising a heavy chain variable region and a light chain variable region shown in SEQ ID NOs: 249 and 250, respectively.

In some embodiments, the antibody is a monoclonal antibody. In some embodiments, the antibody is a human, humanized, or chimeric antibody. In some embodiments, the anti-DLL antibody is a bispecific antibody. In some embodiments, the anti-DLL antibody binds to DLL4 and VEGF.

In some embodiments, the Wnt pathway inhibitor inhibits at least one protein selected from a Wnt, an LRP, and a Fzd. In some embodiments, the Wnt pathway inhibitor inhibits LRP5, LRP6, or both LRP5 and LRP6. In some embodiments, the Wnt pathway inhibitor is an anti-LRP antibody. In some embodiments, the anti-LRP antibody is selected from:
a) an antibody comprising HVR-H1, HVR-H2, HVR-H3, HVR-L1, HVR-L2, and HVR-L3 shown in SEQ ID NOs: 198-203, respectively;
b) an antibody comprising a heavy chain variable region and a light chain variable region shown in SEQ ID NOs: 196 and 197, respectively;
c) an antibody comprising HVR-H1, HVR-H2, HVR-H3, HVR-L1, HVR-L2, and HVR-L3 shown in SEQ ID NOs: 206-211, respectively;
d) an antibody comprising a heavy chain variable region and a light chain variable region shown in SEQ ID NOs: 204 and 205, respectively;
e) a bispecific antibody comprising a first half antibody comprising HVR-H1, HVR-H2, HVR-H3, HVR-L1, HVR-L2, and HVR-L3 shown in SEQ ID NOs: 198-203, respectively, and a second half antibody comprising HVR-H1, HVR-H2, HVR-H3, HVR-L1, HVR-L2, and HVR-L3 shown in SEQ ID NOs: 206-211, respectively;
f) a bispecific antibody comprising a first half antibody comprising a heavy chain variable region and a light chain variable region shown in SEQ ID NOs: 196 and 197, respectively, and a second half antibody comprising a heavy chain variable region and a light chain variable region shown in SEQ ID NOs: 204 and 205, respectively;
g) an antibody comprising a heavy chain variable region and a light chain variable region shown in SEQ ID NOs: 220 and 221, respectively;
h) an antibody comprising HVR-H1, HVR-H2, HVR-H3, HVR-L1, HVR-L2, and HVR-L3 shown in SEQ ID NOs: 214-219, respectively; and
i) an antibody comprising a heavy chain variable region and a light chain variable region shown in SEQ ID NOs: 212 and 213, respectively.

In some embodiments, the antibody is a monoclonal antibody. In some embodiments, the antibody is a human, humanized, or chimeric antibody.

In some embodiments, the Wnt pathway inhibitor inhibits at least one Fzd. In some embodiments, the Wnt pathway inhibitor is an anti-Fzd antibody. In some embodiments, the anti-Fzd antibody is an antibody selected from:
- a) an antibody comprising HVR-H1, HVR-H2, HVR-H3, HVR-L1, HVR-L2, and HVR-L3 shown in SEQ ID NOs: 224-229, respectively;
- b) an antibody comprising a heavy chain variable region and a light chain variable region shown in SEQ ID NOs: 222 and 223, respectively
- c) an antibody comprising HVR-H1, HVR-H2, HVR-H3, HVR-L1, HVR-L2, and HVR-L3 shown in SEQ ID NOs: 232-237, respectively; and
- d) an antibody comprising a heavy chain variable region and a light chain variable region shown in SEQ ID NOs: 230 and 231, respectively.

In some embodiments, the antibody is a monoclonal antibody. In some embodiments, the antibody is a human, humanized, or chimeric antibody.

In some embodiments, the Wnt pathway inhibitor inhibits at least one R-spondin (RSPO). In some embodiments, the Wnt pathway inhibitor is an anti-RSPO antibody. In some embodiments, the anti-RSPO antibody is selected from:
- a) an antibody comprising HVR-H1, HVR-H2, HVR-H3, HVR-L1, HVR-L2, and HVR-L3 shown in SEQ ID NOs: 300-305, respectively;
- b) an antibody comprising a heavy chain variable region and a light chain variable region shown in SEQ ID NOs: 306 and 307, respectively;
- c) an antibody comprising HVR-H1, HVR-H2, HVR-H3, HVR-L1, HVR-L2, and HVR-L3 shown in SEQ ID NOs: 308-313, respectively;
- d) an antibody comprising a heavy chain variable region and a light chain variable region shown in SEQ ID NOs: 314 and 315, respectively;
- e) an antibody comprising HVR-H1, HVR-H2, HVR-H3, HVR-L1, HVR-L2, and HVR-L3 shown in SEQ ID NOs: 316-321, respectively; and
- f) an antibody comprising a heavy chain variable region and a light chain variable region shown in SEQ ID NOs: 322 and 323, respectively.

In some embodiments, the antibody is a monoclonal antibody. In some embodiments, the antibody is a human, humanized, or chimeric antibody.

In some embodiments, the Wnt pathway inhibitor is a soluble Fzd. In some embodiments, the soluble Fzd comprises an Fzd extracellular domain and an Fc. In some embodiments, the soluble Fzd is a soluble Fzd8. In some embodiments, the soluble Fzd8 comprises the sequence of SEQ ID NO: 240 or SEQ ID NO: 257. In some embodiments, the soluble Fzd consists the sequence of SEQ ID NO: 240 or SEQ ID NO: 257.

In some embodiments, the Wnt pathway inhibitor inhibits at least one Wnt. In some embodiments, the Wnt pathway inhibitor is an anti-Wnt antibody. In some embodiments, the antibody is a monoclonal antibody. In some embodiments, the antibody is a human, humanized, or chimeric antibody.

In some embodiments, the Wnt pathway inhibitor is a small molecule. In some embodiments, the Wnt pathway inhibitor is selected from LGK974 (2-(2',3-dimethyl-[2,4'-bipyridin]-5-yl)-N-(5-(pyrazin-2-yl)pyridin-2-yl)acetamide), AVN316 (Avalon Pharmaceuticals), and PRI-724 (Prism Pharma Co.).

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

I. Definitions

Figure 1:
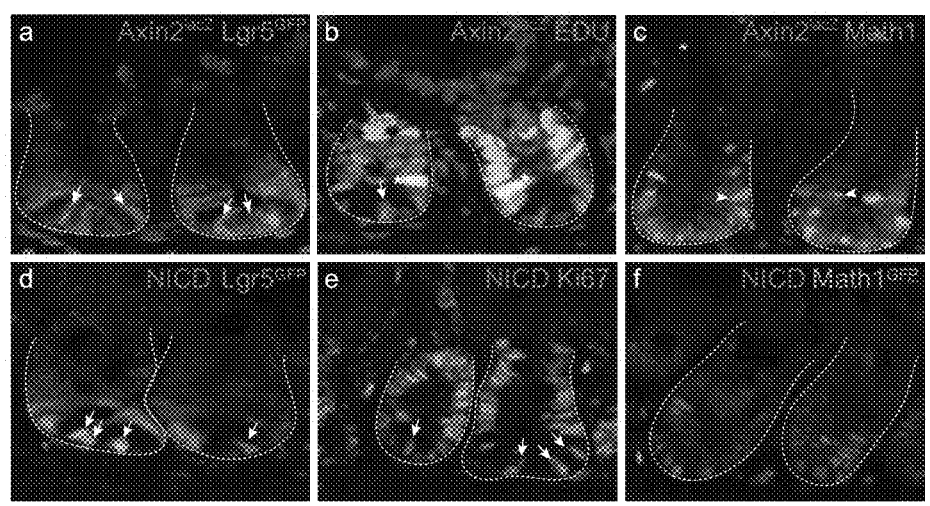
FIG. 1. Distribution of Wnt and Notch signaling in crypts of the mouse small intestine. (a) Wnt signaling is active in crypt base columnar cells (CBCs). $Lgr5^{GFP}$ (green) and $Axin2^{LacZ}$ (red) expression are co-incident in CBCs (arrows). (b) Wnt signaling is present in proliferating CBCs and transit amplifying (TA) cells. $Axin2^{LacZ}$ (red) expression overlaps with EdU incorporation (green) in cells at the base of the crypt (arrows) and in TA cells (asterisks) adjacent to CBCs. (c) Wnt signaling is present in secretory cell progenitors. $Axin2^{LacZ}$ expression (red) overlaps with secretory cell progenitors marked by $Math1^{GFP}$ (green, arrowheads). (d) Notch signaling is also present in CBCs as the active form of Notch1 (NICD, red) is localized to the nuclei of CBCs (green, arrows). (e) Notch signaling is present in proliferating CBCs and TA cells. NICD (red) overlaps with Ki67 staining (green) in CBCs (arrows) and TA cells. (f) Notch signaling (red) is absent from secretory progenitor cells (green).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "alleviates" or "alleviation" as used herein, refers to a reduction in a condition, such as an adverse event or toxicity associated with Notch pathway inhibition. A condition is considered to be alleviated if the incidence or severity of the condition is reduced by at least 10%. In some embodiments, the incidence or severity of the condition is reduced by at least 15%, or at least 20%, or at least 25%, or at least 30%, or at least 35%, or at least 40%, or at least 50%, or at least 60%, or at least 70%, or at least 80%, or at least 90%.

The term "anti-Delta-like (DLL) antibody" and "antibody that binds Delta-like (DLL)" refer to an antibody that is capable of binding DLL1, DLL4, or DLL1 and DLL4 (DLL1/4) with sufficient affinity such that the antibody is useful as a diagnostic and/or therapeutic agent in targeting DLL. In one embodiment, the extent of binding of an anti-DLL antibody to an unrelated, non-DLL protein is less than about 10% of the binding of the antibody to DLL as measured, e.g., by a radioimmunoassay (RIA). In certain embodiments, an antibody that binds to DLL has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-DLL antibody binds to an epitope of Jagged that is conserved among DLL from different species. The terms "anti-DLL1 antibody" and "an antibody that binds to DLL1" refer to an antibody that is capable of binding DLL1 with sufficient affinity such that the antibody is useful as a diagnostic and/or therapeutic agent in targeting DLL1. The terms "anti-DLL4 antibody" and "an antibody that binds to DLL4" refer to an antibody that is capable of binding DLL4 with sufficient affinity such that the antibody is useful as a diagnostic and/or therapeutic agent in targeting DLL4. The terms "anti-DLL1/4 antibody" and "an antibody that binds to DLL1/4" refer to an antibody that is capable of binding DLL1 and DLL4 with sufficient affinity such that the antibody is useful as a diagnostic and/or therapeutic agent in targeting DLL1 and DLL4. In some embodiments, an anti-DLL antibody inhibits DLL activity. In some such embodiments, an anti-DLL antibody may be referred to as an antagonist anti-DLL antibody. Nonlimiting exemplary anti-DLL antibodies are described, e.g., in U.S. Pat. No. 7,803,377; U.S. Publication No. 2010/0196385; 2014/0093521; 2013/0323248; and 2013/0164295.

The terms "anti-Jagged antibody" and "an antibody that binds to Jagged" refer to an antibody that is capable of binding Jagged1, Jagged2, or Jagged1 and Jagged2 ("Jagged1/2") with sufficient affinity such that the antibody is useful as a diagnostic and/or therapeutic agent in targeting Jagged. In one embodiment, the extent of binding of an anti-Jagged antibody to an unrelated, non-Jagged protein is less than about 10% of the binding of the antibody to Jagged as measured, e.g., by a radioimmunoassay (RIA). In certain embodiments, an antibody that binds to Jagged has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$ M to $10^{-13}$ M). In certain embodiments, an anti-Jagged antibody binds to an epitope of Jagged that is conserved among Jagged from different species. The terms "anti-Jagged1 antibody" and "an antibody that binds to Jagged1" refer to an antibody that is capable of binding Jagged1 with sufficient affinity such that the antibody is useful as a diagnostic and/or therapeutic agent in targeting Jagged1. The terms "anti-Jagged2 antibody" and "an antibody that binds to Jagged2" refer to an antibody that is capable of binding Jagged2 with sufficient affinity such that the antibody is useful as a diagnostic and/or therapeutic agent in targeting Jagged2. The terms "anti-Jagged1/2 antibody" and "an antibody that binds to Jagged1/2" refer to an antibody that is capable of binding Jagged1 and Jagged2 with sufficient affinity such that the antibody is useful as a diagnostic and/or therapeutic agent in targeting Jagged1 and Jagged2. In some embodiments, an anti-Jagged antibody inhibits Jagged activity. In some such embodiments, an anti-Jagged antibody may be referred to as an antagonist anti-Jagged antibody. Nonlimiting exemplary anti-Jagged antibodies are described, e.g., in U.S. Publication No. 20140010810 (anti-Jagged1/2 antibodies); 2012/0301489; 2008/0317760; and PCT Publication No. 2014/028446.

The term "anti-Notch antibody" or "an antibody that binds to Notch" refers to an antibody that is capable of binding one or more of Notch1, Notch2, Notch3, and Notch4 with sufficient affinity such that the antibody is useful as a diagnostic and/or therapeutic agent in targeting Notch. Preferably, the extent of binding of an anti-Notch antibody to an unrelated, non-Notch protein is less than about 10% of the binding of the antibody to Notch as measured, e.g., by a radioimmunoassay (RIA). In certain embodiments, an antibody that binds to Notch has a dissociation constant (Kd) of ≤1 µM, ≤100 nM, ≤10 nM, ≤1 nM, or ≤0.1 nM. In certain embodiments, an anti-Notch antibody binds to an epitope of Notch that is conserved among Notch from different species, e.g., rodents (mice, rats) and primates. The term "anti-Notch antibody" includes anti-Notch NRR antibodies and antibodies that bind to other regions of Notch, such as the EGF-like repeat domain. In some embodiments, an anti-Notch antibody inhibits Notch activity. In some such embodiments, an anti-Notch antibody may be referred to as an antagonist anti-Notch antibody. The term "anti-Notch antibody" includes anti-Notch1 antibodies, anti-Notch2 antibodies, anti-Notch3 antibody, and anti-Notch4 antibodies, including antibodies that bind to more than one Notch.

The term "anti-Notch1 antibody" or "an antibody that binds to Notch1" refers to an antibody that is capable of binding Notch1 with sufficient affinity such that the antibody is useful as a diagnostic and/or therapeutic agent in targeting Notch1. Preferably, the extent of binding of an anti-Notch1 antibody to an unrelated, non-Notch protein is less than about 10% of the binding of the antibody to Notch1 as measured, e.g., by a radioimmunoassay (RIA). In certain embodiments, an antibody that binds to Notch1 has a dissociation constant (Kd) of ≤1 µM, ≤100 nM, ≤10 nM, ≤1 nM, or ≤0.1 nM. In certain embodiments, an anti-Notch1 antibody binds to an epitope of Notch that is conserved among Notch from different species, e.g., rodents (mice, rats) and primates. The term "anti-Notch1 antibody" includes anti-Notch1 NRR antibodies and antibodies that bind to other regions of Notch1, such as the EGF-like repeat domain. In some embodiments, an anti-Notch1 antibody inhibits Notch activity. In some such embodiments, an anti-Notch1 antibody may be referred to as an antagonist anti-Notch1 antibody. In some embodiments, an anti-Notch1 antibody binds to Notch1 and at least one other Notch, such as Notch2 and/or Notch3. Nonlimiting exemplary antagonist anti-Notch1 antibodies are described, e.g., in U.S. Pat. Nos. 8,404,237; 8,088,617; 8,435,513; 8,460,661; U.S. Publication Nos. 2013/0266594; 2012/0213786; 2011/0311552; 2009/0258026; 2012/0093813. Nonlimiting exemplary anti-Notch1 antibodies that bind the EGF-like repeat domain are described, e.g., in U.S. Pat. Nos. 8,088,617; 8,460,661; 8,404,237.

The term "anti-Notch1 NRR antibody" or "an antibody that binds to Notch1 NRR" refers to an anti-Notch1 antibody that is capable of binding Notch1 NRR with sufficient affinity such that the antibody is useful as a diagnostic and/or therapeutic agent in targeting Notch1. Preferably, the extent of binding of an anti-Notch1 NRR antibody to an unrelated, non-Notch protein is less than about 10% of the binding of the antibody to Notch1 NRR as measured, e.g., by a radioimmunoassay (RIA). In certain embodiments, an antibody that binds to Notch1 NRR has a dissociation constant (Kd) of ≤1 µM, ≤100 nM, ≤10 nM, ≤1 nM, or ≤0.1 nM. In certain embodiments, an anti-Notch1 NRR antibody binds to an epitope of Notch that is conserved among Notch from different species, e.g., rodents (mice, rats) and primates. In some embodiments, an anti-Notch1 NRR antibody inhibits Notch activity. In some such embodiments, an anti-Notch1 NRR antibody may be referred to as an antagonist anti-Notch1 NRR antibody. Nonlimiting exemplary antagonist anti-Notch1 NRR antibodies are described, e.g., in U.S. Pat. No. 8,435,513; and U.S. Publication Nos. 2013/0266594; 2012/0213786; 2009/0258026; 2012/0093813.

The term "anti-Notch2 antibody" or "an antibody that binds to Notch2" refers to an antibody that is capable of binding Notch2 with sufficient affinity such that the antibody is useful as a diagnostic and/or therapeutic agent in targeting Notch2. Preferably, the extent of binding of an anti-Notch2 antibody to an unrelated, non-Notch protein is less than about 10% of the binding of the antibody to Notch2 as measured, e.g., by a radioimmunoassay (RIA). In certain embodiments, an antibody that binds to Notch2 has a dissociation constant (Kd) of ≤1 µM, ≤100 nM, ≤10 nM, ≤1 nM, or ≤0.1 nM. In certain embodiments, an anti-Notch2 antibody binds to an epitope of Notch that is conserved among Notch from different species, e.g., rodents (mice, rats) and primates. The term "anti-Notch2 antibody" includes anti-Notch2 NRR antibodies and antibodies that bind to other regions of Notch2, such as the EGF-like repeat domain. In some embodiments, an anti-Notch2 antibody inhibits Notch activity. In some such embodiments, an anti-Notch2 antibody may be referred to as an antagonist anti-Notch2 antibody. In some embodiments, an anti-Notch2 antibody binds to Notch2 and at least one other Notch, such as Notch1 and/or Notch3. Nonlimiting exemplary antagonist anti-Notch2 antibodies are described, e.g., in U.S. Pat. Nos. 8,425,903 and 8,226,943 (anti-Notch 2/3 antibodies), 8,404,239; 8,206,713; 7,919,092; and U.S. Publication Nos. 2013/0323266 (anti-Notch 2/3 antibodies). Nonlimiting exemplary anti-Notch2 antibodies that bind the EGF-like repeat domain are described, e.g., in U.S. Pat. Nos. 8,425,903 and 8,226,943 (anti-Notch 2/3 antibodies); U.S. Pat. Nos. 8,206,713; 7,919,092; 8,404,239; and U.S. Publication Nos. 2013/0323266 (anti-Notch 2/3 antibodies); 2010/0080808.

The term "anti-Notch2 NRR antibody" or "an antibody that binds to Notch2 NRR" refers to an antibody that is capable of binding Notch2 NRR with sufficient affinity such that the antibody is useful as a diagnostic and/or therapeutic agent in targeting Notch2. Preferably, the extent of binding of an anti-Notch2 NRR antibody to an unrelated, non-Notch protein is less than about 10% of the binding of the antibody to Notch2 NRR as measured, e.g., by a radioimmunoassay (RIA). In certain embodiments, an antibody that binds to Notch2 NRR has a dissociation constant (Kd) of ≤1 µM, ≤100 nM, ≤10 nM, ≤1 nM, or ≤0.1 nM. In certain embodiments, an anti-Notch2 NRR antibody binds to an epitope of Notch that is conserved among Notch from different species, e.g., rodents (mice, rats) and primates. In some embodiments, an anti-Notch2 NRR antibody inhibits Notch activity. In some such embodiments, an anti-Notch2 NRR antibody may be referred to as an antagonist anti-Notch2 NRR antibody. Nonlimiting exemplary antagonist anti-Notch2 NRR antibodies are described, e.g., in U.S. Pat. No. 8,404,239; and U.S. Publication No. 2010/0080808.

The term "anti-Notch3 antibody" or "an antibody that binds to Notch3" refers to an antibody that is capable of binding Notch3 with sufficient affinity such that the antibody is useful as a diagnostic and/or therapeutic agent in targeting Notch3. Preferably, the extent of binding of an anti-Notch3 antibody to an unrelated, non-Notch protein is less than about 10% of the binding of the antibody to Notch3 as measured, e.g., by a radioimmunoassay (RIA). In certain embodiments, an antibody that binds to Notch3 has a dissociation constant (Kd) of ≤1 µM, ≤100 nM, ≤10 nM, ≤1 nM, or ≤0.1 nM. In certain embodiments, an anti-Notch3 antibody binds to an epitope of Notch that is conserved among Notch from different species, e.g., rodents (mice, rats) and primates. The term "anti-Notch3 antibody" includes anti-Notch3 NRR antibodies and antibodies that bind to other regions of Notch3, such as the EGF-like repeat domain. In some embodiments, an anti-Notch3 antibody inhibits Notch activity. In some such embodiments, an anti-Notch3 antibody may be referred to as an antagonist anti-Notch3 antibody. In some embodiments, an anti-Notch3 antibody binds to Notch3 and at least one other Notch, such as Notch1 and/or Notch2. Nonlimiting exemplary antagonist anti-Notch3 antibodies are described, e.g., in U.S. Pat. Nos. 7,994,285; 7,935,791; 8,513,388; 8,329,868; 8,148,106; 8,425,903 and 8,226,943 (anti-Notch 2/3 antibodies); U.S. Publication Nos. 2012/0328608; 2013/0323266 (anti-Notch 2/3 antibodies); 2013/0323257. Nonlimiting exemplary anti-Notch3 antibodies that bind the EGF-like repeat domain are described, e.g., in U.S. Pat. Nos. 8,513,388; 8,425,903 and 8,226,943 (anti-Notch 2/3 antibodies); and U.S. Publication Nos. 2013/0323266 (anti-Notch 2/3 antibodies); 2013/0323257.

The term "anti-Notch3 NRR antibody" or "an antibody that binds to Notch3 NRR" refers to an antibody that is capable of binding Notch3 NRR with sufficient affinity such that the antibody is useful as a diagnostic and/or therapeutic agent in targeting Notch3. Preferably, the extent of binding of an anti-Notch3 NRR antibody to an unrelated, non-Notch protein is less than about 10% of the binding of the antibody to Notch3 NRR as measured, e.g., by a radioimmunoassay (RIA). In certain embodiments, an antibody that binds to Notch3 NRR has a dissociation constant (Kd) of $\leq 1$ µM, $\leq 100$ nM, $\leq 10$ nM, $\leq 1$ nM, or $\leq 0.1$ nM. In certain embodiments, an anti-Notch3 NRR antibody binds to an epitope of Notch that is conserved among Notch from different species, e.g., rodents (mice, rats) and primates. In some embodiments, an anti-Notch3 NRR antibody inhibits Notch activity. In some such embodiments, an anti-Notch3 NRR antibody may be referred to as an antagonist anti-Notch3 NRR antibody. Nonlimiting exemplary antagonist anti-Notch3 NRR antibodies are described, e.g., in U.S. Pat. No. 7,935,791; U.S. Publication No. 2012/0328608.

The term "anti-Notch4 antibody" or "an antibody that binds to Notch4" refers to an antibody that is capable of binding Notch4 with sufficient affinity such that the antibody is useful as a diagnostic and/or therapeutic agent in targeting Notch4. Preferably, the extent of binding of an anti-Notch4 antibody to an unrelated, non-Notch protein is less than about 10% of the binding of the antibody to Notch4 as measured, e.g., by a radioimmunoassay (RIA). In certain embodiments, an antibody that binds to Notch4 has a dissociation constant (Kd) of $\leq 1$ µM, $\leq 100$ nM, $\leq 10$ nM, $\leq 1$ nM, or $\leq 0.1$ nM. In certain embodiments, an anti-Notch4 antibody binds to an epitope of Notch that is conserved among Notch from different species, e.g., rodents (mice, rats) and primates. In some embodiments, an anti-Notch4 antibody inhibits Notch activity. In some such embodiments, an anti-Notch4 antibody may be referred to as an antagonist anti-Notch4 antibody. In some embodiments, an anti-Notch4 antibody binds to Notch4 and at least one other Notch.

The term "anti-LRP antibody" or "an antibody that binds to LRP" refers to an antibody that is capable of binding a low-density lipoprotein receptor-related protein (LRP) with sufficient affinity such that the antibody is useful as a diagnostic and/or therapeutic agent in targeting LRP. Preferably, the extent of binding of an anti-LRP antibody to an unrelated, non-LRP protein is less than about 10% of the binding of the antibody to LRP as measured, e.g., by a radioimmunoassay (RIA). In certain embodiments, an antibody that binds to LRP has a dissociation constant (Kd) of $\leq 1$ µM, $\leq 100$ nM, $\leq 10$ nM, $\leq 1$ nM, or $\leq 0.1$ nM. In certain embodiments, an anti-LRP antibody binds to an epitope of LRP that is conserved among LRP from different species, e.g., rodents (mice, rats) and primates. In some embodiments, an anti-LRP antibody inhibits LRP activity. In some such embodiments, an anti-LRP antibody may be referred to as an antagonist anti-LRP antibody. The term "anti-LRP antibody" includes, but is not limited to, anti-LRP5 antibodies and anti-LRP6 antibodies, and antibodies that bind both LRP5 and LRP6 (anti-LRP5/6 antibodies). Nonlimiting exemplary antagonist anti-LRP antibodies are described, e.g., in U.S. Publication Nos. 2013/0183320; 2011/0256127; 2011/0243963; 2013/0064823; and 2012/0276089 (anti-LRP5/6 antibodies).

The term "anti-LRP5 antibody" or "an antibody that binds to LRP5" refers to an antibody that is capable of binding a low-density lipoprotein receptor-related protein (LRP) 5 with sufficient affinity such that the antibody is useful as a diagnostic and/or therapeutic agent in targeting LRP5. Preferably, the extent of binding of an anti-LRP5 antibody to an unrelated, non-LRP protein is less than about 10% of the binding of the antibody to LRP5 as measured, e.g., by a radioimmunoassay (RIA). In certain embodiments, an antibody that binds to LRP5 has a dissociation constant (Kd) of $\leq 1$ µM, $\leq 100$ nM, $\leq 10$ nM, $\leq 1$ nM, or $\leq 0.1$ nM. In certain embodiments, an anti-LRP5 antibody binds to an epitope of LRP that is conserved among LRP5 from different species, e.g., rodents (mice, rats) and primates. In some embodiments, an anti-LRP5 antibody inhibits LRP5 activity. In some such embodiments, an anti-LRP5 antibody may be referred to as an antagonist anti-LRP5 antibody. Nonlimiting exemplary antagonist anti-LRP5 antibodies are described, e.g., in U.S. Publication No. 2013/0183320.

The term "anti-LRP6 antibody" or "an antibody that binds to LRP6" refers to an antibody that is capable of binding a low-density lipoprotein receptor-related protein (LRP) 6 with sufficient affinity such that the antibody is useful as a diagnostic and/or therapeutic agent in targeting LRP6. Preferably, the extent of binding of an anti-LRP6 antibody to an unrelated, non-LRP protein is less than about 10% of the binding of the antibody to LRP6 as measured, e.g., by a radioimmunoassay (RIA). In certain embodiments, an antibody that binds to LRP6 has a dissociation constant (Kd) of $\leq 1$ µM, $\leq 100$ nM, $\leq 10$ nM, $\leq 1$ nM, or $\leq 0.1$ nM. In certain embodiments, an anti-LRP6 antibody binds to an epitope of LRP6 that is conserved among LRP6 from different species, e.g., rodents (mice, rats) and primates. In some embodiments, an anti-LRP6 antibody inhibits LRP6 activity. In some such embodiments, an anti-LRP6 antibody may be referred to as an antagonist anti-LRP6 antibody. In some embodiments, an anti-LRP6 antibody is a bispecific antibody. Nonlimiting exemplary antagonist anti-LRP6 antibodies are described, e.g., in U.S. Publication Nos. 2011/0256127; 2011/0243963.

The term "anti-Wnt antibody" or "an antibody that binds to Wnt" refers to an antibody that is capable of binding Wnt with sufficient affinity such that the antibody is useful as a diagnostic and/or therapeutic agent in targeting Wnt. Preferably, the extent of binding of an anti-Wnt antibody to an unrelated, non-Wnt protein is less than about 10% of the binding of the antibody to Wnt as measured, e.g., by a radioimmunoassay (RIA). In certain embodiments, an antibody that binds to Wnt has a dissociation constant (Kd) of $\leq 1$ µM, $\leq 100$ nM, $\leq 10$ nM, $\leq 1$ nM, or $\leq 0.1$ nM. In certain embodiments, an anti-Wnt antibody binds to an epitope of Wnt that is conserved among Wnt from different species, e.g., rodents (mice, rats) and primates. In some embodiments, an anti-Wnt antibody inhibits Wnt activity. In some such embodiments, an anti-Wnt antibody may be referred to as an antagonist anti-Wnt antibody. In some embodiments, an anti-Wnt antibody binds to one or more Wnt proteins selected from Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, and Wnt16. In some embodiments, an anti-Wnt antibody binds to one or more Wnt proteins selected from Wnt1, Wnt2, Wnt2B, Wnt3, Wnt3A, Wnt7A, Wnt7B, Wnt8A, Wnt8B, Wnt10A, and Wnt10B. In some embodiments, an anti-Wnt antibody binds to one or more Wnt proteins selected from Wnt3, Wnt3A, Wnt5A, Wnt5B, and Wnt9B. Nonlimiting exemplary anti-Wnt antibodies are described, e.g., in U.S. Publication No. 2013/0045209.

The term "anti-Frizzled antibody" or "an antibody that binds to Frizzled" or "anti-Fzd antibody" or "antibody that binds Fzd" refers to an antibody that is capable of binding Frizzled (or Fzd) with sufficient affinity such that the antibody is useful as a diagnostic and/or therapeutic agent in targeting Frizzled. Preferably, the extent of binding of an anti-Frizzled antibody to an unrelated, non-Frizzled protein is less than about 10% of the binding of the antibody to Frizzled as measured, e.g., by a radioimmunoassay (RIA). In certain embodiments, an antibody that binds to Frizzled has a dissociation constant (Kd) of ≤1 µM, ≤100 nM, ≤10 nM, ≤1 nM, or ≤0.1 nM. In certain embodiments, an anti-Frizzled antibody binds to an epitope of Frizzled that is conserved among Frizzled from different species, e.g., rodents (mice, rats) and primates. In some embodiments, an anti-Frizzled antibody inhibits Frizzled activity. In some such embodiments, an anti-Frizzled antibody may be referred to as an antagonist anti-Frizzled antibody. In some embodiments, an anti-Frizzled antibody binds to one or more Frizzled proteins selected from Fzd1, Fzd2, Fzd3, Fzd4, Fzd5, Fzd6, Fzd7, Fzd8, Fzd9, and Fzd10. In some embodiments, an anti-Frizzled antibody binds to Fzd7 and/or Fzd8. In some embodiments, an anti-Frizzled antibody binds to Fzd1, Fzd2, Fzd5, Fzd7, and/or Fzd8. Nonlimiting exemplary antagonist anti-Frizzled antibodies are described, e.g., in U.S. Pat. Nos. 7,982,013; 8,507,442 (Fzd1, Fzd2, Fzd5, Fzd7, and Fzd8); and U.S. Publication No. 2013/0295106; 2012/0027778; 2013/0095104 (Fzd10).

The term "anti-RSPO antibody" or "an antibody that binds to RSPO" refers to an antibody that is capable of binding an R-spondin protein (RSPO) with sufficient affinity such that the antibody is useful as a diagnostic and/or therapeutic agent in targeting an RSPO. Preferably, the extent of binding of an anti-RSPO antibody to an unrelated, non-RSPO protein is less than about 10% of the binding of the antibody to RSPO as measured, e.g., by a radioimmunoassay (RIA). In certain embodiments, an antibody that binds to an RSPO has a dissociation constant (Kd) of ≤1 µM, ≤100 nM, ≤10 nM, ≤1 nM, or ≤0.1 nM. In certain embodiments, an anti-RSPO antibody binds to an epitope of RSPO that is conserved among RSPO from different species, e.g., rodents (mice, rats) and primates. In some embodiments, an anti-RSPO antibody inhibits RSPO activity. In some such embodiments, an anti-RSPO antibody may be referred to as an antagonist anti-RSPO antibody. In some embodiments, an anti-RSPO antibody binds at least one RSPO selected from RSPO1, RSPO2, and RSPO3. In some embodiments, an anti-RSPO antibody binds RSPO1. In some embodiments, an anti-RSPO antibody binds RSPO2 and RSPO3. In some embodiments, an anti-RSPO antibody is a bispecific antibody. Nonlimiting exemplary antagonist anti-RSPO antibodies are described, e.g., in U.S. Publication No. 2013/0209473; PCT Publication No. WO 2014/012007; U.S. Pat. No. 8,802,097.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

A "blocking" antibody or an "antagonist" antibody is one which significantly inhibits (either partially or completely) a biological activity of the antigen it binds.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "Delta-like" or "DLL" as used herein, refers to any native DLL from any vertebrate source, including mammals such as primates (e.g. humans) and rodents (e.g., mice and rats), unless otherwise indicated. The term encompasses "full-length," unprocessed DLL as well as any form of DLL that results from processing in the cell. The term also encompasses naturally occurring variants of DLL, e.g., splice variants or allelic variants. A nonlimiting exemplary human DLL1 is shown in SEQ ID NO: 17 (precursor; exemplary mature form is amino acids 18-723 of SEQ ID NO: 17). A nonlimiting exemplary human DLL4 is shown in SEQ ID NO: 18 (precursor; exemplary mature form is amino acids 27-685 of SEQ ID NO: 18).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "Frizzled" or "Fzd" as used herein, refers to any native Fzd from any vertebrate source, including mammals such as primates (e.g. humans) and rodents (e.g., mice and rats), unless otherwise indicated. The term encompasses "full-length," unprocessed Fzd as well as any form of Fzd that results from processing in the cell. The term also encompasses naturally occurring variants of Fzd, e.g., splice variants or allelic variants. A nonlimiting exemplary human Fzd7 is shown in SEQ ID NO: 19 (precursor; exemplary mature form is amino acids 33-574 of SEQ ID NO: 19). A nonlimiting exemplary human Fzd8 is shown in SEQ ID NO: 20 (precursor; exemplary mature form is amino acids 28-694 of SEQ ID NO: 20).

The term "soluble Frizzled," "Frizzled ECD," "Frizzled trap," and "Frizzled decoy" are used interchangeably herein to refer to a fragment of a Fzd protein that lacks a transmembrane domain and an intracellular domain, and which retains the ability to bind Wnt. In some embodiments, a soluble Fzd is capable of binding one or more, two or more, three or more, or four or more human Wnt proteins selected from Wnt1, Wnt2, Wnt2b, Wnt3, Wnt3a, Wnt7a, Wnt7b, Wnt8a, Wnt8b, Wnt10a, and Wnt10b. In some embodiments, a soluble Fzd is capable of binding Wnt1, Wnt2, Wnt3, Wnt3a, and Wnt7b. A soluble Fzd may be fused to a heterologous moiety, such as an Fc. In some embodiments, a soluble Fzd7 comprises amino acids 33 to 257 of SEQ ID NO: 19, or a fragment thereof that is capable of binding Wnt. In some embodiments, a soluble Fzd7 comprises amino acids 45 to 167 of SEQ ID NO: 19. In some embodiments, a soluble Fzd8 comprises amino acids 28 to 275 of SEQ ID NO: 20, or a fragment thereof that is capable of binding Wnt. In some embodiments, a soluble Fzd8 comprises amino acids 31 to 155 of SEQ ID NO: 20. Nonlimiting exemplary soluble Fzds include 54F28 Fzd8-Fc and FZD8CRD. See U.S. Pat. Nos. 7,723,477; 7,947,277; Publication No. 2013/0034551; 2010/0317098.

The terms "full length antibody," "intact antibody," and "whole antibody" are used herein interchangeably to refer to an antibody having a structure substantially similar to a native antibody structure or having heavy chains that contain an Fc region as defined herein.

The terms "gamma-secretase inhibitor" or "γ-secretase inhibitor" are used interchangeably to refer to inhibitors of gamma secretase, a protease complex involved in processing of certain type I integral membrane proteins, such as Notch. Nonlimiting exemplary gamma-secretase inhibitors include tarenflurbil (Flurizan), semagacestat (LY450139), avagacestat, MK-0752 (3-((1r,4s)-4-(4-chlorophenylsulfonyl)-4-(2,5-difluorophenyl)cyclohexyl)propanoic acid), N—[N-(3,5-Difluorophenacetyl)-L-alanyl]-S-phenylglycine t-butyl ester (DAPT), (2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide (compound E), and N-[(1S)-2-[[(7S)-6,7-Dihydro-5-methyl-6-oxo-5H-dibenz[b,d]azepin-7-yl]amino]-1-methyl-2-oxoethyl]-3,5-difluorobenzeneacetamide (DBZ). Nonlimiting exemplary gamma-secretase inhibitors include those described, for example, in U.S. Pat. Nos. 6,756,511; 6,890,956; 6,984,626; 7,049,296; 7,101,895; 7,138,400; 7,144,910; 7,183,303; 8,377,886.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262:732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-[target] antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "Jagged" or "Jag," as used herein, refers to any native Jagged from any vertebrate source, including mammals such as primates (e.g. humans) and rodents (e.g., mice and rats), unless otherwise indicated. The term encompasses "full-length," unprocessed Jagged as well as any form of Jagged that results from processing in the cell. The term also encompasses naturally occurring variants of Jagged, e.g., splice variants or allelic variants. The amino acid sequence of exemplary human and murine Jagged1 and Jagged2 are shown in SEQ ID NOS: 1-4. A nonlimiting exemplary human Jagged1 is shown in SEQ ID NO: 1 (precursor; exemplary mature form is amino acids 34-1218 of SEQ ID NO: 1). A nonlimiting exemplary human Jagged2 is shown in SEQ ID NO: 3 (precursor; exemplary mature form is amino acids 24-1238 of SEQ ID NO: 3).

The term "low-density lipoprotein receptor-related protein" or "LRP," as used herein, refers to any native LRP from any vertebrate source, including mammals such as primates (e.g. humans) and rodents (e.g., mice and rats), unless otherwise indicated. The term encompasses "full-length," unprocessed LRP as well as any form of LRP that results from processing in the cell. The term also encompasses naturally occurring variants of LRP, e.g., splice variants or allelic variants. A nonlimiting exemplary human LRP5 is shown in SEQ ID NO: 21 (precursor; exemplary mature form is amino acids 32-1615 of SEQ ID NO: 21). A nonlimiting exemplary human LRP6 is shown in SEQ ID NO: 22 (precursor; exemplary mature form is amino acids 20-1613 of SEQ ID NO: 22).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "Notch," as used herein, refers to any native Notch (Notch1-4) from any vertebrate source, including mammals such as primates (e.g. humans) and rodents (e.g., mice and rats), unless otherwise indicated. The term encompasses "full-length," unprocessed Notch as well as any form of Notch that results from processing in the cell. The term also encompasses naturally occurring variants of Notch, e.g., splice variants or allelic variants. The term Notch encompasses Notch1, Notch2, Notch3, and Notch4.

The term "Notch1," as used herein, refers to any native Notch1 from any vertebrate source, including mammals such as primates (e.g. humans) and rodents (e.g., mice and rats), unless otherwise indicated. The term encompasses "full-length," unprocessed Notch1 as well as any form of Notch1 that results from processing in the cell. The term also encompasses naturally occurring variants of Notch1, e.g., splice variants or allelic variants. A nonlimiting exemplary human Notch1 amino acid sequence is shown in SEQ ID NO: 9 (precursor; exemplary mature form is amino acids 19-2555 of SEQ ID NO: 9).

The term "Notch2," as used herein, refers to any native Notch2 from any vertebrate source, including mammals such as primates (e.g. humans) and rodents (e.g., mice and rats), unless otherwise indicated. The term encompasses "full-length," unprocessed Notch2 as well as any form of Notch2 that results from processing in the cell. The term also encompasses naturally occurring variants of Notch2, e.g., splice variants or allelic variants. A nonlimiting exemplary human Notch2 amino acid sequence is shown in SEQ ID NO: 10 (precursor; exemplary mature form is amino acids 26-2471 of SEQ ID NO: 10).

The term "Notch3," as used herein, refers to any native Notch3 from any vertebrate source, including mammals such as primates (e.g. humans) and rodents (e.g., mice and rats), unless otherwise indicated. The term encompasses "full-length," unprocessed Notch1 as well as any form of Notch3 that results from processing in the cell. The term also encompasses naturally occurring variants of Notch3, e.g., splice variants or allelic variants. A nonlimiting exemplary human Notch3 amino acid sequence is shown in SEQ ID NO: 11 (precursor; exemplary mature form is amino acids 40-2321 of SEQ ID NO: 11).

The term "Notch4," as used herein, refers to any native Notch4 from any vertebrate source, including mammals such as primates (e.g. humans) and rodents (e.g., mice and rats), unless otherwise indicated. The term encompasses "full-length," unprocessed Notch1 as well as any form of Notch4 that results from processing in the cell. The term also encompasses naturally occurring variants of Notch4, e.g., splice variants or allelic variants. A nonlimiting exemplary human Notch4 amino acid sequence is shown in SEQ ID NO: 12 (precursor; exemplary mature form is amino acids 24-2003 of SEQ ID NO: 12).

The term "Notch1 activity" refers to Notch1 signaling. An agent (e.g., an antibody) that "inhibits Notch1 activity" significantly decreases Notch1 signaling relative to the level of Notch1 signaling observed in an appropriate control under substantially identical conditions. In certain embodiments, Notch1 activity may be assessed by a suitable reporter assay, as described, e.g., in U.S. Publication No. 2009/0258026. In certain embodiments, Notch1 activity may be assessed by measuring vascular network density in a corneal pocket assay or mouse retinal model of angiogenesis, as described, e.g., in U.S. Publication No. 2009/0258026. In certain embodiments, the decrease in Notch1 signaling is at least 2-, 3-, 4-, 5-, or 10-fold below the level observed in the control.

The term "Notch1 NRR" refers to a region of Notch1 consisting of the three LNR modules (LNR-A, LNR-B, and LNR-C) and the HD domain (HD-N and HD-C). Exemplary human and mouse Notch1 NRR sequences are shown in SEQ ID NOs: 13 and 14, respectively. A further exemplary human Notch1 NRR has the sequence of amino acids 1307-1732 of SEQ ID NO: 9. The Notch1 NRR may consist of non-covalently linked fragments, e.g., that result from the processing of Notch1 at S1, as well as a single contiguous polypeptide sequence. By way of example, human Notch1 NRR may consist of amino acids 1307-1732 of human Notch1 (SEQ ID NO: 9).

The term "Notch2 activity" refers to Notch2 signaling. An agent (e.g., an antibody) that "inhibits Notch2 activity" significantly decreases Notch2 signaling relative to the level of Notch2 signaling observed in an appropriate control under substantially identical conditions. In certain embodiments, Notch2 activity may be assessed by a suitable reporter assay, as described, e.g., in U.S. Pat. No. 8,404,239. In certain embodiments, Notch2 activity may be assessed by measuring generation of marginal B zone cells, as described, e.g., in U.S. Pat. No. 8,404,239. In certain embodiments, the decrease in Notch2 signaling is at least 2-, 3-, 4-, 5-, or 10-fold below the level observed in the control.

The term "Notch2 NRR" refers to a region of Notch2 consisting of the three LNR modules (LNR-A, LNR-B, and LNR-C) and the HD domain (HD-N and HD-C). Exemplary human and mouse Notch2 NRR sequences are shown in SEQ ID NOs: 15 and 16, respectively. The Notch2 NRR may consist of non-covalently linked fragments, e.g., that result from the processing of Notch2 at S1, as well as a single contiguous polypeptide sequence. By way of example, human Notch2 NRR may consist of amino acids 1422-1677 of human Notch2 (SEQ ID NO: 10), or alternatively, amino acids 1422-1608 of SEQ ID NO: 10 noncovalently linked to amino acids 1609-1677 of SEQ ID NO: 10.

The term "Notch3 activity" refers to Notch3 signaling. An agent (e.g., an antibody) that "inhibits Notch3 activity" significantly decreases Notch3 signaling relative to the level of Notch3 signaling observed in an appropriate control under substantially identical conditions. In certain embodiments, Notch3 activity may be assessed by a suitable reporter assay, as described, e.g., in U.S. Publication No. 2013/0144040. In certain embodiments, Notch3 activity may be assessed using an apoptosis assay, cell migration assay, invasion assay, and/or morphology assay, as described, e.g., in U.S. Publication No. 2013/0144040. In certain embodiments, the decrease in Notch3 signaling is at least 2-, 3-, 4-, 5-, or 10-fold below the level observed in the control.

The term "Notch3 NRR" refers to a region of Notch3 consisting of the three LNR modules (LNR-A, LNR-B, and LNR-C) and the HD domain (HD-N and HD-C). Exemplary human and mouse Notch3 NRR sequences are shown in SEQ ID NOs: 15 and 16, respectively. The Notch3 NRR may consist of non-covalently linked fragments, e.g., that result from the processing of Notch3 at S1, as well as a single contiguous polypeptide sequence. By way of example, human Notch3 NRR may consist of amino acids 1378-1640 of human Notch3 (SEQ ID NO: 11).

The term "Notch4 activity" refers to Notch4 signaling. An agent (e.g., an antibody) that "inhibits Notch4 activity" significantly decreases Notch4 signaling relative to the level of Notch4 signaling observed in an appropriate control under substantially identical conditions. In certain embodiments, the decrease in Notch4 signaling is at least 2-, 3-, 4-, 5-, or 10-fold below the level observed in the control.

As used herein, the term "Notch-mediated disorder" means a condition or disease which is characterized by the overexpression and/or hypersensitivity of one or more Notch receptors. Specifically it includes conditions associated with cancers such as non-small cell lung cancer, ovarian cancer, and T-cell acute lymphoblastic leukemia. Other cancers including pancreatic, prostate cancer, plasma cell neoplasms (e.g., multiple myeloma, plasma cell leukemia and extramedullary plasmacytoma), neuroblastoma and extramedullary plasmacytoma are also encompassed by this term. Other types of Notch-mediated disorders include lymphoma, Alagille syndrome, liver disease involving aberrant vascularization, neurologic diseases, diabetes, diseases involving vascular cell fate, and rheumatoid arthritis.

The term "Notch pathway inhibitor" or "inhibitor of Notch pathway" as used herein refers to an agent that inhibits Notch activity. A Notch pathway inhibitor may be an antibody, a soluble receptor, a small molecule, or the like. Nonlimiting exemplary Notch pathway inhibitors include anti-Notch antibodies (including, but not limited to, anti-Notch1 antibodies, anti-Notch2 antibodies, anti-Notch3 antibodies, and anti-Notch4 antibodies, and antibodies that bind to more than one Notch), anti-Jagged antibodies (including, but not limited to, anti-Jagged1 antibodies, anti-Jagged2 antibodies, and antibodies that bind to more than one Jagged); gamma secretase inhibitors; and anti-DLL antibodies (including, but not limited to, anti-DLL1 antibodies and anti-DLL4 antibodies, and antibodies that bind to more than one DLL).

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "toxicity" associated with Notch pathway inhibition as used herein refers to adverse events occurring in individuals receiving Notch pathway inhibitors. Nonlimiting examples of such toxicity include secretory metaplasia, diarrhea, gastrointestinal bleeding, liver toxicity (including, but not limited to, sinusoidal dilation, centrilobular hepatocyte atrophy, bile ductular proliferation, and elevated alanine aminotransferase), lung toxicity (including, but not limited to, necrotic lesions), heart toxicity (including, but not limited to, necrotic lesions), subcutaneous tumors, and thymic atrophy. See, e.g., van Es et al., 2005, *Nature* 435: 959-963; Yan et al., 2010, *Nature* 463: E6-7.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "Wnt" as used herein, refers to any native Wnt from any vertebrate source, including mammals such as primates (e.g. humans) and rodents (e.g., mice and rats), unless otherwise indicated. The term encompasses "full-length," unprocessed Wnt as well as any form of Wnt that results from processing in the cell. The term also encompasses naturally occurring variants of Wnt, e.g., splice variants or allelic variants. The human Wnt gene family of secreted ligands has includes at least 19 members (e.g., Wnt-1 (RefSeq.: NM-005430), Wnt-2 (RefSeq.: NM-003391), Wnt-2B (Wnt-13) (RefSeq.: NM-004185), Wnt-3 (RefSeq.: NM-030753), Wnt3a (RefSeq.: NM-033131), Wnt-4 (RefSeq.: NM-030761), Wnt-5A (RefSeq.: NM-003392), Wnt-5B (RefSeq.: NM-032642), Wnt-6 (RefSeq.: NM-006522), Wnt-7A (RefSeq.: NM-004625), Wnt-7B (RefSeq.: NM-058238), Wnt-8A (RefSeq.: NM-058244), Wnt-8B (RefSeq.: NM-003393), Wnt-9A (Wnt-14) (RefSeq.: NM-003395), Wnt-9B (Wnt-15) (RefSeq.: NM-003396), Wnt-10A (RefSeq.: NM-025216), Wnt-10B (RefSeq.: NM-003394), Wnt-11 (RefSeq.: NM-004626), Wnt-16 (RefSeq.: NM-016087)). Each member has varying degrees of sequence identity but all contain 23-24 conserved cysteine residues which show highly conserved spacing. See McMahon, A P et al., *Trends Genet.* 1992; 8: 236-242; Miller, J R. *Genome Biol.* 2002; 3(1): 3001.1-3001.15.

The term "Wnt pathway inhibitor" or "inhibitor of Wnt pathway" as used herein refers to an agent that inhibits Wnt activity. A Wnt pathway inhibitor may be an antibody, a soluble receptor, a small molecule, or the like. Nonlimiting exemplary Wnt pathway inhibitors include small molecule inhibitors (including, but not limited to, Wnt-059 (2-(4-(2-methylpyridin-4-yl)phenyl)-N-(4-(pyridin-3-yl)phenyl)acetamide), LGK974 (see Liu et al., 2013, *PNAS*, 110:20224-9)) anti-Wnt antibodies (including, but not limited to, antibodies that bind to more than one Wnt; see, e.g., U.S. Publication No. 2013/0045209); anti-LRP antibodies (including, but not limited to, anti-LRP5 antibodies, anti-LRP6 antibodies, anti-LRP5/6 antibodies, and other antibodies that bind to more than one LRP); anti-Fzd antibodies (including, but not limited to, anti-Fzd7 antibodies and antibodies that bind to more than one Fzd); soluble Fzd receptors (including, but not limited to, soluble Fzd8); and small molecules that inhibit β-catenin (e.g., PRI-724, Prism Pharma Co.).

II. Compositions and Methods

In one aspect, the invention is based, in part, on the finding that Wnt pathway inhibition alleviates the toxicity associated with Notch pathway inhibition. In certain embodiments, methods of treating cancer are provided, wherein the method comprises administering at least one Wnt pathway inhibitor to an individual who has received, is receiving, or will receive Notch pathway inhibitor therapy. Accordingly, the invention provides methods, compositions, kits, and articles of manufacture related to coordinated Notch pathway inhibition and Wnt pathway inhibition.

A. Notch Pathway Inhibitors

In some embodiments, the invention provides Notch pathway inhibitors. Notch pathway inhibitors include, but are not limited to, small molecules such as gamma secretase inhibitors, and antibodies that bind to one or more proteins involved in Notch signaling. Nonlimiting exemplary antibodies that bind to one or more proteins involved in Notch signaling include anti-Notch antibodies, anti-Jagged antibodies, and anti-DLL antibodies. Also provided are bispecific antibodies comprising a first antigen binding region that binds to one or more proteins involved in Notch signaling and a second antigen binding region that binds to one or more proteins involved in Notch signaling or a second antigen binding region that binds to an antigen not directly involved in Notch signaling, such as VEGF.

1. Anti-Notch Antibodies

In some embodiments, anti-Notch antibodies are provided. Anti-Notch antibodies include, but are not limited to, anti-Notch NRR antibodies and anti-Notch antibodies that bind to the EGF-like repeat region. In some such embodiments, an anti-Notch antibody binds to Notch1. In some embodiments, an anti-Notch antibody binds to Notch2. In some embodiments, an anti-Notch antibody binds to Notch3. In some embodiments, an anti-Notch antibody binds to Notch4. In some embodiments, an anti-Notch antibody binds to more than one Notch. In some embodiments, an anti-Notch antibody binds to Notch1 and Notch2. In some embodiments, an anti-Notch antibody binds to Notch2 and Notch3.

Anti-Notch antibodies useful in the methods of the invention include, but are not limited to, the anti-Notch antibodies described in U.S. Pat. Nos. 8,404,237; 8,404,239; 8,088,617; 8,435,513; 8,460,661; 8,425,903; 8,226,943; 8,206,713; 7,919,092; 7,994,285; 7,935,791; 8,513,388; 8,329,868; and 8,148,106; and U.S. Publication Nos. 2013/0266594; 2012/0213786; 2011/0311552; 2009/0258026; 2013/0323266; 2010/0080808; 2012/0328608; 2012/0093813; and 2013/0323257. In some embodiments, an anti-Notch antibody comprises the HVRs of any of the anti-Notch antibodies described in the patents and applications listed above.

In some embodiments, an anti-Notch antibody comprises the HVRs of, or the variable regions of, antibody 59R5, described in U.S. Pat. No. 7,919,092. In some embodiments, an anti-Notch antibody is antibody 59R5, described in U.S. Pat. No. 7,919,092. In a Phase 1a study in patients with solid tumors, 58% of patients experienced diarrhea, with 14% experiencing grade 3 or higher diarrhea. Further, a significant correlation between diarrhea grade and does of antibody 59R5 was found. See Dupont, "OMP-59R5: a Novel Therapeutic Antibody in Clinical Development for Patients with Cancer," available at www.oncomed.com/presentations/OMP-59R5_Ph1a_Presenation_PEP.pdf.

In some embodiments, an anti-Notch antibody comprises the HVRs of, or the variable regions of, antibody 52M51 or a humanized version such as 52M51H4L3, described in U.S. Pat. No. 8,435,513. In some embodiments, an anti-Notch antibody is antibody 52M51 or a humanized version such as 52M51H4L3, described in U.S. Pat. No. 8,435,513. In a first-in-human phase I study in patients with advanced solid tumors, 64% of patients experienced diarrhea. See Davis et al., "A first-in-human phase I study of the novel cancer stem cell (CSC) targeting antibody OMP-52M51 (anti-Notch1) administered intravenously to patients with certain advanced solid tumors," available at www.oncomed.com/presentations/OMP-52M51%20Ph1a_AACR-NCI-EORTC2013.pdf.

In some embodiments, an anti-Notch antibody comprises the HVRs of, or the variable regions of, antibody A, A-1, A-2, or A-3, described in U.S. Publication No. 2009/0258026. In some embodiments, an anti-Notch antibody comprises the HVRs of, or the variable regions of, antibody A-2, described in U.S. Publication No. 2009/0258026. In some embodiments, an anti-Notch antibody is antibody A, A-1, A-2, or A-3, described in U.S. Publication No. 2009/0258026. In some embodiments, an anti-Notch antibody is antibody A-2, described in U.S. Publication No. 2009/0258026.

In some embodiments, an anti-Notch antibody comprises the HVRs of, or the variable regions of, antibody D, D-1, D-2, or D-3, described in U.S. Pat. No. 8,404,239. In some embodiments, an anti-Notch antibody comprises the HVRs of, or the variable regions of, antibody D-3, described in U.S. Pat. No. 8,404,239. In some embodiments, an anti-Notch antibody is antibody D, D-1, D-2, or D-3, described in U.S. Pat. No. 8,404,239. In some embodiments, an anti-Notch antibody is antibody D-3, described in U.S. Pat. No. 8,404,239.

In some embodiments, an anti-Notch antibody comprises the HVRs of, or the variable regions of, antibody 256A-4 or 256A-8, described in U.S. Pat. No. 8,329,868. In some embodiments, an anti-Notch antibody is antibody 256A-4 or 256A-8, described in U.S. Pat. No. 8,329,868. In some embodiments, an anti-Notch antibody comprises the HVRs of, or the variable regions of, antibody 256A-4, described in U.S. Pat. No. 8,329,868. In some embodiments, an anti-Notch antibody is antibody 256A-4, described in U.S. Pat. No. 8,329,868.

In some embodiments, an anti-Notch antibody comprises the HVRs of, or the variable regions of, antibody 255A-71, 255A-77, or 256A-13, described in U.S. Pat. No. 8,513,388. In some embodiments, an anti-Notch antibody is antibody 255A-71, 255A-77, or 256A-13, described in U.S. Pat. No. 8,513,388.

In some embodiments, an anti-Notch antibody comprises the HVRs of, or the variable regions of, antibody N248A, described in U.S. Publication No. 2012/0093813. In some embodiments, an anti-Notch antibody is antibody N248A, described in U.S. Publication No. 2012/0093813.

2. Anti-Jagged Antibodies

In some embodiments, anti-Jagged antibodies are provided. In some such embodiments, an anti-Jagged antibody binds to Jagged1 and Jagged2.

Anti-Jagged antibodies useful in the methods of the invention include, but are not limited to, the anti-Jagged antibodies described in U.S. Publication Nos. 2014/0010810; 2012/0301489; 2008/0317760; PCT Publication No. 2014/028446; and PCT Publication No. 2014/111704. In some embodiments, an anti-Jagged antibody comprises the HVRs of any of the anti-Jagged antibodies described in the patents and applications listed above.

In some embodiments, an anti-Jagged antibody comprises the HVRs of, or the variable regions of, antibody 4D11, described in U.S. Publication No. 2014/0010810. In some embodiments, an anti-Jagged antibody is antibody 4D11 or 5342-1204-4D11, described in U.S. Publication No. 2014/0010810.

In some embodiments, an anti-Jagged antibody comprises the HVRs of, or the variable regions of, antibody 64R7, described in U.S. Publication No. 2012/0301489. In some embodiments, an anti-Jagged antibody is antibody 64R7, described in U.S. Publication No. 2012/0301489.

In some embodiments, an anti-Jagged antibody comprises the HVRs of, or the variable regions of, antibody 64M14, described in U.S. Publication No. 2008/0317760, and deposited with the ATCC under deposit number PTA-10416. In some embodiments, an anti-Jagged antibody is antibody 64M14, described in U.S. Publication No. 2008/0317760.

In some embodiments, an anti-Jagged antibody comprises the HVRs of, or the variable regions of, antibody 133R0201, described in U.S. Publication No. 2012/0301489. In some embodiments, an anti-Jagged antibody is antibody 133R0201, described in U.S. Publication No. 2012/0301489.

In some embodiments, an anti-Jagged antibody comprises the HVRs of, or the variable regions of, antibody 133R0203, described in U.S. Publication No. 2012/0301489. In some embodiments, an anti-Jagged antibody is antibody 133R0203, described in U.S. Publication No. 2012/0301489.

In some embodiments, an anti-Jagged antibody comprises the HVRs of, or the variable regions of, antibody 133R0205, described in U.S. Publication No. 2012/0301489. In some embodiments, an anti-Jagged antibody is antibody 133R0205, described in U.S. Publication No. 2012/0301489.

In some embodiments, an anti-Jagged antibody comprises the HVRs of, or the variable regions of, antibody 64M51, described in U.S. Publication No. 2012/0301489. In some embodiments, an anti-Jagged antibody is antibody 64M51, described in U.S. Publication No. 2012/0301489.

In some embodiments, an anti-Jagged antibody comprises the HVRs of, or the variable regions of, antibody 64R1B, described in U.S. Publication No. 2012/0301489. In some embodiments, an anti-Jagged antibody is antibody 64R1B, described in U.S. Publication No. 2012/0301489.

In some embodiments, an anti-Jagged antibody comprises the HVRs of, or the variable regions of, antibody J1-65D or antibody J1-183D or a variant of one of those antibodies, described in U.S. Publication No. 2014/111704 (see, e.g., Table 5 and FIGS. 23 and 24). In some embodiments, an anti-Jagged antibody is antibody J1-65D or antibody J1-183D or a variant of one of those antibodies, described in U.S. Publication No. 2014/111704.

In some embodiments, an anti-Jagged antibody comprises the HVRs of, or the variable regions of, antibody A, A-1, or A-2, described in PCT Publication No. WO 2014/028446. In some embodiments, an anti-Jagged antibody is antibody A, A-1, or A-2, described in PCT Publication No. WO 2014/028446. In some embodiments, an anti-Jagged antibody comprises the HVRs of, or the variable regions of, antibody A-2, described in PCT Publication No. WO 2014/028446. In some embodiments, an anti-Jagged antibody is antibody A-2, described in PCT Publication No. WO 2014/028446.

In some embodiments, an anti-Jagged antibody comprises the HVRs of, or the variable regions of, antibody B, B-1, B-2, B-3, or B-4, described in PCT Publication No. WO 2014/028446. In some embodiments, an anti-Jagged antibody is antibody B, B-1, B-2, B-3, or B-4, described in PCT Publication No. WO 2014/028446. In some embodiments, an anti-Jagged antibody comprises the HVRs of, or the variable regions of, antibody B-3, described in PCT Publication No. WO 2014/028446. In some embodiments, an anti-Jagged antibody is antibody B-3, described in PCT Publication No. WO 2014/028446.

In some embodiments, an anti-Jagged antibody comprises the HVRs of, or the variable regions of, antibody C-1, described in PCT Publication No. WO 2014/028446. In some embodiments, an anti-Jagged antibody is antibody C-1, described in PCT Publication No. WO 2014/028446.

3. Anti-DLL Antibodies

In some embodiments, anti-DLL antibodies are provided. In some such embodiments, an anti-DLL antibody binds to DLL1 and/or DLL4. In some embodiments, an anti-DLL antibody is a bispecific antibody comprising a first antigen binding site that binds to DLL and a second antigen biding site that binds to a different antigen. In some embodiments, an anti-DLL antibody is a bispecific antibody comprising a first antigen binding site that binds to DLL and a second antigen biding site that binds to VEGF.

Anti-DLL antibodies useful in the methods of the invention include, but are not limited to, the anti-DLL antibodies described in U.S. Pat. No. 7,803,377; U.S. Publication No. 2010/0196385; 2014/0093521; 2013/0323248; and 2013/0164295. In some embodiments, an anti-DLL antibody comprises the HVRs of any of the anti-DLL antibodies described in the patents and applications listed above.

In some embodiments, an anti-DLL antibody comprises the HVRs of, or the variable regions of, antibody YW26.82, described in U.S. Pat. No. 7,803,377. In some embodiments, an anti-DLL antibody is antibody YW26.82, described in U.S. Pat. No. 7,803,377.

In some embodiments, an anti-DLL antibody comprises the HVRs of, or the variable regions of, antibody OMP-21M18, described in U.S. Publication No. 2013/0323265. In some embodiments, an anti-DLL antibody is antibody OMP-21M18, described in U.S. Publication No. 2013/0323265. In some embodiments, an anti-DLL antibody comprises the HVRs of, or the variable regions of, an antibody encoded by the plasmid having ATCC deposit no. PTA-8425 or PTA-8427. See U.S. Publication No. 2013/0323265. In some embodiments, an anti-DLL antibody is demcizumab.

In some embodiments, an anti-DLL antibody is a bispecific antibody that binds DLL4 and VEGF. In some embodiments, an anti-DLL antibody comprises the HVRs of, or the variable regions of, an anti-DLL4 antibody or bispecific antibody described in U.S. Patent No. 2013/0164295. In some embodiments, an anti-DLL antibody is an anti-DLL4 antibody or bispecific antibody that described in U.S. Patent No. 2013/0164295. In some embodiments, an anti-DLL antibody is a bispecific antibody comprising the HVRs of, or the variable regions of, anti-VEGF/anti-DLL4 bispecific antibody 219R45-MB-21M18 or 219R45-MB-21R83, described in U.S. Publication No. 2013/0164295. In some embodiments, an anti-DLL antibody is anti-VEGF/anti-DLL4 bispecific antibody 219R45-MB-21M18 or 219R45-MB-21R83, described in U.S. Publication No. 2013/0164295.

4. Gamma Secretase Inhibitors

In some embodiments, gamma secretase inhibitors are provided. Nonlimiting exemplary gamma secretase inhibitors include tarenflurbil (Flurizan), semagacestat (LY450139), avagacestat, MK-0752 (3-((1r,4s)-4-(4-chlorophenylsulfonyl)-4-(2,5-difluorophenyl)cyclohexyl)propanoic acid), N—[N-(3,5-Difluorophenacetyl)-L-alanyl]-S-phenylglycine t-butyl ester (DAPT), (2S)-2-{[(3,5-Difluorophenyl)acetyl]amino}-N-[(3S)-1-methyl-2-oxo-5-phenyl-2,3-dihydro-1H-1,4-benzodiazepin-3-yl] propanamide (compound E), and N-[(1S)-2-[[(7S)-6,7-Dihydro-5-methyl-6-oxo-5H-dibenz[b,d]azepin-7-yl] amino]-1-methyl-2-oxoethyl]-3,5-difluorobenzeneacetamide (DBZ). U.S. Pat. Nos. 6,756,511; 6,890,956; 6,984,626; 7,049,296; 7,101,895; 7,138,400; 7,144,910; 7,183,303; 8,377,886.

B. Wnt Pathway Inhibitors

In some embodiments, the invention provides Wnt pathway inhibitors. Wnt pathway inhibitors include, but are not limited to, small molecules, polypeptides, and antibodies that bind to one or more proteins involved in Wnt signaling. Nonlimiting exemplary antibodies that bind to one or more proteins involved in Wnt signaling include anti-LRP antibodies, anti-Frizzled antibodies, anti-RSPO antibodies, and anti-Wnt antibodies. Also provided are bispecific antibodies comprising a first antigen binding region that binds to one or more proteins involved in Wnt signaling and a second antigen binding region that binds to one or more proteins involved in Wnt signaling or a second antigen binding region that binds to an antigen not directly involved in Wnt. Also provided are soluble receptor inhibitors of the Wnt pathway, including but not limited to, soluble Fzd receptors. Also provided are small molecule inhibitors of the Wnt pathway, including but not limited to, small molecules that inhibit β-catenin.

1. Anti-LRP Antibodies

In some embodiments, anti-LRP antibodies are provided. In some such embodiments, an anti-LRP antibody binds to LRP5 and/or LRP6. In some embodiments, an anti-LRP antibody is a bispecific or biparatopic antibody comprising a first antigen binding site that binds to an LRP (such as LRP6) and a second antigen biding site that binds to an LRP (such as LRP6). In some embodiments, an anti-LRP antibody binds to both LRP5 and LRP6.

Anti-LRP antibodies useful in the methods of the invention include, but are not limited to, the anti-LRP antibodies described in U.S. Publication Nos. 2013/0183320; 2011/0256127; 2011/0243963; 2013/0064823; and 2012/0276089. In some embodiments, an anti-LRP antibody comprises the HVRs of any of the anti-LRP antibodies described in the patents and applications listed above.

In some embodiments, an anti-LRP antibody comprises the HVRs of, or the variable regions of, antibody YW211.31.62 and/or YW210.09, described in U.S. Publication No. 2011/0256127. In some embodiments, an anti-LRP antibody is antibody YW211.31.62 or YW210.09, described in U.S. Publication No. 2011/0256127. In some embodiments, an anti-LRP antibody is a bispecific antibody comprising a first antigen binding region comprising the HVRs of, or the variable regions of, antibody YW211.31.62, and a second antigen binding region comprising HVRs of, or the variable regions of, antibody YW210.09. In some embodiments, an anti-LRP antibody is bispecific antibody YW211.31.62/YW210.09.

In some embodiments, an anti-LRP antibody comprises the HVRs of, or the variable regions of, a biparatopic antibody described in U.S. Publication No. 2013/0064823. In some embodiments, an anti-LRP antibody is a biparatopic antibody described in U.S. Publication No. 2013/0064823.

In some embodiments, an anti-LRP antibody comprises the HVRs of, or the variable regions of, antibody P6C.51.61, described in U.S. Publication No. 2013/0183320. In some embodiments, an anti-LRP antibody is antibody P6C.51.61, described in U.S. Publication No. 2013/0183320.

In some embodiments, an anti-LRP antibody comprises the HVRs of, or the variable regions of, antibody 7E5C8, described in U.S. Publication No. 2012/0276089. In some embodiments, an anti-LRP antibody is antibody 7E5C8, described in U.S. Publication No. 2012/0276089.

2. Anti-Frizzled Antibodies

In some embodiments, anti-Frizzled antibodies are provided. In some embodiments, an anti-Frizzled antibody binds Fzd7. In some embodiments, an anti-Frizzled antibody binds more than one Frizzled. In some embodiments, an anti-Frizzled antibody binds one or more Fzds selected from Fzd1, Fzd2, Fzd5, Fzd7, and Fzd8. In some embodiments, an anti-Frizzled antibody binds Fzd5 and/or Fzd8. In some embodiments, an anti-Frizzled antibody binds Fzd10.

Anti-Frizzled antibodies useful in the methods of the invention include, but are not limited to, the anti-Frizzled antibodies described in U.S. Pat. Nos. 7,982,013; 8,507,442; U.S. Publication Nos. 2013/0295106; 2012/0027778; and 2013/0095104. In some embodiments, an anti-Frizzled antibody comprises the HVRs of any of the anti-Frizzled antibodies described in the patents and applications listed above.

In some embodiments, an anti-Fzd antibody comprises the HVRs of, or the variable regions of, antibody 18R5, described in U.S. Pat. No. 8,507,442. In some embodiments, an anti-Fzd antibody is antibody 18R5, described in U.S. Pat. No. 8,507,442.

In some embodiments, an anti-Fzd antibody comprises the HVRs of, or the variable regions of, antibody B9L9.3, described in U.S. Publication No. 2013/0095104. In some embodiments, an anti-Fzd antibody is a humanized antibody huB9L9.3, described in U.S. Publication No. 2013/0095104.

3. Anti-Wnt Antibodies

In some embodiments, anti-Wnt antibodies are provided. In some embodiments, an anti-Wnt antibody binds to at least one Wnt selected from Wnt1, Wnt2, Wnt2b, Wnt3, Wnt3a, Wnt7a, Wnt7b, Wnt8a, Wnt8b, Wnt10a, and Wnt10b. In some embodiments, an anti-Wnt antibody binds to two or more Wnts selected from Wnt1, Wnt2, Wnt2b, Wnt3, Wnt3a, Wnt7a, Wnt7b, Wnt8a, Wnt8b, Wnt10a, and Wnt10b.

Anti-Wnt antibodies useful in the methods of the invention include, but are not limited to, the anti-Wnt antibodies described in U.S. Publication No. 2013/0045209. In some embodiments, an anti-Wnt antibody comprises the HVRs of any of the anti-Wnt antibodies described in U.S. Publication No. 2013/0045209 (including, but not limited to, an anti-Wnt antibody comprising the HVRs of an antibody selected from 250M1, 250M2, 250M3, 250M6, 250M8, 250M11, 250M13, 250M17, 250M19, 25024, and 250M25).

4. Anti-RSPO Antibodies

In some embodiments, anti-RSPO antibodies are provided. In some embodiments, an anti-RSPO antibody binds at least one RSPO selected from RSPO1, RSPO2, and RSPO3. In some embodiments, an anti-RSPO antibody binds RSPO1. In some embodiments, an anti-RSPO antibody binds RSPO2. In some embodiments, an anti-RSPO antibody binds RSPO2 and RSPO3.

Anti-RSPO antibodies useful in the methods of the invention include, but are not limited to, the anti-RSPO antibodies described in U.S. Publication No. 2013/0209473; PCT Publication No. WO 2014/012007; U.S. Pat. No. 8,802,097. In some embodiments, an anti-RSPO antibody comprises the HVRs of any of the anti-RSPO antibodies described in the patent and applications listed above.

In some embodiments, an anti-RSPO antibody comprises the HVRs of, or the variable regions of, antibody 131R010, described in PCT Publication No. WO 2014/012007. In some embodiments, an anti-RSPO antibody is antibody 131R010, described in PCT Publication No. WO 2014/012007.

In some embodiments, an anti-RSPO antibody comprises the HVRs of, or the variable regions of, antibody 89M5 or 130M23, described in U.S. Pat. No. 8,802,097. In some embodiments, an anti-RSPO antibody is antibody 89M5 or 130M23, described in U.S. Pat. No. 8,802,097.

5. Soluble Frizzled Receptors

In some embodiments, soluble Frizzled receptors are provided. In some embodiments, a soluble Frizzled receptor comprises the Fri domain of a Frizzled receptor selected from Fzd4, Fzd5, Fzd6, Fzd7, Fzd8, and Fzd10. See, e.g., U.S. Pat. Nos. 7,723,477 and 7,947,277. In some embodiments, a soluble Frizzled receptor comprises the Fri domain of Fzd8. In some embodiments, a soluble Frizzled receptor comprises the Fri domain of Fzd4. In some embodiments, a soluble Frizzled receptor comprises the Fri domain of Fzd5. In some embodiments, a soluble Frizzled receptor is fused to an Fc domain.

Soluble Frizzleds useful in the methods of the invention include, but are not limited to, the soluble Frizzled described in U.S. Pat. No. 7,723,477. In some embodiments, a soluble Frizzled is 54F28, described in U.S. Pat. No. 7,723,477.

Soluble Frizzleds useful in the methods of the invention include, but are not limited to, the soluble Frizzled described in U.S. Pat. No. 7,947,277. In some embodiments, a soluble Frizzled is a soluble Fzd8, described in U.S. Pat. No. 7,947,277.

6. Other Wnt Pathway Inhibitors

In some embodiments, small molecule and polypeptide inhibitors of the Wnt pathway are provided. In some embodiments, a Wnt pathway inhibitor is a polypeptide described in U.S. Pat. No. 8,551,789. In some embodiments, a Wnt pathway inhibitor is a peptide described in U.S. Publication No. 2013/0273058.

Nonlimiting exemplary small molecule inhibitors of the Wnt pathway are described, e.g., in U.S. Pat. Nos. 8,445,491; 8,450,340; U.S. Publication No. 2013/0296344; 2013/0190258; 2013/0267495; 2013/0225576; 2014/0031374; 2014/0005164; and Landman et al., 2013, *Arthritis Research & Therapy* 15:R93 (PKF115-584, PKF118-310, and CGP049090); Chen et al., 2009, *Nat. Chem. Biol.* 5: 100-7 (IWP-2). Further small molecule inhibitors of the Wnt pathway include, but are not limited to, CCT036477 (Santa Cruz Biotechnology), IWR-1 endo and exo (Santa Cruz Biotechnology), FH535 (Santa Cruz Biotechnology), LGK974 (2-(2',3-dimethyl-[2,4'-bipyridin]-5-yl)-N-(5-(pyrazin-2-yl)pyridin-2-yl)acetamide), Wnt-C59 (2-(4-(2-methylpyridin-4-yl)phenyl)-N-(4-(pyridin-3-yl)phenyl)acetamide), AVN316 (Avalon Pharmaceuticals), and PRI-724 (Prism Pharma Co.).

In a further aspect, any of the antibodies according to any of the above embodiments may incorporate any of the features, singly or in combination, as described in Sections 1-7 below:

7. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$ M, e.g., from $10^{-9}$M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

8. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

9. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

10. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

11. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for a first antigen selected from Notch1, Notch2, Notch3, Notch4, Jagged 1, and Jagged2; and the other is for a second antigen selected from the same list. In certain embodiments, one of the binding specificities is for a first antigen selected from Notch1, Notch2, Notch3, Notch4, Jagged 1, and Jagged2; and the other is for a second antigen not selected from the same list. In certain embodiments, bispecific antibodies may bind to two different epitopes of the same antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to a first antigen as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE 1-continued

| Original Residue | Exemplary Substitutions | Preferred Substitutions |
| --- | --- | --- |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). In some embodiments, an IgG1 constant region comprising an N297G or N297A mutation substantially lacks effector function. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA*

82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., THIOMAB antibodies, in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

C. Recombinant Methods and Compositions

Antibodies may be produced using recombinant methods and compositions, e.g., as described in U.S. Pat. No. 4,816, 567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N. J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

D. Assays

Antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with any of the antibodies described herein for binding to human antigen. In certain embodiments, such a competing antibody binds to the same epitope that is bound by an antibody described herein.

Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to antigen. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying antibodies having biological activity. Biological activity may include, e.g., inhibition of the Notch pathway or inhibition of the Wnt pathway. In certain other embodiments, an antibody of the invention is tested for its ability to inhibit expression of a reporter gene that is responsive to the Notch pathway and/or the Wnt pathway. Nonlimiting exemplary assays are provided in the Examples. In certain embodiments, an antibody of the invention is tested for such biological activity. Antibodies having such biological activity in vivo and/or in vitro are also provided.

E. Immunoconjugates

The invention also provides immunoconjugates comprising an antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAM, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

F. Methods and Compositions for Diagnostics and Detection

In certain embodiments, any of the antibodies provided herein is useful for detecting the presence of its respective antigen in a biological sample. The term "detecting" as used herein encompasses quantitative or qualitative detection. In certain embodiments, a biological sample comprises a cell or tissue, such as cancerous tissues.

In one embodiment, an antibody for use in a method of diagnosis or detection is provided. In a further aspect, a method of detecting the presence of an antigen in a biological sample is provided. In certain embodiments, the method comprises contacting the biological sample with an antibody as described herein under conditions permissive for binding of the antibody to its antigen, and detecting whether a complex is formed between the antibody and antigen. Such method may be an in vitro or in vivo method. In one embodiment, an anti-antibody is used to select subjects eligible for therapy with the antibody, e.g. where the antigen is a biomarker for selection of patients.

Exemplary disorders that may be diagnosed using an antibody of the invention include cancer, e.g., breast cancer, lung cancer, brain cancer, cervical cancer, colon cancer, liver cancer, bile duct cancer, pancreatic cancer, skin cancer, B-cell malignancies, and T-cell malignancies.

In certain embodiments, labeled antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

G. Pharmaceutical Formulations

Pharmaceutical formulations of an antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a cytotoxic agent, e.g., a chemotherapeutic agent. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Methods of alleviating the toxicity associated with Notch pathway inhibition are provided. In some embodiments, the method comprises administering at least one Wnt pathway inhibitor before, during, or after treatment with at least one Notch pathway inhibitor.

In one aspect, Notch pathway inhibitors and Wnt pathway inhibitors for use as medicaments are provided. In further aspects, Notch pathway inhibitors and Wnt pathway inhibitors for use in treating a disease or disorder associated with aberrant Notch signaling, e.g., cancer, are provided. In certain embodiments, Notch pathway inhibitors and Wnt pathway inhibitors for use in methods of treatment are provided. In certain embodiments, Notch pathway inhibitors and Wnt pathway inhibitors for use in methods of treating Notch-mediated disorders are provided. In certain embodiments, the invention provides Notch pathway inhibitors and Wnt pathway inhibitors for use in a method of treating an individual having a cancer comprising administering to the individual an effective amount of a Notch pathway inhibitor and an effective amount of a Wnt pathway inhibitor. In further embodiments, the invention provides Notch pathway inhibitors and Wnt pathway inhibitors for use in inhibiting lung cancer growth. In certain embodiments, the invention provides an Notch pathway inhibitors and Wnt pathway inhibitors for use in a method of reducing lung cancer growth in an individual comprising administering to the individual an effective of at least one Notch pathway inhibitor and an effective amount of at least one Wnt pathway inhibitor to reduce lung cancer growth with less toxicity than with the at least one Notch pathway inhibitor alone. In certain embodiments, the invention provides Notch pathway inhibitors and Wnt pathway inhibitors for use in methods of reducing breast cancer growth in an individual comprising administering to the individual an effective of at least one Notch pathway inhibitor and an effective amount of at least one Wnt pathway inhibitor to reduce breast cancer growth with less toxicity than with the at least one Notch pathway inhibitor alone. An "individual" according to any of the above embodiments is preferably a human.

In some embodiments, the method comprises administering an anti-Notch antibody, including but not limited to, an anti-Notch antibody described herein, and an anti-LRP antibody, including but not limited to, an anti-LRP antibody described herein. In some embodiments, the method comprises administering an anti-Notch antibody, including but not limited to, an anti-Notch antibody described herein, and an anti-Fzd antibody, including but not limited to, an anti-Fzd antibody described herein. In some embodiments, the method comprises administering an anti-Notch antibody, including but not limited to, an anti-Notch antibody described herein, and an anti-Wnt antibody, including but not limited to, an anti-Wnt antibody described herein. In some embodiments, the method comprises administering an anti-Notch antibody, including but not limited to, an anti-Notch antibody described herein, and an anti-RSPO antibody, including but not limited to, an anti-RSPO antibody described herein. In some embodiments, the method comprises administering an anti-Notch antibody, including but not limited to, an anti-Notch antibody described herein, and a soluble Frizzled receptor, including but not limited to, a soluble Frizzled receptor described herein. In some embodiments, the method comprises administering an anti-Notch antibody, including but not limited to, an anti-Notch antibody described herein, and a small molecule Wnt pathway inhibitor, including but not limited to, a small molecule Wnt pathway inhibitor described herein.

In some embodiments, the method comprises administering an anti-Jagged antibody, including but not limited to, an anti-Jagged antibody described herein, and an anti-LRP antibody, including but not limited to, an anti-LRP antibody described herein. In some embodiments, the method comprises administering an anti-Jagged antibody, including but not limited to, an anti-Jagged antibody described herein, and an anti-Fzd antibody, including but not limited to, an anti-Fzd antibody described herein. In some embodiments, the method comprises administering an anti-Jagged antibody, including but not limited to, an anti-Jagged antibody described herein, and an anti-Wnt antibody, including but not limited to, an anti-Wnt antibody described herein. In some embodiments, the method comprises administering an anti-Jagged antibody, including but not limited to, an anti- Jagged antibody described herein, and a soluble Frizzled receptor, including but not limited to, a soluble Frizzled receptor described herein. In some embodiments, the method comprises administering an anti-Jagged antibody, including but not limited to, an anti-Jagged antibody described herein, and a small molecule Wnt pathway inhibitor, including but not limited to, a small molecule Wnt pathway inhibitor described herein.

In some embodiments, the method comprises administering an anti-DLL antibody, including but not limited to, an anti-DLL antibody described herein, and an anti-LRP antibody, including but not limited to, an anti-LRP antibody described herein. In some embodiments, the method comprises administering an anti-DLL antibody, including but not limited to, an anti-DLL antibody described herein, and an anti-Fzd antibody, including but not limited to, an anti-Fzd antibody described herein. In some embodiments, the method comprises administering an anti-DLL antibody, including but not limited to, an anti-DLL antibody described herein, and an anti-Wnt antibody, including but not limited to, an anti-Wnt antibody described herein. In some embodiments, the method comprises administering an anti-DLL antibody, including but not limited to, an anti-DLL antibody described herein, and a soluble Frizzled receptor, including but not limited to, a soluble Frizzled receptor described herein. In some embodiments, the method comprises administering an anti-DLL antibody, including but not limited to, an anti-DLL antibody described herein, and a small molecule Wnt pathway inhibitor, including but not limited to, a small molecule Wnt pathway inhibitor described herein.

In some embodiments, the method comprises administering a gamma secretase inhibitor, including but not limited to, a gamma secretase inhibitor described herein, and an anti-LRP antibody, including but not limited to, an anti-LRP antibody described herein. In some embodiments, the method comprises administering a gamma secretase inhibitor, including but not limited to, a gamma secretase inhibitor described herein, and an anti-Fzd antibody, including but not limited to, an anti-Fzd antibody described herein. In some embodiments, the method comprises administering a gamma secretase inhibitor, including but not limited to, a gamma secretase inhibitor described herein, and an anti-Wnt antibody, including but not limited to, an anti-Wnt antibody described herein. In some embodiments, the method comprises administering a gamma secretase inhibitor, including but not limited to, a gamma secretase inhibitor described herein, and a soluble Frizzled receptor, including but not limited to, a soluble Frizzled receptor described herein. In some embodiments, the method comprises administering a gamma secretase inhibitor, including but not limited to, a gamma secretase inhibitor described herein, and a small molecule Wnt pathway inhibitor, including but not limited to, a small molecule Wnt pathway inhibitor described herein.

In some embodiments, the method comprises administering to an individual an effective amount of an anti-Notch antibody comprising the HVRs or variable regions of an antibody selected from A-2, D-3, and 256A-4 and an effective amount of a Wnt pathway inhibitor, including but not limited to, a Wnt pathway inhibitor described herein. In some embodiments, the method comprises administering to an individual an effective amount of an anti-Notch antibody comprising the HVRs or variable regions of an antibody selected from A-2, D-3, and 256A-4 and an effective amount of an anti-LRP antibody or bispecific antibody comprising the HVRs or variable regions of an antibody selected from YW211.31.62 and/or YW210.09. In some embodiments, the method comprises administering to an individual an effective amount of an anti-Notch antibody comprising the HVRs or variable regions of an antibody selected from A-2, D-3, and 256A-4 and an effective amount of an anti-LRP antibody comprising the HVRs or variable regions of P6C.51.61. In some embodiments, the method comprises administering to an individual an effective amount of an anti-Notch antibody comprising the HVRs or variable regions of an antibody selected from A-2, D-3, and 256A-4 and an effective amount of a soluble Fzd8 receptor, such as FZD8CRD.

In some embodiments, the method comprises administering to an individual an effective amount of an anti-Notch antibody comprising the HVRs or variable regions of 59R5 and an effective amount of a Wnt pathway inhibitor, including but not limited to, a Wnt pathway inhibitor described herein. In some embodiments, the method comprises administering to an individual an effective amount of an anti-Notch antibody comprising the HVRs or variable regions of 59R5 and an effective amount of an anti-Frizzled antibody comprising the HVRs or variable regions of 18R5. In some embodiments, the method comprises administering to an individual an effective amount of an anti-Notch antibody comprising the HVRs or variable regions of 59R5 and an effective amount of an anti-RSPO antibody comprising the HVRs or variable regions of an antibody selected from 13R10, 13R102, 13R103, 89M5, and 130M23. In any of the embodiments described herein, the method may comprise administering to an individual an effective amount of an anti-Notch antibody comprising the HVRs or variable regions of 59R5 and an effective amount of soluble Frizzled receptor 54F28. In any of the embodiments described herein, the method may comprise administering to an individual an effective amount of an anti-Notch antibody comprising the HVRs or variable regions of 59R5 and an effective amount of an anti-LRP antibody comprising the HVRs or variable regions of 7E5C8.

In some embodiments, the method comprises administering to an individual an effective amount of an anti-Notch antibody comprising the HVRs or variable regions of 52M51 and an effective amount of a Wnt pathway inhibitor, including but not limited to, a Wnt pathway inhibitor described herein. In some embodiments, the method comprises administering to an individual an effective amount of an anti-Notch antibody comprising the HVRs or variable regions of 52M51 and an effective amount of an anti-Frizzled antibody comprising the HVRs or variable regions of 18R5. In some embodiments, the method comprises administering to an individual an effective amount of an anti-Notch antibody comprising the HVRs or variable regions of 52M51 and an effective amount of an anti-RSPO antibody comprising the HVRs or variable regions of an antibody selected from 13R10, 13R102, 13R103, 89M5, and 130M23. In any of the embodiments described herein, the method may comprise administering to an individual an effective amount of an anti-Notch antibody comprising the HVRs or variable regions of 52M51 and an effective amount of soluble Frizzled receptor 54F28. In any of the embodiments described herein, the method may comprise administering to an individual an effective amount of an anti-Notch antibody comprising the HVRs or variable regions of 52M51 and an effective amount of an anti-LRP antibody comprising the HVRs or variable regions of 7E5C8.

In some embodiments, the method comprises administering to an individual an effective amount of an anti-Notch antibody comprising the HVRs or variable regions of N248A and an effective amount of a Wnt pathway inhibitor, including but not limited to, a Wnt pathway inhibitor described herein.

In some embodiments, the method comprises administering to an individual an effective amount of an anti-Jagged antibody comprising the HVRs or variable regions of an antibody selected from A-2, B-3, and C-1 and an effective amount of a Wnt pathway inhibitor, including but not limited to, a Wnt pathway inhibitor described herein. In some embodiments, the method comprises administering to an individual an effective amount of an anti-Jagged antibody comprising the HVRs or variable regions of an antibody selected from A-2, B-3, and C-1 and an effective amount of an anti-LRP antibody or bispecific antibody comprising the HVRs or variable regions of an antibody selected from YW211.31.62 and/or YW210.09. In some embodiments, the method comprises administering to an individual an effective amount of an anti-Jagged antibody comprising the HVRs or variable regions of an antibody selected from A-2, B-3, and C-1 and an effective amount of an anti-LRP antibody comprising the HVRs or variable regions of P6C.51.61. In some embodiments, the method comprises administering to an individual an effective amount of an anti-Jagged antibody comprising the HVRs or variable regions of an antibody selected from A-2, B-3, and C-1 and an effective amount of a soluble Fzd8 receptor, such as FZD8CRD.

In some embodiments, the method comprises administering to an individual an effective amount of an anti-Jagged antibody comprising the HVRs or variable regions of an antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B and an effective amount of a Wnt pathway inhibitor, including but not limited to, a Wnt pathway inhibitor described herein. In some embodiments, the method comprises administering to an individual an effective amount of anti-Jagged antibody comprising the HVRs or variable regions of an antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B, and an effective amount of an anti-Frizzled antibody comprising the HVRs or variable regions of 18R5. In some embodiments, the method comprises administering to an individual an effective amount of anti-Jagged antibody comprising the HVRs or variable regions of an antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B, and an effective amount of an anti-RSPO antibody comprising the HVRs or variable regions of an antibody selected from 13R10, 13R102, 13R103, 89M5, and 130M23. In any of the embodiments described herein, the method may comprise administering to an individual an effective amount of anti-Jagged antibody comprising the HVRs or variable regions of an antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B, and an effective amount of soluble Frizzled receptor 54F28. In any of the embodiments described herein, the method may comprise administering to an individual an effective amount of an anti-Jagged antibody comprising the HVRs or variable regions of an antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B, and an effective amount of an anti-LRP antibody comprising the HVRs or variable regions of 7E5C8.

In some embodiments, the method comprises administering to an individual an effective amount of an anti-Jagged antibody comprising the HVRs or variable regions of 4D11 or 5342-1204-4D11 and an effective amount of a Wnt pathway inhibitor, including but not limited to, a Wnt pathway inhibitor described herein.

In some embodiments, the method comprises administering to an individual an effective amount of an anti-DLL antibody comprising the HVRs or variable regions of YW26.82 and an effective amount of a Wnt pathway inhibitor, including but not limited to, a Wnt pathway inhibitor described herein. In some embodiments, the method comprises administering to an individual an effective amount of an anti-DLL antibody comprising the HVRs or variable regions of YW26.82 and an effective amount of an anti-LRP antibody or bispecific antibody comprising the HVRs or variable regions of an antibody selected from YW211.31.62 and/or YW210.09. In some embodiments, the method comprises administering to an individual an effective amount of an anti-DLL antibody comprising the HVRs or variable regions of YW26.82 and an effective amount of an anti-LRP antibody comprising the HVRs or variable regions of P6C.51.61. In some embodiments, the method comprises administering to an individual an effective amount of an anti-DLL antibody comprising the HVRs or variable regions of YW26.82 and an effective amount of a soluble Fzd8 receptor, such as FZD8CRD.

In some embodiments, the method comprises administering to an individual an effective amount of an anti-DLL antibody comprising the HVRs or variable regions of an antibody selected from 21M18, 305B83, 219R45-MB-21M18, or 219R45-MB-21R83 and an effective amount of a Wnt pathway inhibitor, including but not limited to, a Wnt pathway inhibitor described herein. In some embodiments, the method comprises administering to an individual an effective amount of an anti-DLL antibody comprising the HVRs or variable regions of an antibody selected from 21M18, 305B83, 219R45-MB-21M18, or 219R45-MB-21R83 and an effective amount of an anti-Frizzled antibody comprising the HVRs or variable regions of 18R5. In some embodiments, the method comprises administering to an individual an effective amount of an anti-DLL antibody comprising the HVRs or variable regions of an antibody selected from 21M18, 305B83, 219R45-MB-21M18, or 219R45-MB-21R83 and an effective amount of an anti-RSPO antibody comprising the HVRs or variable regions of an antibody selected from 13R10, 13R102, 13R103, 89M5, and 130M23. In any of the embodiments described herein, the method may comprise administering to an individual an effective amount of an anti-DLL antibody comprising the HVRs or variable regions of an antibody selected from 21M18, 305B83, 219R45-MB-21M18, or 219R45-MB-21R83 and an effective amount of soluble Frizzled receptor 54F28. In any of the embodiments described herein, the method may comprise administering to an individual an effective amount of an anti-DLL antibody comprising the HVRs or variable regions of an antibody selected from 21M18, 305B83, 219R45-MB-21M18, or 219R45-MB-21R83 and an effective amount of an anti-LRP antibody comprising the HVRs or variable regions of 7E5C8.

In some embodiments, the method comprises administering to an individual an effective amount of a Notch pathway inhibitor, including but not limited to, a Notch pathway inhibitor described herein and an effective amount of an anti-LRP antibody or bispecific antibody comprising the HVRs or variable regions of an antibody selected from YW211.31.62 and/or YW210.09. In some embodiments, the method comprises administering to an individual an effective amount of a Notch pathway inhibitor, including but not limited to, a Notch pathway inhibitor described herein and an effective amount of a biparatropic antibody described in U.S. Publication No. 2013/0064823. In some embodiments, the method comprises administering to an individual an effective amount of a Notch pathway inhibitor, including but not limited to, a Notch pathway inhibitor described herein and an effective amount of an anti-LRP antibody comprising the HVRs or variable regions of P6C.51.61.

In some embodiments, the method comprises administering to an individual an effective amount of a Notch pathway inhibitor, including but not limited to, a Notch pathway inhibitor described herein and an effective amount of an anti-Frizzled antibody comprising the HVRs or variable regions of 18R5. In some embodiments, the method comprises administering to an individual an effective amount of a Notch pathway inhibitor, including but not limited to, a Notch pathway inhibitor described herein and an effective amount of an anti-Frizzled antibody comprising the HVRs or variable regions of B9L9.3.

In some embodiments, the method comprises administering to an individual an effective amount of a Notch pathway inhibitor, including but not limited to, a Notch pathway inhibitor described herein and an effective amount of an anti-Wnt antibody comprising the HVRs or variable regions of an anti-Wnt antibody described in U.S. Publication No. 2013/0045209.

In some embodiments, the method comprises administering to an individual an effective amount of a Notch pathway inhibitor, including but not limited to, a Notch pathway inhibitor described herein and an effective amount of soluble Frizzled 54F28. In some embodiments, the method comprises administering to an individual an effective amount of a Notch pathway inhibitor, including but not limited to, a Notch pathway inhibitor described herein and an effective amount of a soluble Fzd8 receptor, such as FZD8CRD.

In some embodiments, the method comprises administering to an individual an effective amount of a Notch pathway inhibitor, including but not limited to, a Notch pathway inhibitor described herein and an effective amount of a Wnt pathway inhibitor selected from LGK974, AVN316, and PRI-724.

In some embodiments, methods of alleviating the toxicity associated with Notch pathway inhibition are provided. Nonlimiting examples of such toxicity include secretory metaplasia, diarrhea, gastrointestinal bleeding, liver toxicity (including, but not limited to, sinusoidal dilation, centrilobular hepatocyte atrophy, bile ductula proliferation, and elevated alanine aminotransferase), lung toxicity (including, but not limited to, necrotic lesions), heart toxicity (including, but not limited to, necrotic lesions), subcutaneous tumors, and thymic atrophy. See, e.g., van Es et al., 2005, *Nature* 435: 959-963; Yan et al., 2010, *Nature* 463: E6-7. In some embodiments, the toxicity is diarrhea.

In some embodiments, the method comprises administering to an individual who has received, is receiving, or is going to receive at least one a Notch pathway inhibitor, at least one Wnt pathway inhibitor. The at least one Wnt pathway inhibitor may be administered prior to administration of the at least one Notch pathway inhibitor, at the same time as administration of the at least one Notch pathway inhibitor, or after administration of the at least one Notch pathway inhibitor.

In some embodiments, the method comprises administering to an individual who has received, is receiving, or is going to receive an anti-Notch antibody comprising the HVRs or variable regions of an antibody selected from A-2, D-3, and 256A-4, an effective amount of a Wnt pathway inhibitor, including but not limited to a Wnt pathway inhibitor described herein. In some embodiments, the method comprises administering to an individual who has received, is receiving, or is going to receive an anti-Notch antibody comprising the HVRs or variable regions of an antibody selected from A-2, D-3, and 256A-4, an effective amount of an anti-LRP antibody or bispecific antibody comprising the HVRs or variable regions of an antibody selected from YW211.31.62 and/or YW210.09. In some embodiments, the method comprises administering to an individual who has received, is receiving, or is going to receive an anti-Notch antibody comprising the HVRs or variable regions of an antibody selected from A-2, D-3, and 256A-4, an effective amount of an anti-LRP antibody comprising the HVRs or variable regions of P6C.51.61. In some embodiments, the method comprises administering to an individual who has received, is receiving, or is going to receive an anti-Notch antibody comprising the HVRs or variable regions of an antibody selected from A-2, D-3, and 256A-4, an effective amount of a soluble Fzd8 receptor, such as FZD8CRD.

In some embodiments, the method comprises administering to an individual who has received, is receiving, or is going to receive anti-Notch antibody 59R5, an effective amount of a Wnt pathway inhibitor, including but not limited to a Wnt pathway inhibitor described herein. In some embodiments, the method comprises administering to an individual who has received, is receiving, or is going to receive anti-Notch antibody 59R5, an effective amount of anti-Frizzled antibody 18R5. In some embodiments, the method comprises administering to an individual who has received, is receiving, or is going to receive anti-Notch antibody 59R5, an effective amount of an anti-RSPO antibody comprising the HVRs or variable regions of an antibody selected from 13R10, 13R102, 13R103, 89M5, and 130M23. In some embodiments, the method comprises administering to an individual who has received, is receiving, or is going to receive anti-Notch antibody 59R5, an effective amount of soluble Frizzled receptor 54F28. In some embodiments, the method comprises administering to an individual who has received, is receiving, or is going to receive anti-Notch antibody 59R5, an effective amount of anti-LRP antibody 7E5C8.

In some embodiments, the method comprises administering to an individual who has received, is receiving, or is going to receive anti-Notch antibody 52M51, an effective amount of a Wnt pathway inhibitor, including but not limited to a Wnt pathway inhibitor described herein. In some embodiments, the method comprises administering to an individual who has received, is receiving, or is going to receive anti-Notch antibody 52M51, an effective amount of anti-Frizzled antibody 18R5. In some embodiments, the method comprises administering to an individual who has received, is receiving, or is going to receive anti-Notch antibody 52M51, an effective amount of an anti-RSPO antibody comprising the HVRs or variable regions of an antibody selected from 13R10, 13R102, 13R103, 89M5, and 130M23. In some embodiments, the method comprises administering to an individual who has received, is receiving, or is going to receive anti-Notch antibody 52M51, an effective amount of soluble Frizzled receptor 54F28. In some embodiments, the method comprises administering to an individual who has received, is receiving, or is going to receive anti-Notch antibody 52M51, an effective amount of anti-LRP antibody 7E5C8.

In some embodiments, the method comprises administering to an individual who has received, is receiving, or is going to receive an anti-Notch antibody comprising the HVRs or variable regions of N248A, an effective amount of a Wnt pathway inhibitor, including but not limited to, a Wnt pathway inhibitor described herein.

In some embodiments, the method comprises administering to an individual who has received, is receiving, or is going to receive an anti-Jagged antibody comprising the HVRs or variable regions of an antibody selected from A-2, B-3, and C-1, an effective amount of a Wnt pathway inhibitor, including but not limited to, a Wnt pathway inhibitor described herein. In some embodiments, the method comprises administering to an individual who has received, is receiving, or is going to receive an anti-Jagged antibody comprising the HVRs or variable regions of an antibody selected from A-2, B-3, and C-1, an effective amount of an anti-LRP antibody or bispecific antibody comprising the HVRs or variable regions of an antibody selected from YW211.31.62 and/or YW210.09. In some embodiments, the method comprises administering to an individual who has received, is receiving, or is going to receive an anti-Jagged antibody comprising the HVRs or variable regions of an antibody selected from A-2, B-3, and C-1, an effective amount of an anti-LRP antibody comprising the HVRs or variable regions of P6C.51.61. In some embodiments, the method comprises administering to an individual who has received, is receiving, or is going to receive an anti-Jagged antibody comprising the HVRs or variable regions of an antibody selected from A-2, B-3, and C-1, an effective amount of a soluble Fzd8 receptor, such as FZD8CRD.

In some embodiments, the method comprises administering to an individual who has received, is receiving, or is going to receive an anti-Jagged antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B, an effective amount of a Wnt pathway inhibitor, including but not limited to a Wnt pathway inhibitor described herein. In some embodiments, the method comprises administering to an individual who has received, is receiving, or is going to receive an anti-Jagged antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B; an effective amount of anti-Frizzled antibody 18R5. In some embodiments, the method comprises administering to an individual who has received, is receiving, or is going to receive an anti-Jagged antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B; an effective amount of an anti-RSPO antibody comprising the HVRs or variable regions of an antibody selected from 13R10, 13R102, 13R103, 89M5, and 130M23. In some embodiments, the method comprises administering to an individual who has received, is receiving, or is going to receive anti-Jagged antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B; an effective amount of soluble Frizzled receptor 54F28. In some embodiments, the method comprises administering to an individual who has received, is receiving, or is going to receive anti-Jagged antibody selected from anti-Jagged antibody 64R7, anti-Jagged antibody 64M14, anti-Jagged antibody 133R0201, anti-Jagged antibody 133R0203, anti-Jagged antibody 133R0205, anti-Jagged antibody 64M51, and anti-Jagged antibody 64R1B; an effective amount of anti-LRP antibody 7E5C8.

In some embodiments, the method comprises administering to an individual who has received, is receiving, or is going to receive an anti-Jagged antibody comprising the HVRs or variable regions of 4D11 or 5342-1204-4D11, an effective amount of a Wnt pathway inhibitor, including but not limited to, a Wnt pathway inhibitor described herein.

In some embodiments, the method comprises administering to an individual who has received, is receiving, or is going to receive an anti-DLL antibody comprising the HVRs or variable regions of YW26.82, an effective amount of a Wnt pathway inhibitor, including but not limited to, a Wnt pathway inhibitor described herein. In some embodiments, the method comprises administering to an individual who has received, is receiving, or is going to receive an anti-DLL antibody comprising the HVRs or variable regions of YW26.82, an effective amount of an anti-LRP antibody or bispecific antibody comprising the HVRs or variable regions of an antibody selected from YW211.31.62 and/or YW210.09. In some embodiments, the method comprises administering to an individual who has received, is receiving, or is going to receive an anti-DLL antibody comprising the HVRs or variable regions of YW26.82, an effective amount of an anti-LRP antibody comprising the HVRs or variable regions of P6C.51.61. In some embodiments, the method comprises administering to an individual who has received, is receiving, or is going to receive an anti-DLL antibody comprising the HVRs or variable regions of YW26.82, an effective amount of a soluble Fzd8 receptor, such as FZD8CRD.

In some embodiments, the method comprises administering to an individual who has received, is receiving, or is going to receive an anti-DLL antibody selected from 21M18, 305B83, 219R45-MB-21M18, and 219R45-MB-21R83, an effective amount of a Wnt pathway inhibitor, including but not limited to a Wnt pathway inhibitor described herein. In some embodiments, the method comprises administering to an individual who has received, is receiving, or is going to receive an anti-DLL antibody selected from 21M18, 305B83, 219R45-MB-21M18, and 219R45-MB-21R83, an effective amount of anti-Frizzled antibody 18R5. In some embodiments, the method comprises administering to an individual who has received, is receiving, or is going to receive an anti-DLL antibody selected from 21M18, 305B83, 219R45-MB-21M18, and 219R45-MB-21R83, an effective amount of soluble Frizzled receptor 54F28. In some embodiments, the method comprises administering to an individual who has received, is receiving, or is going to receive an anti-DLL antibody selected from 21M18, 305B83, 219R45-MB-21M18, and 219R45-MB-21R83, an effective amount of anti-LRP antibody 7E5C8.

In some embodiments, the method comprises administering to an individual who has received, is receiving, or is going to receive a Notch pathway inhibitor, including but not limited to, a Notch pathway inhibitor described herein, an effective amount of an anti-LRP antibody or bispecific antibody comprising the HVRs or variable regions of an antibody selected from YW211.31.62 and/or YW210.09. In some embodiments, the method comprises administering to an individual who has received, is receiving, or is going to receive a Notch pathway inhibitor, including but not limited to, a Notch pathway inhibitor described herein, an effective amount of a biparatropic antibody described in U.S. Publication No. 2013/0064823. In some embodiments, the method comprises administering to an individual who has received, is receiving, or is going to receive a Notch pathway inhibitor, including but not limited to, a Notch pathway inhibitor described herein, an effective amount of an anti-LRP antibody comprising the HVRs or variable regions of P6C.51.61.

In some embodiments, the method comprises administering to an individual who has received, is receiving, or is going to receive a Notch pathway inhibitor, including but not limited to, a Notch pathway inhibitor described herein, an effective amount of an anti-Frizzled antibody comprising the HVRs or variable regions of 18R5. In some embodiments, the method comprises administering to an individual who has received, is receiving, or is going to receive a Notch pathway inhibitor, including but not limited to, a Notch pathway inhibitor described herein, an effective amount of an anti-Frizzled antibody comprising the HVRs or variable regions of B9L9.3.

In some embodiments, the method comprises administering to an individual who has received, is receiving, or is going to receive a Notch pathway inhibitor, including but not limited to, a Notch pathway inhibitor described herein, an effective amount of an anti-Wnt antibody comprising the HVRs or variable regions of an anti-Wnt antibody described in U.S. Publication No. 2013/0045209.

In some embodiments, the method comprises administering to an individual who has received, is receiving, or is going to receive a Notch pathway inhibitor, including but not limited to, a Notch pathway inhibitor described herein, an effective amount of soluble Frizzled 54F28. In some embodiments, the method comprises administering to an individual who has received, is receiving, or is going to receive a Notch pathway inhibitor, including but not limited to, a Notch pathway inhibitor described herein, an effective amount of a soluble Fzd8 receptor, such as FZD8CRD.

In some embodiments, the method comprises administering to an individual who has received, is receiving, or is going to receive a Notch pathway inhibitor, including but not limited to, a Notch pathway inhibitor described herein, an effective amount of a Wnt pathway inhibitor selected from LGK974, AVN316, and PRI-724.

In some embodiments, at least one dose of the at least one Wnt pathway inhibitor is administered less than 1 hour, less than 2 hours, less than 4 hours, less than 6 hours, less than 8 hours, less than 12 hours, less than 24 hours, less than 36 hours, or less than 48 hours before administration of at least one dose of at least one Notch pathway inhibitor. In some embodiments, at least one dose of the at least one Wnt pathway inhibitor is administered within 4 hours (i.e., anytime from 4 hours before to 4 hours after), or within 3 hours, or within 2 hours, or within 1 hour, of administration of at least one dose of at least one Notch pathway inhibitor. In some embodiments, at least one dose of the at least one Wnt pathway inhibitor is administered less than 1 hour, less than 2 hours, less than 4 hours, less than 6 hours, less than 8 hours, less than 12 hours, less than 24 hours, less than 36 hours, or less than 48 hours after administration of at least one dose of at least one Notch pathway inhibitor.

In a further aspect, the invention provides for the use of Notch pathway inhibitors and Wnt pathway inhibitors in the manufacture or preparation of a medicament. In one embodiment, the medicament is for treatment of a disease or disorder associated with aberrant Notch signaling. In one embodiment, the medicament is for treatment of a cancer. In a further embodiment, the medicament is for use in a method of treating a cancer comprising administering to an individual having a cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a disease or disorder associated with aberrant Notch signaling. In one embodiment, the method comprises administering to an individual having such disease or disorder an effective amount of at least one Notch pathway inhibitor and an effective amount of at least one Wnt pathway inhibitor. In one embodiment, the method comprises administering to an individual having a cancer an effective amount of at least one Notch pathway inhibitor and an effective amount of at least one Wnt pathway inhibitor. In one such embodiment, the method further comprises administering to the individual an effective amount of at least one additional therapeutic agent, as described below. An "individual" according to any of the above embodiments may be a human.

In a further aspect, the invention provides a method for inhibiting cancer cell growth in an individual. In one embodiment, the method comprises administering to the individual an effective amount of at least one Notch pathway inhibitor and an effective amount of at least one Wnt pathway inhibitor to inhibit cancer cell growth. In one embodiment, an "individual" is a human.

In a further aspect, the invention provides pharmaceutical formulations comprising any of the Notch pathway inhibitors and/or any of the Wnt pathway inhibitors provided herein, e.g., for use in any of the above therapeutic methods. In one embodiment, a pharmaceutical formulation comprises any of the Notch pathway inhibitors and/or any of the Wnt pathway inhibitors provided herein and a pharmaceutically acceptable carrier. In another embodiment, a pharmaceutical formulation comprises any of the Notch pathway inhibitors and/or any of the Wnt pathway inhibitors provided herein and at least one additional therapeutic agent, e.g., as described below.

Notch pathway inhibitors and Wnt pathway inhibitors of the invention can be used either alone or in combination with other agents in a therapy. For instance, the inhibitors of the invention may be co-administered with at least one additional therapeutic agent. In certain embodiments, an additional therapeutic agent is a cytotoxic agent. In certain embodiments, an additional therapeutic agent is an antibody.

Such combination therapies noted above encompass combined administration (where two or more therapeutic agents are included in the same or separate formulations), and separate administration, in which case, administration of the inhibitor of the invention can occur prior to, simultaneously, and/or following, administration of the additional therapeutic agent or agents. In one embodiment, administration of at least one Notch pathway inhibitor and administration of at least one Wnt pathway inhibitor occur within about one month, or within about one, two or three weeks, or within about one, two, three, four, five, or six days, of each other. Inhibitors of the invention can also be used in combination with radiation therapy.

An inhibitor of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Inhibitors of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The inhibitor need not be, but is optionally formulated with one or more agents currently used to prevent or treat the disorder in question. The effective amount of such other agents depends on the amount of inhibitor present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an inhibitor of the invention (when used alone or in combination with one or more other additional therapeutic agents) will depend on the type of disease to be treated, the type of inhibitor, the severity and course of the disease, whether the inhibitor is administered for preventive or therapeutic purposes, previous therapy, the patient's clinical history and response to the inhibitor, and the discretion of the attending physician. The inhibitor is suitably administered to the patient at one time or over a series of treatments. Depending on the type and severity of the disease, about 1 μg/kg to 15 mg/kg (e.g. 0.1 mg/kg-10 mg/kg) of inhibitor can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the inhibitor would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the inhibitor). An initial higher loading dose, followed by one or more lower doses may be administered. An exemplary dosing regimen comprises administering an initial loading dose of about 4 mg/kg, followed by a weekly maintenance dose of about 2 mg/kg of the inhibitor. However, other dosage regimens may be useful. The progress of this therapy is easily monitored by conventional techniques and assays.

It is understood that any of the above formulations or therapeutic methods may be carried out using an immunoconjugate in place of or in addition to the antibodies discussed above.

I. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an inhibitor of the invention. The label or package insert indicates that the composition is used for treating the condition of choice. Moreover, the article of manufacture may comprise (a) a first container with a composition contained therein, wherein the composition comprises a Notch pathway inhibitor; and (b) a second container with a composition contained therein, wherein the composition comprises a Wnt pathway inhibitor. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1. Materials and Methods

Mice

All procedures were performed while observing UCSF regulations and guidelines. Mouse strains used: C57Bl/6, Lgr5GFPiresCreER (Jax strain stock number 008875), Bmi1CreER (Jax strain stock number 010531), Axin2lacZ (Jax strain stock number 009120), Math1GFP (Jax strain stock number 013593), and R26RFP (Jax strain stock number 007908). The intestine was flushed and stretched out with 4% PFA after cardiac perfusion on a cold glass plate. Alternating 2 cm pieces were collected in two cassettes. One cassette was fixed for 4 hr with 4% PFA, followed by a 30% sucrose incubation overnight at 4° C. Tissues were embedded in frozen OCT and sectioned at 7 μm. The other cassette was fixed overnight with 4% PFA and processed for paraffin embedding and sectioned at 2 μm. For lineage tracing, $Lgr5^{CreER/+};Rosa^{RFP/+}$ mice were treated with Tamoxifen dissolved in corn oil at 0.08 mg/g, IP, at the time point indicated in the figure panels. For blocking antibody treatments, dosing of α-Notch1 and α-Notch2 blocking antibodies was given at 1 mg/kg each, by intraperitoneal injection as indicated in the figure panels. α-LRP6 blocking antibody was given at 30 mg/kg, IP. FZD8CRD was given at 10 mg/k every 24 hours.

Immunohistochemistry and Immunofluorescence

Immunohistochemistry was performed using Dako Envision+ system-HRP polymer detection kit. For immunofluorescence staining, samples were blocked with Dako protein-free blocking solution. Primary and secondary antibodies were diluted in Dako antibody diluent and staining conditions are summarized in Table S1. Secondary antibodies were from Jackson Immunology.

TABLE S1

Antibodies used in this study.

| Antigen | Catalog# | dilution | Processing | Species | Company |
|---|---|---|---|---|---|
| B-gal | 559761 | 5000 | frozen | rabbit | MP bioscience |
| GFP | TP401 | 5000 | paraffin/Frozen | rabbit | Torrey Pines |
| GFP | NB100-1614 | 3000 | paraffin/Frozen | chicken | Novus |
| Dll4 | AF1389 | 100 | frozen | goat | R&D systems |
| NICD | 4147 | 100 | paraffin | rabbit | Cell signaling |
| Full-length Notch | 3608 | 100 | Paraffin | rabbit | Cell signaling |
| Dll1 | ab10554 | 200 | frozen | rabbit | abcam |
| Math1 | SC-98520 | 300 | Paraffin/frozen | rabbit | Santa Cruz |
| ckit | af1356 | 300 | Paraffin/frozen | goat | R&Dsystems |
| ki67 | TEC3 | 300 | paraffin | rat | Dako |
| ki67 | rm-9106-s | 300 | Paraffin/frozen | rabbit | Thermo |
| EdU | c10337 | 500 | Paraffin/frozen | | Invitrogen |
| Sox9 | ab5535 | 300 | Paraffin/frozen | rabbit | Millipore |
| EphB3 | AF432 | 100 | Paraffin/frozen | goat | R&D systems |
| RFP | 600-401-379 | 1000 | Paraffin/frozen | rabbit | Rockland |
| b-catenin | c2206 | 6000 | paraffin | rabbit | Sigma |
| Lysozyme | A0099 | 10000 | Paraffin/frozen | rabbit | Dako |

Construction of the LRP6 Bispecific Antibody

Two LRP6 specific antibodies were identified and optimized from human synthetic antibody libraries (Gong et al., 2010). YW210.09 binds to the E1 domain of LRP6 and YW211.31.57 binds to the E3E4 domain of LRP6. We used knobs-into-holes engineering (Ridgeway et al., 1996) to construct a bispecific IgG hybrid with YW211.31.62 and YW210.09 heavy chain heterodimers (Gong, Bourhis et al. 2010; U.S. Publication No. 2011/0256127). Antibodies were cloned into E. coli expression vectors that expressed full length IgG (Simmons et al., 2002). YW210.09 was cloned into the IgG vector with a Knob mutation, while YW211.31.57 was cloned into the IgG vector with a Hole mutation. The bispecific antibody was developed using a method to express heavy-light half antibodies that are subsequently combined to form an intact bispecific immunoglobulin. Detailed protocols of half antibody expression, purification and assembly are described (Spiess et al., 2013). The final bispecific antibody was characterized by Intact and Reduced Mass Spectrometric Analysis and size exclusion chromatography.

Isolation of Crypts for qRTPCR and Microarray Analysis

Four groups of C57B1/6 mice were injected IP with 1 mg/kg Notch1 and Notch2 blocking antibodies, 30 mg/kg Lrp6 blocking antibody, 1 mg/kg Notch1, Notch2 and 30 mg/kg Lrp6 blocking antibodies, or 30 mg/kg anti-ragweed antibody. 24 hr later, isolated small intestines were opened longitudinally, and washed with cold PBS. The tissue was then chopped into 5 mm pieces and incubated in cold chelation buffer (2 mM EDTA, 0.5 mM DL-Dithiothreitol in PBS) for 30 min on ice. Chelation buffer was then removed and tissue fragments were vigorously resuspended in cold PBS using a 10 mL pipette. The process was repeated until individual crypts were released from the tissue chunks. The crypt suspension fractions were pooled and strained through a 70 micron filter. Crypts were pelleted and RNA was extracted using the Qiagen RNeasy mini kit.

Microarray Analysis

RNA samples were hybridized against Agilent Mouse GE 4×44K v2 Microarrays using Universal Mouse RNA in the control channel. Data were processed with ExpressionPlot version 3.5 standard Agilent pipeline, which uses R 3.0.0, and limma 3.6.7. Briefly, (1) background outliers (>50 intensity) were reset to median background intensity in both channels, (2) background correction was performed using the background Correct function with the "normexp" method with an offset of 50, (3) within-array normalization was performed using the normalize WithinArraysfunction with the "loess" method, (4) replicate probes were averaged using theaveReps function, (5) between-array normalization was performed using the normalizeBetweenArrays function with the "Aquantile" method, (6) control probes (those not beginning with "A_" followed by a digit) were discarded, (7) probe expression levels were summarized as log 2 of expression ratio, (8) to obtain gene levels, one probe was selected per gene using by maximizing the inter-quartile range, (9) limma was used for differential expression analysis. Complete data are provided in Table 2. Further analysis to obtain final gene lists was performed using ExpressionPlot: genomebiology.com/2011/12/7/R69.

Example 2. Localization of Wnt and Notch Signaling in the Intestinal Crypt

To investigate the role of the Notch and Wnt pathways in maintaining crypt homeostasis, it was determined which cells within the crypts receive Notch and Wnt signaling. Wnt signaling is required for ISC maintenance (Fevr, Robine et al. 2007; van Es, Haegebarth et al. 2012), and expression of Lgr5$^{GFP}$ and the Wnt reporter Axin2$^{LacZ}$ was detected in CBCs (FIG. 1A,B). Axin2$^{LacZ}$ expression was also detected in proliferating TA cells (FIG. 1B), reflecting Wnt signaling in these cycling cells. Approximately 76% of crypts analyzed showed that Math1$^{GFP}$ expression also overlapped with the Wnt reporter in cells near the border of the stem cell compartment and TA zone (FIG. 1C, arrowheads; n=3, ≥100 crypts per mouse analyzed). These findings are consistent with the notion that Wnt signaling plays an active role in specifying progenitors for the secretory cell fate (Pinto, Gregorieff et al. 2003).

Lgr5 is a Wnt target gene and an established marker of CBCs. It was found that CBCs marked by Lgr5$^{GFP}$ were also positive for the transcriptionally active form of Notch (NICD) (FIG. 1D), confirming that the Notch pathway is active in ISCs. Nuclear NICD staining was also detected in the most proximal proliferating TA cells relative to the crypt bottom (FIG. 1E). NICD staining and the secretory progenitor marker Math1$^{GFP}$ never overlapped in these cells (FIG. 1F; n=3, ≥100 crypts per sample analyzed), consistent with the role of Notch signaling in contributing primarily to absorptive lineages (Fre, Huyghe et al. 2005; van Es, van Gijn et al. 2005). These results reinforce the notion that both pathways are active in CBCs. However, the complete lack of NICD in Math1$^{GFP}$ and Axin2$^{LacZ}$ double positive progenitors indicates that Notch and Wnt signaling pathways also have divergent functions during cell fate specification.

Example 3. Notch Signaling Blockade Impairs ISC Function

Figure 2:
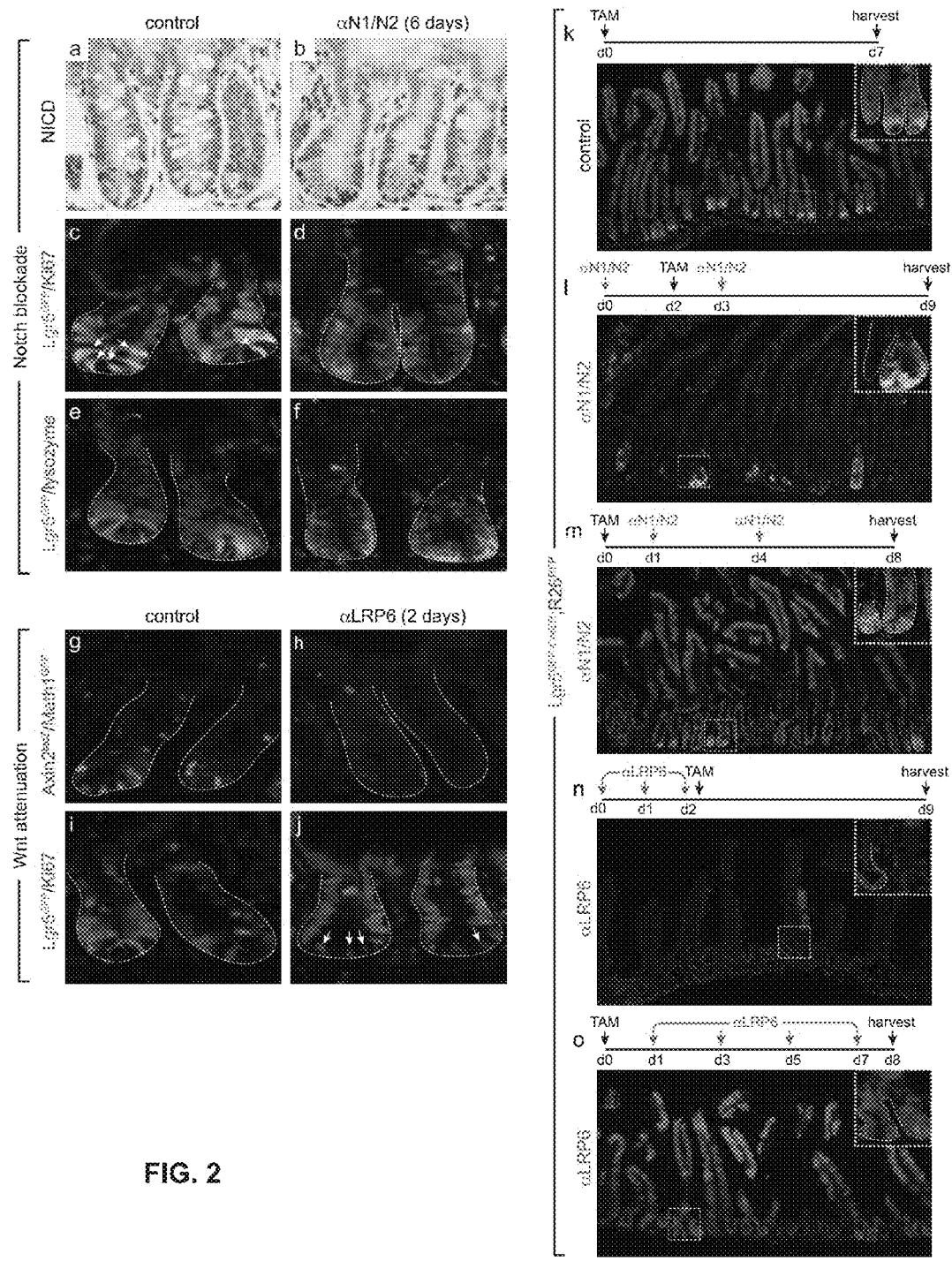
FIG. 2. Loss of Notch signaling perturbs the function of Lgr5-positive stem cells. (a) Control crypts show a normal distribution of NICD staining in CBCs and TA cells. (b) Combined treatment with anti-Notch1 and anti-Notch2 blocking antibodies (αN1/N2) effectively down-regulates Notch signaling. NICD immunostaining is absent from crypts that were treated with αN1/N2 over 6 days. (c) Control crypts show a normal distribution of $Lgr5^{GFP}$ expression in proliferating CBCs and a subset of TA cells (arrows). (d) Notch blockade causes an increase in $Lgr5^{GFP}$ expression (green) and a decrease in proliferating cells (red) in the TA zone. (e) Lgr5-positive CBCs (green) are largely non-overlapping with lysozyme-positive Paneth cells (red). (f) Notch blockade causes secretory cell hyperplasia. Increased Lysozyme expressing cells (red) are present after 6 days αN1/N2 treatment. (g) Control crypts showing distribution of Wnt signaling ($Axin2^{LacZ}$, red) and secretory cell progenitors ($Math1^{GFP}$, green). (h) Wnt attenuation with anti-LRP6 (αLRP6) blocking antibody inhibits secretory cell differentiation. αLRP6 treatment down-regulates $Axin2^{LacZ}$ (red) and $Math1^{GFP}$ (green). (i) Control crypts showing $Lgr5^{GFP}$ expression (green) and proliferating Ki67-positive cells (red). (j) Wnt attenuation with αLRP6 blocking antibody down-regulates $Lgr5^{GFP}$ expression (absence of green staining) without affecting proliferating CBCs (red, arrows). (k) Lineage tracing experiments using $Lgr5^{CreER/+}$; $Rosa^{RFP/+}$ mice show widespread labeling of crypts and villi 7 days post induction with Tamoxifen (TAM). (1) Treatment with αN1/N2 before and after induction with TAM causes decreased lineage tracing from Lgr5-positive cells. (m) Lgr5-positive stem cells were first induced to undergo recombination with TAM and then treated with αN1/N2 on days 1 and 4. (n) αLRP6 treatment causes a loss of lineage tracing from Lgr5-positive cells if provided before induction with TAM. (o) αLRP6 treatment does not affect lineage tracing if provided after induction with TAM.

Based on the observations that both the Notch and Wnt signaling pathways are active in ISCs, their respective roles were tested by reducing the levels of signaling through the use of pharmacological agents. Established antibodies that specifically block the activity of Notch receptors 1 and 2 (Wu, Cain-Hom et al. 2010) were used, as well as a bispecific antibody that inhibits the activity of the Wnt co-receptor LRP6 (Example 1: Materials and methods). Inhibiting Notch1 and Notch2 together effectively blocked Notch signaling, based on a complete loss of NICD accumulation in ISCs and TA cells, and induced a loss of CBC morphology (FIG. 2A,B). Notch inhibition also decreased proliferation associated with the TA zone (FIG. 2C,D) and a substantially increased expression of the Paneth cell marker lysozyme (FIG. 2E,F). These results indicated that this dosing scheme effectively blocked Notch signaling in the small intestine.

Figure 3:
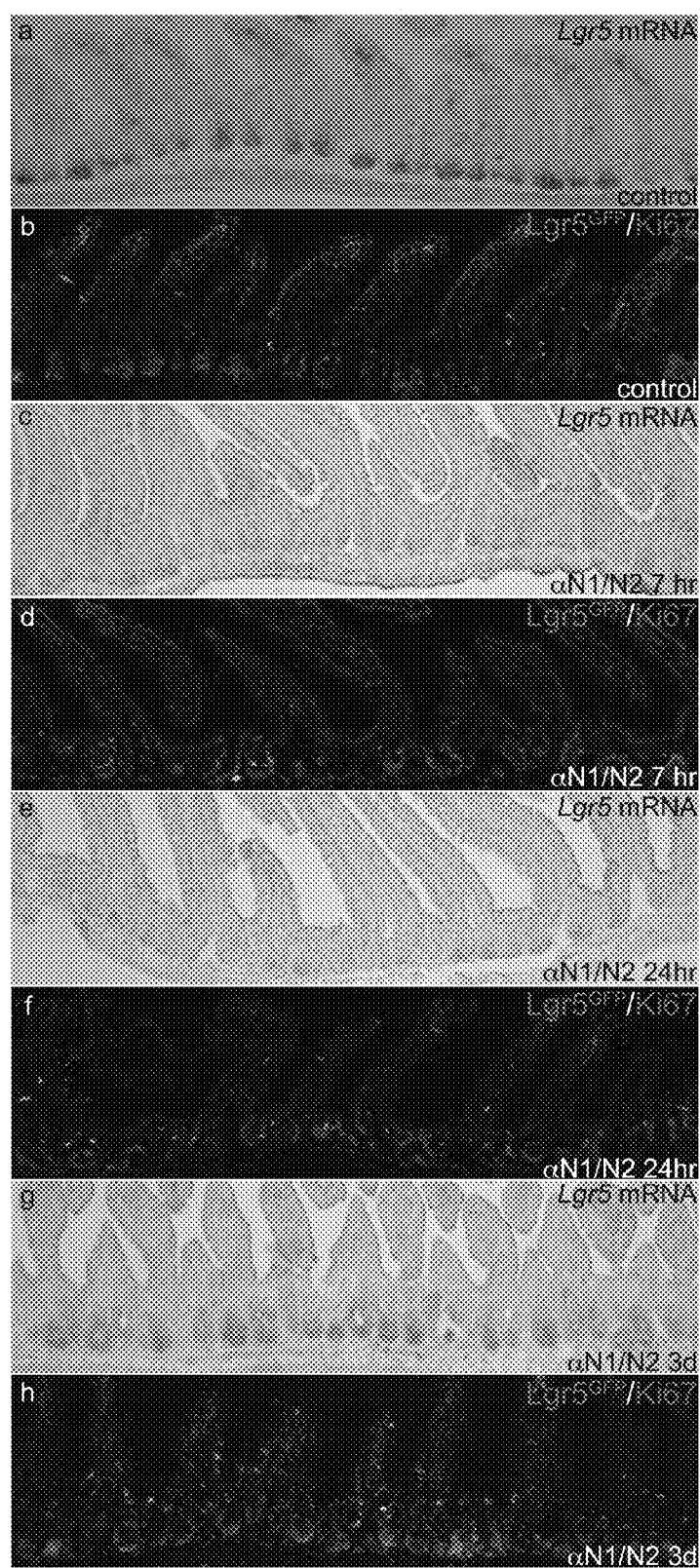
FIG. 3. Lgr5 expression is initially suppressed by Notch blockade and is re-established over time. (a) In situ hybridization showing Lgr5 mRNA distribution in control intestine. (b) $Lgr5^{GFP}$ (green) expression in control intestine. (c) Lgr5 mRNA is absent 7 hours post Notch blockade. (d) $Lgr5^{GFP}$ is absent 7 hours post Notch blockade. (e) Lgr5 mRNA is absent 24 hours post Notch blockade. (f) $Lgr5^{GFP}$ is absent 24 hours post Notch blockade. (g) Lgr5 mRNA in crypts recovers 3 days post Notch blockade. (h) $Lgr5^{GFP}$ in crypts recovers 3 days post Notch blockade.
Figure 4:
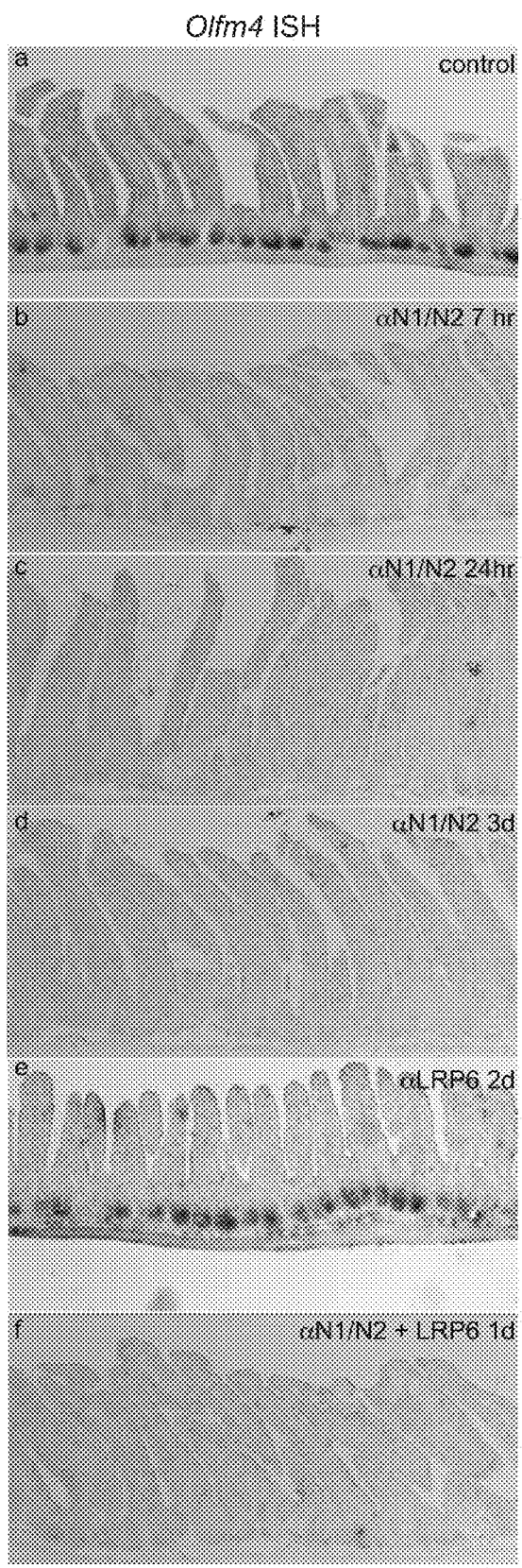
FIG. 4. The Notch target gene and ISC marker Olfm4 is sensitive to Notch blockade but not Wnt signaling attenuation. (a) In situ hybridization showing Olfm4 mRNA distribution in control intestine. (b-d) Olfm4 gene expression is repressed by Notch blockade. (e) Olfm4 mRNA is unaffected by LRP6 blockade. (f) Olfm4 mRNA is repressed in crypts treated with combined Notch/LRP6 blockade.
Figure 5:
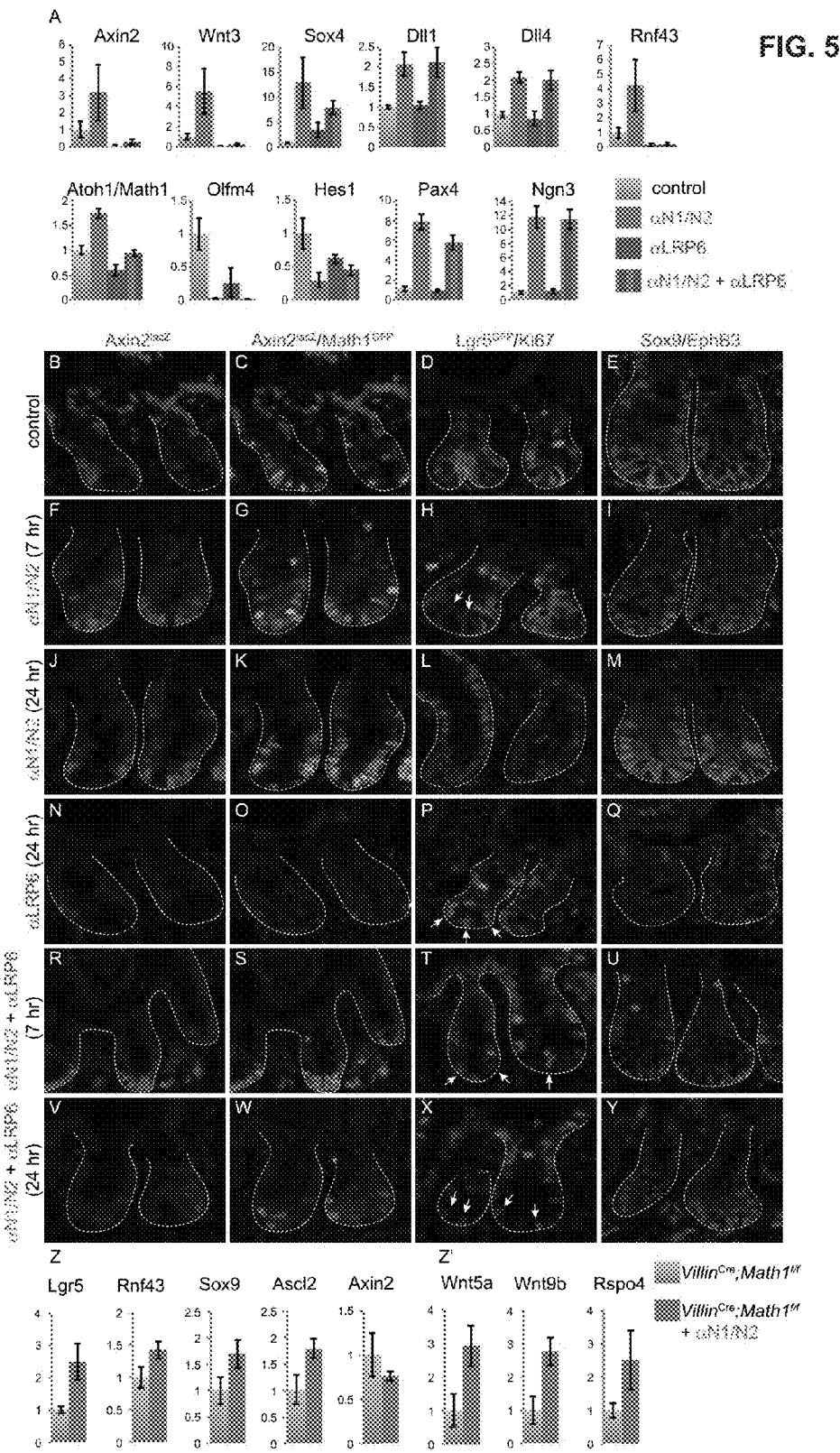
FIG. 5. Notch blockade leads to Wnt signaling up-regulation. (A) Fold changes in gene expression relative to controls after antibody treatments. mRNA was purified from isolated crypts. Results are mean±SEM. (B) Control crypts showing $Axin2^{LacZ}$ staining (red). (C) Combined $Axin2^{LacZ}$ (red) and $Math1^{GFP}$ (green) staining. (D) Control crypts showing expression of $Lgr5^{GFP}$ (green) and proliferating cells (Ki67, red). (E) Control crypts showing antibody staining of the Wnt targets SOX9 (red) and EPHB3 (green) at the base of the crypt. (F) 7 hour timepoint during Notch blockade shows an increase in the Wnt reporter $Axin2^{LacZ}$ (G) 7 hour timepoint shows a normal distribution of $Math1^{GFP}$ relative to controls. (H) At 7 hour timepoint during Notch blockade, $Lgr5^{GFP}$-positive CBCs are still present but have stopped proliferating (arrows). (I) 7 hour timepoint during Notch blockade shows increasing intensity of SOX9-positive nuclei at the base of the crypt (red). (J) 24 hour timepoint during Notch blockade shows an increased in $Axin2^{LacZ}$ staining. (K) 24 hour timepoint during Notch blockade shows an increased distribution of $Math1^{GFP}$ staining (green). (L) At 24 hour timepoint during Notch blockade, $Lgr5^{GFP}$ (green) and proliferating cells (red) are largely absent from the base of the crypt. (M) 24 hour timepoint during Notch blockade shows increased staining and distribution of the Wnt targets SOX9 and EPHB3. (N,O) 24 hour timepoint during LRP6 blockade shows absence of $Axin2^{LacZ}$ (M, red) and loss of $Math1^{GFP}$ expression (N) in treated crypts. Arrows in (N) point to residual $Math1^{GFP}$ expression at base of crypt. (P) 24 hour timepoint during LRP6 blockade shows an absence of $Lgr5^{GFP}$ (green) and a normal distribution of Ki67 staining in CBCs (arrows). (Q) 24 hour timepoint during LRP6 blockade shows near complete down-regulation of the Wnt targets SOX9 and EPHB3. (R) 7 hour timepoint during combined Notch/LRP6 blockade shows a reduced distribution of $Axin2^{LacZ}$ relative to Notch blockade alone (E). (S) 7 hour timepoint during combined Notch/LRP6 blockade shows rescued of $Math1^{GFP}$ expression pattern. (T) 7 hour timepoint during combined Notch/LRP6 blockade shows a loss of $Lgr5^{GFP}$ expression and a rescued distribution of Ki67-positive cells at the base of the crypt. (U) 7 hour timepoint during combined Notch/LRP6 blockade shows the Wnt target genes Sox9 and EphB3 remain down-regulated. (V) 24 hour timepoint during combined Notch/LRP6 blockade shows that $Axin2^{LacZ}$ expression is reduced relative to (I). (W) 24 hour timepoint during combined Notch/LRP6 blockade shows that $Math1^{GFP}$ expression is reduced relative to (J). (X) 24 hour timepoint during combined Notch/LRP6 blockade shows a rescued distribution of Ki67-positive cells including CBCs (arrows). (Y) 24 hour timepoint during combined Notch/LRP6 blockade shows the Wnt target genes Sox9 and EphB3 remain down-regulated. (Z) Relative levels of Wnt target gene expression in Villin Cre;$Math1^{fl/fl}$ mice treated with Notch blocking antibodies. (Z') Levels of Wnt5a, Wnt9b, and Rspo4 increase in Villin Cre;$Math1^{fl/fl}$ mice treated with Notch blocking antibodies.

The ISC markers Lgr5 and Olfm4 were down-regulated 7 hours after Notch antibody treatment (FIG. 3A-D and FIG. 4A,B), suggesting that stem cell maintenance was affected by Notch pathway inhibition. In addition, the number of proliferating CBCs marked by Lgr5$^{GFP}$ and Ki67 staining expression was greatly reduced 24 hours after Notch blockade (FIG. 5D,L and FIG. 3F). Surprisingly, Lgr5 expression recovered 72 hours following initiation of Notch blockade, and Lgr5 was ectopically expressed throughout the crypt base and extended upward to the region normally occupied by TA cells (FIG. 3G,H). On the other hand, expression of the Notch target gene Olfm4 (VanDussen, Carulli et al. 2012) remained down regulated during the entire Notch blockade (FIG. 4A-D). The differential effect of Notch inhibition on the expression of these two stem cell markers may reflect distinct pathway requirements. Nevertheless, the extended loss of Olfm4 expression, coupled with the results on stem cell activity described below, suggest that Olfm4 down regulation correlates with loss of stem cell activity. Increased levels of Lgr5 at later timepoints are likely due to the Lgr5 responsiveness to Wnt signaling, as described below.

Treatment of mice with the anti-Lrp6 blocking antibody led to a marked reduction in secretory cell progenitors (FIG. 2G,H), consistent with previous reports linking Wnt to secretory differentiation (Farin et al., 2012; Pinto, Gregorieff et al. 2003) and with the observation that Axin2$^{LacZ}$ overlaps with Math1$^{GFP}$ expression. Paneth cells, marked by the presence of lysozyme staining, were maintained in the presence of anti-LRP6 treatment (data not shown). Attenuation of the Wnt pathway also led to the loss of Lgr5$^{GFP}$ expression in CBCs while maintaining normal crypt proliferation in the intestine (FIG. 2I,J). This result raises the possibility that different Wnt signaling thresholds are required to maintain Lgr5 levels vs. maintaining proliferation. Although a near complete down-regulation of Axin2$^{LacZ}$ levels in mice treated with anti-Lrp6 blocking antibody was observed (FIG. 2H), it is possible that the Axin2$^{LacZ}$ reporter is insensitive to very low levels of Wnt signaling or that input(s) from other signaling pathway(s) play a role in maintaining TA cell proliferation during anti-Lrp6 blockade.

Figure 6:
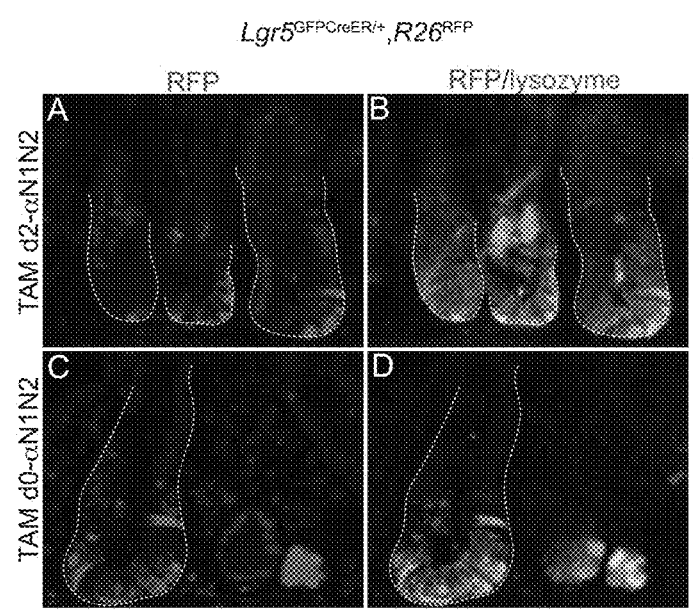
FIG. 6. CBCs convert to secretory cells during Notch blockade. (A) RFP-positive cells derived from Lgr5 expressing cells during Notch blockade. (B) Overlap of RFP-positive cells and Lysozyme expressing secretory cells (green) merged panels) when αN1/N2 is injected before induction with Tamoxifen. (C) RFP-positive cells derived from Lgr5 expressing cells during Notch blockade. (D) Overlap of RFP-positive cells and Lysozyme expressing secretory cells (green) merged panels) when αN1/N2 is injected after induction with Tamoxifen.

To more definitively determine if normal CBC stem cell multipotency requires Notch and Wnt signaling, genetic lineage tracing experiments were performed using Lgr5$^{CreER/+}$;Rosa$^{RFP/+}$ mice. First, mice were given Notch blocking antibodies before induction of recombination with Tamoxifen (Tam). Compared with control mice where Notch signaling is left intact (FIG. 2K), treatment with Notch blocking antibodies before Tam induction completely prevented lineage tracing from Lgr5-expressing cells (FIG. 2L). In samples from these mice, RFP-marked cells were present at the crypt base (FIG. 2L, inset) and expressed the secretory marker lysozyme (FIG. 6B), indicating that CBCs had converted directly into Paneth cells during Notch blockade. In addition, Notch blocking antibodies were injected following tamoxifen-induced recombination. Under these conditions, lineage tracing from the base of the crypts was almost completely absent with patchy lineage tracing remaining in cells near the top of villi (FIG. 2M). RFP marked cells were also detected at the crypt base (FIG. 2M) and expressed lysozyme (FIG. 6D), indicating that a small population of CBCs had given rise to Paneth cells during Notch blockade. Together, these results show that Notch signaling is required for CBC stem cell activity.

Treating mice with the Lrp6 blocking antibody before induction with Tam caused a complete loss of Lgr5 lineage tracing events (FIG. 2N). To differentiate between lost stem cell activity and suppression of Lgr5 expression through Wnt signaling attenuation, recombination was induced in CBCs followed by Lrp6 blocking antibody treatments. This led to un-interrupted lineage tracing similar to that observed in control mice (FIG. 2O), indicating that CBC stem cells function normally under LRP6 signaling attenuation, and that the loss of lineage tracing seen in the pre-Tam treatments was likely due to loss of Lgr5 expression. This observation was corroborated by the presence of proliferating CBCs and Olfm4 expression in the anti-Lrp6 treated animals (FIG. 2J, FIG. 4E).

Example 4. Notch Blockade Leads to Wnt Signaling Up-Regulation, which Promotes Secretory Cell Hyperplasia The down-regulation of Math1$^{GFP}$ expression by administration of the Lrp6 blocking antibody is consistent with a role for Wnt signaling in promotion of secretory cell fate decisions. Indeed, down-regulation of Math1$^{GFP}$ expression was detected as early as 24 hours after anti-Lrp6 injection (FIG. 5O). As a result, Wnt signaling readouts during Notch blockade were examined. By 7 hours after injection with the Notch blocking antibodies, intestinal crypts showed a pronounced increase in Axin2$^{LacZ}$ expression (FIG. 5B,F) without an apparent increase in Math1$^{GFP}$ expression (FIG. 5C,G). Notch signaling has been shown to repress expression of Math1 in the intestine (Fre, Huyghe et al. 2005; van Es, van Gijn et al. 2005), and a substantial increase in Math1$^{GFP}$ expression was similarly detected by 24 hours post treatment (FIG. 5A,K). Interestingly, at this time point, Math1$^{GFP}$-positive cells overlapped with Axin2$^{LacZ}$ expression, which was increased (FIG. 5A,J), indicating that the Notch secretory hyperplasia phenotype correlated with cells that were actively undergoing high levels of Wnt signaling.

As a result of these observations, gene expression analysis using expression microarrays followed by qPCR validation on isolated intestinal crypts from mice treated with Notch blocking antibodies for 24 hours was performed (FIG. 5A and Tables 2-4). The top differentially expressed genes were bona fide Notch targets (Olfm4 (log 2(fold change)=−4.07))

and Neurog3 (log 2(fold change)=3.83)(Fre, Huyghe et al. 2005; VanDussen, Carulli et al. 2012). In addition, up-regulation of several known Wnt target genes was also detected. The ligand Wnt3 was strongly up regulated, as were the Wnt target genes Kit, Ccl9, Sox4, Rnf43, Tnfsrf25. In addition to the Wnt targets, several known regulators of secretory cell differentiation such as Atoh1/Math1, Dll4, Dll1, Pax4, Foxa2, and Nkx2-2, Rfx6, and Neurog3 were also up regulated. Within the set of anti-Notch up-regulated genes, two groups were distinguished based on responsiveness to co-treatment with anti-LRP6. One group showed a greater than 2 fold decrease in expression relative to anti-Notch treatment alone and included Wnt3 and Atoh1/Math1 (Table 4), whereas the other showed minimal responsiveness to anti-LRP6 treatment and included Pax4 (<2 fold, Table 5). Several of the minimally responsive genes have been identified previously in screens for Wnt target genes (de Lau et al., 2011), suggesting that treatment with the anti-LRP6 antibody represents an incomplete Wnt signaling blockade. Expression of other Wnt targets based on the microarray results such as Sox9 and EphB3 was monitored and it was found that they were also increased during the early Notch blockade (FIG. 5E,I,M). Thus, the immunofluorescence and microarray results indicated that Notch signaling attenuates Wnt signaling, preventing secretory differentiation in the intestinal epithelium.

TABLE 2

Genes downregulated after anti-Notch treatment.

| gene symbol | gene name | log2(fold change) |
| --- | --- | --- |
| Olfm4 | olfactomedin 4 | −4.07 |
| Rbp7 | retinol binding protein 7, cellular | −3.18 |
| C3 | complement component 3 | −1.75 |
| Cyp1a1 | cytochrome P450, family 1, subfamily a, polypeptide 1 | −1.74 |
| Ugt2b5 | UDP glucuronosyltransferase 2 family, polypeptide B5 | −1.73 |
| Ctse | cathepsin E | −1.68 |
| Ugt2b38 | UDP glucuronosyltransferase 2 family, polypeptide B38 | −1.57 |
| Cnn3 | calponin 3, acidic | −1.52 |
| Ugt2b36 | UDP glucuronosyltransferase 2 family, polypeptide B36 | −1.46 |
| Akp3 | alkaline phosphatase 3, intestine, not Mn requiring | −1.45 |
| Ascl2 | achaete-scute complex homolog 2 (Drosophila) | −1.45 |
| Tmprss15 | transmembrane protease, serine 15 | −1.44 |
| Adck3 | aarF domain containing kinase 3 | −1.43 |
| Cbr3 | carbonyl reductase 3 | −1.43 |
| Aqp8 | aquaporin 8 | −1.43 |
| Dcn | decorin | −1.39 |
| Sema5a | sema domain, seven thrombospondin repeats (type 1 and type 1-like), transmembrane domain (TM) and short cytoplasmic domain, (semaphorin) 5A | −1.39 |
| Pdk4 | pyruvate dehydrogenase kinase, isoenzyme 4 | −1.33 |
| Cybrd1 | cytochrome b reductase 1 | −1.29 |
| Acsm3 | acyl-CoA synthetase medium-chain family member 3 | −1.29 |
| Rspo1 | R-spondin homolog (Xenopus laevis) | −1.28 |
| Lum | lumican | −1.27 |
| Slc40a1 | solute carrier family 40 (iron-regulated transporter), member 1 | −1.27 |
| Cyp39a1 | cytochrome P450, family 39, subfamily a, polypeptide 1 | −1.23 |
| Ugt2b37 | UDP glucuronosyltransferase 2 family, polypeptide B37 | −1.22 |
| Slc16a9 | solute carrier family 16 (monocarboxylic acid transporters), member 9 | −1.22 |
| Shmt1 | serine hydroxymethyltransferase 1 (soluble) | −1.2 |
| Msln | mesothelin | −1.18 |
| Nkx6-3 | NK6 homeobox 3 | −1.16 |
| Add3 | adducin 3 (gamma) | −1.15 |
| Impa2 | inositol (myo)-1(or 4)-monophosphatase 2 | −1.15 |
| Rarres2 | retinoic acid receptor responder (tazarotene induced) 2 | −1.14 |
| Ugt2b35 | UDP glucuronosyltransferase 2 family, polypeptide B35 | −1.14 |
| Wt1 | Wilms tumor 1 homolog | −1.14 |
| Slc14a1 | solute carrier family 14 (urea transporter), member 1 | −1.13 |
| Upk3b | uroplakin 3B | −1.13 |
| Pbk | PDZ binding kinase | −1.11 |
| Akr1c12 | aldo-keto reductase family 1, member C12 | −1.11 |
| 1110020G09Rik | RIKEN cDNA 1110020G09 gene | −1.1 |
| Clu | clusterin | −1.1 |
| Cth | cystathionase (cystathionine gamma-lyase) | −1.09 |
| Akr1c14 | aldo-keto reductase family 1, member C14 | −1.09 |
| C1ra | complement component 1, r subcomponent A | −1.07 |
| Cenpp | centromere protein P | −1.07 |
| Angpt2 | angiopoietin 2 | −1.06 |
| Rgn | regucalcin | −1.06 |
| Ptgis | prostaglandin I2 (prostacyclin) synthase | −1.05 |
| Adamts2 | a disintegrin-like and metallopeptidase (reprolysin type) with thrombospondin type 1 motif, 2 | −1.05 |
| Fabp4 | fatty acid binding protein 4, adipocyte | −1.03 |
| Scn2b | sodium channel, voltage-gated, type II, beta | −1.03 |
| Snx7 | sorting nexin 7 | −1.03 |
| Kcnq1 | potassium voltage-gated channel, subfamily Q, member 1 | −1.03 |
| Lmcd1 | LIM and cysteine-rich domains 1 | −1.03 |

TABLE 2-continued

Genes downregulated after anti-Notch treatment.

| gene symbol | gene name | log2(fold change) |
| --- | --- | --- |
| Aldh1a3 | aldehyde dehydrogenase family 1, subfamily A3 | −1.02 |
| Slpi | secretory leukocyte peptidase inhibitor | −1.02 |
| Stmn1 | stathmin 1 | −1.02 |
| Hpdl | 4-hydroxyphenylpyruvate dioxygenase-like | −1.01 |
| Aqp4 | aquaporin 4 | −1 |

TABLE 3

Genes upregulated after anti-Notch treatment.

| gene symbol | gene name | log2(fold change) |
| --- | --- | --- |
| Neurog3 | neurogenin 3 | 3.83 |
| Cbfa2t3 | core-binding factor, runt domain, alpha subunit 2, translocated to, 3 (human) | 2.52 |
| Gfra3 | glial cell line derived neurotrophic factor family receptor alpha 3 | 2.44 |
| Kit | kit oncogene | 2.42 |
| Rcor2 | REST corepressor 2 | 2.4 |
| Cacna1a | calcium channel, voltage-dependent, P/Q type, alpha 1A subunit | 2.24 |
| Ccl9 | chemokine (C—C motif) ligand 9 | 2.21 |
| Rfx6 | regulatory factor X, 6 | 2.21 |
| Kcnh3 | potassium voltage-gated channel, subfamily H (eag-related), member 3 | 2.15 |
| C2cd4b | C2 calcium-dependent domain containing 4B | 2.15 |
| Celf3 | CUGBP, Elav-like family member 3 | 2.14 |
| Fcgbp | Fc fragment of IgG binding protein | 2.09 |
| Selm | selenoprotein M | 2.04 |
| Rasa4 | RAS p21 protein activator 4 | 2.01 |
| Vldlr | very low density lipoprotein receptor | 1.98 |
| Pax4 | paired box gene 4 | 1.97 |
| Atoh1 | atonal homolog 1 (Drosophila) | 1.96 |
| Gm5595 | predicted gene 5595 | 1.96 |
| Airn | antisense Igf2r RNA | 1.93 |
| Qsox1 | quiescin Q6 sulfhydryl oxidase 1 | 1.91 |
| Wnt3 | wingless-related MMTV integration site 3 | 1.91 |
| Rapgef3 | Rap guanine nucleotide exchange factor (GEF) 3 | 1.91 |
| Spdef | SAM pointed domain containing ets transcription factor | 1.9 |
| Fut2 | fucosyltransferase 2 | 1.88 |
| Phf21b | PHD finger protein 21B | 1.85 |
| Itga6 | integrin alpha 6 | 1.82 |
| Retnlb | resistin like beta | 1.82 |
| Dll1 | delta-like 1 (Drosophila) | 1.82 |
| Ern2 | endoplasmic reticulum (ER) to nucleus signalling 2 | 1.81 |
| Fut1 | fucosyltransferase 1 | 1.8 |
| Serpina9 | serine (or cysteine) peptidase inhibitor, elude A (alpha-1 antiproteinase, antitrypsin), member 9 | 1.79 |
| Hrh3 | histamine receptor H3 | 1.78 |
| Slc17a9 | solute carrier family 17, member 9 | 1.75 |
| Insm1 | insulinoma-associated 1 | 1.75 |
| Rap1gap | Rap1 GTPase-activating protein | 1.7 |
| Ffar2 | free fatty acid receptor 2 | 1.69 |
| Pla2g2a | phospholipase A2, group IIA (platelets, synovial fluid) | 1.66 |
| Rep15 | RAB15 effector protein | 1.65 |
| Creb3l4 | cAMP responsive element binding protein 3-like 4 | 1.65 |
| Chrm1 | cholinergic receptor, muscarinic 1, CNS | 1.65 |
| Gpr20 | G protein-coupled receptor 20 | 1.64 |
| Slc15a2 | solute carrier family 15 (H+/peptide transporter), member 2 | 1.64 |
| Gadd45g | growth arrest and DNA-damage-inducible 45 gamma | 1.62 |
| Sytl2 | synaptotagmin-like 2 | 1.61 |
| Creb3l1 | cAMP responsive element binding protein 3-like 1 | 1.61 |
| Gsdma2 | gasdermin A2 | 1.6 |
| Tmem44 | transmembrane protein 44 | 1.6 |
| Phlda1 | pleckstrin homology-like domain, family A, member 1 | 1.58 |
| Rassf6 | Ras association (RalGDS/AF-6) domain family member 6 | 1.58 |
| Atp2a3 | ATPase, Ca++ transporting, ubiquitous | 1.57 |
| Syt13 | synaptotagmin XIII | 1.55 |
| Wtip | WT1-interacting protein | 1.55 |
| Sox4 | SRY-box containing gene 4 | 1.53 |
| Dmpk | dystrophia myotonica-protein kinase | 1.51 |

TABLE 3-continued

Genes upregulated after anti-Notch treatment.

| gene symbol | gene name | log2(fold change) |
|---|---|---|
| Tecpr1 | tectonin beta-propeller repeat containing 1 | 1.5 |
| Pdia5 | protein disulfide isomerase associated 5 | 1.5 |
| Bhlha15 | basic helix-loop-helix family, member a15 | 1.49 |
| Myo5c | myosin VC | 1.49 |
| Utrn | utrophin | 1.48 |
| Tnfrsf25 | tumor necrosis factor receptor superfamily, member 25 | 1.47 |
| Hepacam2 | HEPACAM family member 2 | 1.46 |
| Celsr3 | cadherin, EGF LAG seven-pass G-type receptor 3 (flamingo homolog, Drosophila) | 1.45 |
| Hpd | 4-hydroxyphenylpyruvic acid dioxygenase | 1.44 |
| Lama5 | laminin, alpha 5 | 1.43 |
| Galnt12 | UDP-N-acetyl-alpha-D-galactosamine: polypeptide N-acetylgalactosaminyltransferase 12 | 1.43 |
| Gm14207 | predicted gene 14207 | 1.42 |
| Gcnt3 | glucosaminyl (N-acetyl) transferase 3, mucin type | 1.42 |
| Eya2 | eyes absent 2 homolog (Drosophila) | 1.41 |
| Efcab4a | EF-hand calcium binding domain 4A | 1.41 |
| Pde2a | phosphodiesterase 2A, cGMP-stimulated | 1.41 |
| Unc5a | unc-5 homolog A (C. elegans) | 1.41 |
| Dll4 | delta-like 4 (Drosophila) | 1.39 |
| Tubb2b | tubulin, beta 2B class IIB | 1.38 |
| Foxa2 | forkhead box A2 | 1.35 |
| Cd97 | CD97 antigen | 1.34 |
| Thbs1 | thrombospondin 1 | 1.33 |
| Pnma2 | paraneoplastic antigen MA2 | 1.33 |
| Kcnk6 | potassium inwardly-rectifying channel, subfamily K, member 6 | 1.33 |
| Dok7 | docking protein 7 | 1.31 |
| Txndc5 | thioredoxin domain containing 5 | 1.29 |
| Hgfac | hepatocyte growth factor activator | 1.29 |
| Olfm1 | olfactomedin 1 | 1.27 |
| Scnn1a | sodium channel, nonvoltage-gated 1 alpha | 1.26 |
| Gm11937 | predicted gene 11937 | 1.26 |
| Fxyd3 | FXYD domain-containing ion transport regulator 3 | 1.26 |
| Fam174b | family with sequence similarity 174, member B | 1.25 |
| Slc34a1 | solute carrier family 34 (sodium phosphate), member 1 | 1.24 |
| Slc2a10 | solute carrier family 2 (facilitated glucose transporter), member 10 | 1.23 |
| Nkx2-2 | NK2 transcription factor related, locus 2 (Drosophila) | 1.23 |
| Cfi | complement component factor i | 1.23 |
| L1td1 | LINE-1 type transposase domain containing 1 | 1.23 |
| Agr2 | anterior gradient 2 (Xenopus laevis) | 1.23 |
| Ica1 | islet cell autoantigen 1 | 1.23 |
| Ttc39a | tetratricopeptide repeat domain 39A | 1.22 |
| Hpca | hippocalcin | 1.21 |
| Dnajc10 | DnaJ (Hsp40) homolog, subfamily C, member 10 | 1.21 |
| Fsd1l | fibronectin type III and SPRY domain containing 1-like | 1.21 |
| Rundc3a | RUN domain containing 3A | 1.2 |
| B3galt5 | UDP-Gal:betaGlcNAc beta 1,3-galactosyltransferase, polypeptide 5 | 1.2 |
| Slc27a3 | solute carrier family 27 (fatty acid transporter), member 3 | 1.2 |
| Xlr3b | X-linked lymphocyte-regulated 3B | 1.2 |
| Foxa3 | forkhead box A3 | 1.2 |
| Slc43a1 | solute carrier family 43, member 1 | 1.18 |
| Sidt1 | SID1 transmembrane family, member 1 | 1.18 |
| Cd200 | CD200 antigen | 1.16 |
| Pla2g10 | phospholipase A2, group X | 1.16 |
| Chst4 | carbohydrate (chondroitin 6/keratan) sulfotransferase 4 | 1.13 |
| 4930404N11Rik | RIKEN cDNA 4930404N11 gene | 1.13 |
| Galnt7 | UDP-N-acetyl-alpha-D-galactosamine: polypeptide N-acetylgalactosaminyltransferase 7 | 1.13 |
| Gm5796 | predicted gene 5796 | 1.13 |
| C630004H02Rik | RIKEN cDNA C630004H02 gene | 1.12 |
| St6galnac6 | ST6 (alpha-N-acetyl-neuraminyl-2,3-beta-galactosyl-1,3)-N-acetylgalactosaminide alpha-2,6-sialyltransferase 6 | 1.12 |
| Capn8 | calpain 8 | 1.11 |
| Mansc1 | MANSC domain containing 1 | 1.11 |
| Rnf150 | ring finger protein 150 | 1.11 |
| BC057022 | cDNA sequence BC057022 | 1.1 |
| Wars | tryptophanyl-tRNA synthetase | 1.1 |
| Casz1 | castor homolog 1, zinc finger (Drosophila) | 1.09 |
| Hk2 | hexokinase 2 | 1.09 |
| Tbc1d2 | TBC1 domain family, member 2 | 1.09 |
| D10Bwg1379e | DNA segment, Chr 10, Brigham & Women's Genetics 1379 expressed | 1.09 |

TABLE 3-continued

Genes upregulated after anti-Notch treatment.

| gene symbol | gene name | log2(fold change) |
|---|---|---|
| Lrrc27 | leucine rich repeat containing 27 | 1.08 |
| Neurod2 | neurogenic differentiation 2 | 1.08 |
| Gm20558 | predicted gene, 20558 | 1.08 |
| Pecr | peroxisomal trans-2-enoyl-CoA reductase | 1.08 |
| C2cd4a | C2 calcium-dependent domain containing 4A | 1.08 |
| Mcf2l | mcf.2 transforming sequence-like | 1.08 |
| Gm13023 | predicted gene 13023 | 1.07 |
| Sgsm1 | small G protein signaling modulator 1 | 1.07 |
| Igdcc4 | immunoglobulin superfamily, DCC subclass, member 4 | 1.07 |
| Rn4.5s | 4.5S RNA | 1.07 |
| Slc23a3 | solute carrier family 23 (nucleobase transporters), member 3 | 1.06 |
| Fry1 | furry homolog-like (Drosophila) | 1.06 |
| Vwa5b2 | von Willebrand factor A domain containing 5B2 | 1.06 |
| Fkbp11 | FK506 binding protein 11 | 1.05 |
| Nsf | N-ethylmaleimide sensitive fusion protein | 1.04 |
| Krt7 | keratin 7 | 1.04 |
| Ptpro | protein tyrosine phosphatase, receptor type, O | 1.03 |
| Cmtm7 | CKLF-like MARVEL transmembrane domain containing 7 | 1.03 |
| Inf2 | inverted formin, FH2 and WH2 domain containing | 1.03 |
| Tat | tyrosine aminotransferase | 1.03 |
| Serpina10 | serine (or cysteine) peptidase inhibitor, Glade A (alpha-1 antiproteinase, antitrypsin), member 10 | 1.03 |
| Krtap10-10 | keratin associated protein 10-10 | 1.03 |
| Slc7a4 | solute carrier family 7 (cationic amino acid transporter, y+ system), member 4 | 1.03 |
| Tmem132a | transmembrane protein 132A | 1.03 |
| Naip1 | NLR family, apoptosis inhibitory protein 1 | 1.02 |
| Hsp90b1 | heat shock protein 90, beta (Grp94), member 1 | 1.02 |
| Pqlc1 | PQ loop repeat containing 1 | 1.02 |
| Pdia4 | protein disulfide isomerase associated 4 | 1.02 |
| Zc3h7a | zinc finger CCCH type containing 7 A | 1.02 |
| Map3k15 | mitogen-activated protein kinase kinase kinase 15 | 1.01 |
| Mex3a | mex3 homolog A (C. elegans) | 1.01 |
| Sgsm3 | small G protein signaling modulator 3 | 1.01 |
| Rmrp | RNA component of mitochondrial RNAase P | 1.01 |

TABLE 4

Genes downregulated after anti-Notch and anti-Lrp6 treatment.

| gene symbol | gene name | log2 (fold change) due to Notch Blockade | log2(fold change) Notch-_Lrp6 relative to Notch |
|---|---|---|---|
| Cbfa2t3 | core-binding factor, runt domain, alpha subunit 2, translocated to, 3 (human) | 2.52 | −1.43 |
| Kit | kit oncogene | 2.42 | −1.28 |
| Rcor2 | REST corepressor 2 | 2.4 | −0.958 |
| Cacna1a | calcium channel, voltage-dependent, P/Q type, alpha 1A subunit | 2.24 | −1.13 |
| Rfx6 | regulatory factor X, 6 | 2.21 | −1.34 |
| Kcnh3 | potassium voltage-gated channel, subfamily H (eag-related), member 3 | 2.15 | −1.23 |
| C2cd4b | C2 calcium-dependent domain containing 4B | 2.15 | −1.47 |
| Celf3 | CUGBP, Elav-like family member 3 | 2.14 | −1.35 |
| Fcgbp | Fc fragment of IgG binding protein | 2.09 | −1.22 |
| Rasa4 | RAS p21 protein activator 4 | 2.01 | −1.07 |
| Vldlr | very low density lipoprotein receptor | 1.98 | −1.38 |
| Gm5595 | predicted gene 5595 | 1.96 | −1.18 |
| Atoh1 | atonal homolog 1 (Drosophila) | 1.96 | −0.928 |
| Airn | antisense Igf2r RNA | 1.93 | −1.74 |
| Wnt3 | wingless-related MMTV integration site 3 | 1.91 | −1.22 |
| Rapgef3 | Rap guanine nucleotide exchange factor (GEF) 3 | 1.91 | −1.38 |
| Qsox1 | quiescin Q6 sulfhydryl oxidase 1 | 1.91 | −1.27 |
| Spdef | SAM pointed domain containing ets transcription factor | 1.9 | −0.955 |
| Fut2 | fucosyltransferase 2 | 1.88 | −1.73 |
| Phf21b | PHD finger protein 21B | 1.85 | −1.42 |
| Dll1 | delta-like 1 (Drosophila) | 1.82 | −1.05 |
| Itga6 | integrin alpha 6 | 1.82 | −1.13 |
| Retnlb | resistin like beta | 1.82 | −1.29 |
| Ern2 | endoplasmic reticulum (ER) to nucleus signalling 2 | 1.81 | −1.27 |
| Fut1 | fucosyltransferase 1 | 1.8 | −1.18 |
| 14581 | growth factor independent 1 | 1.77 | −1.26 |
| Slc17a9 | solute carrier family 17, member 9 | 1.75 | −1.55 |
| Rap1gap | Rap1 GTPase-activating protein | 1.7 | −0.982 |
| Ffar2 | free fatty acid receptor 2 | 1.69 | −1.27 |
| Pla2g2a | phospholipase A2, group IIA (platelets, synovial fluid) | 1.66 | −1.21 |
| Chrm1 | cholinergic receptor, muscarinic 1, CNS | 1.65 | −1.38 |

TABLE 4-continued

Genes downregulated after anti-Notch and anti-Lrp6 treatment.

| gene symbol | gene name | log2(fold change) due to Notch Blockade | log2(fold change) Notch-_Lrp6 relative to Notch |
|---|---|---|---|
| Slc15a2 | solute carrier family 15 (H+/peptide transporter), member 2 | 1.64 | -1.61 |
| Gpr20 | G protein-coupled receptor 20 | 1.64 | -1.21 |
| Gadd45g | growth arrest and DNA-damage-inducible 45 gamma | 1.62 | -1.06 |
| Sytl2 | synaptotagmin-like 2 | 1.61 | -1.25 |
| Gsdma2 | gasdermin A2 | 1.6 | -1.41 |
| Rassf6 | Ras association (RalGDS/AF-6) domain family member 6 | 1.58 | -1.14 |
| Atp2a3 | ATPase, Ca++ transporting, ubiquitous | 1.57 | -1.04 |
| Wtip | WT1-interacting protein | 1.55 | -1.48 |
| Dmpk | dystrophia myotonica-protein kinase | 1.51 | -1.05 |
| Pdia5 | protein disulfide isomerase associated 5 | 1.5 | -0.946 |
| Tecpr1 | tectonin beta-propeller repeat containing 1 | 1.5 | -1.06 |
| Myo5c | myosin VC | 1.49 | -1.11 |
| Utrn | utrophin | 1.48 | -1.39 |
| Tnfrsf25 | tumor necrosis factor receptor superfamily, member 25 | 1.47 | -1.47 |
| Celsr3 | cadherin, EGF LAG seven-pass G-type receptor 3 (flamingo homolog, Drosophila) | 1.45 | -1.2 |
| Galnt12 | UDP-N-acetyl-alpha-D-galactosamine:polypeptide N-acetylgalactosaminyltransferase 12 | 1.43 | -0.924 |
| Lama5 | laminin, alpha 5 | 1.43 | -1.39 |
| Gcnt3 | glucosaminyl (N-acetyl) transferase 3, mucin type | 1.42 | -0.903 |
| Pde2a | phosphodiesterase 2A, cGMP-stimulated | 1.41 | -0.951 |
| Eya2 | eyes absent 2 homolog (Drosophila) | 1.41 | -0.91 |
| Dll4 | delta-like 4 (Drosophila) | 1.39 | -0.956 |
| 1300002K09Rik | RIKEN cDNA 1300002K09 gene | 1.36 | -0.96 |
| 1810019D21Rik | RIKEN cDNA 1810019D21 gene | 1.35 | -1.2 |
| Cd97 | CD97 antigen | 1.34 | -1.06 |
| Thbs1 | thrombospondin 1 | 1.33 | -1.09 |
| Kcnk6 | potassium inwardly-rectifying channel, subfamily K, member 6 | 1.33 | -1.08 |
| L1td1 | LINE-1 type transposase domain containing 1 | 1.23 | -1.02 |
| Slc2a10 | solute carrier family 2 (facilitated glucose transporter), member 10 | 1.23 | -0.95 |
| Cfi | complement component factor i | 1.23 | -1.12 |
| Slc27a3 | solute carrier family 27 (fatty acid transporter), member 3 | 1.2 | -1.13 |
| B3galt5 | UDP-Gal: betaGlcNAc beta 1,3-galactosyltransferase, polypeptide 5 | 1.2 | -1.44 |
| Cd200 | CD200 antigen | 1.16 | -1.41 |
| Chst4 | carbohydrate (chondroitin 6/keratan) sulfotransferase 4 | 1.13 | -0.949 |
| St6galnac6 | ST6 (alpha-N-acetyl-neuraminyl-2,3-beta-galactosyl-1,3)-N-acetylgalactosaminide alpha-2,6-sialyltransferase 6 | 1.12 | -1.01 |
| Capn8 | calpain 8 | 1.11 | -0.966 |
| Hk2 | hexokinase 2 | 1.09 | -0.903 |
| Rn4.5s | 4.5S RNA | 1.07 | -1.23 |
| Nsf | N-ethylmaleimide sensitive fusion protein | 1.04 | -1.27 |
| Serpina10 | serine (or cysteine) peptidase inhibitor, Glade A (alpha-1 antiproteinase, antitrypsin), member 10 | 1.03 | -0.933 |
| Hsp90b1 | heat shock protein 90, beta (Grp94), member 1 | 1.02 | -1.26 |
| Zc3h7a | zinc finger CCCH type containing 7 A | 1.02 | -1.11 |
| Pdia4 | protein disulfide isomerase associated 4 | 1.02 | -1.11 |
| Chpf2 | chondroitin polymerizing factor 2 | 1 | -1.35 |

TABLE 5

Gene expression changes after anti-Notch and combination anti-Notch/anti-Lrp6 treatment.

| gene symbol | gene name | log2(fold change) Notch treatment | log2(fold change) Notch_LRP6 relative to Notch |
|---|---|---|---|
| Neurog3 | neurogenin 3 | 3.83 | -0.548 |
| Gfra3 | glial cell line derived neurotrophic factor family receptor alpha 3 | 2.44 | -0.463 |
| Rcor2 | REST corepressor 2 | 2.41 | -0.965 |
| Ccl9 | chemokine (C-C motif) ligand 9 | 2.21 | -0.713 |
| Selm | selenoprotein M | 2.05 | -0.632 |
| Pax4 | paired box gene 4 | 1.97 | -0.824 |
| Atoh1 | atonal homolog 1 (Drosophila) | 1.96 | -0.927 |
| Spdef | SAM pointed domain containing ets transcription factor | 1.91 | -0.96 |
| Serpina9 | serine (or cysteine) peptidase inhibitor, Glade A (alpha-1 antiproteinase, antitrypsin), member 9 | 1.79 | -0.565 |
| Hrh3 | histamine receptor H3 | 1.78 | -0.694 |
| Insm1 | insulinoma-associated 1 | 1.75 | -0.0589 |
| Rap1gap | Rap1 GTPase-activating protein | 1.71 | -0.989 |

TABLE 5-continued

Gene expression changes after anti-Notch and combination anti-Notch/anti-Lrp6 treatment.

| gene symbol | gene name | log2(fold change) Notch treatment | log2(fold change) Notch_LRP6 relative to Notch |
|---|---|---|---|
| Rep15 | RAB15 effector protein | 1.65 | −0.864 |
| Creb3l4 | cAMP responsive element binding protein 3-like 4 | 1.65 | −0.697 |
| Creb3l1 | cAMP responsive element binding protein 3-like 1 | 1.62 | −0.887 |
| Phlda1 | pleckstrin homology-like domain, family A, member 1 | 1.6 | −0.679 |
| Tmem44 | transmembrane protein 44 | 1.6 | −0.715 |
| Syt13 | synaptotagmin XIII | 1.56 | −0.702 |
| Sox4 | SRY-box containing gene 4 | 1.53 | −0.333 |
| Pdia5 | protein disulfide isomerase associated 5 | 1.5 | −0.949 |
| Bhlha15 | basic helix-loop-helix family, member a15 | 1.49 | −0.8 |
| Hepacam2 | HEPACAM family member 2 | 1.46 | −0.824 |
| Galnt12 | UDP-N-acetyl-alpha-D-galactosamine: polypeptide N-acetylgalactosaminyltransferase 12 | 1.45 | −0.938 |
| Hpd | 4-hydroxyphenylpyruvic acid dioxygenase | 1.44 | −0.685 |
| 5330417C22Rik | RIKEN cDNA 5330417O22 gene | 1.44 | −0.805 |
| Pde2a | phosphodiesterase 2A, cGMP-stimulated | 1.42 | −0.958 |
| Gm14207 | predicted gene 14207 | 1.42 | −0.369 |
| Efcab4a | EF-hand calcium binding domain 4A | 1.41 | −0.823 |
| Gcnt3 | glucosaminyl (N-acetyl) transferase 3, mucin type | 1.41 | −0.903 |
| Unc5a | unc-5 homolog A (C. elegans) | 1.41 | −0.829 |
| Eya2 | eyes absent 2 homolog (Drosophila) | 1.4 | −0.909 |
| Dll4 | delta-like 4 (Drosophila) | 1.39 | −0.956 |
| Tubb2b | tubulin, beta 2B class IIB | 1.38 | −0.23 |
| Foxa2 | forkhead box A2 | 1.35 | −0.355 |
| 1300002K09Rik | RIKEN cDNA 1300002K09 gene | 1.35 | −0.959 |
| Pnma2 | paraneoplastic antigen MA2 | 1.33 | −0.419 |
| Dok7 | docking protein 7 | 1.31 | −0.801 |
| Txndc5 | thioredoxin domain containing 5 | 1.31 | −0.865 |
| Hgfac | hepatocyte growth factor activator | 1.29 | −0.863 |
| Gm11937 | predicted gene 11937 | 1.27 | 0.0122 |
| Olfm1 | olfactomedin 1 | 1.27 | −0.369 |
| Agr2 | anterior gradient 2 (Xenopus laevis) | 1.27 | −0.761 |
| Fxyd3 | FXYD domain-containing ion transport regulator 3 | 1.26 | −0.248 |
| Scnn1a | sodium channel, nonvoltage-gated 1 alpha | 1.26 | −0.718 |
| Fam174b | family with sequence similarity 174, member B | 1.25 | −0.626 |
| Slc34a1 | solute carrier family 34 (sodium phosphate), member 1 | 1.24 | −0.775 |
| Dnajc10 | DnaJ (Hsp40) homolog, subfamily C, member 10 | 1.24 | −0.645 |
| Ica1 | islet cell autoantigen 1 | 1.23 | −0.735 |
| Slc2a10 | solute carrier family 2 (facilitated glucose transporter), member 10 | 1.23 | −0.95 |
| Nkx2-2 | NK2 transcription factor related, locus 2 (Drosophila) | 1.23 | −0.66 |
| Ttc39a | tetratricopeptide repeat domain 39A | 1.22 | −0.768 |
| Hpca | hippocalcin | 1.21 | −0.787 |
| Fsd1l | fibronectin type III and SPRY domain containing 1-like | 1.21 | −0.822 |
| Rundc3a | RUN domain containing 3A | 1.2 | −0.619 |
| 2210020M01Rik | RIKEN cDNA 2210020M01 gene | 1.2 | −0.817 |
| Foxa3 | forkhead box A3 | 1.2 | −0.488 |
| Xlr3b | X-linked lymphocyte-regulated 3B | 1.2 | −0.6 |
| Sidt1 | SID1 transmembrane family, member 1 | 1.19 | −0.894 |
| Slc43a1 | solute carrier family 43, member 1 | 1.18 | −0.758 |
| Pla2g10 | phospholipase A2, group X | 1.16 | −0.679 |
| Wars | tryptophanyl-tRNA synthetase | 1.14 | −0.433 |
| C630004H02Rik | RIKEN cDNA C630004H02 gene | 1.13 | |
| Galnt7 | UDP-N-acetyl-alpha-D-galactosamine: polypeptide N-acetylgalactosaminyltransferase 7 | 1.13 | |
| Chst4 | carbohydrate (chondroitin 6/keratan) sulfotransferase 4 | 1.13 | |
| 4930404N11Rik | RIKEN cDNA 4930404N11 gene | 1.13 | |
| Gm5796 | predicted gene 5796 | 1.12 | |
| Hk2 | hexokinase 2 | 1.11 | |

TABLE 5-continued

Gene expression changes after anti-Notch and combination anti-Notch/anti-Lrp6 treatment.

| gene symbol | gene name | log2(fold change) Notch treatment | log2(fold change) Notch_LRP6 relative to Notch |
|---|---|---|---|
| Rnf150 | ring finger protein 150 | 1.11 | |
| Capn8 | calpain 8 | 1.11 | |
| Mansc1 | MANSC domain containing 1 | 1.11 | |
| Tbc1d2 | TBC1 domain family, member 2 | 1.1 | |
| BC057022 | cDNA sequence BC057022 | 1.1 | |
| D10Bwg1379e | DNA segment, Chr 10, Brigham & Women's Genetics 1379 expressed | 1.09 | |
| Mcf2l | mcf.2 transforming sequence-like | 1.09 | |
| Casz1 | castor homolog 1, zinc finger (Drosophila) | 1.09 | |
| Pecr | peroxisomal trans-2-enoyl-CoA reductase | 1.08 | |
| C2cd4a | C2 calcium-dependent domain containing 4A | 1.08 | |
| Lrrc27 | leucine rich repeat containing 27 | 1.08 | |
| Neurod2 | neurogenic differentiation 2 | 1.08 | |
| Gm20558 | predicted gene, 20558 | 1.08 | |
| Gm13023 | predicted gene 13023 | 1.07 | |
| Igdcc4 | immunoglobulin superfamily, DCC subclass, member 4 | 1.07 | |
| Sgsm1 | small G protein signaling modulator 1 | 1.06 | |
| Slc23a3 | solute carrier family 23 (nucleobase transporters), member 3 | 1.06 | |
| Inf2 | inverted formin, FH2 and WH2 domain containing | 1.06 | |
| Fryl | furry homolog-like (Drosophila) | 1.06 | |
| Vwa5b2 | von Willebrand factor A domain containing 5B2 | 1.06 | |
| Fkbp11 | FK506 binding protein 11 | 1.05 | |
| Krt7 | keratin 7 | 1.04 | |
| Tmem132a | transmembrane protein 132A | 1.04 | |
| Krtap10-10 | keratin associated protein 10-10 | 1.04 | |
| Cmtm7 | CKLF-like MARVEL transmembrane domain containing 7 | 1.03 | |
| Slc7a4 | solute carrier family 7 (cationic amino acid transporter, y+ system), member 4 | 1.03 | |
| Ptpro | protein tyrosine phosphatase, receptor type, O | 1.02 | |
| Naip1 | NLR family, apoptosis inhibitory protein 1 | 1.02 | |
| Pqlc1 | PQ loop repeat containing 1 | 1.02 | |
| Tat | tyrosine aminotransferase | 1.02 | |
| Serpina10 | serine (or cysteine) peptidase inhibitor, Glade A (alpha-1 antiproteinase, antitrypsin), member 10 | 1.02 | |
| Rmrp | RNA component of mitochondrial RNAase P | 1.01 | |
| Map3k15 | mitogen-activated protein kinase kinase kinase 15 | 1.01 | |
| Sgsm3 | small G protein signaling modulator 3 | 1.01 | |
| Mex3a | mex3 homolog A (C. elegans) | 1.01 | |

Figure 9:
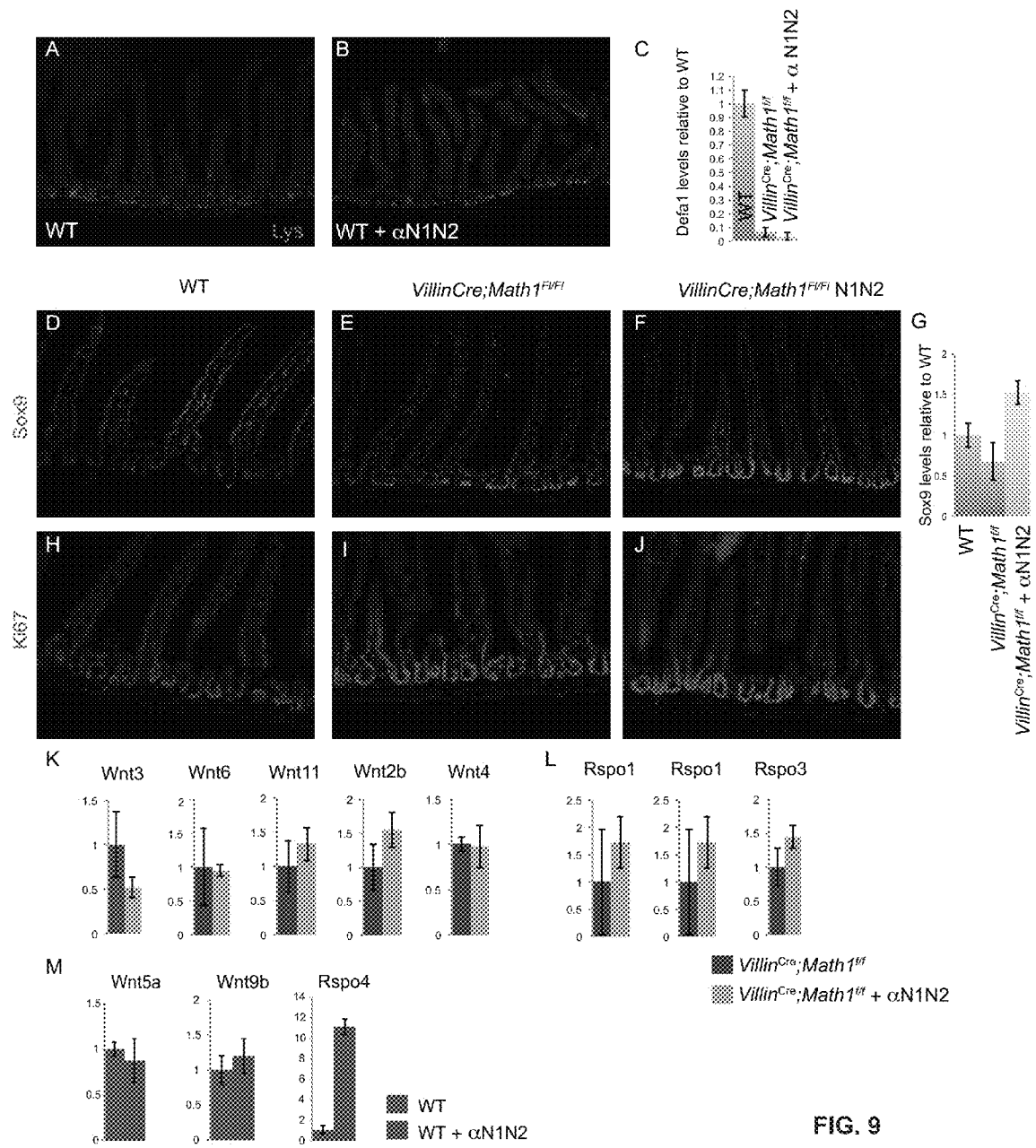
FIG. 9. Wnt signaling up-regulation in Villin Cre; $Math1^{fl/fl}$ mice. (A,B) Lysozyme staining in WT duodenum (A) and WT duodenum treated with Notch antibodies for 24 hours (B). (C) Defa1 levels in duodenum from treated (3 day Notch antibody-treated) and control Villin Cre;Math1$^{fl/fl}$ mice relative to WT. (D-F) SOX9 staining in duodenum from WT, untreated Villin Cre;Math1$^{fl/fl}$ mice, and Villin Cre;Math1$^{fl/fl}$ mice treated with Notch antibodies for 3 days. (H-J) Ki67 staining in duodenum from WT, untreated Villin Cre;Math1$^{fl/fl}$ mice, and Villin Cre;Math1$^{fl/fl}$ mice treated with Notch antibodies for 3 days. (K) Wnt isoform levels in Notch 3 day treated Villin Cre;Math1$^{fl/fl}$ mice relative to untreated. (L) Rspondin1-3 levels Notch 3 day treated Villin Cre;Math1$^{fl/fl}$ mice relative to untreated. (M) Wnt5a, Wnt9b, and Rspo4 levels in Notch 3 day treated WT mice relative to WT untreated.

Example 5. Wnt Signaling Up-Regulation Occurs Independently of Paneth Cell Hyperplasia Paneth cells are a major source of Wnt3 in the small intestine, which led us to ask if Paneth cell hyperplasia represents the sole mechanism by which Wnt signaling up-regulation is achieved during Notch blockade. Levels of the Paneth cell marker Defa1 (microarray data not shown) and lysozyme staining in the small intestine (FIG. 9A,B) were not significantly increased at the 24 hour time point. To test if Paneth cells are required for a Wnt response, we blocked Notch signaling in Villin Cre;Math1$^{fl/fl}$ mice that lack both secretory progenitors as well as differentiated secretory cells, including Paneth cells. Villin Cre;Math1$^{fl/fl}$ mice had significantly reduced levels of Defa1 that did not change with Notch blockade (FIG. 9C). These mice, like their control littermates, appeared to have increased Ki67 and SOX9 staining after Notch blockade (FIG. 9D-J), which suggested to us that Wnt signaling was up-regulated even in the complete absence of Paneth cells. To test this idea, we examined the levels of Wnt target genes, Wnt isoforms, and Rspondin1-4 in the intestines of Villin Cre;Math1$^{fl/fl}$ treated mice. Although Wnt3 was not up-regulated in mice lacking Paneth cells (FIG. 9K), consistent with the notion that Wnt3 is produced by Paneth cells, we observed a consistent up-regulation of several Wnt target genes (FIG. 5Z), as well as mesenchyme derived Wnt5a and epithelium derived Wnt9b (FIG. 5Z'). Of note, Wnt9b was previously shown to compensate for loss of Wnt3 in an organoid growth assay (Farin et al., 2012) and Wnt5a has also been shown to enhance proliferation in the small intestine (Cervantes et al., 2009). In addition, the Wnt signaling agonist Rspondin-4 (Rspo4) was significantly increased in both WT and Villin Cre;Math1$^{fl/fl}$ treated mice (FIG. 9M and FIG. 5Z').

From these results, we conclude that, although the Paneth cells are likely an important source of Wnt proteins when Notch signaling is blocked in control mice, the small intestine can still mount a Wnt response in the absence of Paneth cells. Moreover, the activation of the Wnt pathway due to loss of Notch signaling in control mice most likely results at least in part from an initial amplification of Wnt signaling through up-regulation of the canonical ligand Wnt9b and Wnt signaling agonist Rspo4. Subsequent Wnt3 production stemming from ongoing Paneth cell hyperplasia may then lock in place the secretory cell fate decision.

Example 6. Co-Treatment with Notch and Wnt Blocking Antibodies Rescues Secretory Cell Metaplasia To functionally determine whether elevated Wnt signaling was responsible for the Notch phenotype, co-treatment with Notch and Lrp6 blocking antibodies was tested. Further microarray analysis was performed, and demonstrated that genes up regulated under Notch blockade could be partially or completely repressed by co-treatment with Lrp6 blocking antibodies; interestingly, such genes included Wnt3 and the pro-secretory fate genes Math1, Dll1, Dll4, Pax4 and Ngn3 (FIG. 5A). Without intending to be bound by any particular theory, this suggested that up-regulated Wnt signaling caused the mis-regulation of pro-secretory genes during Notch blockade.

Figure 7:
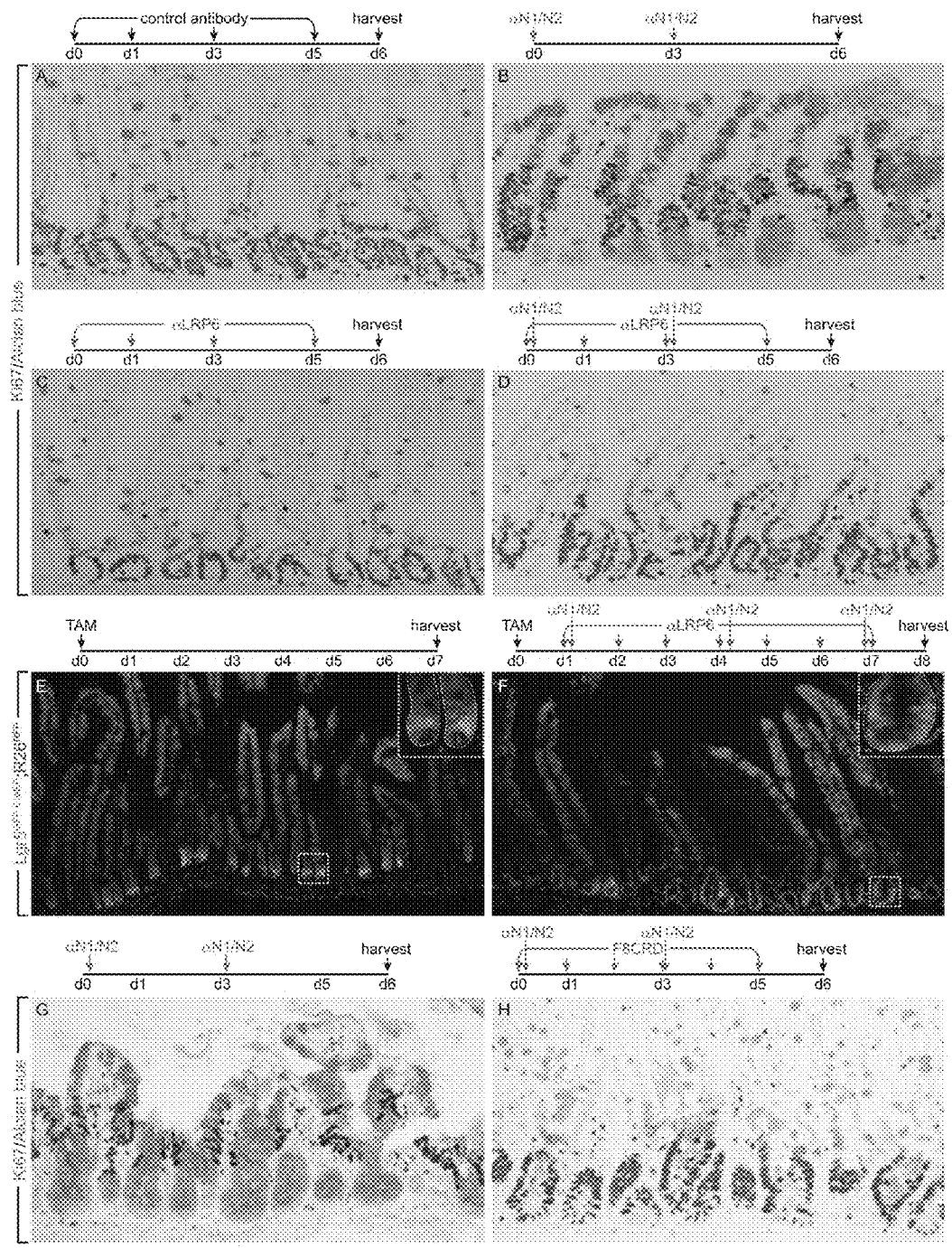
FIG. 7. Co-treatment with Notch and Wnt blocking antibodies rescues secretory cell metaplasia and ISC activity. (A) Control ileum showing proliferating cells (Ki67, brown) and Alcian Blue stained Goblet cells. (B) Notch blockade causes goblet cell metaplasia. Increased presence of Alcian Blue stained goblet cells in the crypts is coincident with a loss of proliferating cells. (C) αLRP6 treatment leads to no significant changes in the distribution of Goblet cells or proliferating cells. (D) Combined αN1/N2 and αLRP6 treatment rescues the proliferation defects and Goblet cell metaplasia associated with Notch blockade alone. (E) Lineage tracing experiments using $Lgr5^{CreER/+}$;$Rosa^{RFP/+}$ mice with fully labeled crypts and villi 7 days post induction with Tamoxifen (TAM). Inset shows expression of $Lgr5^{GFP}$ at crypt base. (F) Combined αN1/N2 and αLRP6 treatment rescues stem cell activity, as indicated by a recovery of lineage tracing events from Lgr5-positive stem cells. Inset shows representative fully labeled crypt with suppressed $Lgr5^{GFP}$ expression. (G) Notch blockade causes goblet cell metaplasia. (H) Combined αN1/N2 and FZD8CRD treatment rescues the proliferation defects and Goblet cell metaplasia. (I) Survival curve for αN1/N2 animals (brown line) and αN1/N2+FZD8CRD animals (green line).
Figure 7:
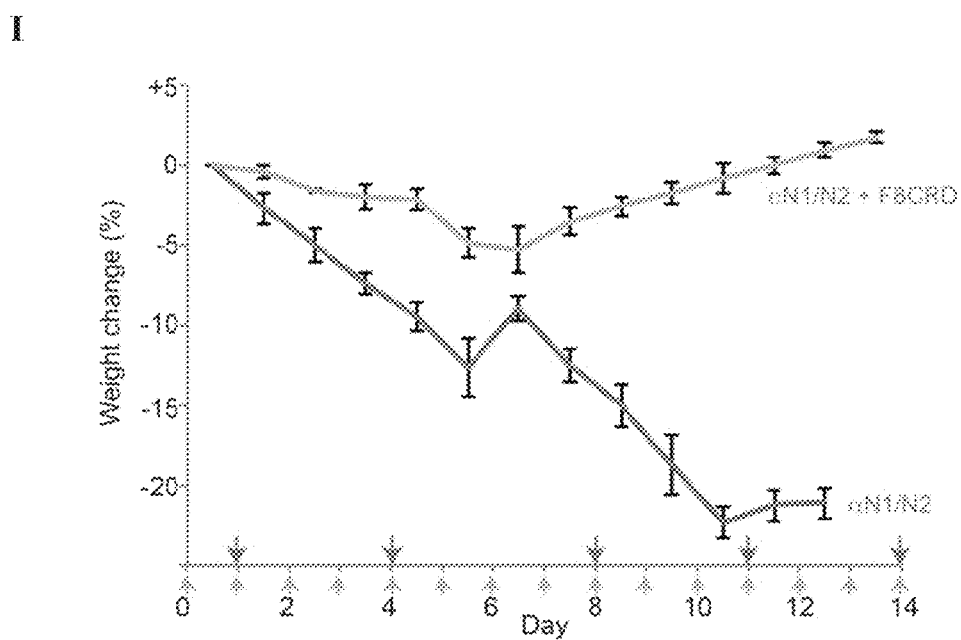

To functionally test whether Wnt attenuation could prevent the secretory cell metaplasia induced by Notch inhibition, secretory cell differentiation and stem cell activity while simultaneously blocking Notch signaling and attenuating Wnt signaling was analyzed. Treatment with Lrp6 blocking antibody alone caused a decrease in the average number of goblet cells per villus compared to controls (6.5 compared to 10.5 goblet cells/villus; n=3, ≥49 villi per sample analyzed). It was observed that the increased goblet cell content and reduced crypt proliferation seen in Notch antibody treated animals was restored to a normal distribution in mice co-treated with Lrp6 blocking antibody (FIG. 7A-D). Thus, co-blockade of Wnt and Notch signaling prevents secretory metaplasia and restores intestine homeostasis. As a definitive test of CBC stem cell activity, $Lgr5^{CreER}$; $Rosa^{RFP}$ mice were treated with both Notch and Lrp6 blocking antibodies after induction of recombination with Tam. Notch and Lrp6 antibody co-treatment dramatically rescued CBC proliferation (FIG. 5T) and stem cell activity (FIG. 7F). CBCs, in this context, no longer express the stem cell markers Lgr5 (inset, FIG. 7F) and Olfm4 (FIG. 4F), indicating that these markers are dispensable for stem cell activity. Together, these data implicate up-regulated Wnt signaling as the mechanism that underlies secretory metaplasia when levels of Notch signaling are reduced.

Figure 8:
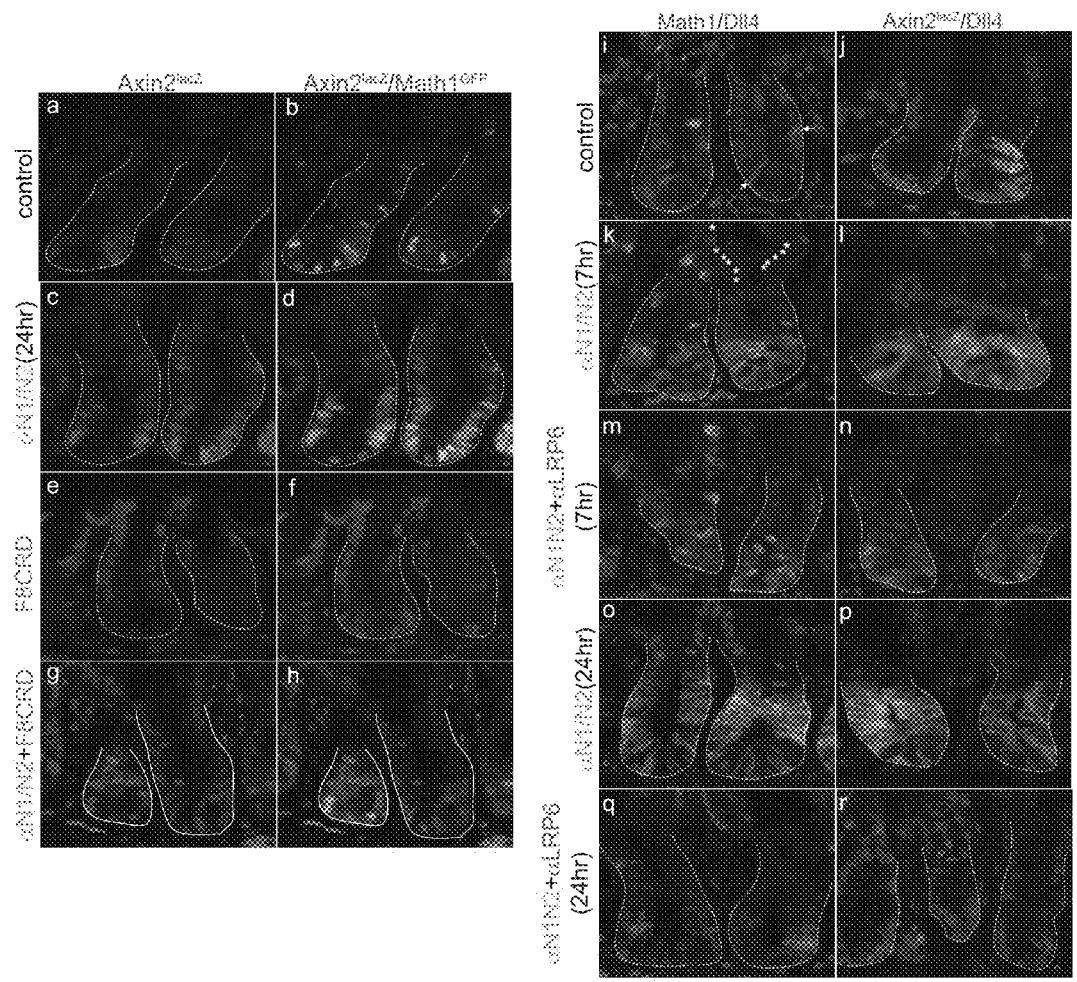
FIG. 8. Treatment with FZD8CRD represses Wnt signaling and secretory cell differentiation, and Dll4 expression correlates with increased secretory cell differentiation. (a) Control crypts showing normal distribution of $Axin2^{LacZ}$. (b) Control crypts showing normal distribution of $Math1^{GFP}$. (c) Notch blockade at the 24 hour timepoint shows an increase in $Axin2^{LacZ}$. (d) Notch blockade at the 24 hour timepoint shows an increase in $Math1^{GFP}$(merged channels). (e) FZD8CRD treatment represses $Axin2^{LacZ}$ and Math1 expression. (f) FZD8CRD treatment represses $Math1^{GFP}$(merged panels). (g) Co-treatment with αN1/N2 and FZD8CRD restores $Axin2^{LacZ}$ (merged panels) to patterns approximating controls. (h) Co-treatment with αN1/N2 and FZD8CRD restores and $Math1^{GFP}$ (merged panels) to patterns approximating controls. (i) Control crypts showing Dll4 (green) and Math1 (red) in secretory progenitor cells. (j) Control crypts showing Dll4 (green) and $Axin2^{LacZ}$ (Wnt signaling, red) are co-expressed. (k) Notch blockade at the 7 hour timepoint shows an increase in Math1 that extends beyond the crypt/villus junction (red, asterisks). (l) Notch blockade at the 7 hour timepoint shows an increase in $Axin2^{LacZ}$ (Wnt signaling, red) that is co-incident with Dll4 staining (green). (m) Notch/LRP6 blockade at the 7 hour timepoint shows increased staining distribution of Math1 (red) and Dll4 (green). (n) Notch/LRP6 blockade at the 7 hour timepoint shows elevated levels of $Axin2^{LacZ}$ (red) co-incident with Dll4 (green). (o) Notch blockade at the 24 hour timepoint shows a substantial increase in Math1 (red) co-incident with Dll4. (p) $Axin2^{LacZ}$ expression correlates with Dll4 and Math1 (shown in G). (q) Notch/LRP6 blockade rescues Math1 (red) and Dll4 expression (green) to normal levels by 24 hours (r) Notch/LRP6 blockade rescues $Axin2^{LacZ}$ (red) and Dll4 (green) expression to normal levels by 24 hours.

To complement the above experiments using the anti-LRP6 antibody, we also tested whether a decoy Wnt receptor, Frizzled 8 CRD (F8CRD) (DeAlmeida et al., 2007), could similarly rescue the effect of Notch antibody blockade. As with single agent anti-LRP6 treatment, F8CRD treatment led to down-regulation of Wnt signaling, as assessed by $Axin2^{LacZ}$, and secretory differentiation, as assessed by $Math1^{GFP}$ (FIG. 8). Combined treatment with Notch antibodies and F8CRD led to complete rescue of the secretory metaplasia phenotype (FIG. 7G,H), reinforcing the notion that Notch blockade leads to secretory conversion in large part through driving an increase in Wnt signaling via upregulation of Wnt ligand expression.

Example 7. Discussion

Notch Signaling Antagonizes Wnt Signaling to Maintain Stem Cell Activity

Previous studies have found that Notch activity plays an essential role in maintaining CBCs and TA cell proliferation while preventing secretory differentiation (van Es, van Gijn et al. 2005; VanDussen, Carulli et al. 2012). The data indicate that Notch signaling is active in CBCs and TA cells and is absent from all secretory progenitors and their differentiated progeny. Using function blocking antibodies against Notch receptors, up-regulation of Wnt signaling shortly after Notch blockade was observed, indicating that Notch signaling antagonizes Wnt signaling in the intestinal epithelium. This finding has surprising implications for how Wnt signaling normally regulates the maintenance and activity of CBC stem cells. First, when Wnt signaling is elevated due to Notch blockade, CBC activity and proliferation in the crypt are severely compromised. These phenotypes are likely meditated through increased Wnt ligand expression, particularly Wnt3, and not other downstream components of the Wnt signaling pathway, as CBC activity and TA cell proliferation could be rescued by attenuating Wnt signaling at the ligand and receptor level with either anti-LRP6 or F8CRD. Second, attenuation of normal Wnt signaling levels with anti-LRP6 or F8CRD had no effect on stem cell activity, such that diminished levels of Wnt signaling were sufficient for normal stem cell function. Together, these results indicate that Notch activity is required for maintaining the proper level of Wnt signaling in the crypt that allows for the simultaneous maintenance and activity of ISCs as well as crypt proliferation.

The finding that anti-LRP6 or F8CRD treatment alone failed to reduce CBC activity and TA proliferation is surprising given the ability of these reagents to suppress Wnt target genes. Potential explanations for why these reagents do not completely eliminate Wnt signaling include technical reasons, such as an inability of F8CRD to completely titrate all WNT3 ligand, or partial blockade of Wnt signaling by the anti-LRP6 antibody; alternatively, signaling events initiated by compensating Wnt pathway components may play a role. These ideas are supported by in vitro studies showing that LRP6 ECD selectively binds a subset of WNTs with high affinity (Bourhis et al., 2010). For instance, LRP6 blocking antibodies have been shown to specifically inhibit WNT3 and WNT3a while potentiating other WNT isoforms in signaling assays (Gong et al., 2010). F8CRD is capable of binding four different WNT isoforms, albeit with highly differing affinities (Bourhis et al., 2010). Aside from Wnt3, additional Wnts and the Lrp5 co-receptor are also expressed in the crypt epithelium (Gregorieff et al., 2005), and these may provide alternative signaling mechanisms that are not fully blocked by F8CRD or anti-LRP6.

Our experiments with the anti-LRP6 antibody point to a differential requirement for Wnt signaling in ISC self-renewal and secretory differentiation. This may reflect functional differences between the LRP6 and LRP5 receptors, although a recent report indicates that these molecules are functionally overlapping (Zhong et al., 2012). Wnt signaling attenuation in our studies caused down-regulation of secretory differentiation, while leaving CBC stem cell activity intact. This points to a model in which lower levels of Wnt signaling are needed for stem cell maintenance and higher levels for secretory cell differentiation, which is similar to the gradient of Wnt activity seen in hair follicle stem cell maintenance and differentiation (Blanpain and Fuchs, 2006). However, ISCs are embedded in a WNT-rich environment (Gregorieff et al., 2005), with the expectation that CBCs transduce the highest levels of Wnt signaling. Our analysis of Wnt activity, as assessed by the Axin2$^{lacZ}$ reporter, shows that cells near the border of the stem cell compartment express Axin2$^{lacZ}$ as strongly or even higher than CBCs (FIG. 1AC). Based on these observations, and together with our findings that the highest intensity of nuclear NICD occurs in CBCs and that high expression of the Notch target gene Olfm4 also occurs in CBCs, we propose that the lower level of Wnt signaling needed for ISC activity is achieved through the antagonistic activity of Notch signaling. In line with this hypothesis, Notch blockade caused an increase in Axin2$^{lacZ}$ expression throughout the crypt, with a particular increase in intensity detected at the crypt base (FIG. 5F,J), along with aberrant secretory cell differentiation and a complete loss of ISC activity. The exact mechanism underlying the collaboration between Notch and Wnt signaling in maintenance of ISCs is still unknown, but our rescue experiments suggest that Notch signaling is dispensable for ISC activity as long as the Wnt signaling output approximates normal levels (FIG. 7F). This notion is supported by published work showing that intestinal homeostasis, and presumably ISC activity, remains intact in Math1 mutants when Notch activity is removed. Conversely, NICD-induced progenitor proliferation is dependent on intact Wnt signaling (Munoz-Descalzo et al., 2011).

Notch and Wnt Signaling Interplay Controls Cell Differentiation

Math1/Atoh1, which is negatively regulated by Notch signaling, is the key mediator of secretory metaplasia after Notch loss of function (Kazanjian, Noah et al. 2010). Math1 deletion has been shown to completely prevent secretory cell metaplasia in animals treated with Notch inhibitors (Kazanjian, Noah et al. 2010). In addition to rescuing secretory cell metaplasia, Math1 deletion also restored proliferation after Notch blockade, suggesting that Math1-mediated cell cycle exit is a factor in maintaining crypt homeostasis. It was found that attenuation of the Wnt pathway by treatment with anti-LRP6 restored the normal distribution of Math1-expressing cells, and this treatment rescued the Notch phenotype, including restoration of proliferation Importantly, the notion that increased Wnt signaling mediates the Notch phenotype through up-regulation of Math1 is substantiated by the observation that Lrp6 blockade represses Math1 expression on its own and that Wnt/β-catenin signaling directly regulates Math1 expression in other contexts (Shi, Cheng et al. 2010). We also found that the up-regulation of Axin2$^{lacZ}$ and other Wnt target genes preceded the activation of Math1 and secretory cell metaplasia. During Notch blockade, the small intestine increases the production of Wnts as well as the agonist Rspo4 in the absence of Math1 and the secretory cell lineage. This strongly suggests that the trigger for secretory cell metaplasia in Notch deficient mice is an immediate hyper-activation of the Wnt pathway. Our data, together with previous studies, indicate that Notch activity is required for maintaining the correct balance of Wnt signaling in the crypt, which allows for simultaneous maintenance of ISCs, proliferation, and differentiation. Interestingly, unlike in perinatal mice (Fre, Huyghe et al. 2005), over-expression of NICD in the adult intestine epithelium does not provide a proliferative advantage, lending support to the hypothesis that a primary role of Notch in adult intestine epithelium is to antagonize Wnt signaling, thereby preventing secretory differentiation through subsequent repression of Math1.

Notch and Wnt signaling may also converge on Dll4 expression to fine-tune the Notch signaling output. Here, it was found that Math1 expression correlates with Dll4 expression (FIG. 8I), and DLL4 protein rapidly accumulates on Math1-expressing secretory cells during Notch blockade, (FIG. 8O). Although it remains unclear if Dll4 is a bona fide Wnt target, overlapping domains of Dll4 expression and Axin2$^{lacZ}$ were detected (FIG. 8J). Elevated levels of Dll4 could down-regulate Notch activity in the cells sending the signal through cis-inhibition, such that Wnt signaling could indirectly attenuate Notch signaling by promoting Math1/Dll4 expression in the secretory lineage. Wnt signaling has multiple roles during differentiation of secretory cells, especially in the case of Paneth cells (Bastide, Darido et al. 2007; Fevr, Robine et al. 2007). In line with this idea, the up-regulation of several key secretory genes due to Notch blockade was partially rescued by the LRP6 blocking antibody, including Math1, Hes1, Pax4, Dll1, Dll4 and Ngn3.

Regulation of Wnt Signaling Outputs by Notch Signaling

The experiments described herein with the anti-LRP6 antibody point to a differential requirement for Wnt signaling in ISC self-renewal and secretory differentiation. This may reflect a functional difference between the LRP6 and LRP5 receptor although a recent report finds the activity of these molecules to be compensatory (Zhong, Baker et al. 2012). Wnt signaling attenuation in these studies caused down-regulation of secretory differentiation, while leaving CBC stem cell activity intact. This suggests that lower levels of Wnt signaling are needed for stem cell maintenance and higher levels for secretory cell differentiation. This scenario is similar to the gradient of Wnt activity seen in hair follicle stem cell maintenance and differentiation (Blanpain and Fuchs 2006). However, ISCs are embedded in a Wnt-rich environment (Gregorieff, Pinto et al. 2005), such that Wnt activity, as assessed by the Axin2$^{lacZ}$ reporter, is strongest at the crypt base and becomes weaker toward the villus (FIG. 1A-C). Thus, based on these observations and the finding that the highest intensity of nuclear NICD occurs in CBCs and that high expression of the Notch target gene Olfm4 also occurs in CBCs, it was proposed that the lower level of Wnt signaling needed for ISC activity is achieved through the antagonistic activity of Notch signaling. In line with this hypothesis, Notch blockade caused an increase in Axin2$^{LacZ}$ expression throughout the crypt, with a particular increase in intensity at the crypt base (FIG. 5F,J), along with aberrant secretory cell differentiation and a complete loss of ISC activity. The exact mechanism underlying the collaboration between Notch and Wnt signaling in maintenance of ISCs is still unknown, but the rescue experiments suggest that Notch signaling is dispensable for ISC activity as long as the Wnt signaling output approximates normal levels (FIG. 7F). This notion is supported by published work showing that intestinal homeostasis, and presumably ISC activity, remain intact in Math1 mutants when Notch activity is removed. Conversely, NICD-induced progenitor proliferation is dependent on intact Wnt signaling (Munoz-Descalzo, Tkocz et al. 2011).

Notch/Wnt Interaction in Other Contexts

The interaction between Wnt and Notch signaling described here may be a common theme in stem cell biology. For example, deletion of the Notch1 receptor in mouse skin causes inappropriate activation of Wnt/β-catenin signaling in the epidermis and impaired differentiation in primary keratinocytes, as well as excess β-catenin accumulation in the eye epithelium leading to Wnt dependent hyper-proliferation (Nicolas, Wolfer et al. 2003). In cardiac progenitors, loss of Notch mimics a gain of function β-catenin phenotype, and in mouse embryonic stem cells, an antagonistic effect of Notch on Wnt signaling was attributed to non-canonical Notch receptor mediated degradation of β-catenin (Kwon, Qian et al. 2009; Kwon, Cheng et al. 2011). This work indicates that Notch signaling normally serves as a natural brake on the Wnt pathway, and that attenuation of Notch signaling releases the brake and allows for high levels of Wnt signaling. Thus, in certain contexts, it may be beneficial to attenuate Notch signaling in order to assist Wnt-mediated injury repair and stem cell-fueled regeneration.

Finally, the interaction between Wnt and Notch signaling in ISCs has important implications for the use of Notch pathway inhibitors. Intestinal goblet cell metaplasia is a major challenge in the development of therapies that block Notch signaling, such as the γ-secretase inhibitors that hold promise for the treatment of Alzheimer disease or of cancers that are caused by mutations in the NOTCH pathway. The intestinal metaplasia disrupts nutrient absorption, and animals succumb due to severe weight loss under long term Notch blockade. By modulation of Wnt signaling, the intestinal metaplasia toxicity and the lethality associated with Notch blockade was overcome. These results suggest that layering Wnt signaling attenuation on top of γ-secretase inhibition or other pathways that block Notch signaling can potentially overcome the intestinal toxicity associated with such treatments, thus allowing for long term dosing with such therapies.

In addition to the above experiments using the anti-LRP6 antibody, a decoy Wnt receptor, Frizzled 8 CRD (FZD8CRD) (DeAlmeida, Miao et al. 2007) was also tested to determine whether it could similarly rescue the effect of Notch antibody blockade. As with anti-Lrp6 treatment alone, FZD8CRD treatment alone led to down-regulation of Wnt signaling, as assessed by $Axin2^{LacZ}$, and secretory differentiation, as assessed by $Math1^{GFP}$ (FIG. 8). Combined treatment with Notch antibodies and FZD8CRD led to complete rescue of the secretory metaplasia phenotype (FIG. 7G-I), and importantly, this treatment combination also rescued the weight loss and lethality induced by Notch blocking antibodies (FIG. 7I). Because Notch signaling plays diverse roles in organ homeostasis and Notch/Wnt interactions may be prevalent in other systems, it cannot be concluded that rescue of weight loss and lethality is the result of secretory cell metaplasia suppression alone. Anti-Lrp6 treatments in combination with Notch antibodies gave similar results in terms of secretory cell metaplasia suppression, however these mice continued to lose weight at a similar rate compared to treatment with anti-Notch alone. Without intending to be bound by any particular theory, it is possible that the FZD8CRD acts less broadly than the LRP6 blockade, and therefore this reagent is able to rescue the effects in the intestine without causing other problems for the animal.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

LIST OF REFERENCES

Andreu, P., S. Colnot, et al. (2005). "Crypt-restricted proliferation and commitment to the Paneth cell lineage following Apc loss in the mouse intestine." *Development* 132(6): 1443-1451.

Andreu, P., G. Peignon, et al. (2008). "A genetic study of the role of the Wnt/beta-catenin signalling in Paneth cell differentiation." *Dev Biol* 324(2): 288-296.

Barker, N., J. H. van Es, et al. (2007). "Identification of stem cells in small intestine and colon by marker gene Lgr5." *Nature* 449(7165): 1003-1007.

Bastide, P., C. Darido, et al. (2007). "Sox9 regulates cell proliferation and is required for Paneth cell differentiation in the intestinal epithelium." *J Cell Biol* 178(4): 635-648.

Blanpain, C. and E. Fuchs (2006). "Epidermal stem cells of the skin." *Annu Rev Cell Dev Biol* 22: 339-373.

Bourhis, E., Tam, C., Franke, Y., Bazan, J. F., Ernst, J., Hwang, J., Costa, M., Cochran, A. G., and Hannoush, R. N. (2010). Reconstitution of a frizzled8.Wnt3a.LRP6 signaling complex reveals multiple Wnt and Dkk1 binding sites on LRP6. The Journal of biological chemistry 285, 9172-9179.

Cervantes, S., Yamaguchi, T. P., and Hebrok, M. (2009). Wnt5a is essential for intestinal elongation in mice. Developmental biology 326, 285-294.

de Lau, W., N. Barker, et al. (2011). "Lgr5 homologues associate with Wnt receptors and mediate R-spondin signalling." *Nature* 476(7360): 293-297.

DeAlmeida, V. I., L. Miao, et al. (2007). "The soluble wnt receptor Frizzled8CRD-hFc inhibits the growth of teratocarcinomas in vivo." *Cancer Res* 67(11): 5371-5379.

Farin, H. F., Van Es, J. H., and Clevers, H. (2012). Redundant sources of Wnt regulate intestinal stem cells and promote formation of Paneth cells. Gastroenterology 143, 1518-1529 e1517.

Fevr, T., S. Robine, et al. (2007). "Wnt/beta-catenin is essential for intestinal homeostasis and maintenance of intestinal stem cells." *Mol Cell Biol* 27(21): 7551-7559.

Fre, S., M. Huyghe, et al. (2005). "Notch signals control the fate of immature progenitor cells in the intestine." *Nature* 435(7044): 964-968.

Gong, Y., E. Bourhis, et al. (2010). "Wnt isoform-specific interactions with coreceptor specify inhibition or potentiation of signaling by LRP6 antibodies." *PLoS One* 5(9): e12682.

Gregorieff, A., D. Pinto, et al. (2005). "Expression pattern of Wnt signaling components in the adult intestine." *Gastroenterology* 129(2): 626-638.

Kazanjian, A., T. Noah, et al. (2010). "Atonal homolog 1 is required for growth and differentiation effects of notch/gamma-secretase inhibitors on normal and cancerous intestinal epithelial cells." *Gastroenterology* 139(3): 918-928, 928 e911-916.

Kim, K. A., Zhao, J., Andarmani, S., Kakitani, M., Oshima, T., Binnerts, M. E., Abo, A., Tomizuka, K., and Funk, W. D. (2006). R-Spondin proteins: a novel link to beta-catenin activation. Cell Cycle 5, 23-26.

Kim, T. H. and R. A. Shivdasani (2011). "Genetic evidence that intestinal Notch functions vary regionally and operate through a common mechanism of Math1 repression." *J Biol Chem* 286(13): 11427-11433.

Korinek, V., N. Barker, et al. (1998). "Depletion of epithelial stem-cell compartments in the small intestine of mice lacking Tcf-4." *Nat Genet* 19(4): 379-383.

Kwon, C., P. Cheng, et al. (2011). "Notch post-translationally regulates beta-catenin protein in stem and progenitor cells." *Nat Cell Biol* 13(10): 1244-1251.

Kwon, C., L. Qian, et al. (2009). "A regulatory pathway involving Notch1/beta-catenin/Isl1 determines cardiac progenitor cell fate." *Nat Cell Biol* 11(8): 951-957.

Munoz-Descalzo, S., K. Tkocz, et al. (2011). "Modulation of the ligand-independent traffic of Notch by Axin and Apc contributes to the activation of Armadillo in *Drosophila.*" *Development* 138(8): 1501-1506.

Nicolas, M., A. Wolfer, et al. (2003). "Notch1 functions as a tumor suppressor in mouse skin." *Nat Genet* 33(3): 416-421.

Pinto, D., A. Gregorieff, et al. (2003). "Canonical Wnt signals are essential for homeostasis of the intestinal epithelium." *Genes Dev* 17(14): 1709-1713.

Ridgway, J. B., Presta, L. G., and Carter, P. (1996). 'Knobs-into-holes' engineering of antibody CH3 domains for heavy chain heterodimerization. Protein engineering 9, 617-621.

Sato, T., J. H. van Es, et al. (2011). "Paneth cells constitute the niche for Lgr5 stem cells in intestinal crypts." *Nature* 469(7330): 415-418.

Shi, F., Y. F. Cheng, et al. (2010). "Beta-catenin up-regulates Atoh1 expression in neural progenitor cells by interaction with an Atoh1 3' enhancer." *J Biol Chem* 285(1): 392-400.

Simmons, L. C., Reilly, D., Klimowski, L., Raju, T. S., Meng, G., Sims, P., Hong, K., Shields, R. L., Damico, L. A., Rancatore, P., et al. (2002). Expression of full-length immunoglobulins in *Escherichia coli*: rapid and efficient production of aglycosylated antibodies. Journal of immunological methods 263, 133-147.

Spiess, C., Bevers, J., 3rd, Jackman, J., Chiang, N., Nakamura, G., Dillon, M., Liu, H., Molina, P., Elliott, J. M., Shatz, W., et al. (2013). Development of a human IgG4 bispecific antibody for dual targeting of interleukin-4 (IL-4) and interleukin-13 (IL-13) cytokines. The Journal of biological chemistry 288, 26583-26593.

Stanger, B. Z., R. Datar, et al. (2005). "Direct regulation of intestinal fate by Notch." *Proc Natl Acad Sci USA* 102 (35): 12443-12448.

van Es, J. H., A. Haegebarth, et al. (2012). "A critical role for the Wnt effector Tcf4 in adult intestinal homeostatic self-renewal." *Mol Cell Biol* 32(10): 1918-1927.

van Es, J. H., P. Jay, et al. (2005). "Wnt signalling induces maturation of Paneth cells in intestinal crypts." *Nat Cell Biol* 7(4): 381-386.

van Es, J. H., M. E. van Gijn, et al. (2005). "Notch/gamma-secretase inhibition turns proliferative cells in intestinal crypts and adenomas into goblet cells." *Nature* 435 (7044): 959-963.

VanDussen, K. L., A. J. Carulli, et al. (2012). "Notch signaling modulates proliferation and differentiation of intestinal crypt base columnar stem cells." *Development* 139(3): 488-497.

Wu, Y., C. Cain-Hom, et al. (2010). "Therapeutic antibody targeting of individual Notch receptors." *Nature* 464 (7291): 1052-1057.

Yan, K. S., L. A. Chia, et al. (2012). "The intestinal stem cell markers Bmi1 and Lgr5 identify two functionally distinct populations." *Proc Natl Acad Sci USA* 109(2): 466-471.

Yang, Q., N. A. Bermingham, et al. (2001). "Requirement of Math1 for secretory cell lineage commitment in the mouse intestine." *Science* 294(5549): 2155-2158.

Zhong, Z., J. J. Baker, et al. (2012). "Lrp5 and Lrp6 play compensatory roles in mouse intestinal development." *J Cell Biochem* 113(1): 31-38.

Zhou, W. J., Z. H. Geng, et al. (2013). "Induction of intestinal stem cells by R-spondin 1 and Slit2 augments chemoradioprotection." *Nature* 501(7465): 107-111.

Table of Sequences

| SEQ ID NO | Description | Sequence |
|---|---|---|
| 1 | Human Jag1 precursor aa 1-33: signal aa 34-1218: mature aa 34-1067: extracellular domain | MRSPRTRGRS GRPLSLLLAL LCALRAKVCG ASGQFELEIL SMQNVNGELQ NGNCCGGARN PGDRKCTRDE CDTYFKVCLK EYQSRVTAGG PCSFGSGSTP VIGGNTFNLK ASRGNDRNRI VLPFSFAWPR SYTLLVEAWD SSNDTVQPDS IIEKASHSGM INPSRQWQTL KQNTGVAHFE YQIRVTCDDY YYGFGCNKFC RPRDDFFGHY ACDQNGNKTC MEGWMGPECN RAICRQGCSP KHGSCKLPGD CRCQYGWQGL YCDKCIPHPG CVHGICNEPW QCLCETNWGG QLCDKDLNYC GTHQPCLNGG TCSNTGPDKY QCSCPEGYSG PNCEIAEHAC LSDPCHNRGS CKETSLGFEC ECSPGWTGPT CSTNIDDCSP NNCSHGGTCQ DLVNGFKCVC PPQWTGKTCQ LDANECEAKP CVNAKSCKNL IASYYCDCLP GWMGQNCDIN INDCLGQCQN DASCRDLVNG YRCICPPGYA GDHCERDIDE CASNPCLNGG HCQNEINRFQ CLCPTGFSGN LCQLDIDYCE PNPCQNGAQC YNRASDYFCK CPEDYEGKNC SHLKDHCRTT PCEVIDSCTV AMASNDTPEG VRYISSNVCG PHGKCKSQSG GKFTCDCNKG FTGTYCHENI NDCESNPCRN GGTCIDGVNS YKCICSDGWE GAYCETNIND CSQNPCHNGG TCRDLVNDFY CDCKNGWKGK TCHSRDSQCD EATCNNGGTC YDEGDAFKCM CPGGWEGTTC NIARNSSCLP NPCHNGGTCV VNGESFTCVC KEGWEGPICA QNTNDCSPHP CYNSGTCVDG DNWYRCECAP GFAGPDCRIN INECQSSPCA FGATCVDEIN GYRCVCPPGH SGAKCQEVSG RPCITMGSVI PDGAKWDDDC NTCQCLNGRI ACSKVWCGPR PCLLHKGHSE CPSGQSCIPI LDDQCFVHPC TGVGECRSSS LQPVKTKCTS DSYYQDNCAN ITFTFNKEMM SPGLTTEHIC SELRNLNILK NVSAEYSIYI ACEPSPSANN EIHVAISAED IRDDGNPIKE ITDKIIDLVS KRDGNSSLIA AVAEVRVQRR PLKNRTDFLV PLLSSVLTVA WICCLVTAFY WCLRKRRKPG SHTHSASEDN TTNNVREQLN QIKNPIEKHG ANTVPIKDYE NKNSKMSKIR THNSEVEEDD MDKHQQKARF AKQPAYTLVD REEKPPNGTP TKHPNWTNKQ DNRDLESAQS LNRMEYIV |
| 2 | Murine Jag1 | MRSPRTRGRP GRPLSLLLAL LCALRAKVCG ASGQFELEIL SMQNVNGELQ NGNCCGGVRN PGDRKCTRDE CDTYFKVCLK EYQSRVTAGG PCSFGSGSTP VIGGNTFNLK ASRGNDRNRI VLPFSFAWPR SYTLLVEAWD SSNDTIQPDS IIEKASHSGM INPSRQWQTL KQNTGIAHFE YQIRVTCDDH YYGFGCNKFC RPRDDFFGHY ACDQNGNKTC MEGWMGPDCN KAICRQGCSP KHGSCKLPGD CRCQYGWQGL YCDKCIPHPG CVHGTCNEPW QCLCETNWGG QLCDKDLNYC GTHQPCLNRG TCSNTGPDKY QCSCPEGYSG PNCEIAEHAC LSDPCHNRGS CKETSSGFEC ECSPGWTGPT CSTNIDDCSP NNCSHGGTCQ DLVNGFKCVC PPQWTGKTCQ LDANECEAKP CVNARSCKNL IASYYCDCLP GWMGQNCDIN |

Table of Sequences

| SEQ ID NO | Description | Sequence |
|---|---|---|
| | | INDCLGQCQN DASCRDLVNG YRCICPPGYA GDHCERDIDE CASNPCLNGG<br>HCQNEINRFQ CLCPTGFSGN LCQLDIDYCE PNPCQNGAQC YNRASDYFCK<br>CPEDYEGKNC SHLKDHCRTT TCEVIDSCTV AMASNDTPEG VRYISSNVCG<br>PHGKCKSQSG GKFTCDCNKG FTGTYCHENI NDCESNPCKN GGTCIDGVNS<br>YKCICSDGWE GAHCENNIND CSQNPCHYGG TCRDLVNDFY CDCKNGWKGK<br>TCHSRDSQCD EATCNNGGTC YDEVDTFKCM CPGGWEGTTC NIARNSSCLP<br>NPCHNGGTCV VNGDSFTCVC KEGWEGPICT QNTNDCSPHP CYNSGTCVDG<br>DNWYRCECAP GFAGPDCRIN INECQSSPCA FGATCVDEIN GYQCICPPGH<br>SGAKCHEVSG RSCITMGRVI LDGAKWDDDC NTCQCLNGRV ACSKVWCGPR<br>PCRLHKSHNE CPSGQSCIPV LDDQCFVRPC TGVGECRSSS LQPVKTKCTS<br>DSYYQDNCAN ITFTFNKEMM SPGLTTEHIC SELRNLNILK NVSAEYSIYI<br>ACEPSLSANN EIHVAISAED IRDDGNPVKE ITDKIIDLVS KRDGNSSLIA<br>AVAEVRVQRR PLKNRTDFLV PLLSSVLTVA WVCCLVTAFY WCVRKRRKPS<br>SHTHSAPEDN TTNNVREQLN QIKNPIEKHG ANTVPIKDYE NKNSKMSKIR<br>THNSEVEEDD MDKHQQKVRF AKQPVYTLVD REEKAPSGTP TKHPNWTNKQ<br>DNRDLESAQS LNRMEYIV |
| 3 | Human Jag2 precursor<br>aa 1-23: signal<br>aa 24-1238: mature<br>aa 24-1080: extracellular domain | MRAQGRGRLP RRLLLLLALW VQAARPMGYF ELQLSALRNV NGELLSGACC<br>DGDGRTTRAG GCGHDECDTY VRVCLKEYQA KVTPTGPCSY GHGATPVLGG<br>NSFYLPPAGA AGDRARARAR AGGDQDPGLV VIPFQFAWPR SFTLIVEAWD<br>WDNDTTPNEE LLIERVSHAG MINPEDRWKS LHFSGHVAHL ELQIRVRCDE<br>NYYSATCNKF CRPRNDFFGH YTCDQYGNKA CMDGWMGKEC KEAVCKQGCN<br>LLHGGCTVPG ECRCSYGWQG RFCDECVPYP GCVHGSCVEP WQCNCETNWG<br>GLLCDKDLNY CGSHHPCTNG GTCINAEPDQ YRCTCPDGYS GRNCEKAEHA<br>CTSNPCANGG SCHEVPSGFE CHCPSGWSGP TCALDIDECA SNPCAAGGTC<br>VDQVDGFECI CPEQWVGATC QLDANECEGK PCLNAFSCKN LIGGYYCDCI<br>PGWKGINCHI NVNDCRGQCQ HGGTCKDLVN GYQCVCPRGF GGRHCELERD<br>ECASSPCHSG GLCEDLADGF HCHCPQGFSG PLCEVDVDLC EPSPCRNGAR<br>CYNLEGDYYC ACPDDFGGKN CSVPREPCPG GACRVIDGCG SDAGPGMPGT<br>AASGVCGPHG RCVSQPGGNF SCICDSGFTG TYCHENIDDC LGQPCRNGGT<br>CIDEVDAFRC FCPSGWEGEL CDTNPNDCLP DPCHSRGRCY DLVNDFYCAC<br>DDGWKGKTCH SREFQCDAYT CSNGGTCYDS GDTFRCACPP GWKGSTCAVA<br>KNSSCLPNPC VNGGTCVGSG ASFSCICRDG WEGRTCTHNT NDCNPLPCYN<br>GGICVDGVNW FRCECAPGFA GPDCRINIDE CQSSPCAYGA TCVDEINGYR<br>CSCPPGRAGP RCQEVIGFGR SCWSRGTPFP HGSSWVEDCN SCRCLDGRRD<br>CSKVWCGWKP CLLAGQPEAL SAQCPLGQRC LEKAPGQCLR PPCEAWGECG<br>AEEPPSTPCL PRSGHLDNNC ARLTLHFNRD HVPQGTTVGA ICSGIRSLPA<br>TRAVARDRLL VLLCDRASSG ASAVEVAVSF SPARDLPDSS LIQGAAHAIV<br>AAITQRGNSS LLLAVTEVKV ETVVTGGSST GLLVPVLCGA FSVLWLACVV<br>LCVWWTRKRR KERERSRLPR EESANNQWAP LNPIRNPIER PGGHKDVLYQ<br>CKNFTPPPRR ADEALPGPAG HAAVREDEED EDLGRGEEDS LEAEKFLSHK<br>FTKDPGRSPG RPAHWASGPK VDNRAVRSIN EARYAGKE |
| 4 | Murine Jag2 | MRARGWGRLP RRLLLLLVLC VQATRPMGYF ELQLSALRNV NGELLSGACC<br>DGDGRTTRAG GCGRDECDTY VRVCLKEYQA KVTPTGPCSY GYGATPVLGG<br>NSFYLPPAGA AGDRARARSR TGGHQDPGLV VIPFQFAWPR SFTLIVEAWD<br>WDNDTTPDEE LLIERVSHAG MINPEDRWKS LHFSGHVAHL ELQIRVRCDE<br>NYYSATCNKF CRPRNDFFGH YTCDQYGNKA CMDGWMGKEC KEAVCKQGCN<br>LLHGGCTVPG ECRCSYGWQG KFCDECVPYP GCVHGSCVEP WHCDCETNWG<br>GLLCDKDLNY CGSHHPCVNG GTCINAEPDQ YLCACPDGYL GKNCERAEHA<br>CASNPCANGG SCHEVPSGFE CHCPSGWSGP TCALDIDECA SNPCAAGGTC<br>VDQVDGFECI CPEQWVGATC QLDANECEGK PCLNAFSCKN LIGGYYCDCL<br>PGWKGINCQI NINDCHGQCQ HGGTCKDLVN GYQCVCPRGF GGRHCELEYD<br>KCASSPCRRG GICEDLVDGF RCHCPRGLSG LHCEVDMDLC EPSPCLNGAR<br>CYNLEGDYYC ACPEDFGGKN CSVPRDTCPG GACRVIDGCG FEAGSRARGV<br>APSGICGPHG HCVSLPGGNF SCICDSGFTG TYCHENIDDC MGQPCRNGGT<br>CIDEVDSFRC FCPSGWEGEL CDINPNDCLP DPCHSRGRCY DLVNDFYCAC<br>DDGWKGKTCH SREFQCDAYT CSNGGTCYDS GDTFRCACPP GWKGSTCTIA<br>KNSSCVPNPC VNGGTCVGSG DSFSCICRDG WEGRTCTHNT NDCNPLPCYN<br>GGICVDGVNW FRCECAPGFA GPDCRINIDE CQSSPCAYGA TCVDEINGYR<br>CSCPPGRSGP RCQEVVIFTR PCWSRGMSFP HGSSWMEDCN SCRCLDGHRD<br>CSKVWCGWKP CLLSGQPSDP SAQCPPGQQC QEKAVGQCLQ PPCENWGECT<br>AEEPLPPSTP CQPRSSHLDN NCARLTLRFN RDQVPQGTTV GAICSGIRAL<br>PATRAAAHDR LLLLLCDRAS SGASAVEVAM SFSPARDLPD SSLIQSTAHA<br>IVAAITQRGN SSLLLAVTEV KVETVVMGGS STGLLVPVLC SVFSVLWLAC<br>VVICVWWTRK RRKERERSRL PRDESTNNQW APLNPIRNPI ERPGGSGLGT<br>GGHKDILYQC KNFTPPPPRA GEALPGPAGH GAGGEDEEDE ELSRGDGDSP<br>EAEKFISHKF TKDPSCSLGR PACWAPGPKV DNRAVRSTKD VRRAGRE |
| 5 | Murine Jag1-DSL-EGF1-4 (mouse Jag1 antigen) | ADLGSQFELE ILSMQNVNGE LQNGNCCGGV RNPGDRKCTR DECDTYFKVC<br>LKEYQSRVTA GGPCSFGSGS TPVIGGNTFN LKASRGNDRN RIVLPFSFAW<br>PRSYTLLVEA WDSSNDTIQP DSIIEKASHS GMINPSRQWQ TLKQNTGIAH<br>FEYQIRVTCD DHYYGFGCNK FCRPRDDFFG HYACDQNGNK TCMEGWMGPD |

Table of Sequences

| SEQ ID NO | Description | Sequence |
|---|---|---|
| | | CNKAICRQGC SPKHGSCKLP GDCRCQYGWQ GLYCDKCIPH PGCVHGTCNE PWQCLCETNW GGQLCDKDLN YCGTHQPCLN RGTCSNTGPD KYQCSCPEGY SGPNCEIAEH ACLSDPCHNR GSCKETSSGF ECECSPGWTG PTCSTNIDDE FGLVPRGSGH HHHHH |
| 6 | human Jag1-DSL-EGF1-4 (human Jag1 antigen) | QFELEILSMQ NVNGELQNGN CCGGARNPGD RKCTRDECDT YFKVCLKEYQ SRVTAGGPCS FGSGSTPVIG GNTFNLKASR GNDRNRIVLP FSFAWPRSYT LLVEAWDSSN DTVQPDSIIE KASHSGMINP SRQWQTLKQN TGVAHFEYQI RVTCDDYYYG FGCNKFCRPR DDFFGHYACD QNGNKTCMEG WMGPECNRAI CRQGCSPKHG SCKLGDCRCQ YGWQGLYCDK CIPHPGCVHG ICNEPWQCLC ETNWGGQLCD KDLNYCGTHQ PCLNGGTCSN TGPDKYQCSC PEGYSGPNCE IAEHACLSDP CHNRGSCKET SLGFECECSP GWTGPTCSTN IDD |
| 7 | murine Jag2-DSL-EGF1-4 (mouse Jag2 antigen) | ADLGSMGYFE LQLSALRNVN GELLSGACCD GDGRTTRAGG CGRDECDTYV RVCLKEYQAK VTPTGPCSYG YGATPVLGGN SFYLPPAGAA GDRARARSRT GGHQDPGLVV IPFQFAWPRS FTLIVEAWDW DNDTTPDEEL LIERVSHAGM INPEDRWKSL HFSGHVAHLE LQIRVRCDEN YYSATCNKFC RPRNDFFGHY TCDQYGNKAC MDGWMGKECK EAVCKQGCNL LHGGCTVPGE CRCSYGWQGK FCDECVPYPG CVHGSCVEPW HCDCETNWGG LLCDKDLNYC GSHHPCVNGG TCINAEPDQY LCACPDGYLG KNCERAEHAC ASNPCANGGS CHEVPSGFEC HCPSGWNGPT CALDIDEEFG LVPRGSGHHH HHH |
| 8 | human Jag2-DSL-EGF1-4 (human Jag2 antigen) | ARPMGYFELQ LSALRNVNGE LLSGACCDGD GRTTRAGGCG HDECDTYVRV CLKEYQAKVT PTGPCSYGHG ATPVLGGNSF YLPPAGAAGD RARARARAGG DQDPGLVVIP FQFAWPRSFT LIVEAWDWDN DTTPNEELLI ERVSHAGMIN PEDRWKSLHF SGHVAHLELQ IRVRCDENYY SATCNKFCRP RNDFFGHYTC DQYGNKACMD GWMGKECKEA VCKQGCNLLH GGCTVPGECR CSYGWQGRFC DECVPYPGCV HGSCVEPWQC NCETNWGGLL CDKDLNYCGS HHPCTNGGTC INAEPDQYRC TCPDGYSGRN CEKAEHACTS NPCANGGSCH EVPSGFECHC PSGWSGPTCA LDIDEEFGLV PRGSGHHHHH H |
| 9 | Human Notch1 precursor (UniProtKB/Swiss-Prot: P46531.4) aa 1-18: signal aa 19-2555: mature aa 20-1426: EGF-like repeat domain aa ~1307-1732: negative regulatory region (NRR) | MPPLLAPLLC LALLPALAAR GPRCSQPGET CLNGGKCEAA NGTEACVCGG AFVGPRCQDP NPCLSTPCKN AGTCHVVDRR GVADYACSCA LGFSGPLCLT PLDNACLTNP CRNGGTCDLL TLTEYKCRCP PGWSGKSCQQ ADPCASNPCA NGGQCLPFEA SYICHCPPSF HGPTCRQDVN ECGQKPGLCR HGGTCHNEVG SYRCVCRATH TGPNCERPYV PCSPSPCQNG GTCRPTGDVT HECACLPGFT GQNCEENIDD CPGNNCKNGG ACVDGVNTYN CRCPPEWTGQ YCTEDVDECQ LMPNACQNGG TCHNTHGGYN CVCVNGWTGE DCSENIDDCA SAACFHGATC HDRVASFYCE CPHGRTGLLC HLNDACISNP CNEGSNCDTN PVNGKAICTC PSGYTGPACS QDVDECSLGA NPCEHAGKCI NTLGSFECQC LQGYTGPRCE IDVNECVSNP CQNDATCLDQ IGEFQCICMP GYEGVHCEVN TDECASSPCL HNGRCLDKIN EFQCECPTGF TGHLCQYDVD ECASTPCKNG AKCLDGPNTY TCVCTEGYTG THCEVDIDEC DPDPCHYGSC KDGVATFTCL CRPGYTGHHC ETNINECSSQ PCRHGGTCQD RDNAYLCFCL KGTTGPNCEI NLDDCASSPC DSGTCLDKID GYECACEPGY TGSMCNINID ECAGNPCHNG GTCEDGINGF TCRCPEGYHD PTCLSEVNEC NSNPCVHGAC RDSLNGYKCD CDPGWSGTNC DINNNECESN PCVNGGTCKD MTSGYVCTCR EGFSGPNCQT NINECASNPC LNQGTCIDDV AGYKCNCLLP YTGATCEVVL APCAPSPCRN GGECRQSEDY ESFSCVCPTG WQGQTCEVDI NECVLSPCRH GASCQNTHGG YRCHCQAGYS GRNCETDIDD CRPNPCHNGG SCTDGINTAF CDCLPGFRGT FCEEDINECA SDPCRNGANC TDCVDSYTCT CPAGFSGIHC ENNTPDCTES SCFNGGTCVD GINSFTCLCP PGFTGSYCQH DVNECDSQPC LHGGTCQDGC GSYRCTCPQG YTGPNCQNLV HWCDSSPCKN GGKCWQTHTQ YRCECPSGWT GLYCDVPSVS CEVAAQRQGV DVARLCQHGG LCVDAGNTHH CRCQAGYTGS YCEDLVDECS PSPCQNGATC TDYLGGYSCK CVAGYHGVNC SEEIDECLSH PCQNGGTCLD LPNTYKCSCP RGTQGVHCEI NVDDCNPPVD PVSRSPKCFN NGTCVDQVGG YSCTCPPGFV GERCEGDVNE CLSNPCDARG TQNCVQRVND FHCECRAGHT GRRCESVING CKGKPCKNGG TCAVASNTAR GFICKCPAGF EGATCENDAR TCGSLRCLNG GTCISGPRSP TCLCLGPFTG PECQFPASSP CLGGNPCYNQ GTCEPTSESP FYRCLCPAKF NGLLCHILDY SFGGGAGRDI PPPLIEEACE LPECQEDAGN KVCSLQCNNH ACGWDGGDCS LNFNDPWKNC TQSLQCWKYF SDGHCDSQCN SAGCLFDGFD CQRAEGQCNP LYDQYCKDHF SDGHCDQGCN SAECEWDGLD CAEHVPERLA AGTLVVVVLM PPEQLRNSSF HFLRELSRVL HTNVVFKRDA HGQQMIFPYY GREEELRKHP IKRAAEGWAA PDALLGQVKA SLLPGGSEGG RRRRELDPMD VRGSIVYLEI DNRQCVQASS QCFQSATDVA AFLGALASLG SLNIPYKIEA VQSETVEPPP PAQLHFMYVA AAAFVLLFFV GCGVLLSRKR RRQHGQLWFP EGFKVSEASK KKRREPLGED SVGLKPLKNA SDGALMDDNQ NEWGDEDLET KKFRFEEPVV LPDLDDQTDH RQWTQQHLDA ADLRMSAMAP TPPQGEVDAD CMDVNVRGPD GFTPLMIASC SGGGLETGNS EEEEDAPAVI SDFIYQGASL HNQTDRTGET ALHLAARYSR SDAAKRLLEA SADANIQDNM GRTPLHAAVS ADAQGVFQIL IRNRATDLDA RMHDGTTPLI LAARLAVEGM LEDLINSHAD VNAVDDLGKS ALHWAAAVNN VDAAVVLLKN GANKDMQNNR EETPLFLAAR EGSYETAKVL LDHFANRDIT DHMDRLPRDI |

Table of Sequences

| SEQ ID NO | Description | Sequence |
|---|---|---|
| | | AQERMHHDIV RLLDEYNLVR SPQLHGAPLG GTPTLSPPLC SPNGYLGSLK PGVQGKKVRK PSSKGLACGS KEAKDLKARR KKSQDGKGCL LDSSGMLSPV DSLESPHGYL SDVASPPLLP SPFQQSPSVP LNHLPGMPDT HLGIGHLNVA AKPEMAALGG GGRLAFETGP PRLSHLPVAS GTSTVLGSSS GGALNFTVGG STSLNGQCEW LSRLQSGMVP NQYNPLRGSV APGPLSTQAP SLQHGMVGPL HSSLAASALS QMMSYQGLPS TRLATQPHLV QTQQVQPQNL QMQQQNLQPA NIQQQQSLQP PPPPPQPHLG VSSAASGHLG RSFLSGEPSQ ADVQPLGPSS LAVHTILPQE SPALPTSLPS SLVPPVTAAQ FLTPPSQHSY SSPVDNTPSH QLQVPEHPFL TPSPESPDQW SSSSPHSNVS DWSEGVSSPP TSMQSQIARI PEAFK |
| 10 | Human Notch2 precursor (UniProtKB/ Swiss-Prot: Q04721.3); aa 1-25: signal aa 26-2471: mature aa 26-1412: EGF-like repeat domain aa ~1422-1677: negative regulatory region (NRR) | MPALRPALLW ALLALWLCCA APAHALQCRD GYEPCVNEGM CVTYHNGTGY CKCPEGFLGE YCQHRDPCEK NRCQNGGTCV AQAMLGKATC RCASGFTGED CQYSTSHPCF VSRPCLNGGT CHMLSRDTEY CTCQVGFTGK ECQWTDACLS HPCANGSTCT TVANQFSCKC LTGFTGQKCE TDVNECDIPG HCQHGGTCLN LPGSYQCQCP QGFTGQYCDS LYVPCAPSPC VNGGTCRQTG DFTFECNCLP GFEGSTCERN IDDCPNHRCQ NGGVCVDGVN TYNCRCPPQW TGQFCTEDVD ECLLQPNACQ NGGTCANRNG GYGCVCNGW SGDDCSENID DCAFASCTPG STCIDRVASF SCMCPEGKAG LLCHLDDACI SNPCHKGALC DTNPLNGQYI CTCPQGYKGA DCTEDVDECA MANSNPCEHA GKCVNTDGAF HCECLKGYAG PRCEMDINEC HSDPCQNDAT CLDKIGGFTC LCMPGFKGVH CELEINECQS NPCVNNGQCV DKVNRFQCLC PPGFTGPVCQ IDIDDCSSTP CLNGAKCIDH PNGYECQCAT GFTGVLCEEN IDNCDPDPCH HGGCQDGIDS YTCICNPGYM GAICSDQIDE CYSSPCLNDG RCIDLVNGYQ CNCQPGTSGV NCEINFDDCA SNPCIHGICM DGINRYSCVC SPGFTGQRCN IDIDECASNP CRKGATCING VNGFRCICPE GPHHPSCYSQ VNECLSNPCI HGNCTGGLSG YKCLCDAGWV GINCEVDKNE CLSNPCQNGG TCDNLVNGYR CTCKKGFKGY NCQVNIDECA SNPCLNQGTC FDDISGYTCH CVLPYTGKNC QTVLAPCSPN PCENAAVCKE SPNFESYTCL CAPGWQGQRC TIDIDECISK PCMNHGLCHN TQGSYMCECP PGFSGMDCEE DIDDCLANPC QNGGSCMDGV NTFSCLCLPG FTGDKCQTDM NECLSEPCKN GGTCSDYVNS YTCKCQAGFD GVHCENNINE CTESSCFNGG TCVDGINSFS CLCPVGFTGS FCLHEINECS SHPCLNEGTC VDGLGTYRCS CPLGYTGKNC QTLVNLCSRS PCKNKGTCVQ KKAESQCLCP SGWAGAYCDV PNVSCDIAAS RRGVLVEHLC QHSGVCINAG NTHYCQCPLG YTGSYCEEQL DECASNPCQH GATCSDFIGG YRCECVPGYQ GVNCEYEVDE CQNQPCQNGG TCIDLVNHFK CSCPPGTRGL LCEENIDDCA RGPHCLNGGQ CMDRIGGYSC RCLPGFAGER CEGDINECLS NPCSSEGSLD CIQLTNDYLC VCRSAFTGRH CETFVDVCPQ MPCLNGGTCA VASNMPDGFI CRCPPGFSGA RCQSSCGQVK CRKGEQCVHT ASGPRCFCPS PRDCESGCAS SPCQHGGSCH PQRQPPYYSC QCAPPFSGSR CELYTAPPST PPATCLSQYC ADKARDGVCD EACNSHACQW DGGDCSLTME NPWANCSSPL PCWDYINNQC DELCNTVECL FDNFECQGNS KTCKYDKYCA DHFKDNHCDQ GCNSEECGWD GLDCAADQPE NLAEGTLVIV VLMPPEQLLQ DARSFLRALG TLLHTNLRIK RDSQGELMVY PYYGEKSAAM KKQRMTRRSL PGEQEQEVAG SKVFLEIDNR QCVQDSDHCF KNTDAAAALL ASHAIQGTLS YPLVSVVSES LTPERTQLLY LLAVAVVIIL FIILLGVIMA KRKRKHGSLW LPEGFTLRRD ASNHKRREPV GQDAVGLKNL SVQVSEANLI GTGTSEHWVD DEGPQPKKVK AEDEALLSEE DDPIDRRPWT QQHLEAADIR RTPSLALTPP QAEQEVDVLD VNVRGPDGCT PLMLASLRGG SSDLSDEDED AEDSSANIIT DLVYQGASLQ AQTDRTGEMA LHLAARYSRA DAAKRLLDAG ADANAQDNMG RCPLHAAVAA DAQGVFQILI RNRVTDLDAR MNDGTTPLIL AARLAVEGMV AELINCQADV NAVDDHGKSA LHWAAAVNNV EATLLLLKNG ANRDMQDNKE ETPLFLAARE GSYEAAKILL DHFANRDITD HMDRLPRDVA RDRMHHDIVR LLDEYNVTPS PPGTVLTSAL SPVICGPNRS FLSLKHTPMG KKSRRPSAKS TMPTSLPNLA KEAKDAKGSR RKKSLSEKVQ LSESSVTLSP VDSLESPHTY VSDTTSSPMI TSPGILQASP NPMLATAAPP APVHAQHALS FSNLHEMQPL AHGASTVLPS VSQLLSHHHI VSPGSGSAGS LSRLHPVPVP ADWMNRMEVN ETQYNEMFGM VLAPAEGTHP GIAPQSRPPE GKHITTPREP LPPIVTFQLI PKGSIAQPAG APQPQSTCPP AVAGPLPTMY QIPEMARLPS VAFPTAMMPQ QDGQVAQTIL PAYHPFPASV GKYPTPPSQH SYASSNAAER TPSHSGHLQG EHPYLTPSPE SPDQWSSSSP HSASDWSDVT TSPTPGGAGG GQRGPGTHMS EPPHNNMQVY A |
| 11 | Human Notch3 precursor (UniProtKB/ Swiss-Prot: Q9UM47.2) aa 1-39: signal aa 40-2321: mature aa 40-1373: EGF-like repeat domain aa ~1378-1640: | MGPGARGRRR RRRPMSPPPP PPPVRALPLL LLLAGPGAAA PPCLDGSPCA NGGRCTQLPS REAACLCPPG WVGERCQLED PCHSGPCAGR GVCQSSVVAG TARFSCRCPR GFRGPDCSLP DPCLSSPCAH GARCSVGPDG RFLCSCPPGY QGRSCRSDVD ECRVGEPCRH GGTCLNTPGS FRCQCPAGYT GPLCENPAVP CAPSPCRNGG TCRQSGDLTY DCACLPGFEG QNCEVNVDDC PGHRCLNGGT CVDGVNTYNC QCPPEWTGQF CTEDVDECQL QPNACHNGGT CFNTLGGHSC VCVNGWTGES CSQNIDDCAT AVCFHGATCH DRVASFYCAC PMGKTGLLCH LDDACVSNPC HEDAICDTNP VNGRAICTCP PGFTGGACDQ DVDECSIGAN PCEHLGRCVN TQGSFLCQCG RGYTGPRCET DVNECLSGPC RNQATCLDRI GQFTCICMAG FTGTYCEVDI DECQSSPCVN GGVCKDRVNG FSCTCPSGFS GSTCQLDVDE CASTPCRNGA KCVDQPDGYE CRCAEGFEGT LCDRNVDDCS |

Table of Sequences

| SEQ ID NO | Description | Sequence |
|---|---|---|
| | negative regulatory region (NRR) | PDPCHHGRCV DGIASFSCAC APGYTGTRCE SQVDECRSQP CRHGGKCLDL VDKYLCRCPS GTTGVNCEVN IDDCASNPCT FGVCRDGINR YDCVCQPGFT GPLCNVEINE CASSPCGEGG SCVDGENGFR CLCPPGSLPP LCLPPSHPCA HEPCSHGICY DAPGGFRCVC EPGWSGPRCS QSLARDACES QPCRAGGTCS SDGMGFHCTC PPGVQGRQCE LLSPCTPNPC EHGGRCESAP GQLPVCSCPQ GWQGPRCQQD VDECAGPAPC GPHGICTNLA GSFSCTCHGG YTGPSCDQDI NDCDPNPCLN GGSCQDGVGS FSCSCLPGFA GPRCARDVDE CLSNPCGPGT CTDHVASFTC TCPPGYGGFH CEQDLPDCSP SSCFNGGTCV DGVNSFSCLC RPGYTGAHCQ HEADPCLSRP CLHGGVCSAA HPGFRCTCLE SFTGPQCQTL VDWCSRQPCQ NGGRCVQTGA YCLCPPGWSG RLCDIRSLPC REAAAQIGVR LEQLCQAGGQ CVDEDSSHYC VCPEGRTGSH CEQEVDPCLA QPCQHGGTCR GYMGGYMCEC LPGYNGDNCE DDVDECASQP CQHGGSCIDL VARYLCSCPP GTLGVLCEIN EDDCGPGPPL DSGPRCLHNG TCVDLVGGFR CTCPPGYTGL RCEADINECR SGACHAAHTR DCLQDPGGGF RCLCHAGFSG PRCQTVLSPC ESQPCQHGGQ CRPSPGPGGG LTFTCHCAQP FWGPRCERVA RSCRELQCPV GVPCQQTPRG PRCACPPGLS GPSCRSFPGS PPGASNASCA AAPCLHGGSC RPAPLAPFFR CACAQGWTGP RCEAPAAAPE VSEEPRCPRA ACQAKRGDQR CDRECNSPGC GWDGGDCSLS VGDPWRQCEA LQCWRLFNNS RCDPACSSPA CLYDNFDCHA GGRERTCNPV YEKYCADHFA DGRCDQGCNT EECGWDGLDC ASEVPALLAR GVLVLTVLLP PEELLRSSAD FLQRLSAILR TSLRFRLDAH GQAMVFPYHR PSPGSEPRAR RELAPEVIGS VVMLEIDNRL CLQSPENDHC FPDAQSAADY LGALSAVERL DFPYPLRDVR GEPLEPPEPS VPLLPLLVAG AVLLLVILVL GVMVARRKRE HSTLWFPEGF SLHKDVASGH KGRREPVGQD ALGMKNMAKG ESLMGEVATD WMDTECPEAK RLKVEEPGMG AEEAVDCRQW TQHHLVAADI RVAPAMALTP PQGDADADGM DVNVRGPDGF TPLMLASFCG GALEPMPTEE DEADDTSASI ISDLICQGAQ LGARTDRTGE TALHLAARYA RADAAKRLLD AGADTNAQDH SGRTPLHTAV TADAQGVFQI LIRNRSTDLD ARMADGSTAL ILAARLAVEG MVEELIASHA DVNAVDELGK SALHWAAAVN NVEATLALLK NGANKDMQDS KEETPLFLAA REGSYEAAKL LLDHFANREI TDHLDRLPRD VAQERLHQDI VRLLDQPSGP RSPPGPHGLG PLLCPPGAFL PGLKAAQSGS KKSRRPPGKA GLGPQGPRGR GKKLTLACPG PLADSSVTLS PVDSLDSPRP FGGPPASPGG FPLEGPYAAA TATAVSLAQL GGPGRAGLGR QPPGGCVLSL GLLNPVAVPL DWARLPPPAP PGPSFLLPLA PGPQLLNPGT PVSPQERPPP YLAVPGHGEE YPAAGAHSSP PKARFLRVPS EHPYLTPSPE SPEHWASPSP PSLSDWSEST PSPATATGAM ATTTGALPAQ PLPLSVPSSL AQAQTQLGPQ PEVTPKRQVL A |
| 12 | Human Notch4 precursor (UniProtKB/Swiss-Prot: Q99466.2) aa 1-23: signal aa 24-2003: mature aa 24-1171: EGF-like repeat domain | MQPPSLLLLL LLLLLLCVSV VRPRGLLCGS FPEPCANGGT CLSLSLGQGT CQCAPGFLGE TCQFPDPCQN AQLCQNGGSC QALLPAPLGL PSSPSPLTPS FLCTCLPGFT GERCQAKLED PCPPSFCSKR GRCHIQASGR PQCSCMPGWT GEQCQLRDFC SANPCVNGGV CLATYPQIQC HCPPGFEGHA CERDVNECFQ DPGPCPKGTS CHNTLGSFQC LCPVGQEGPR CELRAGPCPP RGCSNGGTCQ LMPEKDSTFH LCLCPPGFIG PDCEVNPDNC VSHQCQNGGT CQDGLDTYTC LCPETWTGWD CSEDVDECET QGPPHCRNGG TCQNSAGSFH CVCVSGWGGT SCEENLDDCI AATCAPGSTC IDRVGSFSCL CPPGRTGLLC HLEDMCLSQP CHGDAQCSTN PLTGSTLCLC QPGYSGPTCH QDLDECLMAQ QGPSPCEHGG SCLNTPGSFN CLCPPGYTGS RCEADHNECL SQPCHPGSTC LDLLATFHCL CPPGLEGQLC EVETNECASA PCLNHADCHD LLNGFQCICL PGFSGTRCEE DIDECRSSPC ANGGQCQDQP GAFHCKCLPG FEGPRCQTEV DECLSDPCPV GASCLDLPGA FFCLCPSGFT GQLCEVPLCA PNLCQPKQIC KDQKDKANCL CPDGSPGCAP PEDNCTCHHG HCQRSSCVCD VGWTGPECEA ELGGCISAPC AHGGTCYPQP SGYNCTCPTG YTGPTCSEEM TACHSGPCLN GGSCNPSPGG YYCTCPPSHT GPQCQTSTDY CVSAPCFNGG TCVNRPGTFS CLCAMGFQGP RCEGKLRPSC ADSPCRNRAT CQDSPQGPRC LCPTGYTGGS CQTLMDLCAQ KPCPRNSHCL QTGPSFHCLC LQGWTGPLCN LPLSSCQKAA LSQGIDVSSL CHNGGLCVDS GPSYFCHCPP GFQGSLCQDH VNPCESRPCQ NGATCMAQPS GYLCQCAPGY DGQNCSKELD ACQSQPCHNH GTCTPKPGGF HCACPPGFVG LRCEGDVDEC LDQPCHPTGT AACHSLANAF YCQCLPGHTG QWCEVEIDPC HSQPCFHGGT CEATAGSPLG FICHCPKGFE GPTCSHRAPS CGFHHCHHGG LCLPSPKPGF PPRCACLSGY GGPDCLTPPA PKGCGPPSPC LYNGSCSETT GLGGPGFRCS CPHSSPGPRC QKPGAKGCEG RSGDGACDAG CSGPGGNWDG GDCSLGVPDP WKGCPSHSRC WLLFRDGQCH PQCDSEECLF DGYDCETPPA CTPAYDQYCH DHFHNGHCEK GCNTAECGWD GGDCRPEDGD PEWGPSLALL VVLSPPALDQ QLFALARVLS LTLRVGLWVR KDRDGRDMVY PYPGARAEEK LGGTRDPTYQ ERAAPQTQPL GKETDSLSAG FVVVMGVDLS RCGPDHPASR CPWDPGLLLR FLAAMAAVGA LEPLLGPGLL AVHPHAGTAP PANQLPWPVL CSPVAGVILL ALGALLVLQL IRRRREHGA LWLPPGFTRR PRTQSAPHRR RPPLGEDSIG LKALKPKAEV DEDGVVMCSG PEEGEEVGQA EETGPPSTCQ LWSLSGGCGA LPQAAMLTPP QESEMEAPDL DTRGPDGVTP LMSAVCCGEV QSGTFQGAWL GCPEPWEPLL DGGACPQAHT VGTGETPLHL AARFSRPTAA RRLLEAGANP NQPDRAGRTP LHAAVAADAR EVCQLLLRSR QTAVDARTED GTTPLMLAAR LAVEDLVEEL IAAQADVGAR DKWGKTALHW AAAVNNARAA RSLLQAGADK DAQDNREQTP LFLAAREGAV EVAQLLLGLG AARELRDQAG |

Table of Sequences

| SEQ ID NO | Description | Sequence |
|---|---|---|
| | | LAPADVAHQR NHWDLLTLLE GAGPPEARHK ATPGREAGPF PRARTVSVSV PPHGGGALPR CRTLSAGAGP RGGGACLQAR TWSVDLAARG GGAYSHCRSL SGVGAGGGPT PRGRRFSAGM RGPRPNPAIM RGRYGVAAGR GGRVSTDDWP CDWVALGACG SASNIPIPPP CLTPSPERGS PQLDCGPPAL QEMPINQGGE GKK |
| 13 | Human-Notch1-NRR (uppercase) with Gp67 secretion signal, N-terminal Flag tag, thrombin site C-terminal Flag tag (lower case) | mllvnqshqg fnkehtskmv saivlyvlla aaahsafaad lgsdykdddd kgsgVINGCK GKPCKNGGTC AVASNTARGF ICKCPAGFEG ATCENDARTC GSLRCLNGGT CISGPRSPTC LCLGPFTGPE CQFPASSPCL GGNPCYNQGT CEPTSESPFY RCLCPAKFNG LLCHILDYSF GGGAGRDIPP PLIEEACELP ECQEDAGNKV CSLQCNNHAC GWDGGDCSLN FNDPWKNCTQ SLQCWKYFSD GHCDSQCNSA GCLFDGFDCQ RAEGQCNPLY DQYCKDHFSD GHCDQGCNSA ECEWDGLDCA EHVPERLAAG TLVVVVLMPP EQLRNSSFHH LRELSRVLHT NVVFKRDAHG QQMIFPYYGR EEELRKHPIK RAAEGWAAPD ALLGQVKASL LPGGSEGGRR RRELDPMDVR GSIVYLEIDN RQCVQASSQC FQSATDVAAF LGALASLGSL NIPYKIEAVQ SETVEPPPPA Qefglvprgs ghhhhhh |
| 14 | FLAG-Mouse Notch1 NRR-6His | MGGTAARLGA VILFVVIVGL HGVRGKDYKD DDDKLEVING CRGKPCKNGG VCAVASNTAR GFICRCPAGF EGATCENDAR TCGSLRCLNG GTCISGPRSP TCLCLGSFTG PECQFPASSP CVGSNPCYNQ GTCEPTSENP FYRCLCPAKF NGLLCHILDY SFTGGAGRDI PPPQIEEACE LPECQVDAGN KVCNLQCNNH ACGWDGGDCS LNFNDPWKNC TQSLQCWKYF SDGHCDSQCN SAGCLFDGFD CQLTEGQCNP LYDQYCKDHF SDGHCDQGCN SAECEWDGLD CAEHVPERLA AGTLVLVVLL PPDQLRNNSF HFLRELSHVL HTNVVFKRDA QGGQMIFPYY GHEEELRKHP IKRSTVGWAT SSLLPGTSGG RQRRELDPMD IRGSIVYLEI DNRQCVQSSS QCFQSATDVA AFLGALASLG SLNIPYKIEA VKSEPVEPPL PSQGSGHHHH HH |
| 15 | FLAG-Human-Notch2-NRR-6xHis | KDDDDKGSGD VCPQMPCLNG GTCAVASNMP DGFICRCPPG FSGARCQSSC GQVKCRKGEQ CVHTASGPRC FCPSPRDCES GCASSPCQHG GSCHPQRQPP YYSCQCAPPF SGSRCELYTA PPSTPPATCL SQYCADKARD GVCDEACNSH ACQWDGGDCS LTMENPWANC SSPLPCWDYI NNQCDELCNT VECLFDNFEC QGNSKTCKYD KYCADHFKDN HCNQGCNSEE CGWDGLDCAA DQPENLAEGT LVIVVLMPPE QLLQDARSFL RALGTLLHTN LRIKRDSQGE LMVYPYYGEK SAAMKKQRMT RRSLPGEQEQ EVAGSKVFLE IDNRQCVQDS DHCFKNTDAA AALLASHAIQ GTLSYPLVSV SESSLTPERT EFGLVPRGSG HHHHHH |
| 16 | Mouse Notch2-NRR-FLAG | ADVCPQKPCL NGGTCAVASN MPDGFICRCP PGFSGARCQS SCGQVKCRRG EQCIHTDSGP RCFCLNPKDC ESGCASNPCQ HGGTCYPQRQ PPHYSCRCPP SFGGSHCELY TAPTSTPPAT CQSQYCADKA RDGICDEACN SHACQWDGGD CSLTMEDPWA NCTSTLRCWE YINNQCDEQC NTAECLFDNF ECQRNSKTCK YDKYCADHFK DNHCDQGCNS EECGWDGLDC ASDQPENLAE GTLIIVVLLP PEQLLQDSRS FLRALGTLLH TNLRIKQDSQ GALMVYPYFG EKSAAMKKQK MTRRSLPEEQ EQEQEVIGSK IFLEIDNRQC VQDSDQCFKN TDAAAALLAS HAIQGTLSYP LVSVFSELES PRNARRAGSG DYKDDDDKEN LYFQ |
| 17 | Human DLL1, precursor UniProtKB/ Swiss-Prot: O00548.2 | MGSRCALALA VLSALLCQVW SSGVFELKLQ EFVNKKGLLG NRNCCRGGAG PPPCACRTFF RVCLKHYQAS VSPEPPCTYG SAVTPVLGVD SFSLPDGGGA DSAFSNPIRF PFGFTWPGTF SLIIEALHTD SPDDLATENP ERLISRLATQ RHLTVGEEWS QDLHSSGRTD LKYSYRFVCD EHYYGEGCSV FCRPRDDAFG HFTCGERGEK VCNPGWKGPY CTEPICLPGC DEQHGFCDKP GECKCRVGWQ GRYCDECIRY PGCLHGTCQQ PWQCNCQEGW GGLFCNQDLN YCTHHKPCKN GATCTNTGQG SYTCSCRPGY TGATCELGID ECDPSPCKNG GSCTDLENSY SCTCPPGFYG KICELSAMTC ADGPCFNGGR CSDSPDGGYS CRCPVGYSGF NCEKKIDYCS SSPCSNGAKC VDLGDAYLCR CQAGFSGRHC DDNVDDCASS PCANGGTCRD GVNDFSCTCP PGYTGRNCSA PVSRCEHAPC HNGATCHERG HRYVCECARG YGGPNCQFLL PELPPGPAVV DLTEKLEGQG GPFPWVAVCA GVILVLMLLL GCAAVVVCVR LRLQKHRPPA DPCRGETETM NNLANCQREK DISVSIIGAT QIKNTNKKAD FHGDHSADKN GFKARYPAVD YNLVQDLKGD DTAVRDAHSK RDTKCQPQGS SGEEKGTPTT LRGGEASERK RPDSGCSTSK DTKYQSVYVI SEEKDECVIA TEV |
| 18 | Human DLL4, precursor UniProtKB/ Swiss-Prot: Q9NR61.1 | MAAASRSASG WALLLLVALW QQRAAGSGVF QLQLQEFINE RGVLASGRPC EPGCRTFFRV CLKHFQAVVS PGPCTFGTVS TPVLGTNSFA VRDDSSGGGR NPLQLPFNFT WPGTFSLIIE AWHAPGDDLR PEALPPDALI SKIAIQGSLA VGQNWLLDEQ TSTLTRLRYS YRVICSDNYY GDNCSRLCKK RNDHFGHYVC QPDGNLSCLP GWTGEYCQQP ICLSGCHEQN GYCSKPAECL CRPGWQGRLC NECIPHNGCR HGTCSTPWQC TCDEGWGGLF CDQDLNYCTH HSPCKNGATC SNSGQRSYTC TCRPGYTGVD CELELSECDS NPCRNGGSCK DQEDGYHCLC PPGYYGLHCE HSTLSCADSP CFNGGSCRER NQGANYACEC PPNFTGSNCE KKVDRCTSNP CANGGQCLNR GPSRMCRCRP GFTGTYCELH VSDCARNPCA |

Table of Sequences

| SEQ ID NO | Description | Sequence |
|---|---|---|
| | | HGGTCHDLEN GLMCTCPAGF SGRRCEVRTS IDACASSPCF NRATCYTDLS<br>TDTFVCNCPY GFVGSRCEFP VGLPPSFPWV AVSLGVGLAV LLVLLGMVAV<br>AVRQLRLRRP DDGSREAMNN LSDFQKDNLI PAAQLKNTNQ KKELEVDCGL<br>DKSNCGKQQN HTLDYNLAPG PLGRGTMPGK FPHSDKSLGE KAPLRLHSEK<br>PECRISAICS PRDSMYQSVC LISEERNECV IATEV |
| 19 | Human Frizzled7 (Fzd7), precursor UniProtKB/ Swiss-Prot: O75084.2 | MRDPGAAAPL SSLGLCALVL ALLGALSAGA GAQPYHGEKG ISVPDHGFCQ<br>PISIPLCTDI AYNQTILPNL LGHTNQEDAG LEVHQFYPLV KVQCSPELRF<br>FLCSMYAPVC TVLDQAIPPC RSLCERARQG CEALMNKFGF QWPERLRCEN<br>FPVHGAGEIC VGQNTSDGSG GPGGGPTAYP TAPYLPDLPF TALPPGASDG<br>RGRPAFPFSC PRQLKVPPYL GYRFLGERDC GAPCEPGRAN GLMYFKEEER<br>RFARLWVGVW SVLCCASTLF TVLTYLVDMR RFSYPERPII FLSGCYFMVA<br>VAHVAGFLLE DRAVCVERFS DDGYRTVAQG TKKEGCTILF MVLYFFGMAS<br>SIWWVILSLT WFLAAGMKWG HEAIEANSQY FHLAAWAVPA VKTITILAMG<br>QVDGDLLSGV CYVGLSSVDA LRGFVLAPLF VYLFIGTSFL LAGFVSLFRI<br>RTIMKHDGTK TEKLEKLMVR IGVFSVLYTV PATIVLACYF YEQAFREHWE<br>RTWLLQTCKS YAVPCPPGHF PPMSPDFTVF MIKYLMTMIV GITTGFWIWS<br>GKTLQSWRRF YHRLSHSSKG ETAV |
| 20 | Human Frizzled8 (Fzd8), precursor UniProtKB/ Swiss-Prot: Q9H461.1 | MEWGYLLEVT SLLAALALLQ RSSGAAAASA KELACQEITV PLCKGIGYNY<br>TYMPNQFNHD TQDEAGLEVH QFWPLVEIQC SPDLKFFLCS MYTPICLEDY<br>KKPLPPCRSV CERAKAGCAP LMRQYGFAWP DRMRCDRLPE QGNPDTLCMD<br>YNRTDLTTAA PSPPRRLPPP PPGEQPPSGS GHGRPPGARP PHRGGGRGGG<br>GGDAAAPPAR GGGGGGKARP PGGGAAPCEP GCQCRAPMVS VSSERHPLYN<br>RVKTGQIANC ALPCHNPFFS QDERAFTVFW IGLWSVLCFV STFATVSTFL<br>IDMERFKYPE RPIIFLSACY LFVSVGYLVR LVAGHEKVAC SGGAPGAGGA<br>GGAGGAAAGA GAAGAGAGGP GGRGEYEELG AVEQHVRYET TGPALCTVVF<br>LLVYFFGMAS SIWWVILSLT WFLAAGMKWG NEAIAGYSQY FHLAAWLVPS<br>VKSIAVLALS SVDGDPVAGI CYVGNQSLDN LRGFVLAPLV IYLFIGTMFL<br>LAGFVSLFRI RSVIKQQDGP TKTHKLEKLM IRLGLFTVLY TVPAAVVVAC<br>LFYEQHNRPR WEATHNCPCL RDLQPDQARR PDYAVFMLKY FMCLVVGITS<br>GVWWSGKTL ESWRSLCTRC CWASKGAAVG GGAGATAAGG GGGPGGGGGG<br>GPGGGGGPGG GGGSLYSDVS TGLTWRSGTA SSVSYPKQMP LSQV |
| 21 | Human LRP5, precursor UniProtKB/ Swiss-Prot: O75197.2 | MEAAPPGPPW PLLLLLLLLL ALCGCPAPAA ASPLLLFANR RDVRLVDAGG<br>VKLESTIVVS GLEDAAAVDF QFSKGAVYWT DVSEEAIKQT YLNQTGAAVQ<br>NVVISGLVSP DGLACDWVGK KLYWTDSETN RIEVANLNGT SRKVLFWQDL<br>DQPRAIALDP AHGYMYWTDW GETPRIERAG MDGSTRKIIV DSDIYWPNGL<br>TIDLEEQKLY WADAKLSFIH RANLDGSFRQ KVVEGSLTHP FALTLSGDTL<br>YWTDWQTRSI HACNKRTGGK RKEILSALYS PMDIQVLSQE RQPFFHTRCE<br>EDNGGCSHLC LLSPSEPFYT CACPTGVQLQ DNGRTCKAGA EEVLLLARRT<br>DLRRISLDTP DFTDIVLQVD DIRHAIAIDY DPLEGYVYWT DDEVRAIRRA<br>YLDGSGAQTL VNTEINDPDG IAVDWVARNL YWTDTGTDRI EVTRLNGTSR<br>KILVSEDLDE PRAIALHPVM GLMYWTDWGE NPKIECANLD GQERRVLVNA<br>SLGWPNGLAL DLQEGKLYWG DAKTDKIEVI NVDGTKRRTL LEDKLPHIFG<br>FTLLGDFIYW TDWQRRSIER VHKVKASRDV IIDQLPDLMG LKAVNVAKVV<br>GTNPCADRNG GCSHLCFFTP HATRCGCPIG LELLSDMKTC IVPEAFLVFT<br>SRAAIHRISL ETNNNDVAIP LTGVKEASAL DFDVSNNHIY WTDVSLKTIS<br>RAFMNGSSVE HVVEFGLDYP EGMAVDWMGK NLYWADTGTN RIEVARLDGQ<br>FRQVLVWRDL DNPRSLALDP TKGYIYWTEW GGKPRIVRAF MDGTNCMTLV<br>DKVGRANDLT IDYADQRLYW TDLDTNMIES SNMLGQERVV IADDLPHPFG<br>LTQYSDYIYW TDWNLHSIER ADKTSGRNRT LIQGHLDFVM DILVFHSSRQ<br>DGLNDCMHNN GQCGQLCLAI PGGHRCGCAS HYTLDPSSRN CSPPTTFLLF<br>SQKSAISRMI PDDQHSPDLI LPLHGLRNVK AIDYDPLDKF IYWVDGRQNI<br>KRAKDDGTQP FVLTSLSQGQ NPDRQPHDLS IDIYSRTLFW TCEATNTINV<br>HRLSGEAMGV VLRGDRDKPR AIVVNAERGY LYFTNMQDRA AKIERAALDG<br>TEREVLFTTG LIRPVALVVD NTLGKLFWVD ADLKRIESCD LSGANRLTLE<br>DANIVQPLGL TILGKHLYWI DRQQQMIERV EKTTGDKRTR IQGRVAHLTG<br>IHAVEEVSLE EFSAHPCARD NGGCSHICIA KGDGTPRCSC PVHLVLLQNL<br>LTCGEPPTCS PDQFACATGE IDCIPGAWRC DGFPECDDQS DEEGCPVCSA<br>AQFPCARGQC VDLRLRCDGE ADCQDRSDEA DCDAICLPNQ FRCASGQCVL<br>IKQQCDSFPD CIDGSDELMC EITKPPSDDS PAHSSAIGPV IGIILSLFVM<br>GGVYFVCQRV VCQRYAGANG PFPHEYVSGT PHVPLNFIAP GGSQHGPFTG<br>IACGKSMMSS VSLMGGRGGV PLYDRNHVTG ASSSSSSSTK ATLYPPILNP<br>PPSPATDPSL YNMDMFYSSN IPATARPYRP YIIRGMAPPT TPCSTDVCDS<br>DYSASRWKAS KYYLDLNSDS DPYPPPPTPH SQYLSAEDSC PPSPATERSY<br>FHLFPPPPSP CTDSS |
| 22 | Human LRP6, precursor UniProtKB/ Swiss-Prot: O75581.2 | MGAVLRSLLA CSFCVLLRAA PLLLYANRRD LRLVDATNGK ENATIVVGGL<br>EDAAAVDFVF SHGLIYWSDV SEEAIKRTEF NKTESVQNVV VSGLLSPDGL<br>ACDWLGEKLY WTDSETNRIE VSNLDGSLRK VLFWQELDQP RAIALDPSSG<br>FMYWTDWGEV PKIERAGMDG SSRFIIINSE IYWPNGLTLD YEEQKLYWAD<br>AKLNFIHKSN LDGTNRQAVV KGSLPHPFAL TLFEDILYWT DWSTHSILAC |

-continued

Table of Sequences

| SEQ ID NO | Description | Sequence |
|---|---|---|
| | | NKYTGEGLRE IHSDIFSPMD IHAFSQQRQP NATNPCGIDN GGCSHLCLMS PVKPFYQCAC PTGVKLLENG KTCKDGATEL LLLARRTDLR RISLDTPDFT DIVLQLEDIR HAIAIDYDPV EGYIYWTDDE VRAIRRSFID GSGSQFVVTA QIAHPDGIAV DWVARNLYWT DTGTDRIEVT RLNGTMRKIL ISEDLEEPRA IVLDPMVGYM YWTDWGEIPK IERAALDGSD RVVLVNTSLG WPNGLALDYD EGKIYWGDAK TDKIEVMNTD GTGRRVLVED KIPHIFGFTL LGDYVYWTDW QRRSIERVHK RSAEREVIID QLPDLMGLKA TNVHRVIGSN PCAEENGGCS HLCLYRPQGL RCACPIGFEL ISDMKTCIVP EAFLLFSRRA DIRRISLETN NNNVAIPLTG VKEASALDFD VTDNRIYWTD ISLKTISRAF MNGSALEHVV EFGLDYPEGM AVDWLGKNLY WADTGTNRIE VSKLDGQHRQ VLVWKDLDSP RALALDPAEG FMYWTEWGGK PKIDRAAMDG SERTTLVPNV GRANGLTIDY AKRRLYWTDL DTNLIESSNM LGLNREVIAD DLPHPFGLTQ YQDYIYWTDW SRRSIERANK TSGQNRTIIQ GHLDYVMDIL VFHSSRQSGW NECASSNGHC SHLCLAVPVG GFVCGCPAHY SLNADNRTCS APTTFLLFSQ KSAINRMVID EQQSPDIILP IHSLRNVRAI DYDPLDKQLY WIDSRQNMIR KAQEDGSQGF TVVVSSVPSQ NLEIQPYDLS IDIYSRYIYW TCEATNVINV TRLDGRSVGV VLKGEQDRPR AVVVNPEKGY MYFTNLQERS PKIERAALDG TEREVLFFSG LSKPIALALD SRLGKLFWAD SDLRRIESSD LSGANRIVLE DSNILQPVGL TVFENWLYWI DKQQQMIEKI DMTGREGRTK VQARIAQLSD IHAVKELNLQ EYRQHPCAQD NGGCSHICLV KGDGTTRCSC PMHLVLLQDE LSCGEPPTCS PQQFTCFTGE IDCIPVAWRC DGFTECEDHS DELNCPVCSE SQFQCASGQC IDGALRCNGD ANCQDKSDEK NCEVLCLIDQ FRCANGQCIG KHKKCDHNVD CSDKSDELDC YPTEEPAPQA TNTVGSVIGV IVTIFVSGTV YFICQRMLCP RMKGDGETMT NDYVVHGPAS VPLGYVPHPS SLSGSLPGMS RGKSMISSLS IMGGSSGPPY DRAHVTGASS SSSSSTKGTY FPAILNPPPS PATERSHYTM EFGYSSNSPS THRSYSYRPY SYRHFAPPTT PCSTDVCDSD YAPSRRMTSV ATAKGYTSDL NYDSEPVPPP PTPRSQYLSA EENYESCPPS PYTERSYSHH LYPPPPSPCT DSS |
| 23 | Anti-Notch1 antibody 52M51 heavy chain variable region | QVQLQQSGAE LMKPGASVKI SCKAAGYTMR GYWIEWIKQR PGHGLEWIGQ ILPGTGRTNY NEKFKGKATF TADTSSNTAN MQLSSLTSED SAVYYCARFD GNYGYYAMDY WGQGSSVTVS SA |
| 24 | 52M51 light chain variable region | QAVVTQESAL TTSPGETVTL TCRSSTGAVT TSNYANWVQE KPDHLFTGLI GGTNNRAPGV PARFSGSLIG DKAALTITGA QTEDEAIYFC ALWYSNHWVF GGGTKLTVLG |
| 25 | 52M51H4L3 heavy chain variable region | QVQLVQSGAE VKKPGASVKI SCKVSGYTLR GYWIEWVRQA PGKGLEWIGQ ILPGTGRTNY NEKFKGRVTM TADTSTDTAY MELSSLRSED TAVYYCARFD GNYGYYAMDY WGQGTTVTVS SA |
| 26 | 52M51H4L3 light chain variable region | SGVDSQAVVT QEPSLTVSPG GTVTLTCRSS TGAVTTSNYA NWFQQKPGQA PRTLIGGTNN RAPGVPARFS GSLLGGKAAL TLSGAQPEDE AEYYCALWYS NHWVFGGGTK LTVLG |
| 27 | 52M51 HVR-H1 | RGYWIE |
| 28 | 52M51 HVR-H2 | QILPGTGRTNYNEKFKG |
| 29 | 52M51 HVR-H3 | FDGNYGYYAMDY |
| 30 | 52M51 HVR-L1 | RSSTGAVTTSNYAN |
| 31 | 52M51 HVR-L2 | GTNNRAP |
| 32 | 52M51 HVR-L3 | ALWYSNHWVFGGGTKL |
| 33 | Anti-Notch2/3 antibody 59R5 heavy chain variable region | EVQLVESGGG LVQPGGSLRL SCAASGFTFS SSGMSWVRQA PGKGLEWVSV IASSGSNTYY ADSVKGRFTI SRDNSKNTLY LQMNSLRAED TAVYYCARSI FYTTWGQGTL VTVSS |
| 34 | 59R5 light chain variable region | DIVLTQSPAT LSLSPGERAT LSCRASQSVR SNYLAWYQQK PGQAPRLLIY GASSRATGVP ARFSGSGSGT DFTLTISSLE PEDFAVYYCQ QYSNFPITFG QGTKVEIKR |
| 35 | 59R5 HVR-H1 | SSSGMS |
| 36 | 59R5 HVR-H2 | VIASSGSNTYYADSVK |
| 37 | 59R5 HVR-H3 | SIFYTT |

-continued

| Table of Sequences | | |
|---|---|---|
| SEQ ID NO | Description | Sequence |
| 38 | 59R5 HVR-L1 | RASQSVRSNYL |
| 39 | 59R5 HVR-L2 | GASSRA |
| 40 | 59R5 HVR-L3 | QQYSNFPI |
| 41 | Anti-Notch1 A-2 antibody heavy chain variable region | EVQLVESGGG LVQPGGSLRL SCAASGFTFS SYWIHWVRQA PGKGLEWVAR INPPNRSNQY ADSVKGRFTI SADTSKNTAY LQMNSLRAED TAVYYCARGS GFRWVMDYWG QGTLVTVSS |
| 42 | A-2 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ FYTTPSTFGQ GTKVEIKR |
| 43 | A, A-1, A-2, A-3 HVR-H1 | GFTFSSYWIH |
| 44 | A HVR-H2 | ARINPSNGSTNYADSVKG |
| 45 | A-1 HVR-H2 | ARINPSNGSAHYADSVKG |
| 46 | A-2 HVR-H2 | ARINPSNRSNQYADSVKG |
| 47 | A-3 HVR-H2 | ARINPSNGSTRYADSVKG |
| 48 | A, A-1, A-2, A-3 HVR-H3 | RGSGFRWVMDY |
| 49 | A, A-1, A-2, A-3 HVR-L1 | RASQDVSTAVA |
| 50 | A, A-1, A-2, A-3 HVR-L2 | SASFLYS |
| 51 | A HVR-L3 | QQSYTTPPT |
| 52 | A-1 HVR-L3 | QQSYTTPAT |
| 53 | A-2 HVR-L3 | QQFYTTPST |
| 54 | A-3 HVR-L3 | QQSFSTPAT |
| 55 | Anti-Notch2 D-3 antibody heavy chain variable region | EVQLVESGGG LVQPGGSLRL SCAASGYTFS SYGMSWVRQA PGKGLEWVSY IYPYSGATYY ADSVKGRFTI SADTSKNTAY LQMNSLRAED TAVYYCARHS GYYRISSAMD VWGQGTLVTV SA |
| 56 | D-3 light chain variable region | DIQMTQSPSS LSASVGDRVT ITCRASQNIK RFLAWYQQKP GKAPKLLIYG ASTRESGVPS RFSGSGSGTD FTLTISSLQP EDFATYYCQQ YYRSPHTFGQ GTKVEIKR |
| 57 | D HVR-H1 | GYSFTSYGMS |
| 58 | D-1, D-2, D-3 HVR-H1 | GYTFSSYGMS |
| 59 | D, D-1, D-2, D-3 HVR-H2 | SYIYPYSGATYYADSVKG |
| 60 | D, D-1, D-2, D-3 HVR-H3 | HSGYYRISSAMDV |
| 61 | D HVR-L1 | RASQSISSYLA |
| 62 | D-1 HVR-L1 | RASQSNRRFLA |
| 63 | D-2 HVR-L1 | RASQSVRSFLA |
| 64 | D-3 HVR-L1 | RASQNIKRFLA |
| 65 | D, D-1 HVR-L2 | GASSRAS |

-continued

| Table of Sequences | | |
|---|---|---|
| SEQ ID NO | Description | Sequence |
| 66 | D-2 HVR-L2 | RASIRAS |
| 67 | D-3 HVR-L2 | GASTRES |
| 68 | D HVR-L3 | QQYYSSPLT |
| 69 | D-1 HVR-L3 | QQYYISPLT |
| 70 | D-2 HVR-L3 | QQYYISPWT |
| 71 | D-3 HVR-L3 | QQYYRSPHT |
| 72 | Anti-Notch3 NRR 256-A4 antibody heavy chain variable region | EVQLVESGGG LVQPGGSLKL SCAASGFTFS HYYMSWVRQT PEKRLEWVAY ISNGGGRTDY PDSVKGRFTI SRDNAKNTLH LQMSSLKSED TAMYYCTRLD YFGGSPYFDY WGQGTTLTVS SA |
| 73 | 256-A4 light chain variable region | EIVLTQSPAI TAASLGQKVT ITCSASSSVS YMHWYQQKSG TSPKPWIYEI SKLASGVPPR FSGSGSGTSY SLTISSMEAE DAAIYYCQQW NYPLITFGSG TKLEIKRADA APTV |
| 74 | 256-A4, 256-A8 HVR-H1 | GFTFSHYYMS |
| 75 | 256-A4 HVR-H2 | ISNGGGRTD |
| 76 | 256-A8 HVR-H2 | YINSGGGRTD |
| 77 | 256-A4 HVR-H3 | RLDYFGGSPYFDY |
| 78 | 256-A8 HVR-H3 | LDYYGGSPYFDY |
| 79 | 256-A4, 256-A8 HVR-L1 | SASSSVSYMH |
| 80 | 256-A4, 256-A8 HVR-L2 | EISKLAS |
| 81 | 256-A4, 256-A8 HVR-L3 | QQWNYPLIT |
| 82 | Anti-Notch3 255A-71 antibody heavy chain variable region | SDVQLQESGP GLVKPSQSLS LTCSVTGYSI TSGYYWNWIR QFPGNKLEWM GFISYDGSNN YNPSLKNRIS ITRDTSKNQF FLKLNSVTTE DTATFYCATL YYDYDGNYFD YWGQGTTLTV SSA |
| 83 | 255A-71 light chain variable region | CDIQMTQTTS SLSASLGDRV TISCRTSQDI SNYLNWYQQK PDGTVKLLIY YTSRLHSGVP SRFSGSGSGT DYSLTISNLE QEDIATYFCQ QGNALPLTFG PGTKLELKRA DAAPTV |
| 84 | 255A-71 HVR-H1 | GYSITSGYYWNW |
| 85 | 255A-71 HVR-H2 | ISYDGSNNYN |
| 86 | 255A-71 HVR-H3 | LYYDYDGNYFDY |
| 87 | 255A-71 HVR-L1 | RTSQDISNYLN |
| 88 | 255A-71 HVR-L2 | YTSRLHS |
| 89 | 255A-71 HVR-L3 | QQGNALPT |
| 90 | Anti-Notch3 255A-77 antibody heavy chain variable region | CQVQLQQSGD DLVKPGASVK LSCKASGYTF TSYWINWIKQ RPGQGLEWIG HIGPGSGSTY YNEIFKGKAT LTVDTSSSTA YIQLSSLSSE DSAVYFCVLT RYFYAMDYWG QGTSVTVSSA |
| 91 | 255A-77 light chain variable region | DIVMTQSPSS LAVTAGEKVT MRCKSSQSLL WSVNQNNYLS WYQQKGQPP KLLIYGASIR ESWVPDRFTG SGSGTDFTLT ISNVHVEDLA VYYCQHNHGS FLPLTFGAGT KLELKRADAA PTV |

-continued

| Table of Sequences | | |
|---|---|---|
| SEQ ID NO | Description | Sequence |
| 92 | 255A-77 HVR-H1 | GYTFTSYWIN |
| 93 | 255A-77 HVR-H2 | HIGPGSGSTYYN |
| 94 | 255A-77 HVR-H3 | TRYFYAMDY |
| 95 | 255A-77 HVR-L1 | KSSQSLLWSVNQNNYL |
| 96 | 255A-77 HVR-L2 | GASIRES |
| 97 | 255A-77 HVR-L3 | QHNHGSFLPLT |
| 98 | Anti-Notch3 256-A13 antibody heavy chain variable region | SQVQLQQSGA ELAKPGTSVK MACKASGYTF TTHWMNWVKQ RPGQGLEWIG TINPSNDFTD CNQKFKDKAI LTADKSSSTA YMQLSSLTSE DSAIYYCASG LTARAWFAYW GQGTLVTVSA A |
| 99 | 256-A13 light chain variable region | RATISCRASQ SVTTSNYSYM HWFQQKPGQP PKLLIKYASN LDSGVPARFS GSGSGTDFTL NIHPVEEEDT ATFYCQHSWE IPYTFGGGTN LEIKRADAAP TV |
| 100 | 256-A13 HVR-H1 | GYTFTTHWMNW |
| 101 | 256-A13 HVR-H2 | INPSNDFTDCN |
| 102 | 256-A13 HVR-H3 | TARAWFAY |
| 103 | 256-A13 HVR-L1 | RASQSVTTSNYSYMH |
| 104 | 256-A13 HVR-L2 | YASNLDSG |
| 105 | 256-A13 HVR-L3 | QHSWEIPYT |
| 106 | Anti-Jagged A-2 antibody heavy chain variable region | EVQLVESGGG LVQPGGSLRL SCAASGFTFS NYGIHWVRQA PGKGLEWVGW ITGNGGYSDY ADSVKGRFTI SADTSKNTAY LQMNSLRAED TAVYYCARAG SWFAYWGQGT LVTVSS |
| 107 | Anti-Jagged A-2 antibody light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIK |
| 108 | Anti-Jagged A-2 HVR-H1 | GFTFSNYGIH |
| 109 | Anti-Jagged A-2 HVR-H2 | WITGNGGYSDYADSVKG |
| 110 | Anti-Jagged A-2 HVR-H3 | AGSWFAY |
| 111 | Anti-Jagged A-2 HVR-L1 | RASQDVSTAVA |
| 112 | Anti-Jagged A-2 HVR-L2 | SASFLYS |
| 113 | Anti-Jagged A-2 HVR-L3 | QQSYTTPPT |
| 114 | Anti-Jagged B-3 antibody heavy chain variable region | EVQLVESGGG LVQPGGSLRL SCAASGFTFT SYDIHWVRQA PGKGLEWVGG ISPADGDTDY ANSVKGRFTI SADTSKNTAY LQMNSLRAED TAVYYCARND YDVRFVGSGM DYWGQGTLVT VSS |
| 115 | Anti-Jagged B-3 antibody light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SFTAPPTFGQ GTKVEIK |

Table of Sequences

| SEQ ID NO | Description | Sequence |
|---|---|---|
| 116 | Anti-Jagged B-3 HVR-H1 | GFTFTSYDIH |
| 117 | Anti-Jagged B-3 HVR-H2 | GISPADGDTDYANSVKG |
| 118 | Anti-Jagged B-3 HVR-H3 | NDYDVRFVGSGMDY |
| 119 | Anti-Jagged B-3 HVR-L1 | RASQDVSTAVA |
| 120 | Anti-Jagged B-3 HVR-L2 | SASFLYS |
| 121 | Anti-Jagged B-3 HVR-L3 | QQSFTAPPT |
| 122 | Anti-Jagged C1 antibody heavy chain variable region | EVQLVESGGG LVQPGGSLRL SCAASGFTFT NSDIHWVRQA PGKGLEWVGG ITPADGYTDY ADSVKGRFTI SADTSKNTAY LQMNSLRAED TAVYYCARSY WSSSPGSAFD YWGQGTLVTV SS |
| 123 | Anti-Jagged C1 antibody light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYISPSTFGQ GTKVEIK |
| 124 | Anti-Jagged C1 HVR-H1 | GFTFTNSDIH |
| 125 | Anti-Jagged C1 HVR-H2 | GITPADGYTDYADSVKG |
| 126 | Anti-Jagged C1 HVR-H3 | SYWSSSPGSAFDY |
| 127 | Anti-Jagged C1 HVR-L1 | RASQDVSTAVA |
| 128 | Anti-Jagged C1 HVR-L2 | SASFLYS |
| 129 | Anti-Jagged C1 HVR-L3 | QQSYISPST |
| 130 | Anti-Jagged 4D11 antibody heavy chain variable region | EVQLLESGGG LVQPGGSLRL SCAASGFTFS SYAMSWVRQA PGKGLEWVSS IDPEGRQTYY ADSVKGRFTI SRDNSKNTLY LQMNSLRAED TAVYYCAKDI GGRSAFDYWG QGTLVTVSS |
| 131 | 4D11 light chain variable region | DIQMTQSPSS LSASVGDRVT ITCRASQSIS SYLNWYQQKP GKAPKLLIYA ASSLQSGVPS RFSGSGSGTD FTLTISSLQP EDFATYYCQQ TVVAPPLFGQ GTKVEIKR |
| 132 | Anti-Jagged 64R7 antibody heavy chain variable region | QVQLVESGGG VVQPGRSLRL SCAASGFTFS SYAMHWVRQA PGKGLEWVAV ISYDGSNKYY ADSVKGRFTI SRDNSKNTLY LQMNSLRAED TAVYYCARDK YDIPDAFDIW GQGTLVTVSS |
| 133 | 64R7 antibody light chain variable region | DIRMTQSPSS LSASVGDRVT ITCRASQGIS NDLAWYQQKP GKVPRLLIYA TSTLQSGVPS RFSGSGSATD FTLTISSLQP EDVATYYCQQ SYNAPITFGQ GTRLEIK |
| 134 | 64R7 HVR-H1 | SYAMH |
| 135 | 6487 HVR-H2 | VISYDGSNKYYADSVKG |
| 136 | 64R7 HVR-H3 | DKYDIPDAFDI |
| 137 | 64R7 HVR-L1 | RASQGISNDLA |
| 138 | 64R7 HVR-L2 | ATSTLQS |

Table of Sequences

| SEQ ID NO | Description | Sequence |
|---|---|---|
| 139 | 64R7 HVR-L3 | QQSYNAPI |
| 140 | Anti-Jagged 133R0201 antibody heavy chain variable region | QVQLVESGGG VVQPGRSLRL SCAASGFTFS SYAMHWVRQA PGKGLEWVAA IYPDSSNKYY ADSVKGRFTI SRDNSKNTLY LQMNSLRAED TAVYYCARDK YDIPDAFDIW GQGTLVTVS |
| 141 | Anti-Jagged 133R0201 antibody light chain variable region | DIRMTQSPSS LSASVGDRVT ITCRASQGIS NDLAWYQQKP GKVPRLLIYA TSTLQSGVPS RFSGSGSATD FTLTISSLQP EDVATYYCQQ SYNAPITFGQ GTRLEIK |
| 142 | 133R0201 HVR-H1 | SYAMH |
| 143 | 133R0201 HVR-H2 | AIYPDSSNKYYADSVKG |
| 144 | 133R0201 HVR-H3 | DKYDIPDAFDI |
| 145 | 133R0201 HVR-L1 | RASQGISNDLA |
| 146 | 133R0201 HVR-L2 | ATSTLQS |
| 147 | 133R0201 HVR-L3 | QQSYNAPI |
| 148 | Anti-Jagged 133R0203 antibody heavy chain variable region | QVQLVESGGG VVQPGRSLRL SCAASGFTFS SYAMHWVRQA PGKGLEWVAA ISPEASNKYY ADSVKGRFTI SRDNSKNTLY LQMNSLRAED TAVYYCARDK YDIPDAFDIW GQGTLVTVS |
| 149 | Anti-Jagged 133R0203 antibody light chain variable region | DIRMTQSPSS LSASVGDRVT ITCRASQGIS NDLAWYQQKP GKVPRLLIYA TSTLQSGVPS RFSGSGSATD FTLTISSLQP EDVATYYCQQ SYNAPITFGQ GTRLEIK |
| 150 | 133R0203 HVR-H1 | SYAMH |
| 151 | 133R0203 HVR-H2 | AISPEASNKYYADSVKG |
| 152 | 133R0203 HVR-H3 | DKYDIPDAFDI |
| 153 | 133R0203 HVR-L1 | RASQGISNDLA |
| 154 | 133R0203 HVR-L2 | ATSTLQS |
| 155 | 133R0203 HVR-L3 | QQSYNAPI |
| 156 | Anti-Jagged 133R0205 antibody heavy chain variable region | QVQLVESGGG VVQPGRSLRL SCAASGFTFS SYAMHWVRQA PGKGLEWVAA IYPASSNKYY ADSVKGRFTI SRDNSKNTLY LQMNSLRAED TAVYYCARDK YDIPDAFDIW GQGTLVTVS |

| SEQ ID NO | Description | Sequence |
|---|---|---|
| 157 | Anti-Jagged 133R0205 antibody light chain variable region | DIRMTQSPSS LSASVGDRVT ITCRASQGIS NDLAWYQQKP GKVPRLLIYA TSTLQSGVPS RFSGSGSATD FTLTISSLQP EDVATYYCQQ SYNAPITFGQ GTRLEIK |
| 158 | 133R0205 HVR-H1 | SYAMH |
| 159 | 133R0205 HVR-H2 | AIYPASSNKYYADSVKG |
| 160 | 133R0205 HVR-H3 | DKYDIPDAFDI |
| 161 | 133R0205 HVR-L1 | RASQGISNDLA |
| 162 | 133R0205 HVR-L2 | ATSTLQS |
| 163 | 133R0205 HVR-L3 | QQSYNAPI |
| 164 | Anti-Jagged 64M51 antibody heavy chain variable region | QVQLKQSGAE LVRPGTSVKL SCKTSGYIFT SYWIHWVKQR SGQGLEWIAR IYPGIGSTYY NEKFKDKATL TADKSSSTAY MQLSSLKSED SAVYFCAKNG GFFDYWGQGT TLTVSS |
| 165 | Anti-Jagged 64M51 antibody light chain variable region | DIVLTQSPAS LAVSLGQRAT ISCRASESVD SYGNSFMHWY QQKPGQPPKL LIYRASNLES GIPARFSGSG SRTDFTLTIN PVEADDVATY YCQQSNEDPW TFGGGTKLEI K |
| 166 | 64M51 HVR-H1 | SYNTH |
| 167 | 64M51 HVR-H2 | RIYPGIGSTYYNEKFKD |
| 168 | 64M51 HVR-H3 | NGGFFDY |
| 169 | 64M51 HVR-L1 | RASESVDSYGNSFMH |
| 170 | 64M51 HVR-L2 | RASNLES |
| 171 | 64M51 HVR-L3 | QQSNDPWT |
| 172 | Anti-Jagged 64R1B antibody heavy chain variable region | QVQLQESGPG LVKPSGTLSL TCTVSGDSIS SSNWWSWVRQ PPGQGLEWIG EIFHGENTNY NPSLKSRVTI SVDKSKNQIS LNLTSATAAD TAVYYCARNP GIGAAKFDSW GQGTLVTVSS |
| 173 | Anti-Jagged 64R1B antibody light chain variable region | DIVMTQTPLS LSVTPGQPAS ISCKSSQSLL HSDGKTYLYW YLQKPGQPPQ LLIYEVSNRF SGVPDRFSGS GSGTDFTLKI SRVEAEDVGV YYCMQHIDFP FTFGQGTKLE IK |
| 174 | 64R1B HVR-H1 | SSNWWS |
| 175 | 64R1B HVR-H2 | EIFHGENTNYNPSLKS |
| 176 | 64R1B HVR-H3 | NPGIGAAKFDS |
| 177 | 64R1B HVR-L1 | KSSQSLLHSDGKTYLY |
| 178 | 64M51 HVR-L2 | EVSNRFS |
| 179 | 64M51 HVR-L3 | MQHIDFP |
| 180 | Anti-DLL4 antibody YW26.82 heavy chain variable region | EVQLVESGGG LVQPGGSLRL SCAASGFTFT DNWISWVRQA PGKGLEWVGY ISPNSGFTYY ADSVKGRFTI SADTSKNTAY LQMNSLRAED TAVYYCARDN FGGYFDYWGQ GTLV |

Table of Sequences

| SEQ ID NO | Description | Sequence |
|---|---|---|
| 181 | YW26.82 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTGTVTFGQ GTKVEIKR |
| 182 | YW26.82 HVR-H1 | GFTFTDNWIS |
| 183 | YW26.82 HVR-H2 | GYISPNSGFTYYADSVKG |
| 184 | YW26.82 HVR-H3 | VYYCARDNFGGYFDY |
| 185 | YW26.82 HVR-L1 | RASQDVSTAVA |
| 186 | YW26.82 HVR-L2 | SASFLYS |
| 187 | YW26.82 HVR-L3 | QQSYTGTVT |
| 188 | Anti-DLL4 antibody demcizumab (OMP-21M18) heavy chain variable region | QVQLVQSGAE VKKPGASVKI SCKASGYSFT AYYIHWVKQA PGQGLEWIGY ISSYNGATNY NQKFKGRVTF TTDTSTSTAY MELRSLRSDD TAVYYCARDY DYDVGMDYWG QGTLVTVSS |
| 189 | demcizumab light chain variable region | DIVMTQSPDS LAVSLGERAT ISCRASESVD NYGISFMKWF QQKPGQPPKL LIYAASNQGS GVPDRFSGSG SGTDFTLTIS SLQAEDVAVY YCQQSKEVPW TFGGGTKVEI K |
| 190 | demcizumab HVR-H1 | TAYYIH |
| 191 | demcizumab HVR-H2 | YISSYNGATNYNQKFKG |
| 192 | demcizumab HVR-H3 | RDYDYDVGMDY |
| 193 | demcizumab HVR-L1 | RASESVDNYGISFMK |
| 194 | demcizumab HVR-L2 | AASNQGS |
| 195 | demcizumab HVR-L3 | QQSKEVPWTFGG |
| 196 | αLRP6 YW211.31.62 antibody heavy chain variable region | EVQLVESGGG LVQPGGSLRL SCAASGFTFG YYYISWVRQA PGKGLEWVAE ISPYSGSTYY ADSVKGRFTI SADTSKNTAY LQMNSLRAED TAVYYCALRA RPPIRLHPRG SVMDYWGQ |
| 197 | αLRP6 YW211.31.62 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKR |
| 198 | αLRP6 YW211.31.62 HVR-H1 | YYYIS |
| 199 | αLRP6 YW211.31.62 HVR-H2 | EISPYSGSTYYADSVKG |

-continued

| | Table of Sequences | |
|---|---|---|
| SEQ ID NO | Description | Sequence |
| 200 | αLRP6 YW211.31.62 HVR-H3 | RARPPIRLHPRGSV |
| 201 | αLRP6 YW211.31.62 HVR-L1 | RASQDVSTAVA |
| 202 | αLRP6 YW211.31.62 HVR-L2 | SASFLYS |
| 203 | αLRP6 YW211.31.62 HVR-L3 | QQSYTTPPT |
| 204 | αLRP6 YW210.09 antibody heavy chain variable region | EVQLVESGGG LVQPGGSLRL SCAASGFTFT NSYIHWVRQA PGKGLEWVGW ITPYGGYTNY ADSVKGRFTI SADTSKNTAY LQMNSLRAED TAVYYCARGS GHVNAVKNYG YVMDYWGQ |
| 205 | αLRP6 YW210.09 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKR |
| 206 | αLRP6 YW210.09 HVR-H1 | NSYI |
| 207 | αLRP6 YW210.09 HVR-H2 | WITPYGGYTNYADSVK |
| 208 | αLRP6 YW210.09 HVR-H3 | GSGHVNAVKNYGYV |
| 209 | αLRP6 YW210.09 HVR-L1 | RASQDVSTAVA |
| 210 | αLRP6 YW210.09 HVR-L2 | SASFLYS |
| 211 | αLRP6 YW210.09 HVR-L3 | QQSYTTPPT |
| 212 | αLRP5 P6C.51.61 antibody heavy chain variable region | EVQLVESGGG LVQPGGSLRL SCAASGFTFS SYAMHWVRQA PGKGLEWVSR ISSNGGSTYY ADSVKGRFTI SRDNSKNTLY LQMNSLRAED TAVYYCARWI PQSYPFASYK SGFDYWGQ |
| 213 | αLRP5 P6C.51.61 light chain variable region | DIQMTQSPSS LSASVGDRVT ITCRASQVMG YYLAWYQQKP GKAPKLLIYD ASSLESGVPS RFSGSGSGTD FTLTISSLQP EDFATYYCQQ YYSYPFTFGQ GTKVEIKR |
| 214 | αLRP5 P6C.51.61 HVR-H1 | GFTFSSYAMH |
| 215 | αLRP5 P6C.51.61 HVR-H2 | SR ISSNGGSTYY ADSVKG |
| 216 | αLRP5 P6C.51.61 HVR-H3 | WIPQSYPFASYK SGFDY |
| 217 | αLRP5 P6C.51.61 HVR-L1 | RASQVMG YYLA |
| 218 | αLRP5 P6C.51.61 HVR-L2 | DASSLES |
| 219 | αLRP5 P6C.51.61 HVR-L3 | QQ YYSYPFT |

| SEQ ID NO | Description | Sequence |
|---|---|---|
| 220 | αLRP 7E5C8 antibody heavy chain variable region | QVQLKESGPG LVASSQSLSI TCTVSGFSLS RYSVHWVRQP PGKGLEWLGM IWGGGSTDYN SALKSRLGIS KDNSKSQVFL KMNSLQTDDT AMYYCAGTGS WFAYWGQGTL VTVSA |
| 221 | αLRP antibody 7E5C8 light chain variable region | DIQMTQSPAS LSASVGETVT ITCRASGNIH NYLAWYQQKQ GKSPQLLVYN AKTLADGVPS RFSGSGSGTQ YSLKINSLQP EDFGSYYCQH FWSTPWTFGG GTKLEIK |
| 222 | Anti-Fzd antibody Vantictumab (18R5) heavy chain variable region | EVQLVESGGG LVQPGGSLRL SCAASGFTFS HYTLSWVRQA PGKGLEWVSV ISGDGSYTYY ADSVKGRFTI SSDNSKNTLY LQMNSLRAED TAVYYCARNF IKYVFANWGQ GTLVTVSS |
| 223 | Vantictumab light chain variable region | DIELTQPPSV SVAPGQTARI SCSGDNIGSF YVHWYQQKPG QAPVLVIYDK SNRPSGIPER FSGSNSGNTA TLTISGTQAE DEADYYCQSY ANTLSLVFGG GTKLTVLG |
| 224 | Vantictumab HVR-H1 | GFTFSHYTLS |
| 225 | Vantictumab HVR-H2 | VISGDGSYTYYADSVKG |
| 226 | Vantictumab HVR-H3 | NFIKYVFAN |
| 227 | Vantictumab HVR-L1 | SGDNIGSFYVH |
| 228 | Vantictumab HVR-L2 | DKSNRPSG |
| 229 | Vantictumab HVR-L3 | QSYANTLSL |
| 230 | Anti-Fzd antibody B9L9.3 heavy chain variable region | EVQLVESGGG LVQPGGSLRL SCAASGFTFS SFNMFWVRQA PGKGLEWVAG IDDDGSYPNY GSAVKGRATI SRDNSKNTLY LQMNSLRAED TAVYYCAKSG YGGSWGGYIA DDIDAWGQGT LVTVSS |
| 231 | B9L9.3 light chain variable region | ELTQPPSVSV SPGQTARITC SGDGSYAGSY YYGWYQQKPG QAPVTLIYYN NKRPSGIPER FSGSLSGSTN TLTISGVQAE DEADYYCGSA DNSGAAFGGG TKLTVL |
| 232 | B9L9.3 HVR-H1 | SFNMF |
| 233 | B9L9.3 HVR-H2 | GIDDDGSYPNYGSAVKG |
| 234 | B9L9.3 HVR-H3 | SGYGGSWGGYIADDIDA |
| 235 | B9L9.3 HVR-L1 | SGDGSYAGSYYYG |
| 236 | B9L9.3 HVR-L2 | YNNKRPS |
| 237 | B9L9.3 HVR-L3 | GSADNSGAA |
| 238 | Fzd7 ECD | CQPISIPLCT DIAYNQTILP NLLGHTNQED AGLEVHQFYP LVKVQCSPEL RFFLCSMYAP VCTVLDQAIP PCRSLCERAR QGCEALMNKF GFQWPERLRC ENFPVHGAGE IC |
| 239 | Fzd8 ECD | CQEITVPLCK GIGYNYTYMP NQFNHDTQDE AGLEVHQFWP LVEIQCSPDL KFFLCSMYTP ICLEDYKKPL PPCRSVCERA KAGCAPLMRQ YGFAWPDRMR CDRLPEQGNP DT |

| SEQ ID NO | Description | Sequence |
|---|---|---|
| 240 | 54F28 Fzd8-Fc | ASAKELACQE ITVPLCKGIG YNYTYMPNQF NHDTQDEAGL EVHQFWPLVE IQCSPDLKFF LCSMYTPICL EDYKKPLPPC RSVCERAKAG CAPLMRQYGF AWPDRMRCDR LPEQGNPDTL CMDYNRTDLT TEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 241 | Anti-Notch N248A antibody heavy chain variable region | QVQLQQSGAE LMKPGASVKI SCKATGYTFS NYWMEWVKQR PGHGLEWIGE ILPGRGRTNY NENFKGKATF TADTSSNTVY MQLNSLTSED SAVYYCARFH SSAYYYTMDY WGQRTSVTVS S |
| 242 | N248A antibody light chain variable region | QAVVTQESAL TTSPGETVTL TCRSSTGAVT TSNYANWVQE KPDHLFTGLI GGTNNRAPGI PARFSGSLIG DKAALTITGA QTEDEAIYFC ALWYSNHWVF GGGTKLTVL |
| 243 | N248A HVR-H1 | NYWME |
| 244 | N248A HVR-H2 | EILPGRGRTNYNENFK |
| 245 | N248A HVR-H3 | FHSSAYYYTMDY |
| 246 | N248A HVR-L1 | RSSTGAVTTSNYAN |
| 247 | N248A HVR-L2 | GTNNRAP |
| 248 | N248A HVR-L3 | ALWYSNHWV |
| 249 | Anti-DLL/VEGF 219R45-MB-21R83 heavy chain variable region (anti-DLL arm) | QVQLVQSGAE VKKPGASVKI SCKASGYSFT AYYIHWVKQA PGQGLEWIGY ISNYNRATNY NQKFKGRVTF TTDTSTSTAY MELRSLRSDD TAVYYCARDY DYDVGMDYWG QGTLVTVSS |
| 250 | 219R45-MB-21R83 light chain variable region (anti-DLL arm) | DIVMTQSPDS LAVSLGERAT ISCRASESVD NYGISFMKWF QQKPGQPPKL LIYAASNQGS GVPDRFSGSG SGTDFTLTIS SLQAEDVAVY YCQQSKEVPW TFGGGTKVEI K |
| 251 | 219R45-MB-21R83 HVR-H1 | TAYYIH |
| 252 | 219R45-MB-21R83 HVR-H2 | YISNYNRATNYNQKFK |
| 253 | 219R45-MB-21R83 HVR-H3 | RDYDYDVGMDY |
| 254 | 219R45-MB-21R83 HVR-L1 | RASESVDNYGISFMK |
| 255 | 219R45-MB-21R83 HVR-L2 | AASNQGS |
| 256 | 219R45-MB-21R83 HVR-L3 | QQSKEVPWTFGG |
| 257 | decoy Wnt receptor, Frizzled 8 CRD (FZD8CRD) | MEWGYLLEVT SLLAALAVLQ RSSGAAAASA KELACQEITV PLCKGIGYNY TYMPNQFNHD TQDEAGLEVH QFWPLVEIQC SPDLKFFLCS MYTPICLEDY KKPLPPCRSV CERAKAGCAP LMRQYGFAWP DRMRCDRLPE QGNPDTLCMD YNRTDLESGG GGVTDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 258 | J1-183D HVR-H1 sequence | DYAIH |

Table of Sequences

| SEQ ID NO | Description | Sequence |
|---|---|---|
| 259 | J1-183D_VH and VH_1 HVR-H2 sequence | NTYYGDSKYNQKFKD |
| 260 | J1-183D_VH_2, VH_3, and VH_4 HVR-H2 sequence | NTYYGDSKYAQKFQG |
| 261 | J1-183D HVR-H3 sequence | GYDGFAY |
| 262 | J1-183D HVR-L1 sequence | RTSENIYSYLT |
| 263 | J1-183D_VL and _VL_1 HVR-L2 sequence | NAKILAAGV |
| 264 | J1-183D_VL_2 HVR-L2 sequence | NAKTLASGV |
| 265 | J1-183D_VL_3 HVR-L2 sequence | NAKILDSGV |
| 266 | J1-183D_VL_4 HVR-L2 sequence | HAKILDSGV |
| 267 | J1-183D HVR-L3 sequence | QHHYDIPWT |
| 268 | J1-183D_VL light chain sequence | MSVPTQVLGLLLLWLTDARCDIQLTQSPASLSASVGETVTFTCRTSENIYSYLTWYQQKQGKSPQLLVYNAKILAAGVPSRFSGYGSGTQFSLKINSLQPEDFGTYYCQHHYDIPWTFGGGTKLEIKRT |
| 269 | J1-183D_VL_1 light chain sequence | MSVPTQVLGLLLLWLTDARCDIQMTQSPSSLSASVGDRVTITCRTSENIYSYLTWYQQKPGKAPKLLVYNAKILAAGVPSRFSGSGSGTDFTLTISSLQPEDFATYYCQHHYDIPWTFGGGTKLEIKRT |
| 270 | J1-183D_VL_2 light chain sequence | MSVPTQVLGLLLLWLTDARCDIQMTQSPSSLSASVGDRVTITCRTSENIYSYLTWYQQKPGKAPKLLIYNAKTLASGVPSRFSGSGSGTDFTLTISSLQPEDFATYYCQHHYDIPWTFGGGTKLEIKRT |
| 271 | J1-183D_VL_3 light chain sequence | MSVPTQVLGLLLLWLTDARCDIQMTQSPSSLSASVGDRVTITCRTSENIYSYLTWYQQKPGKAPKLLIYNAKILDSGVPSRFSGSGSGTDFTLTISSLQPEDFATYYCQHHYDIPWTFGGGTKLEIKRT |
| 272 | J1-183D_VL_4 light chain sequence | MSVPTQVLGLLLLWLTDARCDIQMTQSPSSLSASVGDRVTITCRTSENIYSYLTWYQQKPGKAPKLLIYHAKILDSGVPSRFSGSGSGTDFTLTISSLQPEDFATYYCQHHYDIPWTFGGGTKLEIKRT |
| 273 | J1-183D_VH heavy chain sequence | MEWSWVFLFFLSVTTGVHSQVQLQQPGTELVRPGVSVKISCKVSGYAFTDYAIHWIMQSHAKSLEWIGIINTYYGDSKYNQKFKDKATMTVDKSSNTAYMELARLTSEDSAIYYCARGYDGFAYWGQGTLVTVSSASTKGP |
| 274 | J1-183D_VH_1 heavy chain sequence | MEWSWVFLFFLSVTTGVHSQVQLVQSGAELKKPGASVKVSCKVSGYAFTDYAIHWIRQAPGQGLEWMGIINTYYGDSKYNQKFKDRVTMTVDKSTSTAYMELSSLRSEDTAVYYCARGYDGFAYWGQGTLVTVSSASTKGP |
| 275 | J1-183D_VH_2 heavy chain sequence | MEWSWVFLFFLSVTTGVHSQVQLVQSGAELKKPGASVKVSCKVSGYAFTDYAIHWIRQAPGQGLEWMGIINTYYGDSKYAQKFQGRVTMTVDTSTSTAYMELSSLRSEDTAVYYCARGYDGFAYWGQGTLVTVSSASTKGP |
| 276 | J1-183D_VH_3 heavy chain sequence | MEWSWVFLFFLSVTTGVHSQVQLVQSGAELKKPGASVKVSCKVSGYAFTDYAIHWVRQAPGQGLEWMGIINTYYGDSKYAQKFQGRVTMTVDTSTSTAYMELSSLRSEDTAVYYCARGYDGFAYWGQGTLVTVSSASTKGP |
| 277 | J1-183D_VH_4 heavy chain sequence | MEWSWVFLFFLSVTTGVHSQVQLVQSGAEVKKPGASVKVSCKASGYTFTDYAIHWVRQAPGQGLEWMGIINTYYGDSKYAQKFQGRVTMTVDTSTSTAYMELSSLRSEDTAVYYCARGYDGFAYWGQGTLVTVSSASTKGP |
| 278 | J1-65D HVR-H1 | DYEMH |

-continued

| Table of Sequences | | |
|---|---|---|
| SEQ ID NO | Description | Sequence |
| 279 | J1-65D_VH and VH_1 HVR-H2 | QPGGGGTAYNQKFKG |
| 280 | J1-65D_VH_2 HVR-H2 | QPGGGGTAYAQKFKG |
| 281 | J1-65D_VH_3 and VH_4 HVR-H2 | QPGGGGTAYAQKFQG |
| 282 | J1-65D HVR-H3 | RGYDDYPFAY |
| 283 | J1-65D_VL, VL_1, VL_2, and VL_3 HVR-L1 | RASGNIHNYLA |
| 284 | J1-65D_VL_4 HVR-L1 | RASQGIHNYLA |
| 285 | J1-65D_VL HVR-L2 | NAKTLADDI |
| 286 | J1-65D_VL_1 HVR-L2 | NAKTLADDV |
| 287 | J1-65D_VL_2, VL_3, and VL_4 HVR-L2 | NAKTLADAV |
| 288 | J1-65D_VL, VL_1, VL_2, and VL_3 HVR-L3 | QHFWSAPWT |
| 289 | J1-65D_VL_4 HVR-L3 | QQFWSAPWT |
| 290 | J1-65D_VL light chain sequence | MSVPTQVLGLLLLWLTDARCDIQLQSPASLSASVGETVTITCRASGNIHNYLAW YQQKQGKSPQLLVYNAKTLADDIPSRFSGSGSGTQYSLKINSLQPEDFGSYYCQ HFWSAPWTFGGGTKLEIKRT |
| 291 | J1-65D_VL_1 light chain sequence | MSVPTQVLGLLLLWLTDARCDIQMTQSPSSLSASVGDRVTITCRASGNIHNYLA WYQQKPGKAPKLLIYNAKTLADDVPSRFSGSGSGTDYTLTISSLQPEDFATYYC QHFWSAPWTFGGGTKLEIKRT |
| 292 | J1-65D_VL_2 light chain sequence | MSVPTQVLGLLLLWLTDARCDIQMTQSPSSLSASVGDRVTITCRASGNIHNYLA WYQQKPGKAPKLLIYNAKTLADAVPSRFSGSGSGTDYTLTISSLQPEDFATYYC QHFWSAPWTFGGGTKLEIKRT |
| 293 | J1-65D_VL_3 light chain sequence | MSVPTQVLGLLLLWLTDARCDIQMTQSPSSLSASVGDRVTITCRASGNIHNYLA WYQQKPGKAPKLLIYNAKTLADAVPSRFSGSGSGTDYTLTISSLQPEDFATYYC QHFWSAPWTFGQGTKLEIKRT |
| 294 | J1-65D_VL_4 light chain sequence | MSVPTQVLGLLLLWLTDARCDIQMTQSPSSLSASVGDRVTITCRASQGIHNYLA WYQQKPGKAPKLLIYNAKTLADAVPSRFSGSGSGTDYTLTISSLQPEDFATYYC QQFWSAPWTFGQGTKLEIKRT |
| 295 | J1-65D_VH heavy chain sequence | MEWSWVFLFFLSVTTGVHSQVQLQQPGAELVRPGASVKLSCKALGYTFTDYEMH WVKETPVHGLEWIGAIQPGGGGTAYNQKFKGKATLTADKSSSTAYMELSSLTSE DSAVYYCTRRGYDDYPFAYWGQGTLVTVSSASTKGP |
| 296 | J1-65D_VH_1 heavy chain sequence | MEWSWVFLFFLSVTTGVHSQVQLVQSGAELKKPGSSVKVSCKASGYTFTDYEMH WVRQAPGQGLEWMGAIQPGGGGTAYNQKFKGRVTLTADKSTSTAYMELSSLRSE DTAVYYCTRRGYDDYPFAYWGQGTLVTVSSASTKGP |
| 297 | J1-65D_VH_2 heavy chain sequence | MEWSWVFLFFLSVTTGVHSQVQLVQSGAELKKPGSSVKVSCKASGYTFTDYEMH WVRQAPGQGLEWMGAIQPGGGGTAYAQKFKGRVTLTADKSTSTAYMELSSLRSE DTAVYYCTRRGYDDYPFAYWGQGTLVTVSSASTKGP |
| 298 | J1-65D_VH_3 heavy chain sequence | MEWSWVFLFFLSVTTGVHSQVQLVQSGAEVKKPGSSVKVSCKASGYTFTDYEMH WVRQAPGQGLEWMGAIQPGGGGTAYAQKFQGRVTLTADKSTSTAYMELSSLRSE DTAVYYCTRRGYDDYPFAYWGQGTLVTVSSASTKGP |

Table of Sequences

| SEQ ID NO | Description | Sequence |
|---|---|---|
| 299 | J1-65D_VH_4 heavy chain sequence | MEWSWVFLFFLSVTTGVHSQVQLVQSGAEVKKPGSSVKVSCKASGYTFTDYEMH WVRQAPGQGLEWMGAIQPGGGTAYAQKFQGRVTITADKSTSTAYMELSSLRSE DTAVYYCTRRGYDDYPFAYWGQGTLVTVSSASTKGP |
| 300 | 131R010 HVR H1 | KASGYTFT DYS |
| 301 | 131R010 HVR H2 | IYPSNGDS |
| 302 | 131R010 HVR H3 | ATYF ANNFDY |
| 303 | 131R010FIVRL1 | QSVD YDGDSYM |
| 304 | 131R010FIVRL2 | AASNLES |
| 305 | 131R010FIVRL3 | QQSNEDPLT |
| 306 | 131R010 heavy chain variable region | QVQLVQSGAE VKKPGASVKV SCKASGYTFT DYSIHWVRQA PGQGLEWIGY IYPSNGDSGY NQKFKNRVTM TRDTSTSTAY MELSRLRSED TAVYYCATYF ANNFDYWGQG TTLTVSS |
| 307 | 131R010 light chain variable region | DIQMTQSPSS LSASVGDRVT ITCKASQSVD YDGDSYMNWY QQKPGKAPKL LIYAASNLES GVPSRFSGSG SGTDFTLTIS PVQAEDFATY YCQQSNEDPL TFGAGTKLEL KRT |
| 308 | 89M5 HVR-H1 | TGYTMH |
| 309 | 89M5 HVR-H2 | GINPNNGGTTYNQNFKG |
| 310 | 89M5 HVR-H3 | KEFSDGYYFFAY |
| 311 | 89M5 HVR-L1 | KASQDVIFAVA |
| 312 | 89M5 HVR-L2 | WASTRHT |
| 313 | 89M5 HVR-L3 | QQHYSTPW |
| 314 | 89M5 heavy chain variable region | EVQLQQSGPE LVKPGASVKI SCKTSGYTFT GYTMHWVRQS HGKTLEWIGG INPNNGGTTY NQNFKGKATL TVEKSSTTAY LELRSLTSED SALYYCARKE FSDGYYFFAY WGQGTLVTVS A |
| 315 | 89M5 light chain variable region | DIVMTQSHKF MSTSVGDRVN ITCKASQDVI FAVAWYQQKP GQSPKLLIYW ASTRHTGVPD RFTGSVSGTD YTLTISSVQA EDLALYYCQQ HYSTPWTFGG GTKLEIK |
| 316 | 130M23 HVR-H1 | SSYAMS |
| 317 | 130M23 HVR-H2 | SISSGGSTYYPDSVKG |
| 318 | 130M23 HVR-H3 | RGGDPGVYNGDYEDAMDY |
| 319 | 130M23 HVR-L1 | KASQDVSSAVA |
| 320 | 130M23 HVR-L2 | WASTRHT |
| 321 | 130M23 HVR-L3 | QQHYSTP |
| 322 | 130M23 heavy chain variable region | EVKLVESGGG LVKPGGSLKF SCAASGFSFS SYAMSWVRQT PEKRLEWVAS ISSGGSTYYP DSVKGRFTIS RDNVRNILYL QMSSLASEDT AMYFCARGGD PGVYNGDYED AMDYWGQGTS VTVSS |
| 323 | 130M23 light chain variable region | DIVMTQSHKF MSTSVGDRVS ITCKASQDVS SAVAWYQQKP GQSPKLLIYW ASTRHTGVPD RFTNSGSGTD YTLTISSVQA EDLALYYCQQ HYSTPWTFGG GTKLEIK |

What is claimed is:

1. A method of alleviating toxicity associated with Notch pathway inhibition comprising administering to an individual being treated with a Notch pathway inhibitor an effective amount of at least one Wnt pathway inhibitor, wherein the toxicity comprises one or more of diarrhea, gastrointestinal bleeding, and secretory metaplasia.

2. The method of claim 1, wherein the Wnt pathway inhibitor is administered before, at the same time as, or after the individual has been administered at least one dose of a Notch pathway inhibitor.

3. The method of claim 1, wherein administration of at least one Wnt pathway inhibitor alleviates the diarrhea or gastrointestinal bleeding or both.

4. The method of claim 1, wherein the individual is being treated for cancer.

5. The method of claim 4, wherein the method results in reduced toxicity compared to toxicity observed with the at least one Notch pathway inhibitor alone.

6. The method of claim 4, wherein the cancer is selected from breast cancer, lung cancer, brain cancer, cervical cancer, colon cancer, liver cancer, bile duct cancer, pancreatic cancer, skin cancer, B-cell malignancies, and T-cell malignancies.

7. The method of claim 1, wherein the Notch pathway inhibitor is a gamma-secretase inhibitor.

8. The method of claim 1, wherein the Notch pathway inhibitor inhibits at least one protein selected from Notch1, Notch2, Notch3, Notch4, DLL1, DLL4, Jagged1, and Jagged2.

9. The method of claim 8, wherein the Notch pathway inhibitor inhibits Notch1 and Notch2 or inhibits Notch 2 and Notch 3.

10. The method of claim 8, wherein the Notch pathway inhibitor is an anti-Notch antibody.

11. The method of claim 10, wherein the anti-Notch antibody is an anti-Notch NRR antibody or an anti-Notch antibody that binds to the EGF-like repeat domain of Notch.

12. The method of claim 10, wherein the anti-Notch antibody is selected from:
  a) an antibody comprising HVR-H1, HVR-H2, HVR-H3, HVR-L1, HVR-L2, and HVR-L3 shown in SEQ ID NOs: 35 to 40, respectively;
  b) an antibody comprising a heavy chain variable region and a light chain variable region shown in SEQ ID NOs: 33 and 34, respectively;
  c) an antibody comprising HVR-H1, HVR-H2, HVR-H3, HVR-L1, HVR-L2, and HVR-L3 shown in SEQ ID NOs: 27 to 32, respectively;
  d) an antibody comprising a heavy chain variable region and a light chain variable region shown in SEQ ID NOs: 25 and 26, respectively;
  e) an antibody comprising HVR-H1, HVR-H2, HVR-H3, HVR-L1, HVR-L2, and HVR-L3 shown in SEQ ID NOs: 43, 46, 48, 49, 50, and 53, respectively;
  f) an antibody comprising a heavy chain variable region and a light chain variable region shown in SEQ ID NOs: 41 and 42, respectively;
  g) an antibody comprising HVR-H1, HVR-H2, HVR-H3, HVR-L1, HVR-L2, and HVR-L3 shown in SEQ ID NOs: 58 to 60, 64, 67, and 71, respectively;
  h) an antibody comprising a heavy chain variable region and a light chain variable region shown in SEQ ID NOs: 55 and 56, respectively;
  i) an antibody comprising HVR-H1, HVR-H2, HVR-H3, HVR-L1, HVR-L2, and HVR-L3 shown in SEQ ID NOs: 74, 75, 77, and 79-81, respectively; and
  j) an antibody comprising a heavy chain variable region and a light chain variable region shown in SEQ ID NOs: 72 and 73, respectively
  k) an antibody comprising HVR-H1, HVR-H2, HVR-H3, HVR-L1, HVR-L2, and HVR-L3 shown in SEQ ID NOs: 243 to 248, respectively; and
  l) an antibody comprising a heavy chain variable region and a light chain variable region shown in SEQ ID NOs: 241 and 242, respectively.

13. The method of claim 8, wherein the Notch pathway inhibitor inhibits at least one protein selected from Jagged1 and Jagged2.

14. The method of claim 13, wherein the Notch pathway inhibitor is an anti-Jagged antibody.

15. The method of claim 14, wherein the anti-Jagged antibody is selected from:
  a) an antibody comprising HVR-H1, HVR-H2, HVR-H3, HVR-L1, HVR-L2, and HVR-L3 shown in SEQ ID NOs: 108-113, respectively;
  b) an antibody comprising a heavy chain variable region and a light chain variable region shown in SEQ ID NOs: 106 and 107, respectively;
  c) an antibody comprising HVR-H1, HVR-H2, HVR-H3, HVR-L1, HVR-L2, and HVR-L3 shown in SEQ ID NOs: 116-121, respectively;
  d) an antibody comprising a heavy chain variable region and a light chain variable region shown in SEQ ID NOs: 114 and 115, respectively;
  e) an antibody comprising HVR-H1, HVR-H2, HVR-H3, HVR-L1, HVR-L2, and HVR-L3 shown in SEQ ID NOs: 124-129, respectively;
  f) an antibody comprising a heavy chain variable region and a light chain variable region shown in SEQ ID NOs: 122 and 123, respectively;
  g) an antibody comprising a heavy chain variable region and a light chain variable region shown in SEQ ID NOs: 130 and 131, respectively;
  h) an antibody comprising HVR-H1, HVR-H2, HVR-H3, HVR-L1, HVR-L2, and HVR-L3 shown in SEQ ID NOs: 134-139, respectively;
  i) an antibody comprising a heavy chain variable region and a light chain variable region shown in SEQ ID NOs: 132 and 133, respectively;
  j) an antibody comprising HVR-H1, HVR-H2, HVR-H3, HVR-L1, HVR-L2, and HVR-L3 shown in SEQ ID NOs: 142-147, respectively;
  k) an antibody comprising a heavy chain variable region and a light chain variable region shown in SEQ ID NOs: 140 and 141, respectively;
  l) an antibody comprising HVR-H1, HVR-H2, HVR-H3, HVR-L1, HVR-L2, and HVR-L3 shown in SEQ ID NOs: 150-155, respectively;
  m) an antibody comprising a heavy chain variable region and a light chain variable region shown in SEQ ID NOs: 148 and 149, respectively;
  n) an antibody comprising HVR-H1, HVR-H2, HVR-H3, HVR-L1, HVR-L2, and HVR-L3 shown in SEQ ID NOs: 158-163, respectively;
  o) an antibody comprising a heavy chain variable region and a light chain variable region shown in SEQ ID NOs: 156 and 157, respectively;
  p) an antibody comprising HVR-H1, HVR-H2, HVR-H3, HVR-L1, HVR-L2, and HVR-L3 shown in SEQ ID NOs: 166-171, respectively;
  q) an antibody comprising a heavy chain variable region and a light chain variable region shown in SEQ ID NOs: 164 and 165, respectively;
  r) an antibody comprising HVR-H1, HVR-H2, HVR-H3, HVR-L1, HVR-L2, and HVR-L3 shown in SEQ ID NOs: 174-179, respectively;
  s) an antibody comprising a heavy chain variable region and a light chain variable region shown in SEQ ID NOs: 172 and 173, respectively;
  t) an antibody comprising HVR-H1 of SEQ ID NO: 258, HVR-H2 selected from SEQ ID NOs: 259 and 260, HVR-H3 of SEQ ID NO: 261, HVR-L1 of SEQ ID NO: 262, HVR-L2 selected from SEQ ID NOs: 263 to 266, and HVR-L3 of SEQ ID NO: 267;
  u) an antibody comprising a heavy chain variable region selected from SEQ ID NOs: 273 to 277 and a light chain variable region selected from SEQ ID NOs: 268 to 272;
  v) an antibody comprising HVR-H1 of SEQ ID NO: 278, HVR-H2 selected from SEQ ID NOs: 279 to 281, HVR-H3 of SEQ ID NO: 282, HVR-L1 selected from SEQ ID NOs: 283 and 284, HVR-L2 selected from SEQ ID NOs: 285 to 287, and HVR-L3 selected from SEQ ID NOs: 288 and 289; and
  w) an antibody comprising a heavy chain variable region selected from SEQ ID NOs: 295 to 299 and a light chain variable region selected from SEQ ID NOs: 290 to 294.

16. The method of 8, wherein the Notch pathway inhibitor inhibits at least one protein selected from DLL1 and DLL4.

17. The method of claim 16, wherein the Notch pathway inhibitor is an anti-DLL antibody.

18. The method of claim 17, wherein the anti-DLL antibody is an antibody selected from:
  a) an antibody comprising HVR-H1, HVR-H2, HVR-H3, HVR-L1, HVR-L2, and HVR-L3 shown in SEQ ID NOs: 182-187, respectively;
  b) an antibody comprising a heavy chain variable region and a light chain variable region shown in SEQ ID NOs: 180 and 181, respectively;

c) an antibody comprising HVR-H1, HVR-H2, HVR-H3, HVR-L1, HVR-L2, and HVR-L3 shown in SEQ ID NOs: 190-195, respectively;
d) an antibody comprising a heavy chain variable region and a light chain variable region shown in SEQ ID NOs: 188 and 189, respectively;
e) an antibody comprising HVR-H1, HVR-H2, HVR-H3, HVR-L1, HVR-L2, and HVR-L3 shown in SEQ ID NOs: 251-256, respectively; and
f) an antibody comprising a heavy chain variable region and a light chain variable region shown in SEQ ID NOs: 249 and 250, respectively.

19. The method of claim 17, wherein the anti-DLL antibody is a bispecific antibody that binds to DLL4 and VEGF.

20. The method of claim 1, wherein the Wnt pathway inhibitor inhibits at least one protein selected from a Wnt, an LRP, an RSPO, and a Fzd.

21. The method of claim 20, wherein the Wnt pathway inhibitor inhibits LRP5, LRP6, or both LRP5 and LRP6.

22. The method of claim 21, wherein the Wnt pathway inhibitor is an anti-LRP antibody.

23. The method of claim 22, wherein the anti-LRP antibody is selected from:
a) an antibody comprising HVR-H1, HVR-H2, HVR-H3, HVR-L1, HVR-L2, and HVR-L3 shown in SEQ ID NOs: 198-203, respectively;
b) an antibody comprising a heavy chain variable region and a light chain variable region shown in SEQ ID NOs: 196 and 197, respectively;
c) an antibody comprising HVR-H1, HVR-H2, HVR-H3, HVR-L1, HVR-L2, and HVR-L3 shown in SEQ ID NOs: 206-211, respectively;
d) an antibody comprising a heavy chain variable region and a light chain variable region shown in SEQ ID NOs: 204 and 205, respectively;
e) a bispecific antibody comprising a first half antibody comprising HVR-H1, HVR-H2, HVR-H3, HVR-L1, HVR-L2, and HVR-L3 shown in SEQ ID NOs: 198-203, respectively, and a second half antibody comprising HVR-H1, HVR-H2, HVR-H3, HVR-L1, HVR-L2, and HVR-L3 shown in SEQ ID NOs: 206-211, respectively;
f) a bispecific antibody comprising a first half antibody comprising a heavy chain variable region and a light chain variable region shown in SEQ ID NOs: 196 and 197, respectively, and a second half antibody comprising a heavy chain variable region and a light chain variable region shown in SEQ ID NOs: 204 and 205, respectively;
g) an antibody comprising a heavy chain variable region and a light chain variable region shown in SEQ ID NOs: 220 and 221, respectively;
h) an antibody comprising HVR-H1, HVR-H2, HVR-H3, HVR-L1, HVR-L2, and HVR-L3 shown in SEQ ID NOs: 214-219, respectively; and
i) an antibody comprising a heavy chain variable region and a light chain variable region shown in SEQ ID NOs: 212 and 213, respectively.

24. The method of claim 20, wherein the Wnt pathway inhibitor inhibits at least one Fzd.

25. The method of claim 24, wherein the Wnt pathway inhibitor is an anti-Fzd antibody.

26. The method of claim 25, wherein the anti-Fzd antibody is an antibody selected from:
a) an antibody comprising HVR-H1, HVR-H2, HVR-H3, HVR-L1, HVR-L2, and HVR-L3 shown in SEQ ID NOs: 224-229, respectively;
b) an antibody comprising a heavy chain variable region and a light chain variable region shown in SEQ ID NOs: 222 and 223, respectively
c) an antibody comprising HVR-H1, HVR-H2, HVR-H3, HVR-L1, HVR-L2, and HVR-L3 shown in SEQ ID NOs: 232-237, respectively; and
d) an antibody comprising a heavy chain variable region and a light chain variable region shown in SEQ ID NOs: 230 and 231, respectively.

27. The method of claim 24, wherein the Wnt pathway inhibitor is a soluble Fzd.

28. The method of claim 27, wherein the soluble Fzd comprises an Fzd extracellular domain and an Fc.

29. The method of claim 27, wherein the soluble Fzd is a soluble Fzd8.

30. The method of claim 29, wherein the soluble Fzd8 comprises the sequence of SEQ ID NO: 240 or SEQ ID NO: 257.

31. The method of claim 20, wherein the Wnt pathway inhibitor inhibits at least one R-spondin (RSPO).

32. The method of claim 31, wherein the Wnt pathway inhibitor is an anti-RSPO antibody.

33. The method of claim 32, wherein the anti-RSPO antibody is an antibody selected from:
a) an antibody comprising HVR-H1, HVR-H2, HVR-H3, HVR-L1, HVR-L2, and HVR-L3 shown in SEQ ID NOs: 300-305, respectively;
b) an antibody comprising a heavy chain variable region and a light chain variable region shown in SEQ ID NOs: 306 and 307, respectively;
c) an antibody comprising HVR-H1, HVR-H2, HVR-H3, HVR-L1, HVR-L2, and HVR-L3 shown in SEQ ID NOs: 308-313, respectively;
d) an antibody comprising a heavy chain variable region and a light chain variable region shown in SEQ ID NOs: 314 and 315, respectively;
e) an antibody comprising HVR-H1, HVR-H2, HVR-H3, HVR-L1, HVR-L2, and HVR-L3 shown in SEQ ID NOs: 316-321, respectively; and
f) an antibody comprising a heavy chain variable region and a light chain variable region shown in SEQ ID NOs: 322 and 323, respectively.

34. The method of claim 20, wherein the Wnt pathway inhibitor inhibits at least one Wnt.

35. The method of claim 34, wherein the Wnt pathway inhibitor is an anti-Wnt antibody.

36. The method of claim 20, wherein the Wnt pathway inhibitor is a small molecule.

37. The method of claim 36, wherein the Wnt pathway inhibitor is selected from LGK974 (2-(2',3-dimethyl-[2,4'-bipyridin]-5-yl)-N-(5-(pyrazin-2-yl)pyridin-2-yl)acetamide), AVN316 (Avalon Pharmaceuticals), and PRI-724 (Prism Pharma Co.).

* * * * *